(12) United States Patent
Hua et al.

(10) Patent No.: US 12,678,203 B2
(45) Date of Patent: *Jul. 14, 2026

(54) SYSTEMS AND METHODS FOR PEDICLE SCREW STABILIZATION OF SPINAL VERTEBRAE

(71) Applicant: SPINE23 INC., Campbell, CA (US)

(72) Inventors: Sherwin Hua, Hillsborough, CA (US); Natasha Chernishof, San Jose, CA (US)

(73) Assignee: SPINE23 INC., Campbell, CA (US)

( * ) Notice: Subject to any disclaimer, the term of this patent is extended or adjusted under 35 U.S.C. 154(b) by 16 days.

This patent is subject to a terminal disclaimer.

(21) Appl. No.: 18/810,275

(22) Filed: Aug. 20, 2024

(65) Prior Publication Data

US 2024/0407811 A1     Dec. 12, 2024

Related U.S. Application Data

(63) Continuation of application No. 17/743,135, filed on May 12, 2022, now Pat. No. 12,076,058.

(Continued)

(51) Int. Cl.
*A61B 17/70* (2006.01)
(52) U.S. Cl.
CPC ...... *A61B 17/7077* (2013.01); *A61B 17/7032* (2013.01); *A61B 17/7085* (2013.01)
(58) Field of Classification Search
CPC .............. A61B 17/708; A61B 17/7077; A61B 17/7079; A61B 17/7085
See application file for complete search history.

(56) References Cited

U.S. PATENT DOCUMENTS 4,448,191 A     5/1984   Rodnyansky et al.
5,092,866 A     3/1992   Breard et al.
(Continued)

FOREIGN PATENT DOCUMENTS

CN          2782035 Y     5/2006
CN          1972639 A     5/2007
(Continued)

OTHER PUBLICATIONS

U.S. Appl. No. 13/098,325 (U.S. Pat. No. 8,545,541), filed Apr. 29, 2011, System and Method for Wire-Guided Pedicle Screw Stabilization of Spinal Vertebrae.

(Continued)

*Primary Examiner* — Eduardo C Robert
*Assistant Examiner* — Anna V. Little
(74) *Attorney, Agent, or Firm* — KNOBBE, MARTENS, OLSON & BEAR, LLP

(57) ABSTRACT

Disclosed herein are embodiments of a system and embodiments of a method for stabilizing spinal vertebrae through a skin incision. In some embodiments, the system or method can include a first screw having a first screw head, a second screw having a second screw head, and a third screw having a third screw head, a first tower having a distal portion, a proximal portion, and a bend between the distal portion and the proximal portion, a second tower having a distal portion and a proximal portion, the second tower configured to be removably coupled with the second screw at a distal end of the second tower, and a third tower having a distal portion, a proximal portion, and a bend between the distal portion and the proximal portion.

26 Claims, 92 Drawing Sheets

Related U.S. Application Data

(60) Provisional application No. 63/187,859, filed on May 12, 2021.

(56) References Cited

U.S. PATENT DOCUMENTS

| | | | |
|---|---|---|---|
| 5,242,443 A | 9/1993 | Kambin | |
| 5,300,076 A | 4/1994 | Leriche | |
| 5,306,275 A | 4/1994 | Bryan | |
| 5,324,316 A | 6/1994 | Schulman et al. | |
| 5,411,546 A | 5/1995 | Bowald et al. | |
| 5,531,779 A | 7/1996 | Dahl et al. | |
| 5,672,175 A | 9/1997 | Martin | |
| 5,728,097 A | 3/1998 | Mathews | |
| 5,865,842 A | 2/1999 | Knuth et al. | |
| 5,938,689 A | 8/1999 | Fischell et al. | |
| 5,975,085 A | 11/1999 | Rise | |
| 5,980,521 A | 11/1999 | Montague et al. | |
| 6,011,991 A | 1/2000 | Mardirossian | |
| 6,016,449 A | 1/2000 | Fischell et al. | |
| 6,051,017 A | 4/2000 | Loeb et al. | |
| 6,090,113 A | 7/2000 | Le Couedic et al. | |
| 6,175,764 B1 | 1/2001 | Loeb et al. | |
| 6,176,242 B1 | 1/2001 | Rise | |
| 6,181,965 B1 | 1/2001 | Loeb et al. | |
| 6,185,452 B1 | 2/2001 | Schulman et al. | |
| 6,208,881 B1 | 3/2001 | Champeau | |
| 6,208,894 B1 | 3/2001 | Schulman et al. | |
| 6,214,016 B1 | 4/2001 | Williams et al. | |
| 6,227,203 B1 | 5/2001 | Rise et al. | |
| 6,235,028 B1 | 5/2001 | Brumfield et al. | |
| 6,240,316 B1 | 5/2001 | Richmond et al. | |
| 6,263,237 B1 | 7/2001 | Rise | |
| 6,343,226 B1 | 1/2002 | Sunde et al. | |
| 6,427,086 B1 | 7/2002 | Fischell et al. | |
| 6,445,953 B1 | 9/2002 | Bulkes et al. | |
| 6,482,182 B1 | 11/2002 | Carroll et al. | |
| 6,485,491 B1 | 11/2002 | Farris et al. | |
| 6,493,592 B1 | 12/2002 | Leonard et al. | |
| 6,530,929 B1 | 3/2003 | Justis et al. | |
| 6,546,277 B1 | 4/2003 | Franck et al. | |
| 6,549,810 B1 | 4/2003 | Leonard et al. | |
| 6,582,441 B1 | 6/2003 | He et al. | |
| 6,597,954 B1 | 7/2003 | Pless et al. | |
| 6,622,051 B1 | 9/2003 | Bishay et al. | |
| 6,623,490 B1 | 9/2003 | Crane et al. | |
| 6,665,562 B2 | 12/2003 | Gluckman | |
| 6,711,430 B1 | 3/2004 | Ferris et al. | |
| 6,731,976 B2 | 5/2004 | Penn et al. | |
| 6,735,475 B1 | 5/2004 | Whitehurst et al. | |
| 6,764,498 B2 | 7/2004 | Mische | |
| 6,782,292 B2 | 8/2004 | Whitehurst | |
| 6,788,975 B1 | 9/2004 | Whitehurst et al. | |
| 6,793,656 B1 | 9/2004 | Mathews | |
| 6,795,737 B2 | 9/2004 | Gielen et al. | |
| 6,819,956 B2 | 11/2004 | Dilorenzo | |
| 6,830,544 B2 | 12/2004 | Tanner | |
| 6,862,479 B1 | 3/2005 | Whitehurst et al. | |
| 6,871,098 B2 | 3/2005 | Nuttin | |
| 6,916,320 B2 | 7/2005 | Michelson | |
| 6,922,590 B1 | 7/2005 | Whitehurst | |
| 6,929,606 B2 | 8/2005 | Ritland | |
| 6,950,707 B2 | 9/2005 | Whitehurst | |
| 6,959,215 B2 | 10/2005 | Gliner et al. | |
| 6,970,741 B1 | 11/2005 | Whitehurst et al. | |
| 6,978,180 B2 | 12/2005 | Tadlock | |
| 6,990,377 B2 | 1/2006 | Gliner et al. | |
| 7,003,352 B1 | 2/2006 | Whitehurst | |
| 7,006,859 B1 | 2/2006 | Osorio et al. | |
| 7,008,422 B2 | 3/2006 | Foley et al. | |
| 7,011,660 B2 | 3/2006 | Sherman et al. | |
| 7,013,177 B1 | 3/2006 | Whitehurst et al. | |
| 7,063,708 B2 | 6/2006 | Gibson et al. | |
| 7,063,725 B2 | 6/2006 | Foley | |
| 7,066,961 B2 | 6/2006 | Michelson | |
| 7,083,621 B2 | 8/2006 | Shaolian et al. | |
| 7,103,408 B2 | 9/2006 | Haller et al. | |
| 7,107,103 B2 | 9/2006 | Schulman et al. | |
| 7,146,217 B2 | 12/2006 | Firlik et al. | |
| 7,150,737 B2 | 12/2006 | Purdy et al. | |
| 7,151,961 B1 | 12/2006 | Whitehurst et al. | |
| 7,158,333 B1 | 1/2007 | Ardja et al. | |
| 7,167,751 B1 | 1/2007 | Whitehurst et al. | |
| 7,174,212 B1 | 2/2007 | Klehn et al. | |
| 7,179,225 B2 | 2/2007 | Shluzs et al. | |
| 7,179,261 B2 | 2/2007 | Seivol et al. | |
| 7,187,967 B2 | 3/2007 | Kennedy | |
| 7,188,626 B2 | 3/2007 | Foley et al. | |
| 7,209,787 B2 | 4/2007 | Dilorenzo | |
| 7,221,981 B2 | 5/2007 | Gliner | |
| 7,236,830 B2 | 6/2007 | Gliner | |
| 7,236,831 B2 | 6/2007 | Firlik et al. | |
| 7,250,052 B2 | 7/2007 | Landry et al. | |
| 7,255,686 B2 | 8/2007 | Putz | |
| 7,277,758 B2 | 10/2007 | DiLorenzo | |
| 7,282,064 B2 | 10/2007 | Chin | |
| 7,283,856 B2 | 10/2007 | Boling | |
| 7,292,890 B2 | 11/2007 | Whitehurst et al. | |
| 7,295,875 B2 | 11/2007 | Wallace et al. | |
| 7,299,096 B2 | 11/2007 | Balzer et al. | |
| 7,302,298 B2 | 11/2007 | Lowry et al. | |
| 7,305,268 B2 | 12/2007 | Gliner et al. | |
| 7,306,603 B2 | 12/2007 | Boehm, Jr. et al. | |
| 7,326,210 B2 | 2/2008 | Jahng et al. | |
| D565,735 S | 4/2008 | Washbon | |
| 7,353,064 B2 | 4/2008 | Gliner et al. | |
| 7,376,468 B2 | 5/2008 | King et al. | |
| 7,386,350 B2 | 6/2008 | Villims | |
| 7,406,105 B2 | 7/2008 | Delmain et al. | |
| 7,440,806 B1 | 10/2008 | Whitehurst et al. | |
| 7,465,306 B2 | 12/2008 | Pond, Jr. et al. | |
| 7,468,064 B2 | 12/2008 | Bruneau et al. | |
| 7,491,208 B2 | 2/2009 | Pond, Jr. et al. | |
| 7,491,218 B2 | 2/2009 | Landry et al. | |
| 7,493,171 B1 | 2/2009 | Whitehurst et al. | |
| 7,497,869 B2 | 3/2009 | Justis | |
| 7,515,961 B2 | 4/2009 | Germanson et al. | |
| 7,520,879 B2 * | 4/2009 | Justis | A61B 17/7002 |
| | | | 606/86 A |
| 7,527,638 B2 | 5/2009 | Anderson et al. | |
| 7,547,318 B2 | 6/2009 | Birkmeyer et al. | |
| 7,575,581 B2 | 8/2009 | Lovell | |
| 7,588,575 B2 | 9/2009 | Colleran et al. | |
| 7,588,588 B2 | 9/2009 | Spitler et al. | |
| 7,604,658 B2 | 10/2009 | Wilson et al. | |
| 7,666,189 B2 | 2/2010 | Gerber et al. | |
| 7,684,867 B2 | 3/2010 | Jaax et al. | |
| 7,686,814 B2 | 3/2010 | Lim et al. | |
| 7,691,132 B2 | 4/2010 | Landry et al. | |
| 7,708,763 B2 | 5/2010 | Selover et al. | |
| 7,717,944 B2 | 5/2010 | Foley et al. | |
| 7,725,196 B2 | 5/2010 | Machado et al. | |
| 7,736,370 B2 | 6/2010 | Sweeney | |
| 7,749,233 B2 | 7/2010 | Farr et al. | |
| 7,758,584 B2 | 7/2010 | Bankoski et al. | |
| 7,758,617 B2 | 7/2010 | Iott et al. | |
| 7,763,055 B2 | 7/2010 | Foley | |
| 7,776,051 B2 | 8/2010 | Colleran et al. | |
| 7,824,410 B2 | 11/2010 | Simonson et al. | |
| 7,846,093 B2 | 12/2010 | Gorek et al. | |
| 7,875,031 B2 | 1/2011 | Chin et al. | |
| 7,894,912 B2 | 2/2011 | Benabid et al. | |
| 7,917,230 B2 | 3/2011 | Bly | |
| 7,937,160 B2 | 5/2011 | Garabedian et al. | |
| 7,947,045 B2 | 5/2011 | Hestad et al. | |
| 7,955,355 B2 | 6/2011 | Chin | |
| 7,974,696 B1 | 7/2011 | DiLorenzo | |
| 7,991,465 B2 | 8/2011 | Bartic et al. | |
| 8,000,795 B2 | 8/2011 | Lozano | |
| 8,043,343 B2 | 10/2011 | Miller et al. | |
| 8,052,711 B2 | 11/2011 | Hanse et al. | |
| 8,052,720 B2 | 11/2011 | Kuester et al. | |
| 8,060,207 B2 | 11/2011 | Wallace et al. | |
| 8,075,565 B2 | 12/2011 | Wilcox et al. | |
| 8,100,959 B2 | 1/2012 | Que et al. | |

(56) References Cited

U.S. PATENT DOCUMENTS

| | | | |
|---|---|---|---|
| 8,103,350 B2 | 1/2012 | Wallace et al. |
| 8,150,524 B2 | 4/2012 | Maschino et al. |
| 8,209,027 B2 | 6/2012 | Butson et al. |
| 8,216,173 B2 | 7/2012 | Dacey, Jr. et al. |
| 8,216,282 B2 | 7/2012 | Hua |
| 8,282,593 B2 | 10/2012 | Dacey, Jr. et al. |
| 8,333,753 B2 | 12/2012 | Nishtala |
| 8,333,770 B2 | 12/2012 | Hua |
| 8,343,086 B2 | 1/2013 | Dacey, Jr. et al. |
| 8,346,365 B2 | 1/2013 | Lozano |
| 8,366,652 B2 | 2/2013 | Dacey, Jr. et al. |
| 8,366,714 B2 | 2/2013 | Jones et al. |
| 8,401,654 B1 | 3/2013 | Foster et al. |
| 8,417,345 B2 | 4/2013 | Machado et al. |
| 8,460,313 B2 | 6/2013 | Huffmaster |
| 8,515,541 B1 | 8/2013 | Jaax et al. |
| 8,515,542 B2 | 8/2013 | Jaax et al. |
| 8,545,541 B2 | 10/2013 | Hua |
| 8,556,940 B2 | 10/2013 | Hua |
| 8,706,181 B2 | 4/2014 | Stypulkowski et al. |
| 8,721,691 B2 | 5/2014 | Hua |
| 8,731,674 B2 | 5/2014 | Wallace |
| 8,798,754 B2 | 8/2014 | Knudson et al. |
| 8,900,248 B2 | 12/2014 | Biyani |
| 9,179,875 B2 | 11/2015 | Hua |
| 9,198,698 B1 | 12/2015 | Doose et al. |
| 9,307,925 B2 | 4/2016 | Russell et al. |
| 9,327,069 B2 | 5/2016 | Foster et al. |
| 9,352,145 B2 | 5/2016 | Whitehurst et al. |
| 9,402,659 B2 | 8/2016 | McBride |
| 9,402,661 B2 | 8/2016 | Reitblat et al. |
| 9,421,373 B2 | 8/2016 | DiLorenzo |
| 9,480,574 B2 | 11/2016 | Lee et al. |
| 9,630,019 B2 | 4/2017 | Valente et al. |
| 9,636,115 B2 | 5/2017 | Henry et al. |
| 9,642,552 B2 | 5/2017 | Hua |
| 9,724,515 B2 | 8/2017 | Fostick et al. |
| 9,820,668 B2 | 11/2017 | Hua |
| 9,867,978 B1 | 1/2018 | Rapoport et al. |
| 9,877,846 B2 | 1/2018 | Dvorak et al. |
| 9,919,146 B2 | 3/2018 | Hua |
| 9,919,148 B2 | 3/2018 | Howard et al. |
| 9,925,376 B2 | 3/2018 | Hartig et al. |
| 9,955,961 B2 | 5/2018 | Huffmaster et al. |
| 10,004,543 B2 | 6/2018 | Stokes et al. |
| 10,194,960 B1 | 2/2019 | Hammann et al. |
| 10,406,351 B2 | 9/2019 | Hua |
| 10,660,631 B1 | 5/2020 | Boesel et al. |
| 10,702,314 B2 | 7/2020 | Reitblat et al. |
| 10,736,533 B2 | 8/2020 | Hua |
| 10,973,551 B2 | 4/2021 | Hua |
| 11,116,509 B2 | 9/2021 | Follmer et al. |
| 11,160,580 B2 | 11/2021 | Hua |
| 11,759,238 B2 | 9/2023 | Hua |
| 12,076,058 B2 | 9/2024 | Hua et al. |
| 12,268,422 B2 | 4/2025 | Hua |
| 2001/0003156 A1 | 6/2001 | Gill |
| 2002/0151770 A1 | 10/2002 | Noll, III et al. |
| 2003/0028072 A1 | 2/2003 | Fischell et al. |
| 2003/0040753 A1 | 2/2003 | Daum et al. |
| 2003/0088245 A1 | 5/2003 | Woloszko et al. |
| 2003/0093105 A1 | 5/2003 | Huffmaster |
| 2003/0093129 A1 | 5/2003 | Nicolelis et al. |
| 2003/0135147 A1 | 7/2003 | Rosenberg et al. |
| 2003/0171750 A1 | 9/2003 | Chin |
| 2003/0208203 A1 | 11/2003 | Lim et al. |
| 2003/0233125 A1 | 12/2003 | Kaplan et al. |
| 2003/0233126 A1 | 12/2003 | Kaplan et al. |
| 2004/0030236 A1 | 2/2004 | Mazzochi et al. |
| 2004/0082961 A1 | 4/2004 | Teitelbaum |
| 2004/0088024 A1 | 5/2004 | Firlik et al. |
| 2004/0147928 A1 | 7/2004 | Landry et al. |
| 2004/0186532 A1 | 9/2004 | Tadlock |
| 2004/0225335 A1 | 11/2004 | Whitehurst et al. |
| 2004/0243130 A1 | 12/2004 | Biscup |
| 2004/0243207 A1 | 12/2004 | Olson et al. |
| 2004/0267274 A1 | 12/2004 | Patel et al. |
| 2005/0021040 A1 | 1/2005 | Bertagnoli |
| 2005/0049649 A1 | 3/2005 | Luders et al. |
| 2005/0075680 A1 | 4/2005 | Lowry et al. |
| 2005/0101954 A1 | 5/2005 | Simonson |
| 2005/0102006 A1 | 5/2005 | Whitehurst et al. |
| 2005/0131311 A1 | 6/2005 | Leuthardt |
| 2005/0131422 A1 | 6/2005 | Anderson et al. |
| 2005/0137646 A1 | 6/2005 | Wallace et al. |
| 2005/0137652 A1 | 6/2005 | Cauller et al. |
| 2005/0182453 A1 | 8/2005 | Whitehurst et al. |
| 2005/0192570 A1 | 9/2005 | Jackson |
| 2005/0192589 A1 | 9/2005 | Raymond et al. |
| 2005/0203599 A1 | 9/2005 | Garabedian et al. |
| 2005/0228380 A1 | 10/2005 | Moore et al. |
| 2005/0245969 A1 | 11/2005 | Loeb |
| 2005/0251237 A1 | 11/2005 | Kuzma et al. |
| 2005/0267491 A1 | 12/2005 | Kellett et al. |
| 2005/0283203 A1 | 12/2005 | Flaherty et al. |
| 2006/0005845 A1 | 1/2006 | Karr et al. |
| 2006/0025841 A1 | 2/2006 | McIntyre |
| 2006/0030872 A1 | 2/2006 | Culbert et al. |
| 2006/0058854 A1 | 3/2006 | Abrams et al. |
| 2006/0089652 A1 | 4/2006 | Eckman |
| 2006/0095035 A1 | 5/2006 | Jones et al. |
| 2006/0111767 A1 | 5/2006 | Olson et al. |
| 2006/0122597 A1 | 6/2006 | Jones et al. |
| 2006/0173522 A1 | 8/2006 | Osorio |
| 2006/0184143 A1 | 8/2006 | Jolly et al. |
| 2006/0195154 A1 | 8/2006 | Jaax et al. |
| 2006/0206165 A1 | 9/2006 | Jaax et al. |
| 2006/0212087 A1 | 9/2006 | Haller et al. |
| 2006/0212090 A1 | 9/2006 | Lozano et al. |
| 2006/0212091 A1 | 9/2006 | Lozano et al. |
| 2006/0234279 A1 | 10/2006 | Miller et al. |
| 2006/0235279 A1 | 10/2006 | Hawkes et al. |
| 2006/0241600 A1 | 10/2006 | Ensign et al. |
| 2006/0241717 A1 | 10/2006 | Whitehurst et al. |
| 2006/0264942 A1 | 11/2006 | Lim et al. |
| 2006/0264962 A1 | 11/2006 | Chin et al. |
| 2007/0016188 A1 | 1/2007 | Boehm, Jr. et al. |
| 2007/0016198 A1 | 1/2007 | Boehm, Jr. et al. |
| 2007/0016199 A1 | 1/2007 | Boehm, Jr. et al. |
| 2007/0021800 A1 | 1/2007 | Whitehurst et al. |
| 2007/0027498 A1 | 2/2007 | Maschino et al. |
| 2007/0032718 A1 | 2/2007 | Shults et al. |
| 2007/0032839 A1 | 2/2007 | Parramon et al. |
| 2007/0060974 A1 | 3/2007 | Lozano |
| 2007/0078460 A1 | 4/2007 | Frigg et al. |
| 2007/0078503 A1 | 4/2007 | Kuzma et al. |
| 2007/0088417 A1 | 4/2007 | Schouenborg |
| 2007/0093814 A1 | 4/2007 | Callahan, II et al. |
| 2007/0100393 A1 | 5/2007 | Whitehurst et al. |
| 2007/0106143 A1 | 5/2007 | Flaherty |
| 2007/0123954 A1 | 5/2007 | Gielen et al. |
| 2007/0135867 A1 | 6/2007 | Klosterman et al. |
| 2007/0167954 A1 | 7/2007 | Sicvol et al. |
| 2007/0173733 A1 | 7/2007 | Le et al. |
| 2007/0191840 A1 | 8/2007 | Pond, Jr. et al. |
| 2007/0219554 A1 | 9/2007 | Landry et al. |
| 2007/0219854 A1 | 9/2007 | Mueller et al. |
| 2007/0233079 A1 | 10/2007 | Fallin et al. |
| 2007/0233097 A1 | 10/2007 | Anderson et al. |
| 2007/0233158 A1 | 10/2007 | Rodriguez |
| 2007/0239159 A1 | 10/2007 | Altarac et al. |
| 2007/0239259 A1 | 10/2007 | Boylan et al. |
| 2007/0265582 A1 | 11/2007 | Kaplan et al. |
| 2007/0265683 A1 | 11/2007 | Ehrlich |
| 2007/0270815 A1 | 11/2007 | Johnson et al. |
| 2007/0282395 A1 | 12/2007 | Maltan et al. |
| 2007/0282396 A1 | 12/2007 | Overstreet et al. |
| 2007/0299443 A1 | 12/2007 | DiPoto et al. |
| 2007/0299444 A1 | 12/2007 | DiPoto et al. |
| 2008/0004676 A1 | 1/2008 | Osypka et al. |
| 2008/0009864 A1 | 1/2008 | Forton et al. |
| 2008/0009920 A1 | 1/2008 | Gibson et al. |
| 2008/0015582 A1 | 1/2008 | DiPoto et al. |
| 2008/0039838 A1 | 2/2008 | Landry et al. |

(56) References Cited

U.S. PATENT DOCUMENTS

| | | |
|---|---|---|
| 2008/0045957 A1 | 2/2008 | Landry et al. |
| 2008/0046012 A1 | 2/2008 | Covalin et al. |
| 2008/0051782 A1 | 2/2008 | Wu |
| 2008/0071274 A1 | 3/2008 | Ensign |
| 2008/0071323 A1 | 3/2008 | Lowry et al. |
| 2008/0077139 A1 | 3/2008 | Landry et al. |
| 2008/0086130 A1 | 4/2008 | Lake et al. |
| 2008/0097457 A1 | 4/2008 | Warnick |
| 2008/0097519 A1 | 4/2008 | Calderon et al. |
| 2008/0119849 A1 | 5/2008 | Beardsley et al. |
| 2008/0119850 A1 | 5/2008 | Sicvol et al. |
| 2008/0119862 A1* | 5/2008 | Wicker ............... A61B 17/708 |
| | | 606/99 |
| 2008/0125788 A1 | 5/2008 | Cohen et al. |
| 2008/0125817 A1 | 5/2008 | Arnett et al. |
| 2008/0140075 A1 | 6/2008 | Ensign et al. |
| 2008/0140120 A1 | 6/2008 | Hestad et al. |
| 2008/0140132 A1 | 6/2008 | Perez-Cruet |
| 2008/0140154 A1 | 6/2008 | Loeb et al. |
| 2008/0177269 A1 | 7/2008 | Seelig |
| 2008/0183241 A1 | 7/2008 | Bedenbaugh |
| 2008/0208074 A1 | 8/2008 | Snyder et al. |
| 2008/0208302 A1 | 8/2008 | Alexander et al. |
| 2008/0218472 A1 | 9/2008 | Breen et al. |
| 2008/0221582 A1 | 9/2008 | Gia et al. |
| 2008/0249531 A1 | 10/2008 | Patterson |
| 2008/0262318 A1 | 10/2008 | Gorek et al. |
| 2008/0312716 A1 | 12/2008 | Russell |
| 2009/0018599 A1 | 1/2009 | Hastings et al. |
| 2009/0054955 A1 | 2/2009 | Kopell et al. |
| 2009/0062857 A1 | 3/2009 | Ramsay et al. |
| 2009/0082819 A1 | 3/2009 | Blain et al. |
| 2009/0112278 A1 | 4/2009 | Wingeier et al. |
| 2009/0118804 A1 | 5/2009 | Moffitt et al. |
| 2009/0125080 A1 | 5/2009 | Montgomery |
| 2009/0171392 A1 | 7/2009 | Garcia-Bengochea et al. |
| 2009/0187220 A1 | 7/2009 | Hamada |
| 2009/0216278 A1 | 8/2009 | Song |
| 2009/0221878 A1 | 9/2009 | Gorek |
| 2009/0221879 A1 | 9/2009 | Gorek |
| 2009/0222044 A1 | 9/2009 | Gorek |
| 2009/0222045 A1 | 9/2009 | Gorek |
| 2009/0222046 A1 | 9/2009 | Gorek |
| 2009/0234392 A1 | 9/2009 | Dziedzic et al. |
| 2009/0259137 A1 | 10/2009 | Delic et al. |
| 2009/0287061 A1 | 11/2009 | Feigenbaum et al. |
| 2009/0326586 A1 | 12/2009 | Duarte |
| 2010/0004695 A1 | 1/2010 | Stad et al. |
| 2010/0049206 A1 | 2/2010 | Biyani |
| 2010/0114182 A1* | 5/2010 | Wilcox .............. A61B 17/7079 |
| | | 606/86 A |
| 2010/0145176 A1 | 6/2010 | Himes |
| 2010/0168803 A1 | 7/2010 | Hestad et al. |
| 2010/0234792 A1 | 9/2010 | Dacey, Jr. et al. |
| 2010/0234793 A1 | 9/2010 | Dacey, Jr. et al. |
| 2010/0240017 A1 | 9/2010 | Dacey, Jr. et al. |
| 2010/0241048 A1 | 9/2010 | Dacey, Jr. et al. |
| 2010/0241050 A1 | 9/2010 | Dacey, Jr. et al. |
| 2010/0241051 A1 | 9/2010 | Dacey, Jr. et al. |
| 2010/0241052 A1 | 9/2010 | Dacey, Jr. et al. |
| 2010/0241053 A1 | 9/2010 | Dacey, Jr. et al. |
| 2010/0249692 A1 | 9/2010 | Dacey, Jr. et al. |
| 2010/0249844 A1 | 9/2010 | Durrani |
| 2010/0292629 A1 | 11/2010 | Dacey, Jr. et al. |
| 2011/0022088 A1 | 1/2011 | Forton et al. |
| 2011/0077692 A1 | 3/2011 | Jackson |
| 2011/0112590 A1 | 5/2011 | Wu et al. |
| 2011/0172674 A1* | 7/2011 | Bankoski ........... A61B 17/1735 |
| | | 606/86 A |
| 2011/0196426 A1 | 8/2011 | Peukert et al. |
| 2011/0202095 A1 | 8/2011 | Semler et al. |
| 2011/0218560 A1 | 9/2011 | Ramzipoor et al. |
| 2011/0238117 A1 | 9/2011 | Geist et al. |
| 2011/0301647 A1* | 12/2011 | Hua ................... A61B 17/7032 |
| | | 606/279 |
| 2011/0319938 A1* | 12/2011 | Piza Vallespir .... A61B 17/7085 |
| | | 606/279 |
| 2012/0065693 A1 | 3/2012 | Lim et al. |
| 2012/0089187 A1 | 4/2012 | Forton et al. |
| 2012/0109208 A1 | 5/2012 | Justis et al. |
| 2012/0239096 A1* | 9/2012 | Gleeson ............... A61B 17/708 |
| | | 606/86 A |
| 2012/0316609 A1 | 12/2012 | Wall et al. |
| 2013/0096637 A1 | 4/2013 | Richelsoph et al. |
| 2013/0110184 A1* | 5/2013 | Wing ................. A61B 17/7085 |
| | | 606/86 A |
| 2013/0184763 A1 | 7/2013 | McClintock et al. |
| 2013/0289385 A1 | 10/2013 | Lozano et al. |
| 2013/0325069 A1 | 12/2013 | Pereiro de Lamo et al. |
| 2014/0039556 A1 | 2/2014 | Rutschmann et al. |
| 2014/0243714 A1 | 8/2014 | Ward et al. |
| 2014/0350612 A1 | 11/2014 | Leroux et al. |
| 2015/0066088 A1 | 3/2015 | Brinkman et al. |
| 2015/0088210 A1 | 3/2015 | Reitblat et al. |
| 2015/0173810 A1 | 6/2015 | Biedermann et al. |
| 2015/0216568 A1 | 8/2015 | Sanpera Trigueros et al. |
| 2015/0230836 A1 | 8/2015 | Cochran |
| 2015/0374354 A1 | 12/2015 | Boyd et al. |
| 2016/0158051 A1 | 6/2016 | Mische |
| 2016/0166326 A1 | 6/2016 | Bakker et al. |
| 2016/0220821 A1 | 8/2016 | O'Connell et al. |
| 2016/0228693 A1 | 8/2016 | Vardiman |
| 2016/0242827 A1 | 8/2016 | Viljoen et al. |
| 2016/0324542 A1* | 11/2016 | Reitblat ............. A61B 17/7083 |
| 2016/0331410 A1 | 11/2016 | Tsuang et al. |
| 2016/0331971 A1 | 11/2016 | Gill |
| 2016/0367809 A1 | 12/2016 | Patel et al. |
| 2017/0056076 A1 | 3/2017 | Kim et al. |
| 2017/0143966 A1 | 5/2017 | Reymers et al. |
| 2017/0151436 A1 | 6/2017 | Flaherty et al. |
| 2017/0164985 A1 | 6/2017 | Reitblat et al. |
| 2018/0000372 A1 | 1/2018 | Hua |
| 2018/0036037 A1 | 2/2018 | Abell et al. |
| 2018/0070987 A1 | 3/2018 | Su et al. |
| 2018/0303630 A1 | 10/2018 | Lorang et al. |
| 2018/0360514 A1 | 12/2018 | Emery et al. |
| 2019/0069930 A1 | 3/2019 | Su et al. |
| 2019/0090918 A1 | 3/2019 | Jackson |
| 2019/0142470 A1 | 5/2019 | Kim et al. |
| 2019/0183543 A1 | 6/2019 | Hammann et al. |
| 2019/0216453 A1 | 7/2019 | Predick et al. |
| 2019/0216482 A1 | 7/2019 | Huffmaster et al. |
| 2019/0231394 A1 | 8/2019 | Bechtel et al. |
| 2019/0290332 A1 | 9/2019 | Tsuang et al. |
| 2019/0336182 A1 | 11/2019 | Suh et al. |
| 2020/0107865 A1 | 4/2020 | Lu et al. |
| 2021/0121219 A1 | 4/2021 | Huffmaster et al. |
| 2021/0161569 A1 | 6/2021 | Shin et al. |
| 2021/0161579 A1 | 6/2021 | Huffmaster et al. |
| 2022/0031922 A1 | 2/2022 | Tsuji et al. |
| 2022/0387080 A1 | 12/2022 | Hua et al. |
| 2022/0409246 A1 | 12/2022 | Hua |
| 2025/0120750 A1 | 4/2025 | Hua et al. |
| 2025/0387143 A1 | 12/2025 | Hua |

FOREIGN PATENT DOCUMENTS

| | | |
|---|---|---|
| CN | 101022848 A | 8/2007 |
| CN | 201157401 Y | 12/2008 |
| CN | 102293680 A | 12/2011 |
| CN | 103096820 A | 5/2013 |
| CN | 103930059 A | 7/2014 |
| EP | 1 062 973 A1 | 12/2000 |
| EP | 2 155 322 A2 | 2/2010 |
| EP | 2 777 573 A1 | 9/2014 |
| EP | 2 851 022 A1 | 3/2015 |
| EP | 3 092 964 A1 | 11/2016 |
| EP | 2 892 452 B1 | 8/2018 |
| GB | 2330078 A | 4/1999 |
| JP | H10-080431 A | 3/1998 |
| JP | 2005-516697 A | 6/2005 |
| JP | 2005-324017 A | 11/2005 |
| JP | 2006-504505 A | 2/2006 |
| JP | 2007-520319 A | 7/2006 |

(56)                    References Cited

FOREIGN PATENT DOCUMENTS

| | | | |
|---|---|---|---|
| JP | 2006-518655 | A | 8/2006 |
| JP | 2006-528028 | A | 12/2006 |
| JP | 2007-502662 | A | 2/2007 |
| JP | 2007-524463 | A | 8/2007 |
| JP | 2008-509759 | A | 4/2008 |
| JP | 2008-539029 | A | 11/2008 |
| JP | 2013-526905 | A | 6/2013 |
| JP | 2015-061602 | A | 4/2015 |
| KR | 10-1703003 | B1 | 2/2017 |
| KR | 10-2145362 | B1 | 8/2020 |
| RU | 2285483 | C2 | 10/2006 |
| SU | 1771717 | A1 | 10/1992 |
| WO | WO 03/005943 | A2 | 1/2003 |
| WO | WO 03/066153 | A2 | 8/2003 |
| WO | WO 2004/041100 | A1 | 5/2004 |
| WO | WO 2004/075768 | A2 | 9/2004 |
| WO | WO 2005/051306 | A2 | 6/2005 |
| WO | WO 2006/015087 | A2 | 2/2006 |
| WO | WO 2006/019723 | A2 | 2/2006 |
| WO | WO 2006/099462 | A2 | 9/2006 |
| WO | WO 2007/002144 | A2 | 1/2007 |
| WO | WO 2008/039247 | A2 | 4/2008 |
| WO | WO 2008/136802 | A1 | 11/2008 |
| WO | WO 2008/149289 | A2 | 12/2008 |
| WO | WO 2010/039817 | A2 | 4/2010 |
| WO | WO 2010/039817 | A3 | 7/2010 |
| WO | WO 2010/085782 | A2 | 7/2010 |
| WO | WO 2010/039817 | A4 | 9/2010 |
| WO | WO 2011/040986 | A1 | 4/2011 |
| WO | WO 2011/084788 | A2 | 7/2011 |
| WO | WO 2011/123580 | A1 | 10/2011 |
| WO | WO 2011/133583 | A1 | 10/2011 |
| WO | WO 2012/012310 | A2 | 1/2012 |
| WO | WO 2013/059113 | A1 | 4/2013 |
| WO | WO 2014/159757 | A2 | 10/2014 |
| WO | WO 2017/039762 | A1 | 3/2017 |
| WO | WO 2021/092495 | A1 | 5/2021 |
| WO | WO 2021/108709 | A1 | 6/2021 |

OTHER PUBLICATIONS

U.S. Appl. No. 13/246,432 (U.S. Pat. No. 8,216,282),filed Sep. 27, 2011, System and Method for Wire-Guided Pedicle Screw Stabilization of Spinal Vertebrae.
U.S. Appl. No. 13/122,388 (U.S. Pat. No. 8,556,940), filed Apr. 1, 2011, System and Method for Wire-Guided Pedicle Screw Stabilization of Spinal Vertebrae.
U.S. Appl. No. 14/645,167 (U.S. Pat. No. 9,642,552), filed Mar. 11, 2015, Insertion of Medical Devices Through Non-Orthogonal and Orthogonal Trajectories Within the Cranium and Methods of Using.
U.S. Appl. No. 15/483,944 ( Pub. No. 2018/0000372), filed Apr. 10, 2017, Insertion of Medical Devices Through Non-Orthogonal and Orthogonal Trajectories Within the Cranium and Methods of Using.
U.S. Appl. No. 16/132,161, filed Sep. 14, 2018, Insertion of Medical Devices Through Non-Orthogonal and Orthogonal Trajectories Within the Cranium and Methods of Using.
U.S. Appl. No. 16/375,722, filed Apr. 4, 2019, Insertion of Medical Devices Through Non-Orthogonal and Orthogonal Trajectories Within the Cranium and Methods of Using.
U.S. Appl. No. 13/318,462 (U.S. Pat. No. 9,179,875), filed Nov. 1, 2011, Insertion of Medical Devices Through Non-Orthogonal and Orthogonal Trajectories Within the Cranium and Methods of Using.
U.S. Appl. No. 14/202,707 (U.S. Pat. No. 9,820,668), filed Mar. 10, 2014, Insertion of Medical Devices Through Non-Orthogonal and Orthogonal Trajectories Within the Cranium and Methods of Using.
U.S. Appl. No. 15/783,954 (U.S. Pat. No. 10,736,533), filed Oct. 13, 2017, Insertion of Medical Devices Through Non-Orthogonal and Orthogonal Trajectories Within the Cranium and Methods of Using.
U.S. Appl. No. 16/905,700, filed Jun. 18, 2020, Insertion of Medical Devices Through Non-Orthogonal and Orthogonal Trajectories Within the Cranium and Methods of Using.

U.S. Appl. No. 13/082,346 (U.S. Pat. No. 8,721,691), filed Apr. 7, 2011, Systems and Methods for Pedicle Screw Stabilization of Spinal Vertebrae.
U.S. Appl. No. 13/189,432 (U.S. Pat. No. 10,973,551), filed Jul. 22, 2011, Systems and Methods for Pedicle Screw Stabilization of Spinal Vertebrae.
U.S. Appl. No. 13/245,227 (U.S. Pat. No. 8,333,770), filed Sep. 26, 2011, Systems and Methods for Pedicle Screw Stabilization of Spinal Vertebrae.
U.S. Appl. No. 17/025,815 (U.S. Pat. No. 11,579,238), filed Sep. 18, 2020, Systems and Methods for Pedicle Screw Stabilization of Spinal Vertebrae.
U.S. Appl. No. 18/363,505, filed Aug. 1, 2023, Systems and Methods for Pedicle Screw Stabilization of Spinal Vertebrae.
U.S. Appl. No. 14/266,732 (U.S. Pat. No. 9,919,146), filed Apr. 30, 2014, Methods and Systems for Intra Ventricular Brain Stimulation.
U.S. Appl. No. 15/891,231 (U.S. Pat. No. 10,406,351, filed Feb. 7, 2018, Methods and Systems for Intra Ventricular Brain Stimulation.
U.S. Appl. No. 16/516,034, filed Jul. 18, 2019, Methods and Systems for Intra Ventricular Brain Stimulation.
U.S. Appl. No. 16/855,941, (U.S. Pat No. 11,160,580), filed Apr. 22, 2020, Systems and Methods for Pedicle Screw Stabilization of Spinal Vertebrae.
U.S. Appl. No. 17/449,611, filed Sep. 30, 2021, Systems and Methods Pedicle Screw Stabilization of Spinal Vertebrae.
U.S. Appl. No. 17/775,215 (Pub No. 2022/0387080), filed May 6, 2022, Systems and Methods for Pedicle Screw Stabilization of Spinal Vertebrae.
U.S. Appl. No. 17/779,975, (Pub No. 2022/0409246), filed May 25, 2022, Systems, Devices and Methods for Treating a Lateral Curvature of a Spine.
U.S. Appl. No. 17/743,135, (U.S. Pat. No. 12,076,058), filed May 12, 2022, Systems and Methods for Pedicle Screw Stabilization of Spinal Vertebrae.
"Mantis™ Spinal System Surgical Technique", Stryker Spine, Literature No. TLMANST06071, 2006, (Brochure) in 48 pages.
"Mantis® Spinal System Surgical Technique", Stryker Spine, MIMAN-ST-2_Rev-3, 2015, (Brochure) in 48 pages.
2009 K2M Complex Spine Innovations, "Serengeti Minimally Invasive Retractor System, A Simple Approach to Complex Spine", 2 pages, 2009.
2010 K2M Complex Spine Innovations, Mesa Spinal System Lumbar Products for Surgeons Treating Spinal Disorders, 1 page. Downloaded May 6, 2010.
Buchholz, A. et al., "Deformity Correction Through the Use of Reduction Towers: 2-Dimensional Operative Video", Operative Neurosurgery, Aug. 2020, vol. 19, Issue 2, pp. E157-E158.
Buell. T. et al., "Surgical correction of severe adult lumbar scoliosis (major curves ≥ 75°): retrospective analysis with minimum 2-year follow-up", Journal of Neurosurgery Spine, Jun. 2019, vol. 21, pp. 1-14.
Carbunaru, R. et al., "Rechargeable Battery-Powered bion® Microstimulators for Neuromodulation," Proceedings of the 26th Annual International Conference of the IEEE EMBS San Francisco, CA, USA, Sep. 1-5, 2004. 0-7803-B439-3/04/$20.00@2004 IEEE, in 4 pages.
Demura, S. et al., "Influence of Rod Contouring on Rod Strength and Stiffness in Spine Surgery", Orthopedics, Jun. 2015, vol. 38(6), pp. e520-e523.
Ezzyat, Y. et al., "Closed-loop stimulation of temporal cortex rescues functional networks and improves memory", Nature Communications, vol. 9, Feb. 2018, in 8 pages. URL: https://www.nature.com/articles/s41467-017-02753-0.
Giles, Jim, "Electric currents boosts brain power" in Nature, Oct. 26, 2004, in 2 pages.
Hewitt, John, "Rise of the Cyborgs", Extreme Tech, Jan. 14, 2013, in 6 pages. URL: https://www.extremetech.com/extreme/144579-rise-of-the-cyborgs.
Koivisto, A.M. et al., "Poor Cognitive Outcome in Shunt-Responsive Idiopathic Normal Pressure Hydrocephalus", Neurosurgery, Jan. 2013, vol. 72(1), pp. 1-8.

(56) References Cited

OTHER PUBLICATIONS

Kokabu, T. et al., "Identification of optimized rod shapes to guide anatomical spinal reconstruction for adolescent thoracic idiopathic scoliosis", Journal of Orthopaedic Research, Jul. 2018, pp. 3219-3224.

Laxton, A. et al., "Deep Brain Stimulation for the Treatment of Alzheimer Disease and Dementias", World Neurosurgery, Sep./Oct. 2013, 80 (3/4), S28.e1-8.

Lindsey, C. et al., "The Effects of Rod Contouring on Spinal Construct Fatigue Strength", Spine, Jul. 2006, vol. 31, Issue 15, pp. 1680-1687.

Loeb, G. et al., "The BION Devices: Injectable Interfaces with Peripheral Nerves and Muscles." Neurosurg Focus. 2006;20(5) @2006 American Association of Neurological Surgeons Posted Aug. 15, 2006, in 12 pages.

Medtronic CD Horizon® Sextant® II—Rod Insertion System—Surgical Technique, 2010, IRN10910-20-03/0710, in 48 pages.

Medtronic Sofamor Danek METRx™ System Surgical Technique "Minimal Access Spinal Technologies" article, 2004, in 22 pages.

Mims, C., "A Hardware Update for the Human Brain", The Wall Street Journal, Jun. 5, 2017, in 4 pages. URL: https://www.wsj.com/articles/a-hardware-update-for-the-human-brain-1496660400.

Santoni, B.G. et al., "Cortical Bone Trajectory for Lumbar Pedicle Screws", The Spine Journal, 2009, vol. 9, pp. 366-373.

Simonite, Tim. "Brain blanket boosts mind control" in New Scientist. Feb. 15, 2008, posted online, in 3 pages.

Singer, Emily, "Want to Enhance Your Brain Power? Research hints that electrically stimulating the brain can speed learning," MIT Technology Review, Jun. 26, 2008, in 2 pages.

Torres, et al., "Body Fat and Body Weight Reduction Following Hypothalamic Deep Brain Stimulation in Monkeys: an Intraventricular approach", International Journal of Obesity, Feb. 21, 2012, pp. 1537-1544.

International Search Report and Written Opinion dated Sep. 28, 2022, from PCT Application No. PCT/US2022/029030.

* cited by examiner

200
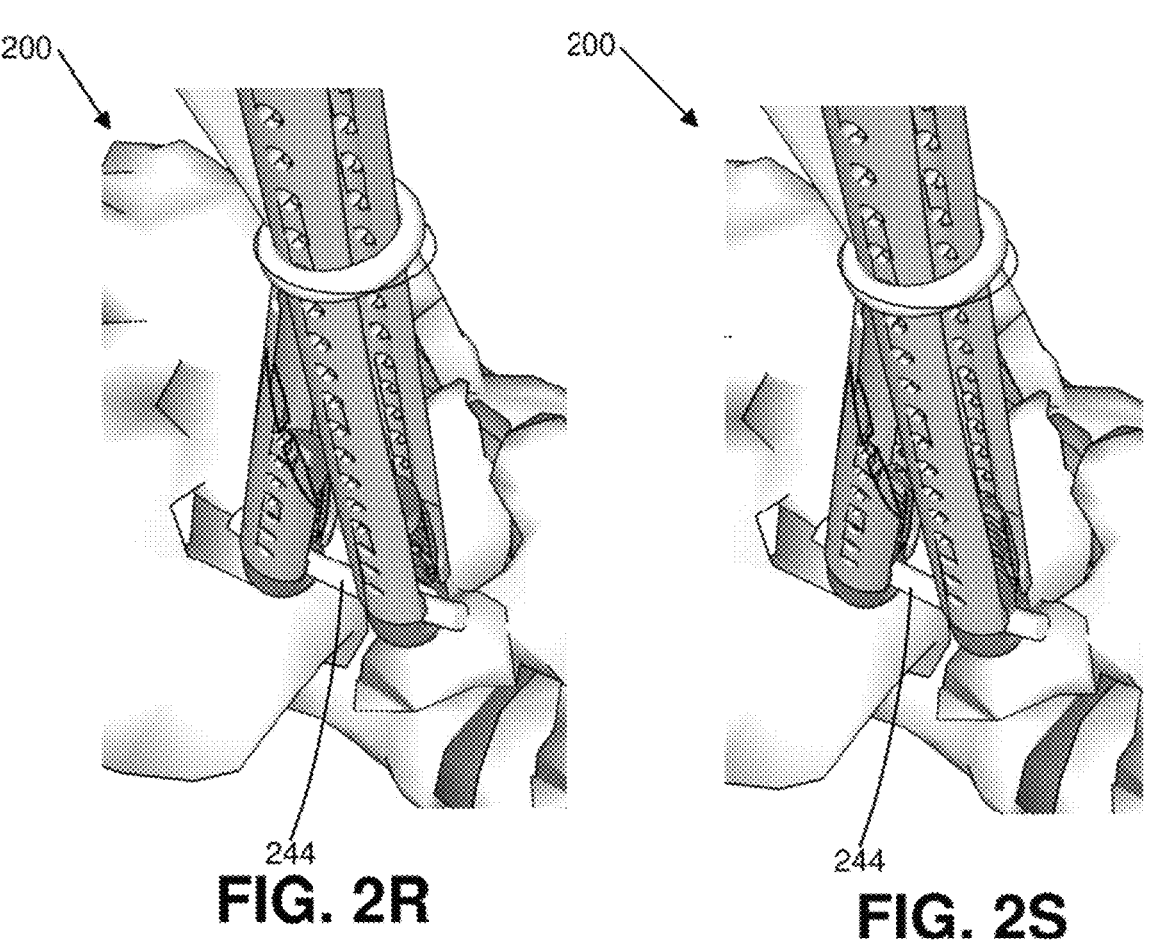
244
FIG. 2R
244
FIG. 2S
200
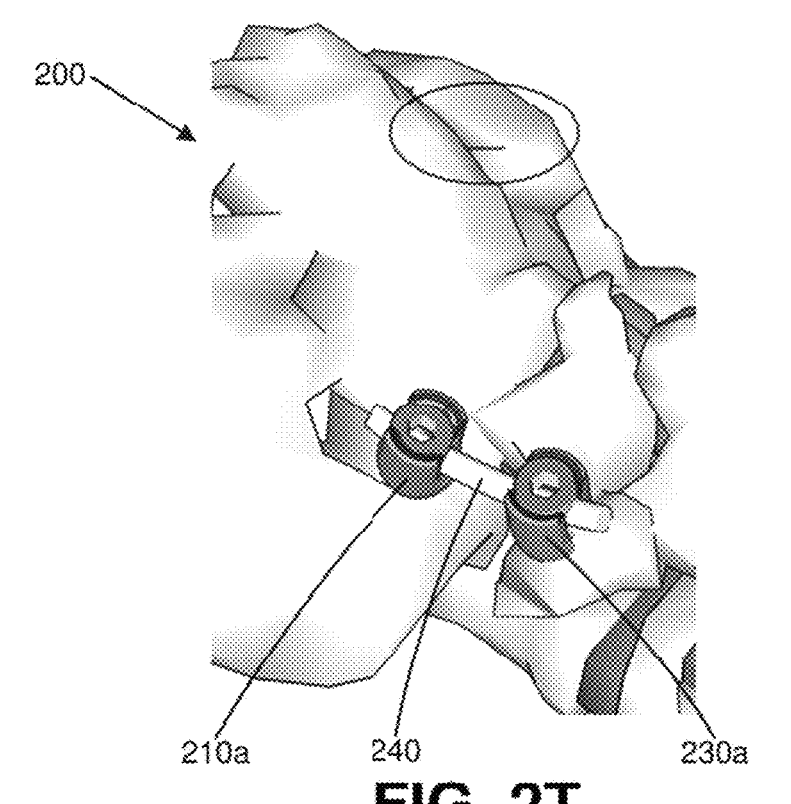
210a          240          230a
FIG. 2T

420

478

476

472

470

420

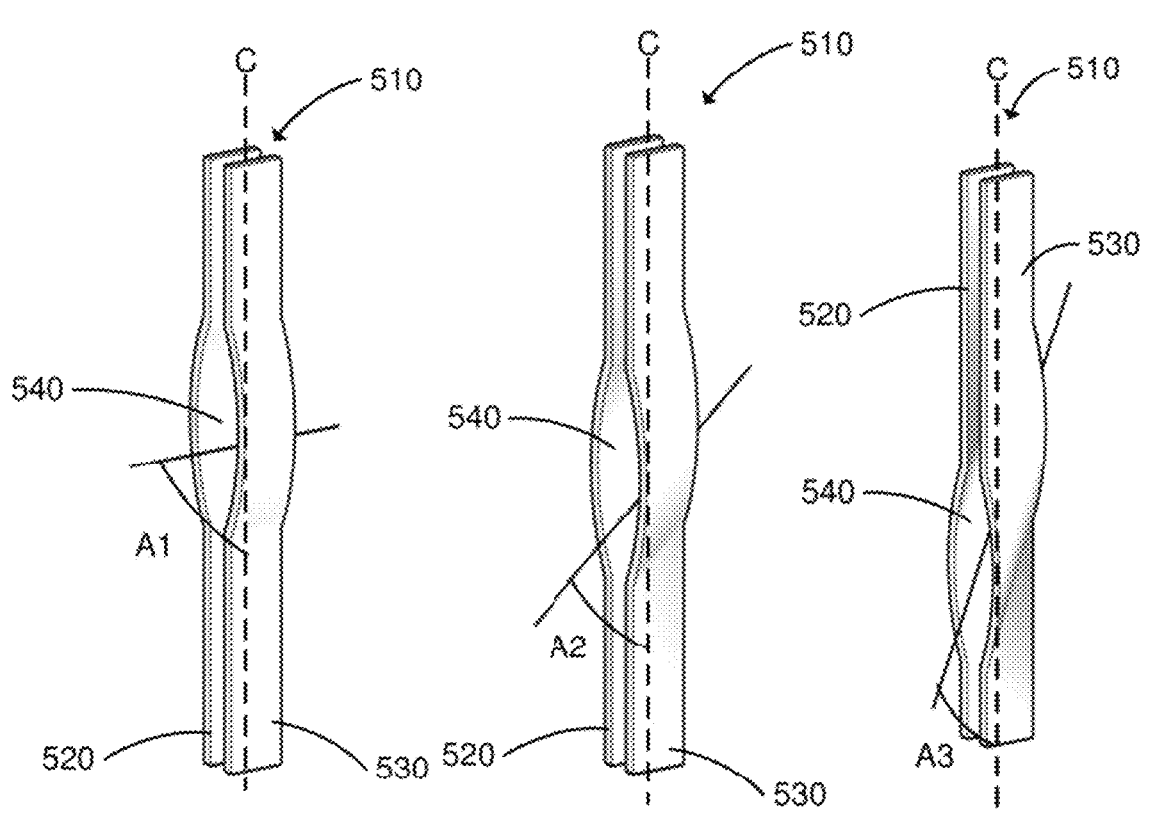
FIG. 5E          FIG. 5F          FIG. 5G
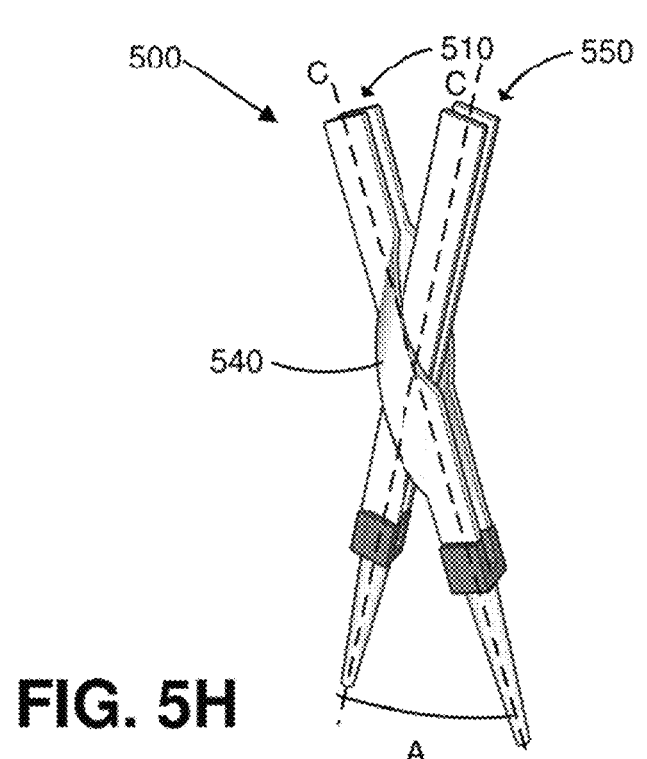
FIG. 5H

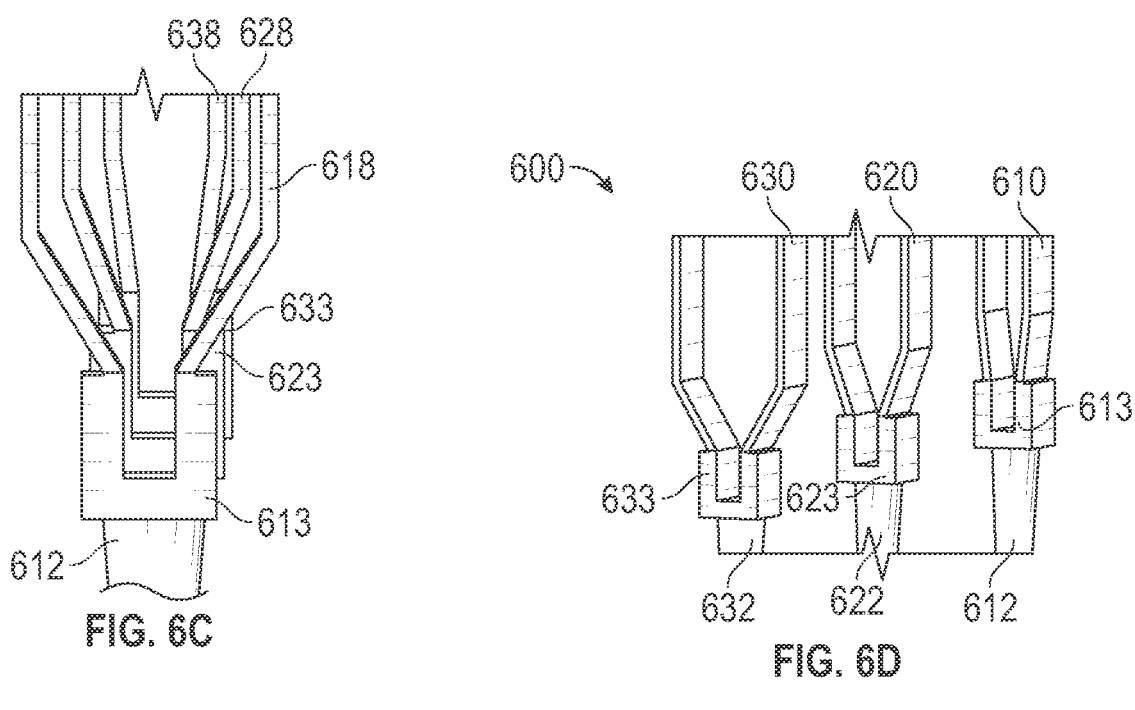
FIG. 6C
FIG. 6D
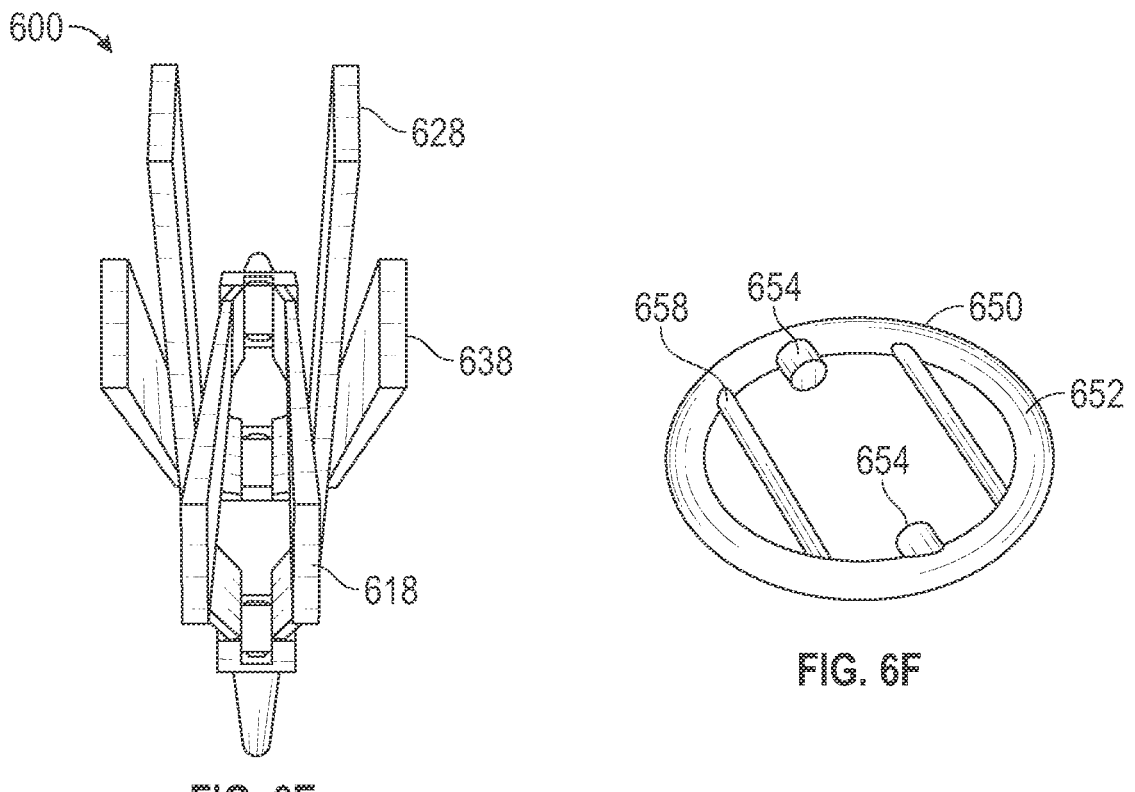
FIG. 6E
FIG. 6F

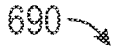
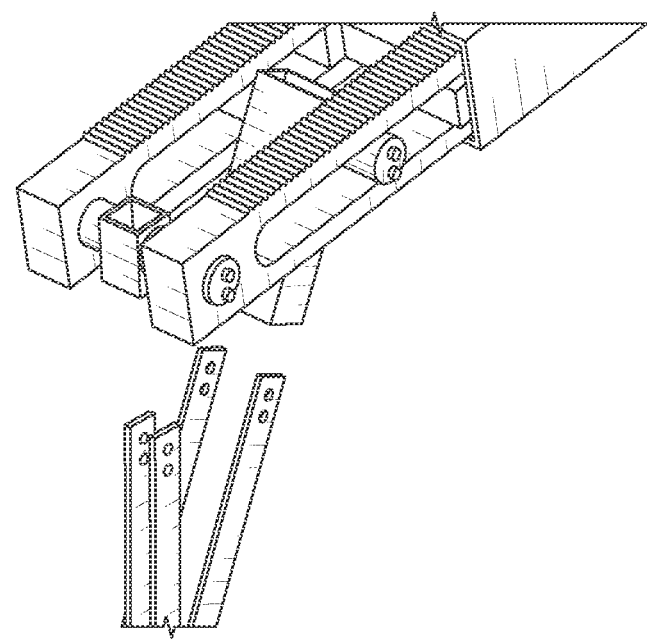
FIG. 6S
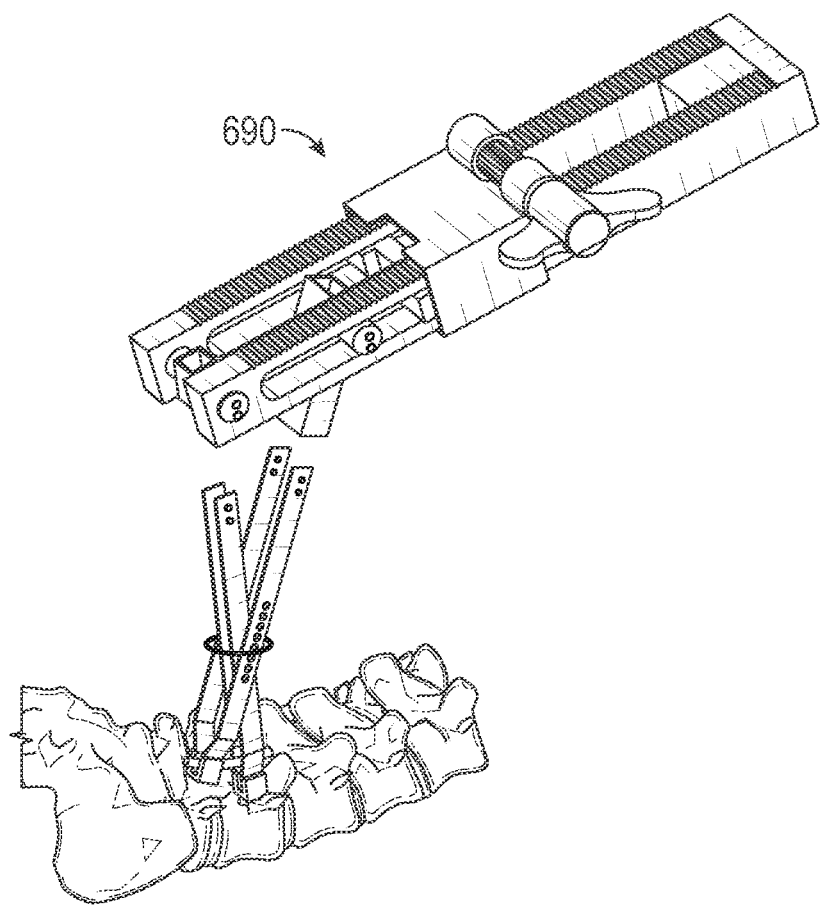
FIG. 6T

690

690

700

712          C          714

704a

730

704          702a 704d          702

704b          702b

700

712          C          714

704a 704          730

702c          702a 704d          702

702d

704b

702b

704c

1632

1600

1630

1606

1602

1612    1624    1616

1800

1800

SYSTEMS AND METHODS FOR PEDICLE SCREW STABILIZATION OF SPINAL VERTEBRAE

PRIORITY CLAIM AND INCORPORATION BY REFERENCE

The present application is a continuation of U.S. patent application Ser. No. 17/743,135, filed on May 12, 2022, titled SYSTEMS AND METHODS FOR PEDICLE SCREW STABILIZATION OF SPINAL VERTEBRAE, which claims priority from U.S. Patent Application No. 62/187,859, filed on May 12, 2021, titled SYSTEMS AND METHODS FOR PEDICLE SCREW STABILIZATION OF SPINAL VERTEBRAE, the contents of which are hereby incorporated by reference herein in its entirety as if fully set forth herein. The benefit of priority is claimed under the appropriate legal basis including, without limitation, under 35 U.S.C. § 119 (e). Any and all applications for which a foreign or domestic priority claim is identified in the Application Data Sheet as filed with the present application are hereby incorporated by reference herein in their entirety and made a part of this specification. The present application also incorporates by reference World Intellectual Property Organization Application No. PCT/US2020/059547, filed on Nov. 6, 2020, titled SYSTEMS AND METHODS FOR PEDICLE SCREW STABILIZATION OF SPINAL VERTEBRAE which claims priority from U.S. Patent Application No. 62/933,321, filed on Nov. 8, 2019, titled SYSTEMS AND METHODS FOR PEDICLE SCREW STABILIZATION OF SPINAL VERTEBRAE, the contents of each of which is hereby incorporated by reference herein in their entirety as if fully set forth herein.

BACKGROUND

Field

Embodiments of the present disclosure relate to devices, systems, and methods for treating the spine, including without limitation devices, systems, and methods for stabilizing adjoining vertebrae in at least the cervical, thoracic, and lumbosacral spine.

Description of the Related Art

While some lower back conditions can be ameliorated with non-surgical approaches, spinal fusion is recommended for certain conditions when non-surgical approaches fail. Non-surgical approaches include medications, physical therapy, chiropractic treatment, traction, epidural steroid injections, facet blocks or rhizotomy, weight loss, smoking cession, and acupuncture. Conditions that commonly serve as indications for spinal fusion or stabilization surgery can be divided generally into three categories: (i) trauma induced, (ii) curvature, and (iii) degenerative.

Trauma induced conditions include fractures and ligamentous injuries. Fractures typically result from an unfortunate incident involving an extraneous force or fall but may also arise from pathologic conditions, such as cancer or osteoporosis. Fractures are often compressive in nature and typically lead to a pathological curving of the spine resulting in a loss of the natural lordotic curvature in the lumbar and cervical spine, known as kyphosis. Fractures of the spine also occur with translational or rotational forces perpendicular to the axis of the spine. These forces result in fractures of the facet or pars interarticularis (pars). If the external forces are large enough, vertebrae can collapse resulting in a burst fracture that can injure all three (3) columns of the vertebrae (anterior, middle, and posterior columns). Many traumatic injuries can heal without surgery, but unstable injuries that pose a risk for neurologic injury and/or pain require stabilization through a procedure such as fusion.

A condition called spondylolisthesis characterized by slippage of the spine bones or vertebrae relative to one another can result from fractures of the pars interarticularis (pars fracture) known as spondylolysis. Spondylolisthesis can also develop from malformation of the facet joints by degenerative arthritis as well as congenital malformation and pathologic conditions such as tumors. If the pars on both sides are fractured, then the spinous process and lamina are essentially completely disconnected from the pedicle and vertebral body. This large fragment is called the Gill body. Pars fractures are actually common in people of all ages (often acquired in the teenage years). While, many of these patients are mildly symptomatic and do not require surgery, those with progressive symptoms may require surgical decompression with or without fusion. Spondylolisthesis results in misalignment of the spine and increases the risk of a nerve becoming entrapped. Nerves travel within the spinal canal bounded by the vertebrae and their roots protrude from the curved openings in the sides of the vertebrae called foramina (singular is foramen). These spinal nerves are suspected to be the source of back and radicular pain when they become entrapped or when the nerve endings become irritated by irregular or abrasive motion around a disc, bone, or joint. Spondylolisthesis can also aggravate or be accompanied by degeneration of disc or facet joint which can lead to axial back pain.

The normal curvature of the lumbar and cervical spine is lordosis, where the posterior aspect of these spinal levels forms a concave curve. The thoracic spine normally has a kyphotic or convex curve. Curvature conditions include straightening of the natural curvature as well as abnormal lordosis, abnormal kyphosis or lateral/rotational bending called scoliosis. Curvature conditions can occur idiopathically during adolescence, e.g., adolescent idiopathic scoliosis, or develop as a secondary problem in situations where spinal muscle activation is abnormal such as cerebral palsy, spina bifida, or tethered cord syndrome. Abnormal spinal curvature is common in spinal degeneration when the discs and joints degenerate asymmetrically leading to a progressive curvature (scoliosis, kyphosis, or lordosis) as the biomechanics of the spine are disrupted. Curvature conditions also occur after trauma with compression or burst fractures or with ligamentous injury. Additionally, curvature conditions can occur iatrogenically after previous spinal surgery where the anatomy and biomechanics of the spine have been altered. Such situations include the removal of the posterior tension band after laminectomy as well as the alteration of physiologic movement after spinal fusion leading to adjacent level compensation and degeneration. Curvature conditions lead to abnormal biomechanical stress on the discs and facet joints accompanied by compensatory measures such as facet or ligamentous hypertrophy. Patients can develop both axial back pain and radicular pain. In patients who have failed conservative therapy and bracing, surgery can be effective. Surgery in these conditions includes decompression of nerve or spinal cord compression as well as fusion or stabilization. Curvature can be corrected through surgery, and fusion prevents further curvature from developing.

Degenerative conditions include spinal arthritis and recurrent disc herniation. Spinal arthritis is the most common indication for fusion and may exist in the form of severe disc degeneration (also called Degenerative Disc Disease, DDD) or facet disease. Degenerative arthritis can also be a cause of spondylolisthesis in addition to traumatic fractures discussed above. Degenerative conditions are generally accompanied by nerve compression causing radicular pain in the distribution of the nerve's receptive field, which usually correlates with and is manifested in arm or leg pain. Pure nerve compression syndromes such as herniated nucleus pulposus (herniated discs) or foraminal stenosis (narrowing of the side foramina canals through which the nerves pass) can often be treated with decompression without fusion. Pure disc degeneration syndromes can be treated with fusion without decompression of the nerves. However, most commonly disc degeneration occurs in combination with nerve compression causing both axial back pain and radicular limb pain. In these circumstances, fusion surgery is combined with nerve decompression surgery.

Fusion functions to eliminate motion in the disc space and facet joints between adjacent vertebrae. The vertebrae provide the rigid structural framework of the spine and the fibrocartilaginous disc space acts as a cushion or shock-absorber. Degradation of the disc space can distort alignment and alter the biomechanical cushion that the disc affords the adjacent vertebrae. This degradation alters the forces impacted upon the vertebrae and results in axial back pain. Fusion is designed to eliminate movement between adjacent vertebrae by either forming a solid bridge of bone across the disk space and/or creating new bone formation in the posterolateral space to provide stabilization, rigidity, and strength. Sometimes fusion involves a bone graft taken from another location in the body (e.g., autograft from the iliac crest in the pelvis) or from an external source, e.g., allograft. Physicians commonly refer to the level of a fusion. A single level fusion involves stabilizing the two vertebral bones adjacent to a diseased disc. A two-level fusion involves stabilizing three adjacent vertebral bones spanning two problematic disc spaces. Each vertebra makes contacts (joints) with adjacent vertebrae at three points, the paired facet joints located posteriorly and the intervertebral disc located anteriorly. Thus, lumbar fusion can be directed either at the posterior facet joints or at the anterior interbody/disc space or both. When an anterior interbody fusion is performed in combination with posterior fusion, the procedure is termed 360° fusion. One commonly used technique of posterolateral fusion is pedicle screw fusion where screws are directed into the pedicle portions and the bodies of adjacent vertebrae and then rods are connected to the screws across the disc spaces. The screws and rods hold the adjacent vertebrae motionless relative to one another and allow the bone graft that is placed either in the interbody (disc) space or in the posterolateral space to grow into solid bone. Conventional pedicle screws and rods are metal, typically titanium (Ti) alloy but have been made from stainless steel, cobalt chrome, and molybdenum rhenium as well. Recently rods have been made from a minimally flexible polymer called polyetheretherketone (PEEK). Other metals have been used and can also be adopted. These can include, for example, cobalt, molybdenum, and other metallic as well as nonmetal polymers.

A newer lumbar pedicle screw technique involves placing screws from a midline incision and placing screws superiorly and laterally instead of the typical trajectory of starting laterally and aiming medically through the pedicle into the vertebral body. This technique has been named Cortical Bone Trajectory (CBT) because the trajectory of the screw transverses more cortical bone in contrast to cancellous bone. Cortical bone is typically harder and thus provides greater pullout strength. Thus cortical bone trajectory allows smaller and shorter screws with a single midline incision instead of bilateral Wiltse style incisions. The issue with CBT screw trajectory is that the superior screw in a lumbar fusion such as L4 trajectory in a L4, L5 TLIF surgery, has a trajectory that is aimed more superiorly and laterally rather than a medical trajectory. The inferior screw can have a parallel trajectory or have a more straight-in trajectory in the sagittal plane (rather than superior direction). This configuration causes a natural crossing of the superior screw with the inferior screw in that the superior screw is aimed superiorly so a minimally invasive spinal (MIS) screw attached to a tower has the tower pointing inferiorly because the screw is directed superiorly. While the inferior screw is directed is a less superior trajectory so the towers attached to these two screws are bound to interfere. Furthermore since the incision is midline and the screws are directed from medial to lateral direction, then the screws from ipsilateral and contralateral sides also are bound to intersect. Thus cortical bone trajectory is a technique that would benefit from towers attached to screws that did not interfere with each other due to the fact that they have interfering trajectories.

Interbody fusion involves placing one or more spacers (typically pre-loaded with bone graft material) within the interbody (disc) space between bony vertebral bodies after the degenerated disc has been cleaned out and removed. Spacers are made from bone grafts, titanium, carbon fiber, or polymers such as PEEK. Interbody fusion can be performed through several approaches including: an anterior approach (anterior lumbar interbody fusion, ALIF), a posterior approach (posterior lumber interbody fusion, PLIF, or transforaminal lumbar interbody fusion, TLIF), or a lateral approach (direct lateral interbody fusion, DLIF™— Medtronic, or extreme lateral interbody fusion, XLIF™— Nuvasive). The aim of these approaches is to remove the degenerated disc and replace the disc with material that induces bony fusion. Alternatively, the disc can be replaced with an artificial joint/disc (discussed below). Each of these interbody approaches has advantages and disadvantages. Anterior procedures allow a very large spacer with large degree of lordosis but require a retroperitoneal dissection and risk injury to the large blood vessels anterior to the lumbar vertebrae. In addition, injury to the nerve plexus anterior to the vertebrae can result in sexual dysfunction. The lateral approach also allows a very large spacer and some lordosisbut is limited to the upper and mid lumbar levels (rostral to L5, S1) because of obstruction by the iliac crest. The posterior interbody approach is more time consuming and typically requires more muscle dissection and retraction. However, the posterior approach allows the placement of the interbody graft, posterior pedicle screw fusion, and decompression of nerves all to occur through the posterior incision(s).

Although anterior and lateral approaches can be performed stand-alone (without posterior instrumentation), many surgeons will back-up or supplement anterior or lateral interbody fusions by placing pedicle screws posteriorly after the interbody cage or graft has been placed. This 360° fusion limits movement more than just an isolated anterior or posterior fusion, and fusion rates are increased. However, in ALIF and lateral interbody (DLIF™, XLIF™) cases, two sets of incisions are required for a 360° fusion.

The posterior approaches (TLIF and PLIF) allow an interbody fusion, pedicle screw fusion, and neural decompression to be done all through the same posterior incision(s). In the TLIF, a single large interbody spacer is inserted on the side ipsilateral to the patient's symptomatic side after neural decompression is completed. If both sides are symptomatic then decompression is required on both sides. A PLIF is performed by placing two interbody spacers, one on each side. Posterior procedures may be done according to: (i) an invasive open procedure in which a large incision and/or several incisions are made, (ii) a percutaneous approach in which small incisions and/or few incisions are made, and potentially (iii) an endoscopic approach in which small incisions are made and all tools and devices are inserted through portals with visualization provided on an external monitor.

As an alternative to fusion, recent advances in interbody stabilization have resulted in the development of artificial disc technology. Artificial discs replace the degenerated discs and allow continued motion at the joint. Both cervical and lumbar artificial discs have been developed. Additionally, dynamic stabilization techniques have been developed for the posterior spine. These posterior techniques utilize pedicle screws and a dynamic rod. Typically the dynamic rod has a mechanism to bend under certain loads or forces, thereby absorbing some stress and strain that is applied to the spine. The advantage of dynamic stabilization is that motion is preserved in the spine. However, the durability of these systems may be an issue. In fusions, the bone graft (interbody or posterolateral) eventually fuses the vertebrae eliminating the need for the spinal instrumentation (screws and rods). However in dynamic stabilization, fusion does not occur, so the screws and dynamic rods will always be subjected to the strain and forces of the spine. Over time, the possibility of loosening of the pedicle screws or mechanical failure may increase. Sometimes the use of a slightly flexible rod such as a rod made of PEEK may actually increase fusion by reducing stress shielding. Stress shielding occurs when rigid fusion constructs shield the vertebral bone in contact with the bone graft from the stresses required to form and remodel bone.

Posterior lumber stabilization (fusion and dynamic stabilization) techniques have evolved into minimally invasive approaches because such minimized exposures reduce patient morbidity and facilitate patients' recovery to function. Blood loss and hospital stays are shorter. The process of performing a minimally invasive pedicle screw fusion is the same as that for dynamic stabilization and involves two basic parts. First, screws are placed percutaneously through the pedicle into the vertebral body. For minimally invasive systems, cannulated screws are placed percutaneously over a fluoroscopically (an X-ray that can be seen on a video screen) guided guidance element. Recent advances also allow screws, either cannulated or noncannulated, to be placed using intraoperative navigation, using robotic guidance, or using virtual reality guidance. Generally, two screws are used on each vertebral body being fused, one on a right side and the other on a left side. A single level fusion involves connecting the vertebral bodies that are next to the disc level that is being fused. For instance, a L5, S1 fusion requires screws to be placed at L5 and S1, usually bilaterally, in order to immobilize the L5, S1 disc. The second part of the process involves connecting the screws with a rod and locking the rod and screws together. In dynamic stabilization, the rod or rod-like device (flexible connector) is bendable, but the process of inserting this bendable rod is the same as that for fusion. For example, a rod-like device (flexible connector), like a rod, fits within the screw heads, but may also include an element (a shock absorber, a spring, etc.) that allows some motion. The variations between different minimally invasive systems mostly arise in the method of placing the rod and locking the rod with the screws through a minimal incision.

Before the intervertebral body spacer is inserted, the damaged or degenerated disc within the disc space must be removed. In the TLIF approach, the disc space is accessed through a facetectomy in which the foramen around the nerve roots is opened with a bone-cutting tool such as an osteotome or a high-speed drill. In the PLIF approach, laminectomies or laminotomies are performed to access the disc space. Both TLIF and PLIF allow for decompression of the spinal thecal sac and the nerve roots; however, the facetectomy in a TLIF allows the maximum decompression of the exiting nerve root on that side. With gentle retraction of the thecal sac, the disc space is easily accessed. Then the instruments used for clearing out the degenerated disc may be inserted into the disc space to complete the discectomy.

Following removal of the disc, the surgeon should prepare the bony surfaces, known as the end plates, of the vertebral bodies on each side of the disc that was removed. Peeling off the end plate with a tool such as a curette induces bleeding which stimulates healing and assimilation of the bone graft to be inserted into the interbody space. The spacer or cage that is to be inserted is typically constructed of bone, titanium, carbon fiber, or polymers such as PEEK. The spacer is usually hollow or at least porous to accommodate bone graft material therein. Bone inducing protein such as bone morphogenetic protein (BMP) is also commonly placed within the spacer. After placing the spacer and bone graft, the rods may be inserted into the pedicle screws and the screws can be tightened to lock the rods in place.

Pedicle screw fusions such as the TLIF can be done open through a single large incision or through a minimally invasive (MIS) approach in which the incision size(s) are smaller, and less tissue is damaged or injured. MIS TLIF typically uses percutaneous pedicle screws where each screw is placed through a small incision just about the side of the diameter of a single screw, screw head, or the largest screw insertion tool. Typically, the placement of the percutaneous screws is straightforward. This is because screws are long and thin and are screwed through the tissue into the bone either directly or over a guidewire that is placed through either fluoroscopic guidance or using stereotactic navigation sometimes with the aid of a surgical robotic. Whereas in the open approach the screws are placed using visually identified anatomic landmarks and fluoroscopic guidance, though navigation and robotic guidance can help in open cases as well. Because percutaneous pedicle screws are placed through small incisions that are barely large enough to fit the screw or screw insertion tools, virtually no visual landmarks are available. There are miniopen approaches where visual landmarks for placing pedicle screws can be identified through tiny incisions using either a microscope or endoscope through either a small tubular retractor or endoscope. The key is that once the pedicle screw tract is located and the guidewire is placed into the pedicle screw tract, then placing a percutaneous pedicle screw over the guidewire is relatively easy. Also stereotactic navigation and robotic guidance has also made placement of pedicle screws relatively easy.

In most of the minimally invasive surgery (MIS) systems used today, a guidance element, such as a wire or guidewire, is placed percutaneously under fluoroscopic guidance through the pedicle. Recent advances also allow screws, either cannulated or noncannulated, to be placed using intraoperative navigation, using robotic guidance, intraoperative CT, or using virtual reality guidance. These methods also allow accurate placement of pedicle screws directly without guidewire and without cannulation. If a guidewire system is used, percutaneous cannulated drills and screw taps are inserted over the guidance element/wire to prepare the tract through the pedicle and vertebral body for pedicle screw insertion. Dilating tubes and a guidance tube or a retractor system can often be used to dilate and hold open the path around the guidance element through skin and muscle to reduce injury to muscle and tissue when pedicle screws and insertion tools are inserted. Pedicle screws are inserted over the guidance elements either with or without passage through a guidance tube/retractor. Again, because of the development and wide spread use of intraoperative navigation to guide pedicle screw placement, some pedicle screws can be placed without the use of predrilling a hole or the use of a guidewire. These systems use intraoperative navigation to directly place the pedicle screw through the tissue into bone without predrilling a hole or tapping the hole. Additionally robotic arms can now be used to also aid in the accurate placement of pedicle screws in addition and often combination with navigation systems.

In MIS pedicle screw fusion, after the pedicle screw has been inserted, there are still critical steps in connecting the screw heads and locking adjacent screws using a rod and locking cap. The insertion of rods that connect the screw heads and locking caps to lock the rod inside the screw heads are currently some of the most difficult steps while using a MIS approach through a minimal incision. In order to place the rod and locking assembly into the screw heads, each screw head is associated with blades or towers that extend upwards from the screwhead through the skin incision. The tower has to accommodate the rod and locking assemblies so it is typically the same size or larger than the maximum diameter of the screw head. Once the towers attached to the screws are in place, the rod is then inserted through one of a variety of methods. The leading MIS system is Sextant™ by Medtronic. In this system, the rod is placed by forming a pendulum like mechanism. The two or three towers (for one or two-level fusion, respectively) are coupled together to align the towers, and the rod is swung around through a separate incision superior or inferior to the towers in a pendulum fashion. Once the rod is swung in place, locking caps are placed through the towers and tightened. Alternatively, most of the existing systems insert the rod through one of the towers and then turn the rod approximately 90° to capture the other screws in the other towers. Inserting the rod through the screw heads in a minimally invasive system is done blindly, e.g., without direct visualization of the screw head. Thus, this process is sometimes tedious and frustrating.

The Sextant™ system and other existing systems that use towers are hindered by both the number of incisions required. The use of a separate tower for each screw requires a separate incision for each tower, or a single incision long enough to accommodate two towers. The Sextant™ system also requires an additional incision for the rod, equaling six incisions (three on each side) for a single level fusion and eight incisions for a two level fusion. The other existing tower systems that use the direct rod insert and turn mechanism still require one incision for each screw and each incision has to be larger than the size of a tower through which the screws are inserted. Typically, each incision is at least 15 mm in length. When the sum of the lengths of all incisions on both sides are totaled, the total length of the current leading minimally invasive systems often are longer than the single midline incision of a traditional "open" approach for a single or two level pedicle screw fusion.

Furthermore none of the current MIS pedicle screw systems has been designed to take advantage of the lumbar lordosis that is typically present in most patients. About 80% of lumbar pedicle screw fusions are performed at the lowest two levels L4 to L5 and L5 to S1. These lowest lumbar levels also typically exhibit the strongest lumbar lordosis such that pedicle screw tracts through L4, L5, S1 and even L3 often intersect near a single point often near the skin similar to spokes on a bicycle tire. For most pedicle screw systems, this lordotic curvature is a hindrance in which the towers of the pedicle screws all intersect and cross. Crossing of the towers make it difficult for these MIS screw systems to allow a rod to be placed through the channels of the towers.

U.S. Pat. No. 7,306,603 entitled "Device and method for percutaneous placement of lumbar pedicle screws and connecting rods" by Frank H. Boehm, Jr., et al. and assigned to Innovative Spinal Technologies (Mansfield, MA), the entirety of which is hereby incorporated by reference, discloses a system of connecting a rod to the pedicle screws using a pin and recesses within the screw heads. According to this system the rod can pivot about a longitudinal axis of the pin between a first position in which the rod is parallel to the longitudinal axis of the screw (e.g., vertically oriented) and a second position in which the rod is transverse to that axis in order to bridge screws on adjacent vertebrae. The '603 Patent teaches various guide systems (see FIGS. 5 and 6), rod holder systems (see FIGS. 8, 9, 10, and 11), and a rod guide system (see FIG. 12) but does not include a sleek, detachable system among them. Rather, the systems illustrated are tower-like with rather bulky dilators (80 and 86 in FIGS. 6 and 8), sheaths (81 in FIG. 6), and/or outer housing (120 in FIGS. 11 and 12). U.S. Publication No. 2008/0140075 entitled "Press-On Pedicle Screw Assembly" by Michael D. Ensign and assigned to Alpinespine, LLC (American Fork, Utah), the entirety of which is hereby incorporated by reference, discloses attaching the rod to screw heads indirectly via a tulip assembly. The tulip assembly has a housing with an inner diameter smaller than an inner diameter of the screw head such that it is easily pressed into position upon the screw head. The rod is then placed by attaching directly to the tulip assembly after connecting the assembly to the screw head. The publication mentions using a Kirschner guidance element (or K-guidance element) for inserting both the pedicle screws and the tulip member (see [0030], [0032], and) [0045]) but does not disclose how the rods are guided into position.

U.S. Publication No. 2008/0097457 entitled "Pedicle screw systems and methods of assembling/installing the same" by David R. Warnick and unassigned, the entirety of which is hereby incorporated by reference, like the '075 Publication, also discloses using a tulip assembly as an intervening means to join a rod to the screws. In this system, rather than a press-on locking mechanism, the structure is tightened by rotating an inner member and outer housing of the tulip assembly relative to one another.

U.S. Pat. No. 7,179,261 entitled "Percutaneous access devices and bone anchor assemblies" by Christopher W. Sicvol, et al. and assigned to Depuy Spine, Inc., the entirety of which is hereby incorporated by reference, describes one of the several tower systems for placement of pedicle screws percutaneously. The patent describes a situation where the angle of the screws intersect, and the towers may interfere with each other. This situation is rather typical in the lordotic lumbar spine, especially the lumbo-sacral (L5, S1) junction. In order to solve this problem, they describe cutouts in the tubes so that two tubes can intersect. Given that the angles of the vertebrae are variable from patient to patient and the depth of the vertebrae from the skin is also highly variable, the variations on the cutouts would have to be numerous. Additionally, when two tubes intersect at the cutout as shown in FIG. 22B in the '261 Patent, the edges of the cutout of one tube interferes or blocks off the lumen of the other tube, and vice versa. This occurs because the muscle and tissue surrounding the tubes will push the tubes together at the section of the cutouts thereby significantly reducing the lumen through which the rod and other elements are inserted. The only way to avoid this interference or blockage of the lumens is to keep the tubes separate that would necessitate a larger incision and would eliminate the need for cutouts in the first place. Additionally a 2 or 3 level fusion requiring 3 or 4 screws that may be intersecting would be problematic if the towers on the screws were intersecting.

SUMMARY OF SOME EXEMPLIFYING EMBODIMENTS

Some embodiments described in this application are directed to systems, devices and/or methods for bone stabilization, such as for stabilizing the spine. In some embodiments, one or more guiding elements may be provided, which may also be referred to herein as guidance elements, guide elements, towers, or extensions or other terms as later described. Guiding elements may be connectable with, attachable to, and/or engageable with bone screws, such as pedicle screws. These guiding elements may be utilized in some embodiments to deliver a connecting member, such as a rod, to bone screws implanted within a patient's vertebrae. Additional systems, devices and methods are described herein, including but not limited to rod insertion devices and guidance tools for drills. The systems, methods and devices of this disclosure each have several innovative aspects, implementations, or aspects, no single one of which is solely responsible for the desirable attributes disclosed herein.

Some embodiments of a system for bone stabilization disclosed herein can have a first guiding element comprising an elongate body having a first longitudinal axis, a proximal end and a distal end, the distal end configured to engage with a first bone screw, a second guiding element comprising an elongate body having a second longitudinal axis, a proximal end and a distal end, the distal end configured to engage with a second bone screw, and an opening provided at an intermediate portion of the first guiding element when in use. In some embodiments, the opening can be sized and configured to allow for passage of the second guiding element therethrough such that the second longitudinal axis is at an angle relative to the first longitudinal axis, wherein the opening is sized and configured to limit movement and/or rotation of the second guiding element along the first longitudinal axis relative to the first guiding element.

Disclosed herein are embodiments of a system for stabilizing spinal vertebrae through a skin incision. In some embodiments, the system can include a first screw having a first screw head, a second screw having a second screw head, and a third screw having a third screw head, a first tower having a distal portion, a proximal portion, and a bend between the distal portion and the proximal portion, a second tower having a distal portion and a proximal portion, the second tower configured to be removably coupled with the second screw at a distal end of the second tower, and a third tower having a distal portion, a proximal portion, and a bend between the distal portion and the proximal portion.

Any embodiments of the devices, systems, and methods disclosed herein can include, in additional embodiments, one or more of the following features, components, and/or details, in any combination with any of the other features, components, and/or details of any other embodiments of the devices, systems, and methods disclosed herein: wherein the first tower can be configured to be removably coupled with the first screw at a distal end of the first tower; wherein the third tower can be configured to be removably coupled with the third screw at a distal end of the third tower; wherein the first tower is configured to removably couple with the first screw such that, when the first tower is coupled with the first screw, an axial centerline of the distal portion of the first tower is approximately collinear with an axial centerline of the first screw; wherein the second tower is configured to removably couple with the second screw such that, when the second tower is coupled with the second screw, an axial centerline of the distal portion of the second tower is approximately collinear with an axial centerline of the second screw; wherein the third tower is configured to removably couple with the third screw such that, when the third tower is coupled with the third screw, an axial centerline of the distal portion of the third tower is approximately collinear with an axial centerline of the third screw; wherein the proximal portion of the first tower extends at an acute, nonzero angle away from the axial centerline of the distal portion of the first tower; wherein the proximal portion of the third tower extends at an acute, nonzero angle away from the axial centerline of the distal portion of the third tower; wherein, in an operable state, the first, second, and third towers are configured to intersect one another; and/or wherein the proximal portions of one or more of the towers (for example and without limitation, the first and third towers or extensions) are configured to be compatible with graspers, coupling mechanisms, and other components of surgical robotic systems.

Also disclosed herein are embodiments of a system for stabilizing spinal vertebrae through a skin incision. In some embodiments, the system can include a first screw having a first screw head, a second screw having a second screw head, and a third screw having a third screw head, a first tower having a distal portion and a proximal portion, a second tower having a distal portion and a proximal portion, the second tower configured to be removably coupled with the second screw at a distal end of the second tower, and a third tower having a distal portion and a proximal portion.

Any embodiments of the devices, systems, and methods disclosed herein can include, in additional embodiments, one or more of the following features, components, and/or details, in any combination with any of the other features, components, and/or details of any other embodiments of the devices, systems, and methods disclosed herein: wherein the first tower can be configured to be removably coupled with the first screw at a distal end of the first tower; wherein the third tower can be configured to be removably coupled with the third screw at a distal end of the third tower; wherein the first tower is configured to removably couple with the first screw such that, when the first tower is coupled with the first screw, an axial centerline of the distal portion of the first tower is approximately collinear with an axial centerline of the first screw; wherein the second tower is configured to removably couple with the second screw such that, when the second tower is coupled with the second screw, an axial centerline of the distal portion of the second tower is approximately collinear with an axial centerline of the second screw; wherein the third tower is configured to removably couple with the third screw such that, when the third tower is coupled with the third screw, an axial centerline of the distal portion of the third tower is approximately collinear with an axial centerline of the third screw; wherein the proximal portion of the first tower extends at an acute, nonzero angle away from the axial centerline of the distal portion of the first tower; wherein the proximal portion of the third tower extends at an acute, nonzero angle away from the axial centerline of the distal portion of the third tower; wherein, in an operable state, the proximal portion of the first tower extends away from the second tower in a first direction; and/or wherein, in an operable state, the proximal portion of the third tower also extends away from the second tower in the first direction.

Also disclosed herein are embodiments of a method of stabilizing spinal vertebrae. In some embodiments, the method can include implanting a first screw that is coupled with a first tower through an incision into a first vertebra, advancing a second tower that is coupled with a second screw through an opening formed in the first tower and implanting the second screw into a second vertebra, advancing a third tower that is coupled with a third screw through the opening formed in the first tower and implanting the third screw into a third vertebra, and moving a proximal portion of the first tower toward a proximal portion of the third tower to move the first vertebra from a first position relative to the third vertebra to a second position relative to the third vertebra.

Also disclosed herein are embodiments of a method of stabilizing spinal vertebrae. In some embodiments, the method can include implanting a first screw that is coupled with a first extension through a single incision into a first vertebra, the first extension having a proximal portion and a distal portion, advancing a second extension that is coupled with a second screw through the single incision and through a first opening formed in the first extension so that an axial centerline of at least a distal portion of the second extension is at an acute angle relative to an axial centerline of at least the distal portion of the first extension, implanting the second screw into a second vertebra, advancing a third extension that is coupled with a third screw through the single incision and through the first opening formed in the first extension so that an axial centerline of at least a distal portion of the third extension is at an acute angle relative to the axial centerline of at least the distal portion of the first extension and is at an acute angle relative to the axial centerline of at least the distal portion of the second extension, and implanting the third screw into a second vertebra.

Any embodiments of the devices, systems, and methods disclosed herein can include, in additional embodiments, one or more of the following features, components, and/or details, in any combination with any of the other features, components, and/or details of any other embodiments of the devices, systems, and methods disclosed herein: wherein, in an operable state, the first, second, and third towers are configured to intersect at or adjacent to a skin level of a patient; wherein, in an operable state, the first, second, and third towers are configured to intersect in an implanted state at or adjacent to a skin level of a patient such that a distance from the skin level to a proximal most end of the distal portion of the first tower is less than or equal to 10% of a length of the distal portion of the first tower and a distance from the skin level to a proximal most end of the distal portion of the third tower is less than or equal to 10% of a length of the distal portion of the third tower; wherein the first tower has an opening therein sized and configured to receive the second tower and the third tower therein such that, in an operable state, an outer wall of a portion of the first tower surrounds an outer surface of a portion of the second and third towers; wherein the opening extends at least through a proximal end of the distal portion of the first tower; wherein the opening extends along the first tower to an edge that is adjacent to a proximal end of the distal portion of the first tower; wherein the proximal portion of the first tower is configured such that, in an operable state of the system, the proximal portion of the first tower also extends at an acute, nonzero angle away from the axial centerline of the proximal portion of the second tower so that the proximal portion of the first tower forms an acute angle relative to the proximal portion of the second tower; wherein the distal portion of the first tower is configured such that, in an operable state of the system, the distal portion of the first tower extends at an acute, nonzero angle away from the axial centerline of the distal portion of the second tower so that the distal portion of the first tower forms an acute angle relative to the distal portion of the second tower; wherein the proximal portion of the third tower is configured such that, in an operable state of the system, the proximal portion of the third tower also extends at an acute, nonzero angle away from the axial centerline of the proximal portion of the second tower so that the proximal portion of the third tower forms an acute angle relative to the proximal portion of the second tower; wherein the distal portion of the third tower is configured such that, in an operable state of the system, the distal portion of the third tower extends at an acute, nonzero angle away from the axial centerline of the distal portion of the second tower so that the distal portion of the third tower forms an acute angle relative to the distal portion of the second tower; and/or wherein the distal portion of the first tower and/or the third tower has a curved cross-sectional profile and the proximal portion of the first tower and/or the third tower has a flat or rectangular cross-sectional profile.

Any embodiments of the devices, systems, and methods disclosed herein can include, in additional embodiments, one or more of the following features, components, and/or details, in any combination with any of the other features, components, and/or details of any other embodiments of the devices, systems, and methods disclosed herein: wherein the first tower is sized and configured such that, in an implanted state, the proximal portion of the first tower extends away from a skin incision in a first direction and the proximal portion of the third tower also extends away from the skin incision in the first direction; wherein, in an operable state, the proximal portion of the third tower is positioned between the proximal portion of the first and second towers; wherein the first tower is sized and configured such that, in an operable state, the proximal portion of the first tower extends away from a skin incision in a first direction and the proximal portion of the third tower also extends away from the skin incision in the first direction; wherein the distal portion of the first tower extends away from the first screw to a height just below the skin incision, or to a height level with the skin of a patient, when the first screw is fully implanted in a first vertebra; wherein the proximal portion of the first tower is configured to be grasped by a surgeon to enable a surgeon to exert a counter-torque force on the first tower about at least the axial centerline of the distal portion of the first tower; wherein, in an operable state, the proximal portion of the third tower is configured to be grasped by a surgeon to enable a surgeon to exert a rotational force on the third tower about at least the axial centerline of the distal portion of the third tower; wherein, in an operable state, the system is configured such that moving the proximal portion of the first tower toward the proximal portion of the third tower will cause a compressive force on at least a first vertebra that the first screw is implanted in relative to a third vertebra that the third screw is implanted in; wherein the first tower and the third tower are sized and configured such that only the proximal portions of the first and third towers are outside of a skin incision when the first screw is implanted in a first vertebra; wherein the system is configured such that the first, second, and third screws are implanted through the same skin incision; wherein the proximal portion of the first tower has a length that is approximately the same as a length of the distal portion of the first tower; wherein the proximal portion of the first tower has a length that is at least 80% of a length of the distal portion of the first tower; wherein the proximal portion of the first tower is removably coupled with the distal portion of the first tower and the proximal portion of the third tower is removably coupled with the distal portion of the third tower; wherein the proximal portion of the first tower is non-removably coupled with the distal portion of the first tower and the proximal portion of the third tower is non-removably coupled with the distal portion of the third tower; wherein the proximal portion of the first tower is integrally formed with the body portion of the first tower; wherein at least the distal portions of the first tower, the second tower, and the third tower have a complete or a partial tubular shape; wherein the first tower has a pair of hooks configured to receive a pair of wires used during an implantation procedure; wherein the hooks are configured to provide a surface against which the third tower can rotate; wherein the first tower has a projection which provides a fulcrum for rotation of the third tower relative to the first tower; wherein the third tower can have an opening formed through a wall portion of the third tower, wherein the opening can be configured to allow the second tower to pass through the opening of the third tower in an operable state and such that at least a portion of a wall of the third portion at least partially surrounds an outside surface of the second tower; wherein the distal portion of the first tower and/or the third tower is open along one side thereof and not fully enclosed; and/or wherein, in an operable state, an axial centerline of both the distal portion of the third tower and the proximal portion of the third tower extend at a nonzero angle away from the axial centerline of the second tower in a same direction.

Any embodiments of the devices, systems, and methods disclosed herein can include, in additional embodiments, one or more of the following features, components, and/or details, in any combination with any of the other features, components, and/or details of any other embodiments of the devices, systems, and methods disclosed herein: wherein at least the distal portion of the first tower and the distal portion of the third tower have an adjustable length; wherein at least the distal portion of the first tower, the distal portion of the second tower, and the distal portion of the third tower are generally cylindrically shaped; wherein the proximal portion of the first tower and the proximal portion of the third tower have a cross-sectional profile having a curved shape; wherein the proximal portion of the first tower and the proximal portion of the third tower have a cross-sectional profile having a semi-circular tubular shape; wherein the proximal portion of the first tower and the proximal portion of the third tower have a planar shape; wherein the device, system, or method can include: a rigid connecting element; a first receiving element coupled with the first screw head; a second receiving element coupled with the second screw head; and a third receiving element coupled with the third screw head; wherein the first, second, and third receiving elements are configured to operably receive the connecting element that, in an operable state, extends between the first, second, and third receiving elements when the first, second, and third screws are implanted in a first, second, and third vertebra, respectively; wherein the first tower has at least one opening extending through a side of the distal portion thereof configured to receive a connecting element that is configured to extend between the first, second, and third screws in an operable state, wherein the second tower has at least one opening extending through a side of the body portion thereof configured to receive a connecting element that is configured to extend between the first, second, and third screws in an operable state, and the third tower has at least one opening extending through a side of the body portion thereof configured to receive a connecting element that is configured to extend between the first, second, and third screws in an operable state; wherein the device, system, or method can include one or more covers configured to selectively couple with the first tower, the second tower, and/or the third tower to selectively cover a channel or an opening of the first tower, the second tower, and/or the third tower and increase a torsional or bending rigidity of the first tower, the second tower, and/or the third tower; and/or wherein the device, system, or method can include two or more of the first towers and/or two or more of the third towers, wherein each of the two or more of the first towers define a different angle between the proximal portion and the distal portion of the first towers and each of the two or more of the third towers define a different angle between the proximal portion and the distal portion of the third towers.

Any embodiments of the devices, systems, and methods disclosed herein can include, in additional embodiments, one or more of the following features, components, and/or details, in any combination with any of the other features, components, and/or details of any other embodiments of the devices, systems, and methods disclosed herein: wherein, in an operable state, the first, second, and third towers are configured to intersect at or adjacent to a skin level of a patient; wherein the device, system, or method can include advancing a connecting element toward the first screw, the second screw, and the third screw and securing the connecting element to the first screw, the second screw, and/or the third screw to prevent the first vertebra from moving back to the first position relative to the third vertebra; wherein the first extension has a proximal portion, a distal portion, and a bend between the proximal and distal portions; wherein the third extension; wherein the first and the third extensions are sized and configured such that the proximal portion of the first and the third extensions are positioned under an outside surface of a patient's skin; and/or wherein the device, system, or method can include advancing the first, the second, and the third extensions through a single incision in a patient's skin.

Any embodiments of the devices, systems, and methods disclosed herein can include, in additional embodiments, one or more of the following features, components, and/or details, in any combination with any of the other features, components, and/or details of any other embodiments of the devices, systems, and methods disclosed herein: wherein the first extension has a bend between the proximal portion of the first extension and the distal portion of the first extension such that an axial centerline of the proximal portion of the first extension is at an acute angle relative to an axial centerline of the distal portion of the first extension; wherein the third extension has a bend between the proximal portion of the third extension and the distal portion of the third extension such that an axial centerline of the proximal portion of the third extension is at an acute angle relative to an axial centerline of the distal portion of the third extension; and/or wherein the device, system, or method can include moving the proximal portion of the first extension toward a proximal portion of the third extension to rotate the first extension relative to the third extension and move the first screw toward the third screw, thereby moving the first vertebra toward the third vertebra.

Some embodiments disclosed herein can be described as follows:

1. A system for bone stabilization, comprising:
a first guiding element comprising an elongate body having a first longitudinal axis, a proximal end and a distal end, the distal end configured to engage with a first bone screw;
a second guiding element comprising an elongate body having a second longitudinal axis, a proximal end and a distal end, the distal end configured to engage with a second bone screw; and
an opening provided at an intermediate portion of the first guiding element when in use, wherein the opening is sized and configured to allow for passage of the second guiding element therethrough such that the second longitudinal axis is at an angle relative to the first longitudinal axis, wherein the opening is sized and configured to limit movement of the second guiding element along the first longitudinal axis.

2. The system of Embodiment 1, wherein the first and second guiding elements each comprise a pair of blades.

3. The system of Embodiment 2, wherein each pair of blades has one or more bends or curves to increase a separation distance between opposing blades when the pair of blades is engaged with a bone screw.

4. The system of Embodiment 1, wherein the first and second guiding elements comprise partial tubes.

5. The system of any one of the previous Embodiments, wherein the opening is provided within an intermediate portion of the first guiding element.

6. The system of any one of Embodiments 1-4, wherein the opening is provided by an external restraint configured to surround at least the first guiding element.

7. A system for bone stabilization, comprising:
a first guiding element comprising an elongate body having a first longitudinal axis, a proximal end and a distal end, the distal end configured to engage with a first bone screw;
a second guiding element comprising an elongate body having a second longitudinal axis, a proximal end and a distal end, the distal end configured to engage with a second bone screw,
wherein the second guiding element is configured to pass through a portion of the first guiding element when the first and second guiding elements are engaged with the first and second bone screws, respectively, and the first and second bone screws are implanted within a patient; and
means for limiting relative movement and creating a fulcrum between the first and second guiding elements when the second guiding element passes through a portion of the first guiding element and when the first and second guiding elements are engaged with the first and second bone screws, respectively, and the first and second bone screws are implanted within a patient.

Some embodiments are directed to a screw comprising one or more features of the foregoing description. Some embodiments are directed to a device, system and/or method as illustrated and/or described. Some embodiments are directed to a method of operating any of the devices or systems of the foregoing description. Further embodiments are described throughout the following description, including but not limited to systems for stabilizing spinal vertebrae, methods for stabilizing spinal vertebrae, guiding assemblies, screws, rod inserters, methods of operating any of the foregoing, and other devices, systems and methods.

BRIEF DESCRIPTION OF THE DRAWINGS

The accompanying drawings, which are incorporated in and constitute a part of the specification, illustrate embodiments of the present disclosure, and together with the general description given above and the detailed description of the embodiments given below, serve to explain the principles of the embodiments of the present disclosure.

FIGS. 5A-5K illustrate another embodiment of a method and a system for stabilizing spinal vertebrae comprising spinal screws.

DETAILED DESCRIPTION OF SOME EXEMPLIFYING EMBODIMENTS

Figure 1A:
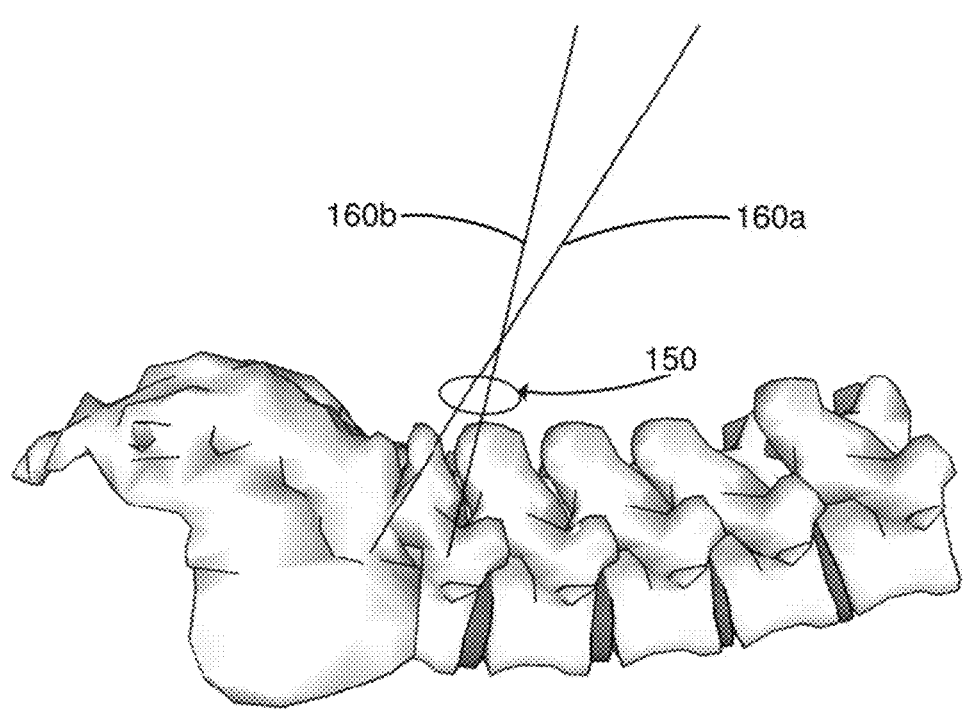
FIGS. 1A-1Z illustrate an embodiment of a method and a system for stabilizing spinal vertebrae comprising pedicle screw including hybrid guidance elements.

Embodiments of the present disclosure relate to medical devices, systems and methods for bone fixation. Specifically, some embodiments disclosed herein can be configured to stabilize adjoining vertebrae in at least the cervical, thoracic, and lumbosacral spine. In addition, some embodiments can be configured to fuse and stabilize vertebrae in the lumbar spine to alleviate axial back pain and radicular pain. Some embodiments can be configured to improve minimally invasive surgical (MIS) approaches to pedicle screw fusion by reducing the number and size of incisions and the size of the medical instruments inserted therein. Further, some embodiments disclosed herein can improve the efficiency of percutaneous lumbar pedicle screw fusion for the surgeon while minimizing the surgical trauma to the patient's tissue.

For example and without limitation, some embodiments of the systems for stabilizing spinal vertebrae disclosed herein are directed towards, but not limited to, improving minimally invasive (optionally adaptable for use with the percutaneous or endoscopic approach) TLIF and PLIF approaches and backing up the ALIF, DLIF™, and XLIF™ approaches. TLIF approaches can provide several advantages including: (i) stabilization of both the anterior and posterior portions of the spine through one or more posterior incision(s); (ii) the ability to fill with bone graft material a greater volume and diversity of spaces (front disc space with the spacer, amongst the screws and rods on the sides, and in the back of vertebrae) increasing the chances of a successful stabilization through the development and solidification of bone; (iii) the spacer placed within the front disc space maintains the natural interbody disc height to reduce pressure on nerve roots (from bone spurs, thickened, ligaments, etc.); and (iv) enhanced safety because the spinal canal is accessed from one side only and this reduces the risk of pinching, stretching, or otherwise agitating the spinal nerves.

Embodiments of the disclosure provide a system, device and/or method for performing a minimally invasive posterior and/or transforaminal lumbar pedicle screw fusion or stabilization procedure. Hereinafter references to "fusion" implicitly include stabilization which offers somewhat greater motion short of completely fusing the bone. Likewise, hereinafter references to "stabilization" implicitly include fusion. The main situations in which a surgeon can use the disclosed system can include a minimally invasive TLIF procedure with either: (i) a micro-lumbar interbody fusion, MLIF™, or (ii) mini-open TLIF on the symptomatic side to decompress the neural compression, and a pedicle screw fusion through a minimally invasive incision on the contralateral side. Similarly, the system disclosed herein would be used bilaterally in a PLIF approach with the decompression and interbody spacer placement performed bilaterally. Alternatively, the disclosed system is ideal for "backing up" (with a minimal posterior incision) anterior interbody fusions (ALIF) and lateral interbody fusions (XLIF™ and DLIF™). MLIF™ collectively encompasses (i) transforaminal lumbar interbody fusions and stabilizations, (ii) posterior lumbar interbody fusions and stabilizations, (iii) anterior lumbar interbody fusions and stabilizations, and (iv) lateral lumbar interbody fusions and stabilizations through a minimally invasive "micro" approach using the guidance system described herein, and (v) posterolateral instrumented fusions where only pedicle screws are placed for posterolateral fusion without using interbody spacers or implants. Since the lateral fusions such as the XLIF or DLIF are truly minimally invasive, a minimal posterior incision for backing up the lateral interbody spacer with pedicle screw fusion would be very complementary. Lateral interbody fusions are becoming more popular and more spine companies are coming out with their own lateral interbody fusion systems. It will be appreciated that although certain embodiments described herein are directed to minimally invasive procedures through a single skin incision, the systems and methods may also be used in open surgery or mini-open procedures through openings in the skin of a patient as desired by the practicing surgeon.

The lumbar spine has a lordotic curvature such that the lowest levels, L4, L5 and S1, have a posteriorly concave orientation or alignment, while the upper levels, L1-L3, are less lordotic. This curvature sets up a unique situation in which the trajectories through the pedicles (the trajectories to insert the pedicle screws) from L2 to S1 are not parallel.

Rather, the trajectories commonly intersect at a point around the level of the skin. This configuration is similar to the spokes of a wheel in which the spokes (trajectories) meet at a common center point (a hub). Given that many patients have such a lordotic configuration of the lumbar spine, it is possible to insert pedicle screws through a single incision centered in the middle of the lumbar curvature. However, if each screw required a separate tower (or tube) (as in conventional tower/tube systems) in order for multiple screws to exist simultaneously, then the sum cross sectional area of the towers/tubes does not permit a single small incision. The towers/tubes interfere with each other and get in the way of one another due to their size. It is also difficult to place the rod through the channels of the towers and into the seats of the pedicle screws when the towers of the pedicle screws are crossed and not aligned in a straight line.

An alternative method is necessary in order to minimize the number and size of incisions. Reducing the number and size of incisions minimizes the tissue trauma needed to place pedicle screws for lumbar stabilization or fusion. An ideal system and procedure would take full advantage of the natural curvature of the lumbar spine in order to provide this reduction. However, the apparatuses and methods of the present application described and claimed herein are not limited to applications in the lumbar vertebrae and may also find use for fusing, stabilizing, or otherwise treating vertebrae in other regions of the spine such as the cervical spine where lordotic curvature is again the typical anatomical alignment.

The number of osteoporotic spinal patients requiring surgical intervention is increasing. Historically this complex group of patients has had complications with bone-screw fixation due to the nature of the bone and types and projection geometries of the screws used, along with their methods of insertion. These complications include implant failure, screw loosening and pullout. Recent research suggests new cortical screws that project in an anteromediolateral direction have advantages over traditional screws projecting in an anteromedial direction. Embodiments of the present disclosure take this research into account and can be used in guiding and placing new cortical screws to project in an anteromediolateral direction in order to overcome many problems of traditional screws in osteoporotic patients. Further, embodiments of the present disclosure can be used to place multiple new cortical screws through a single incision, minimizing trauma to already sensitive osteoporotic patients.

The last steps in pedicle screw fusion can involve rod reduction and final tightening. Rod reduction is typically necessary if there is malalignment in the vertebral bodies such as spondylolisthesis. In this case, the malalignment can be realigned by pulling or pushing on the pedicle screw that is anchored into that vertebrate relative to other screws in other vertebrate. By adjusting the relative position of the screws heads, a preferably bent rod can be lowered into the screw heads and "reduce" the malalignment or spondylolisthesis. In open surgeries, the reduction process is usually performed by rod reduction tools that push the rod into the screw head. In MIS systems, extended threads on the tower or extended tab that extend higher than the screw head can reduce the rod into the screw head by allowing the locking cap to engage with the threads at a higher position thereby capturing the rod at a position higher up or farther away than the final seat of the screw head.

After the rod is reduced and the vertebrate are aligned, the rod can be locked into the screw heads by locking caps. The locking caps are usually tightened to the final torque using a counter-torque instrument. The counter-torque usually is a sleeve that passes over the screw head as well as blades or towers (if present). The counter-torque can have grooves that fit over the screw head and often also the rod in order to provide a counter force when the locking cap is final tightened. The counter-torque can stabilize the screw heads so that any rotation of the screw head during final tightening is minimized.

During the final tightening process, it is also common to provide compression of the screw heads. Compression during final locking is thought to help with the fusion process as any interbody fusion is thought to be more successful under pressure or compression. Compression also helps place pressure upon the interbody spacer and reduces the chance that the spacer will back out, retropulse, or migrate. Compression is also useful to restore lumbar lordosis. Many interbody spacers placed either anteriorly through an ALIF, laterally through an XLIF or DLIF, obliquely through OLIF (oblique lateral interbody fusion), or posteriorly through PLIF or TLIF all can have lordotic profiles. The new expandable cages allow even more significant lordosis. The compression during final tightening can optimize the lordosis through posterior compression during final locking.

Typical pedicle screw system use separate tools for screw insertion, screw alignment, rod insertion, cap insertion, rod reduction, counter-torque, and final tightening. These separate tools all require extra steps at each pedicle screw. Each extra step introduces more irritation of muscle and tissue as well as time. Thus, a system that allows a pedicle screw that is preattached to a tower system that can perform all these tasks without any extra tools is indeed time saving and optimal. Some embodiments disclosed herein describe a system of towers that are removably attached to pedicle screws. In some embodiments:

Towers can cross paths without interference (in situations with lordosis);

Towers can be used to align the screw heads without the need for a separate tool to straighten the screw heads;

Towers can be used to measure the length and curvature of the rod;

Towers can allow easy rod placement and visualization of the rods even in MIS approach and even in large patients where visualization is difficult;

Towers can allow and/or facilitate rod reduction, and reduction of spondylolisthesis;

Towers can allow final tightening under compression or distraction without a separate compression or distraction tool;

Towers can provide counter-torque during final tightening without a counter-torque tool; and/or Towers attached to screws can be placed robotically and allow rod placement, rod reduction, compression, and final tightening with counter-torque all to be performed robotically through a mechanical coupling of parts of the tower system with robotic arms. The robot, navigation system, software can be configured to know the positions of all towers screws, rods and caps at all times.

The intersecting tower system of some embodiments disclosed herein can allow or provide an optimal MIS system where incision size and tissue damage is minimized, surgical steps are optimized, number of tools are minimized, and surgical time is reduced. Previous MIS tower systems are either placed in an awkward configuration where the screw trajectories are crossed due to lumbar lordosis with the towers angled to be parallel to each other. Otherwise, MIS towers are placed though a single incision and the towers are crossed next to each other, making rod insertion, and final tightening very difficult and frustrating. Some embodiments of the present disclosure can avoid these difficulties and can provide an optimized MIS pedicle screw system.

Some embodiments disclosed herein provide a simple method and associated apparatus to place two or more pedicle screws through one small hole. This provides a better cosmetic and functional result with just a single skin incision of small size (approximately 0.5 to 4 cm in length, approximately 0.5 to 3 cm in length, or approximately 1 to 2 cm in length) regardless of the number of screws used. In one embodiment, the single incision is smaller than the sum of the maximum widths of two respective largest elements for each screw that is inserted through the single incision, where an element includes the screw, screw head, rod, locking assembly and associated tools.

Some embodiments disclosed herein are configured to enable a surgeon or other user to insert, position, and manipulate a spinal implant such as a rod and a locking assembly through the same small incision in order to lock the rod within the screws. Certain embodiments provide novel ways to insert a rod into the heads of pedicle screws and ways to lock the rod within the screws through a single small incision. The systems and methods involve in certain embodiments the attachment of guide elements consisting of the following: one or more flexible wires, flexible yet firm extended blades, extended tabs, or towers attached to each pedicle screw head to be used to guide the rod down to the screw. The guide elements are configured and combined so that they can overlap or intersect at or below the skin incision, thereby enabling the use of a small, single skin incision. The screws, rods, and locking assemblies can all be placed through a single small incision and yet still be appropriately interconnected within because of the natural lordotic curvature of the lumbar spine. By attaching at least one guidance element on each side of the screw head, the guidance elements assist to align the screw head. The guidance elements also trap or restrict displacement of the rod, forcing it to fit between them and directly into the screw head.

Compared to U.S. Pat. No. 7,179,261 to Sicvol described above, embodiments of the present disclosure eliminate the need for "cut-outs" where the guide elements intersect. For example, in embodiments utilizing extended tabs or blades, these extended tabs or blades do not have a proximal, distal, or any lumen, and the configuration of guidance elements (extended tabs or blades) for screws at adjacent levels allow the tabs to intersect and overlap completely for any patient with any relative geometries. Thus interference between adjacent guidance elements on adjacent vertebrae is not a problem. Also, in the cut-out tubes taught by the '261 Patent, a rod or other element would still have to be inserted through the tube at some point. The cut-out tubes require that the rod (or other inserted element) is oriented longitudinally parallel to the long axis of the tube as it is directed into the body until it reaches a section with side wall openings or slots distal to the cut-out section, at which point it may optionally be turned perpendicularly to the long axis and directed out of the side wall through the opening or slot. In embodiments of the present disclosure by using guidance elements such as extended blades or extended tabs (from the screw head), the element that is guided by them and inserted along them (e.g., a rod, a locking assembly etc.) does not have to be inserted through any lumen. When a rod is inserted using the blades, the blades can simply be fed through the outer edges of the rod body, through a retaining element or clasp attached to the rod body, or between the outer edges of the rod body and a retaining element (retention thread). Thus, it is possible for the inserted rod or other elements to be oriented perpendicular to the long axis or oriented in any other manner or at any angle during the entire entry pathway. This provides greater flexibility for avoiding interference between adjacent stabilization system pieces and eliminates the need for a surgeon to identify the cut-out sections before turning the screw/rod perpendicularly and/or reorienting it. Furthermore, since there are no lumens proximally or distally with the extended tabs, blades from adjacent levels may overlap and intersect without the need for cutout therefore allowing all blades to exit a single small minimal incision.

The guidance elements can also be used to guide the locking assemblies down to the screw heads for embodiments in which the locking assembly is not part of the screw head itself (and already down there).

Another embodiment is a hybrid system where each screw is placed through short towers or tubes that do not come to the skin surface. Wires, blade or tab extensions are attached to the top of the towers or tubes so that the screw, rod, locking assembly, and tools used for insertion, adjustment, locking, compression, distraction, and removal are guided by the extensions close to the skin but through individual towers or tubes close to the bone and pedicle screw. This hybrid system offers both the advantages of the wires/extended blades/tabs in which many guidance elements can overlap in a single incision at the skin level and the advantages of a tower or tube system are preserved at the bone level. Some surgeons who are comfortable with the tower system but who want the advantages of the blade/tab system may want to use this hybrid system.

Making some of the guidance elements telescopic allows for more guidance elements to fit through a single incision smoothly, thereby advantageously reducing the need to have a larger incision and/or multiple incisions. After insertion, the various guidance elements may be deployed telescopically as needed. Using telescoping components as part of the upwardly directed extended guidance elements allows a rod for stabilizing vertebrae to be inserted into the body through the telescoping components and through the same singular incision, minimizing invasiveness of the procedure.

All combinations and arrangements of towers, tubes, blades, arms, tabs, wires, and other upwardly directed extended guidance elements, either as described herein or in hybrid systems which combine conventional tower/guidance elements as described in the prior art (such as described in the references incorporated by reference throughout this specification) are contemplated as within the spirit and scope of the present disclosure. As used herein, the term guiding or guidance element is intended to include one or more components extending between a screw and a skin incision, preferably directly or indirectly coupled or detachably connected to a screw head, and includes both conventional towers or tubes such as those made of rigid or semi-rigid materials as described in the patents and publications incorporated by reference throughout this specification, as well as the additional embodiments of guiding or guidance elements as described herein. The most suitable selection and arrangement is for the surgeon to determine in each particular case. For example, in one embodiment, there may be telescoping tubes at one level, wires at the next level, and blades at the next level on one side (of the slot for the rod) with blades attached to wires on the other side (of the slot for the rod). Different variations may be selected for each side (medial, lateral) in order to introduce more components through the same incision. The goal is to provide enough guidance elements to properly guide the stabilization rods, locking assemblies, tools, etc. to the pedicle while minimizing the number of incisions and preventing overcrowding. Eliminating overcrowding permits proper visualization so that the surgeon can work comfortably and efficiently.

In some embodiments, a system is provided for performing spine stabilization through an opening in skin of a patient. In some embodiments, the opening may be a single, minimally invasive skin incision. The system comprises a first screw having a screw head and a first guiding element (also referred to herein as a first extension) comprising a height component detachably connected to the first screw, the first screw being configured for implantation in a first vertebra. The system also comprises a second screw having a screw head and a second guiding element detachably connected to the second screw, the second screw configured for implantation in a second vertebra. The first screw with the first guiding element and the second screw with the second guiding element can be delivered into the first and second vertebra.

Other objectives and advantages of embodiments of the disclosure will be set forth in the description which follows. Implicit modifications of the present disclosure based on the explicit descriptions will be, at least in part, obvious from the description, or may be learned by practice of the disclosure. Such subtle, predictable modifications and adaptations are taken to be within the scope of the present disclosure. Additional advantages of the disclosure may be realized and obtained by means of the instrumentalities and combinations particularly pointed out hereinafter.

Figure 1B:
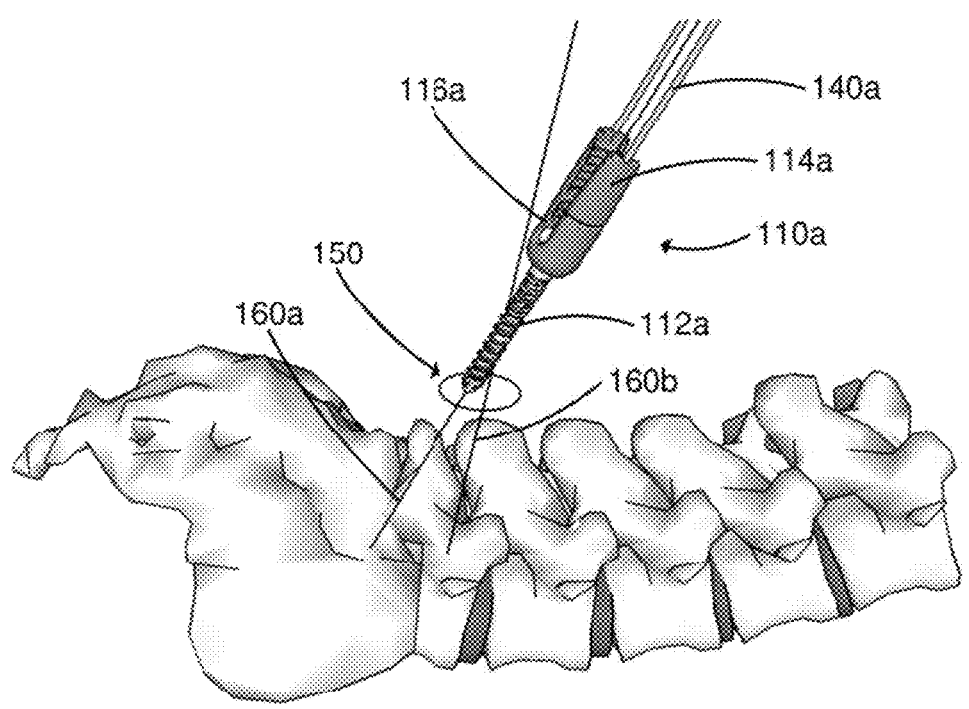
Figure 1C:
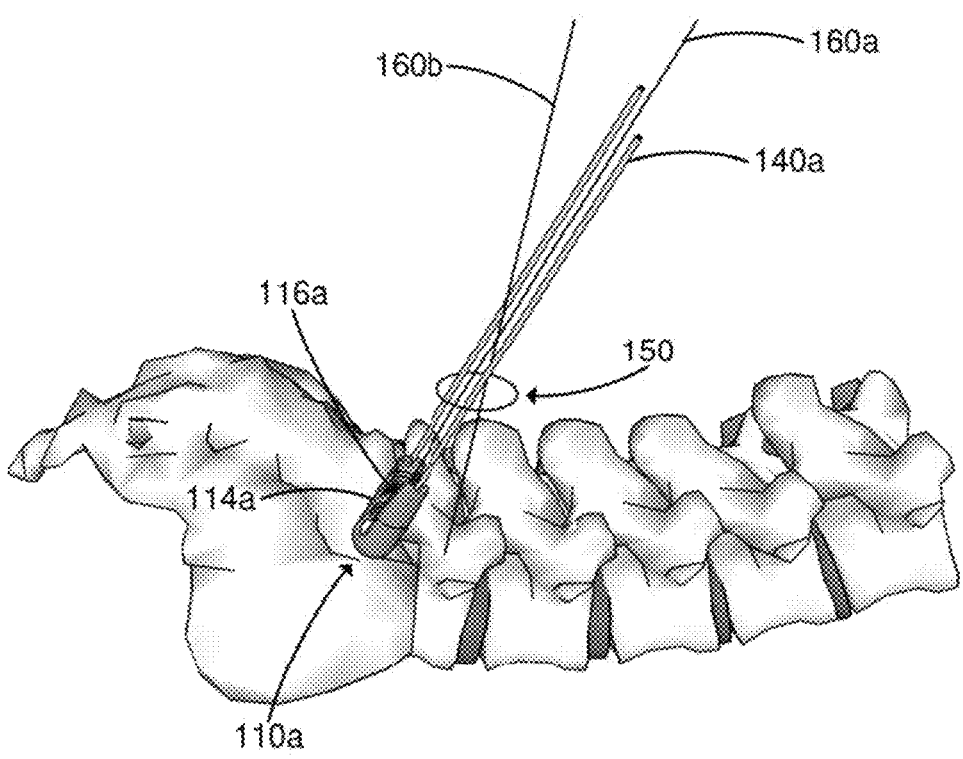

Embodiments disclosed herein include improved systems, apparatuses and methods for guiding one or more screws, rods, and locking assemblies down to the vertebrae and for securing a rod or other spinal implant to stabilize the vertebrae. Embodiments of a device or system for stabilizing spinal vertebrae are disclosed herein, as shown in FIGS. 1A-1Z, though the features of this system may be utilized with all of the other embodiments described throughout this specification. In some embodiments, the system for stabilizing spinal vertebrae can include pedicle screws. In some embodiments, the screw 110 (shown as 110A in some of the figures) can include a bone engaging shaft 112 and a screw head 114. In some examples, the bone engaging shaft 112 is threaded. The bone engaging shaft 112 may be relatively moveable to different angles relative to the screw head 114. In some embodiments, the screw head 114 has generally a U-shape, defining upwardly extending arms that form a channel for receiving a rod 120. The rod 120 may either sit on the head of the bone engaging shaft 112, or may sit on an insert 116 placed in the screw head 114 for receiving the rod 120.

A locking assembly may be built into or attached onto the screw head or be a separate element. Locking assemblies that are separate elements include (but are not limited to) those reliant on caps and set screws. Locking assemblies integrated with the screw head can include (but are not limited to) rotatable mechanisms in which a turn of the screw head traps the rod. The locking assembly may be guided down to the screw before or after insertion of the rod depending upon the details of the locking mechanism used to secure the rod. In some embodiments, the locking assembly is already present on the screw head before the rod is received. In some examples, the rod is inserted into the screw head 114 first and the locking assembly follows. In some embodiments, the upwardly extending arms of the screw head 114 may be internally threaded to receive an externally threaded cap screw that is rotated into the screw head 114 to apply a downward force to a rod 120 sitting in the channel of the screw head 114. This downward force may also then lock the position of the screw head 114 relative to the rod 120.

The guidance elements for directing the rod 120, various locking assembly components (e.g., screw head caps), surgical insertion and manipulation tools, and other components into position may be any type of upwardly directed, extended guidance elements. These guidance elements are preferably detachably connected to the screw heads or screws so that they can be easily removed once a procedure is completed. Suitable guidance elements include: tubes, towers, blades, arms, extended tabs, wires, string, etc. In some embodiments, the guidance elements extended tabs or extended blades run from a site adjacent the screw head up through the incision site. In some examples, the guidance elements can be curved (along one or more axis) or bent (along one or more axis) to accommodate the cap and other components. The guidance elements may also be curved or bent in order to be offset from adjacent elements such that they do not interfere if and when they cross. The curvature may be a permanent rounded shape or they may be flexibly curveable or comprised of foldable panels. The curves and bends may be permanent and pre-formed or adjustable in situ. The extended guidance elements may also be tapered, threaded and/or notched to assist in stabilizing the cap or other components as they are lowered down to the screw head.

In some embodiments, the guidance elements comprise two or more blades that may be offset from each other. In some examples, the offset configuration of the two or more blades allows the two or more blades to cross as the two or more blades do not interfere with each other. In some embodiments, the plurality of blades 132 of the guidance elements 130 of each of the screws 110 can be configured to cross and/or overlap as described above. In some examples, the guidance elements can be offset in any functional manner, and can assume different positions around the screw heads (e.g., for staggered crossing), bending at different positions (e.g., straight to bent), curvatures that are non-intersecting with adjacent elements (blades from adjacent screw head), etc.

The extended tabs/blades or other guidance elements on adjacent screws may be offset such that they do not interfere with one another when they intersect. Rather, as they cross one another, the extended tabs/blades (or other guidance elements) can be configured to smoothly pass by one another. Therefore the extended tabs/blades on adjacent screws can be inserted through the same small incision and manipulated within that incision. This may be achieved by tabs/blades, or other guidance elements, on the inside of one screw and the outside of the other screw. In some embodiments, the tabs/blades for adjacent screws can simply be staggered or misaligned. In some examples, one screw can have a single tab/blade on the medial side while another screw has a single tab/blade on the lateral side. In some embodiments, one screw can have extended tabs, while one or more of the other screws can have flexible wires as guidance elements.

In some embodiments, some of the extended guidance elements (tabs, blades, etc.) on some screw heads may be straight while those on others are bendable or angled, such that the bendable or angled elements cross over the straight ones to exit the body through the same skin level incision. In other embodiments, a first screw is connected to a first extended guidance element in the form of a plurality of blades and a second screw is connected to a second extended guidance element in the form of a plurality of blades. The plurality of blades of the first extended guidance element can overlap and/or intersect with the plurality of blades of the second extended guidance element. Advantageously the first extended guidance element and the second extended guidance element can intersect or overlap at or near a skin level incision. By intersecting or overlapping at or near a skin level incision, this allows both of the guidance elements to extend through a single, small incision.

The extended tabs/blades or other guidance elements are configured to easily detach from the screw head upon completion of directing rods, caps, instruments, and other components precisely to the screw head. This detachment process may occur by any number of means, including break-off along a pre-perforated or notched line, burning or melting at the base of the tabs/blades with an instrument, releasing a mechanical clamp, etc. In some embodiments, the extended guidance elements (e.g. extended tabs, extended blades, etc.) for adjacent screws may be attached to their respective screw heads at different positions along the screw head to produce the offset configuration. In some examples, the extended guidance elements may be attached to their respective screw heads at the same location and bent at different angles to form different configurations that are offset with respect to one another when crossed. For example, the extended guidance elements may be bent to come out of the screw head at different lateral displacements such that they do not interfere with one another. In some embodiments, for a two level fusion, three offset extended guidance elements (tabs, blades, etc.) attached to three adjacent screws can be used. In some examples, for a three level fusion, four offset extended guidance elements attached to four adjacent screw can be used. In some embodiments, for a level four fusion, five offset extended guidance elements attached to five adjacent screws can be used. In a level four fusion, potentially all of the five offset extended guidance elements can be configured to come through the same skin level incision and crossing at some point at or near the same level skin incision.

In some embodiments, the extended tabs/blades/arms and wires can work together in a "hybrid" concept. For example, a first tab/blade/arm can be attached to the screw head and is configured to be easily detachable. Additional tabs/blades/arms between the screw head and distal wires protruding from the skin can be added and/or removed as needed to lengthen or shorten the distance of the guidance trajectory. In some embodiments, the guidance element can include a multitude of breakoff tabs/blades/arms that are attached to one another in series to create a long extended blade. The blade can then be tailored to the appropriate length, such as at the level of the skin incision, by breaking the tabs off at the closest breakoff point to the desired length. In some embodiments, one or more of the breakoff tabs can be attached to a proximal wire to keep track of and locate the tab within the patient.

In some embodiments, flexible guidance wires can be used to direct other guidance element features (e.g., tabs, blades, arms) during insertion and removal. The guidance wires can serve as a guide to direct add-on tab elements into place within the patient. In some examples, a plurality of flexible guidance wires can serve alone as guidance elements to guide rods, tools or locking assembly components to a desired location at or near the spine. In some embodiments, the flexible guidance wires can be part of a "hybrid" concept and can work in conjunction with tabs/blades/arms to guide elements to a desired location. The rods, tools or locking assembly components can be delivered via the guidance elements by hand, or in some embodiments, using a stereotactic guidance mechanism and/or by a robot.

Additional embodiments of systems and methods for pedicle screw stabilization of spinal vertebrae are also disclosed in U.S. Pat. No. 8,721,691, the entire contents of which are hereby incorporated by reference in its entirety.

As used herein, distal is defined as a space farther from a particular location, and proximal is defined as a space closer to the particular location. In some embodiments, a portion of a tab or blade that extends out beyond an incision can be considered a proximal portion, while a portion of a tab or blade that is beneath the incision can be considered a distal portion.

Systems, Devices and Methods of FIGS. 1A-1Z

FIGS. 1A-1Z illustrate an embodiment of the method for implanting a plurality of screws into a plurality of vertebrae and the implantation and securement of a rod. The method disclosed in FIGS. 1A-1Z include the screw 110a and screw 110b illustrated above. Although the method illustrated only includes two screws, the disclosed method can be used for any number of screws to be implanted in any number of vertebrae in any order.

FIG. 1A illustrates a first guidewire 160a and a second guidewire 160b that are positioned at a target location on a first and second vertebra. As illustrated, the first guidewire 160a is directed to a vertebrae that is inferior to the vertebrae that the second guidewire 160b is directed to. Each of the first and second guidewires 160a, 160b are configured to directed a first screw 110a and a second screw 110b to their respective vertebrae. As is illustrated in FIG. 1B, the first screw 110a is directed down the first guidewire 160a. As discussed above, the first screw 110a includes a bone engaging shaft 112a and a screw head 114a and a plurality of wires 140a, 140b, where at least one wire of the plurality of wires 140a is located on either side of the screw head 114a.

Figure 1D:
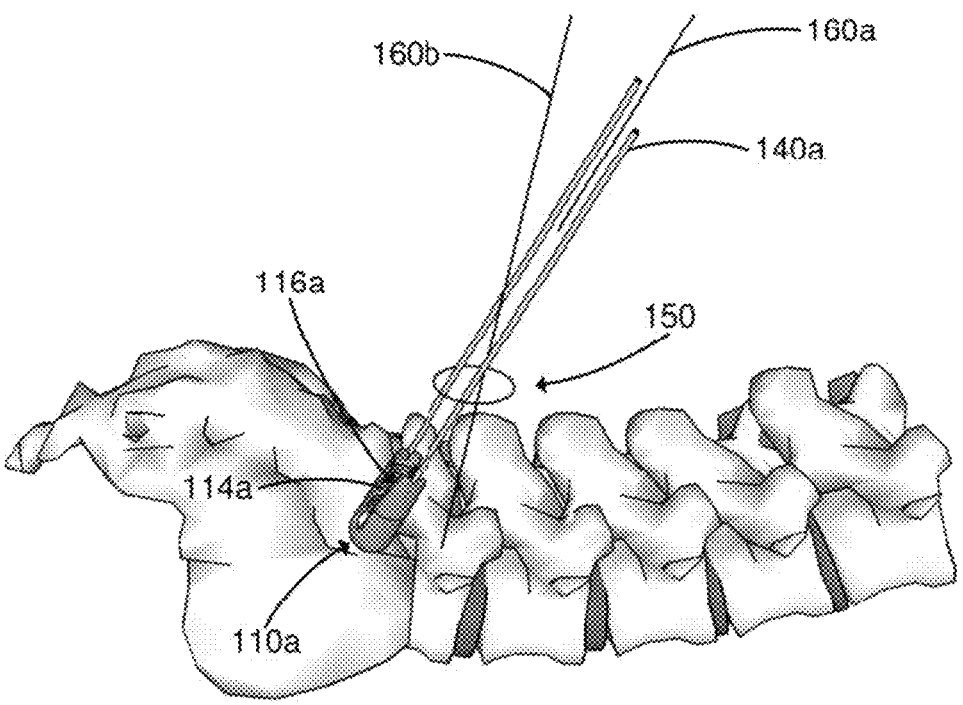
Figure 1E:
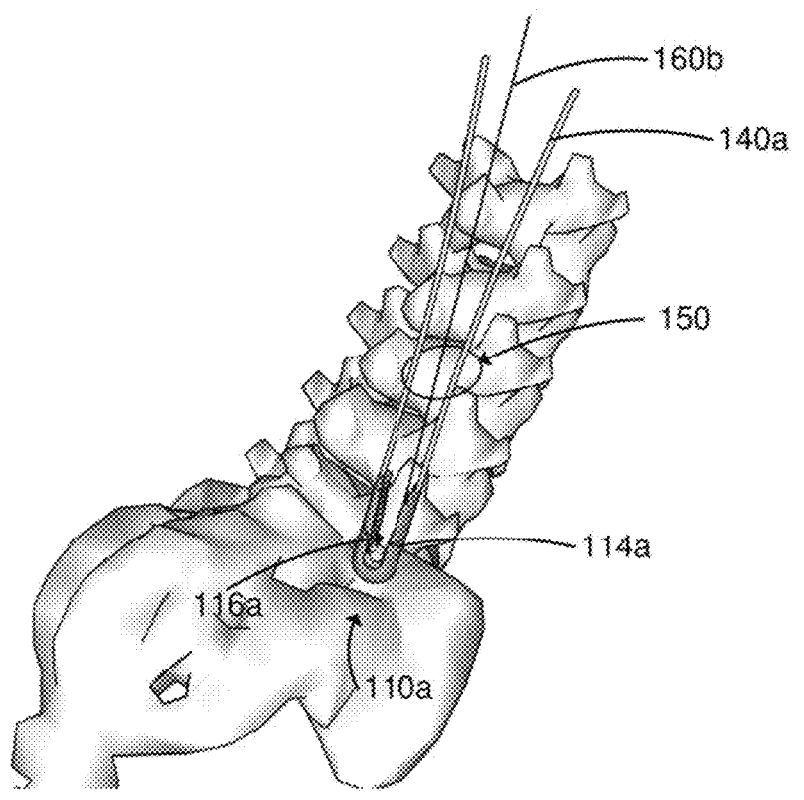

Once the screw 110a is guided to the target location on the first vertebra, as illustrated in FIG. 1D, the bone engaging shaft 112a is screwed into and retained in the first vertebra. As illustrated in FIG. 1E, once the screw 110a is secured, the guidewire 160a is withdrawn out of the body.

Figure 1F:
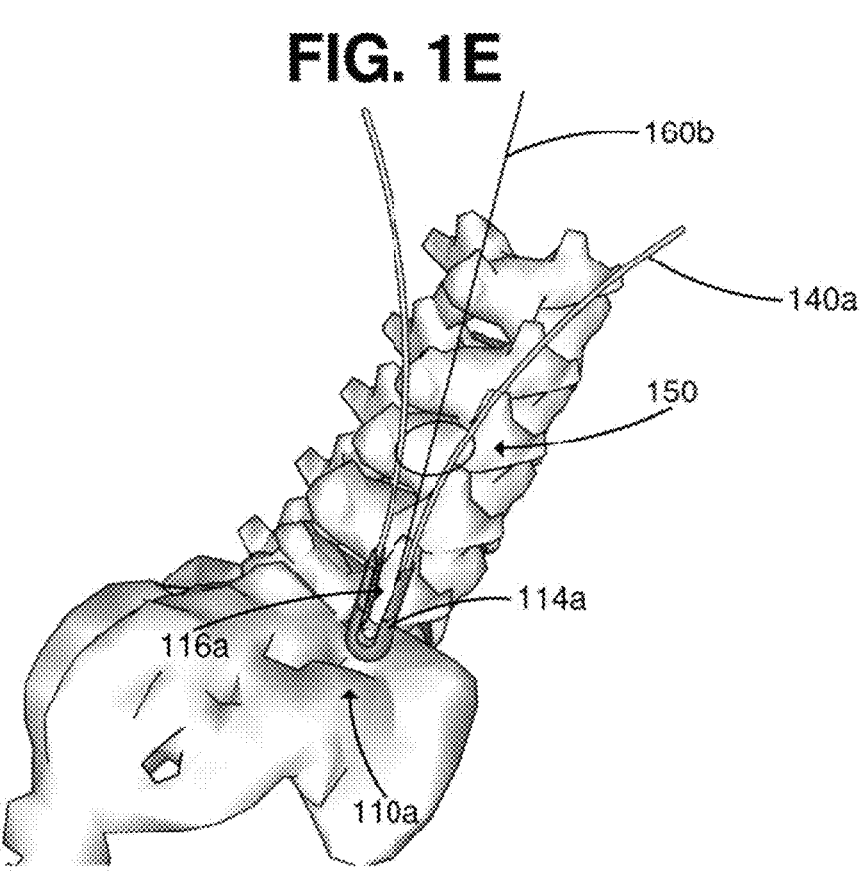

FIG. 1E illustrates a perspective view of the implanted first screw 110a. As illustrated, the wires 140a are attached at a distal end to the screw head 114a such that the proximal end of the wires 140a extend out of the incision 150. To prepare for the implantation of the second screw 110b, the plurality of wires 140a are bent away from each other to increase access to the incision (see FIG. 1F).

Figure 1G:
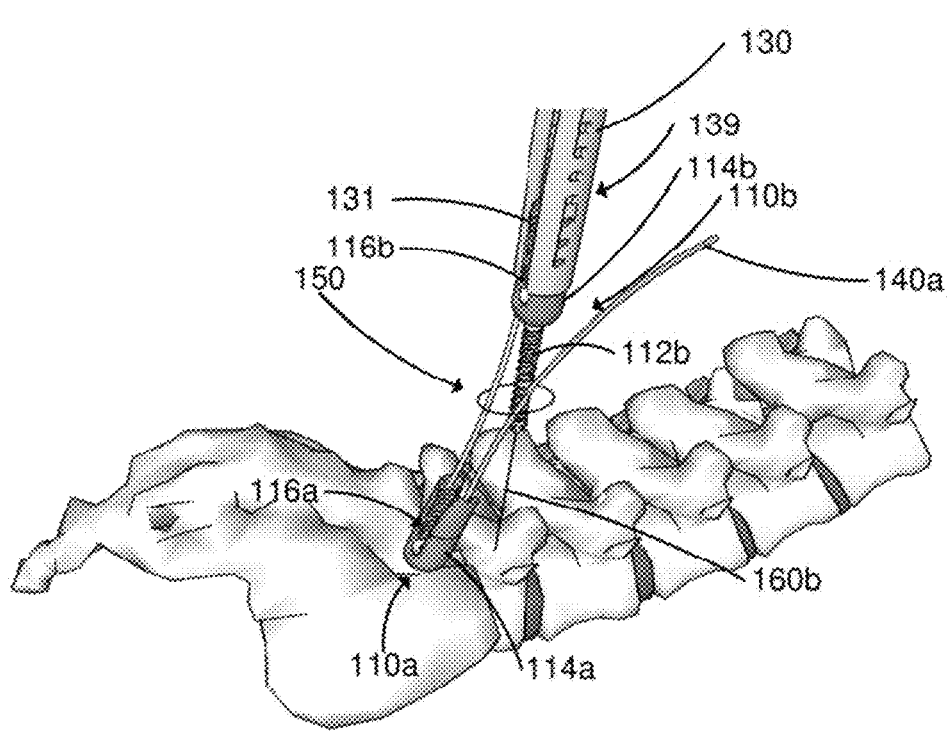
Figure 1H:
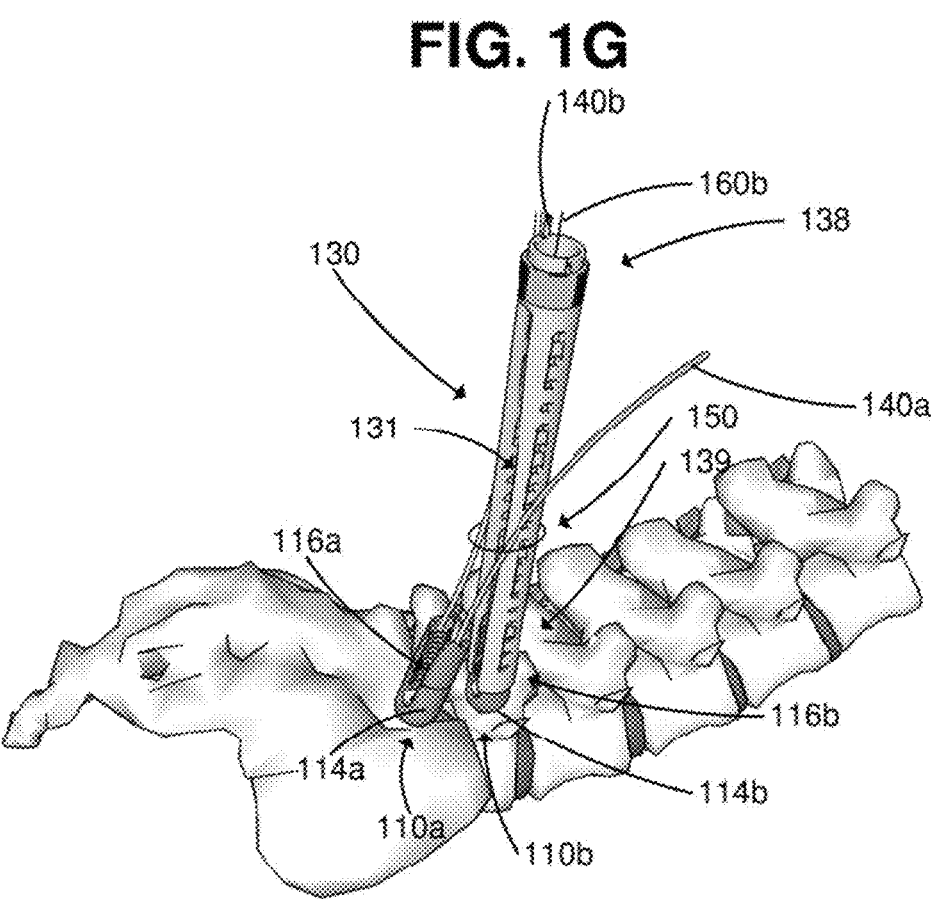

Similar to the implantation of the first screw 110a, the second screw 110b can be guided to the second vertebra by the second guidewire 160b. In some embodiments, as illustrated in FIG. 1G, the second screw 110b can be inserted with the distal end 139 of the tower 130 retained about the proximal end of the screw head 114b. As will be seen more clearly in subsequent figures, the tower 130 is disposed about the plurality of wires 140b. In some examples, as is illustrated in FIG. 1H, the proximal end of the wires 140b extends from the proximal end 138 of the tower 130.

Figure 1I:
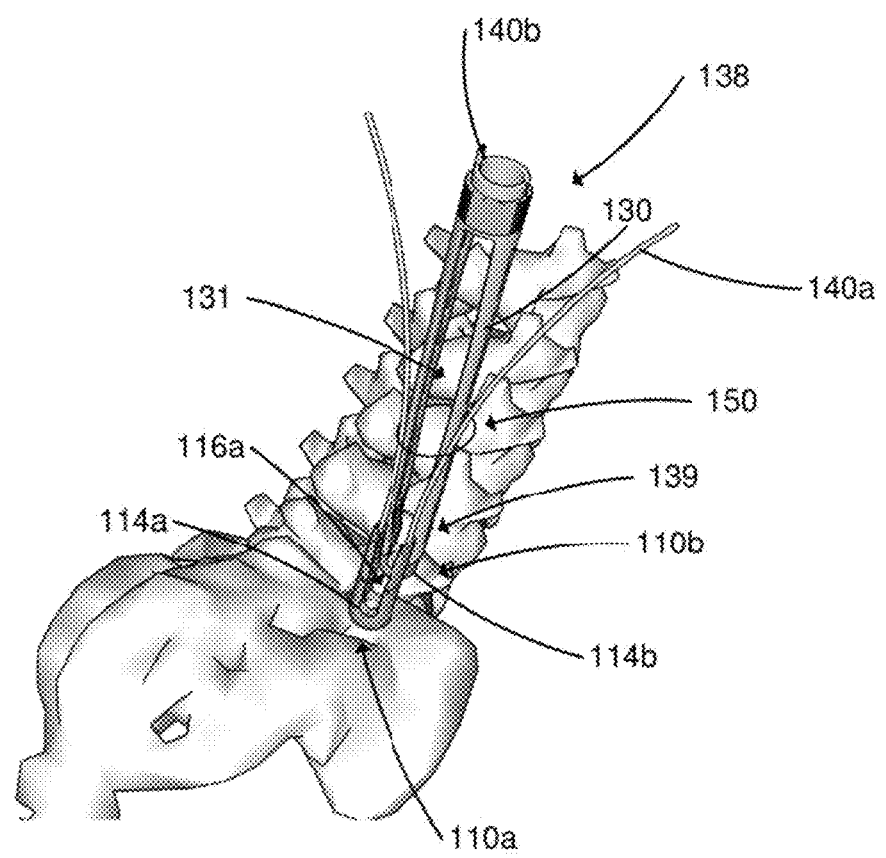

FIG. 1I illustrates a perspective view of the implanted first screw 110a, the implanted second screw 110b, and the tower 130 disposed about the wires 140b and the screw head 114b of the second screw head 114b. As illustrated, the second guidewire 160b has been removed and the plurality of wires 140a remain bent away from each other to allow access to the window 131 of the tower 130.

Figure 1J:
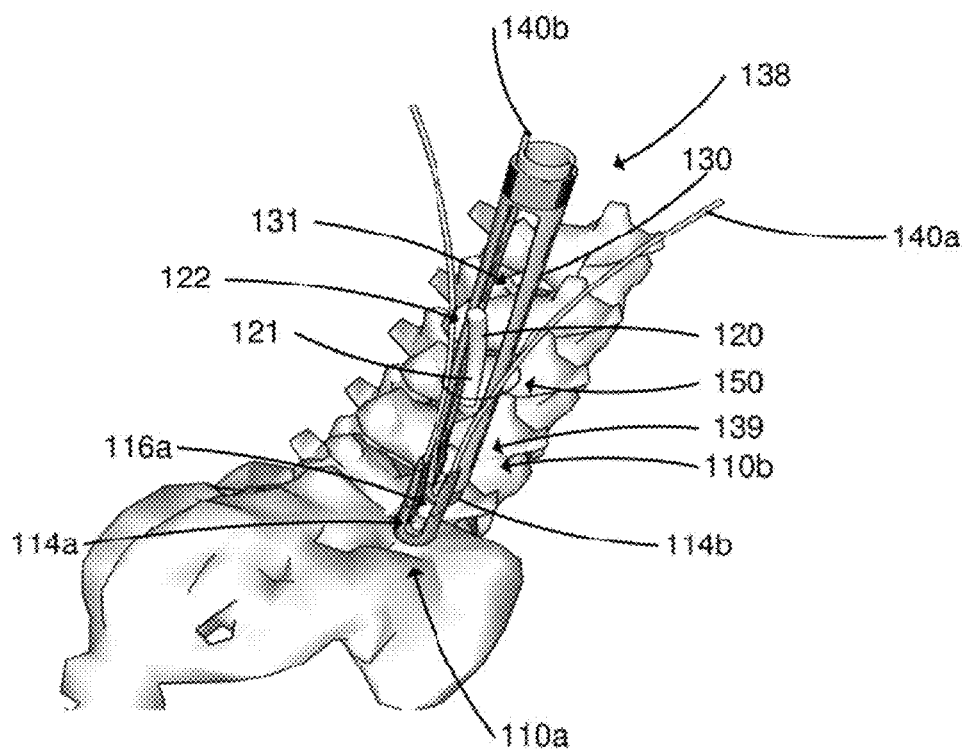
Figures 1K, 1L:
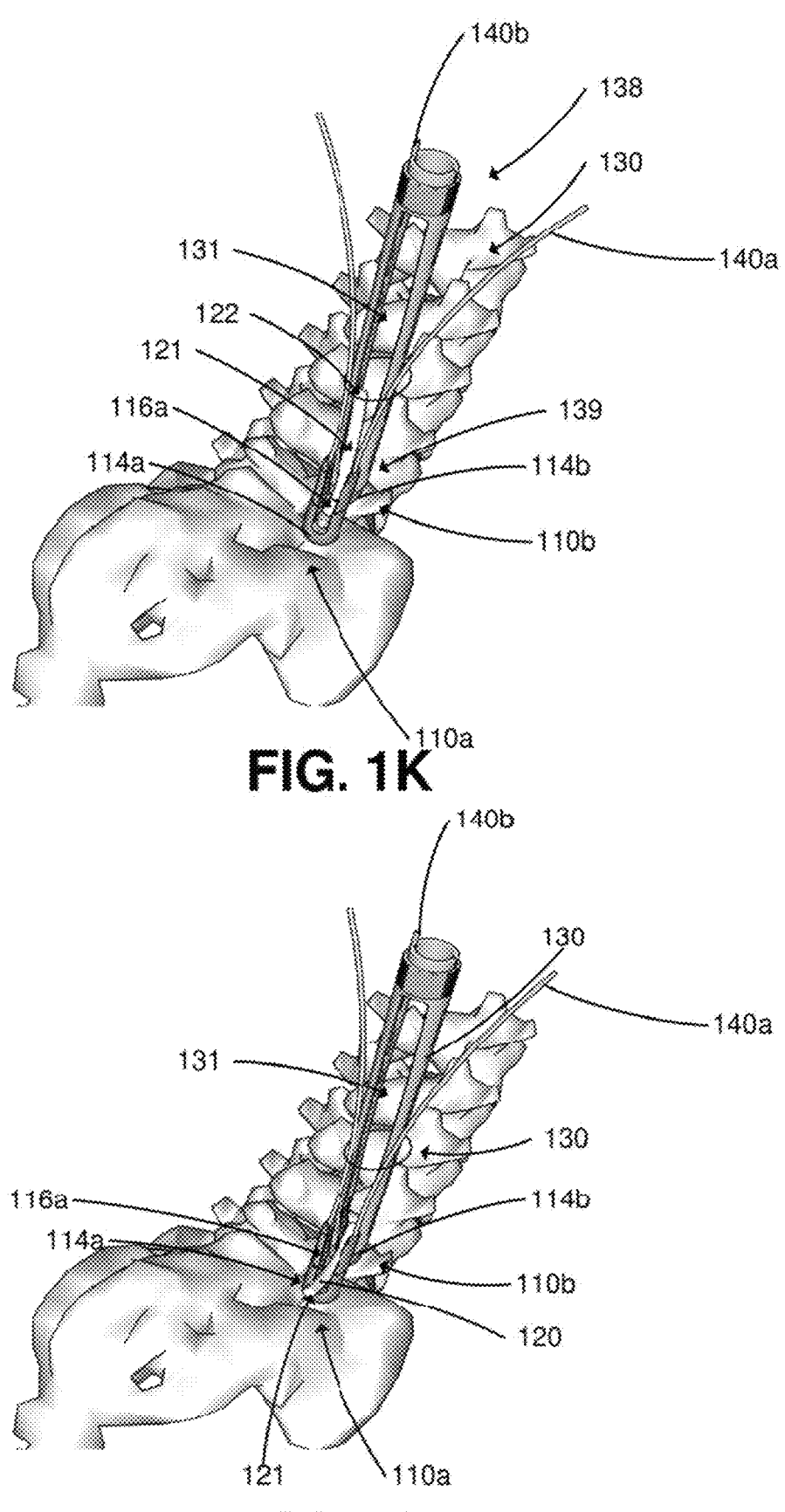

FIGS. 1J-1L illustrate the insertion and placement of the rod 120 into the first insert 116a of the first screw 110a and the second insert 116b of the second screw 110b. In some embodiments, the rod 120 (or other implant) can be inserted through the incision 150 and between the bent wires 140a and the window 131 of the tower 130. In some examples, a first end 121 of the rod 120 is passed through the window 131 of the tower 130. The first end 121 can be guided down the window 131 of the tower 130 and the distal end of the wires 140a until it enters the insert 116a of the first screw head 114a in the first vertebra. In some examples, the second end 122 of the rod 120 is guided down the window 131 until it enters the insert 116b of the second screw head 114a in the second vertebra.

Figures 1M, 1N:
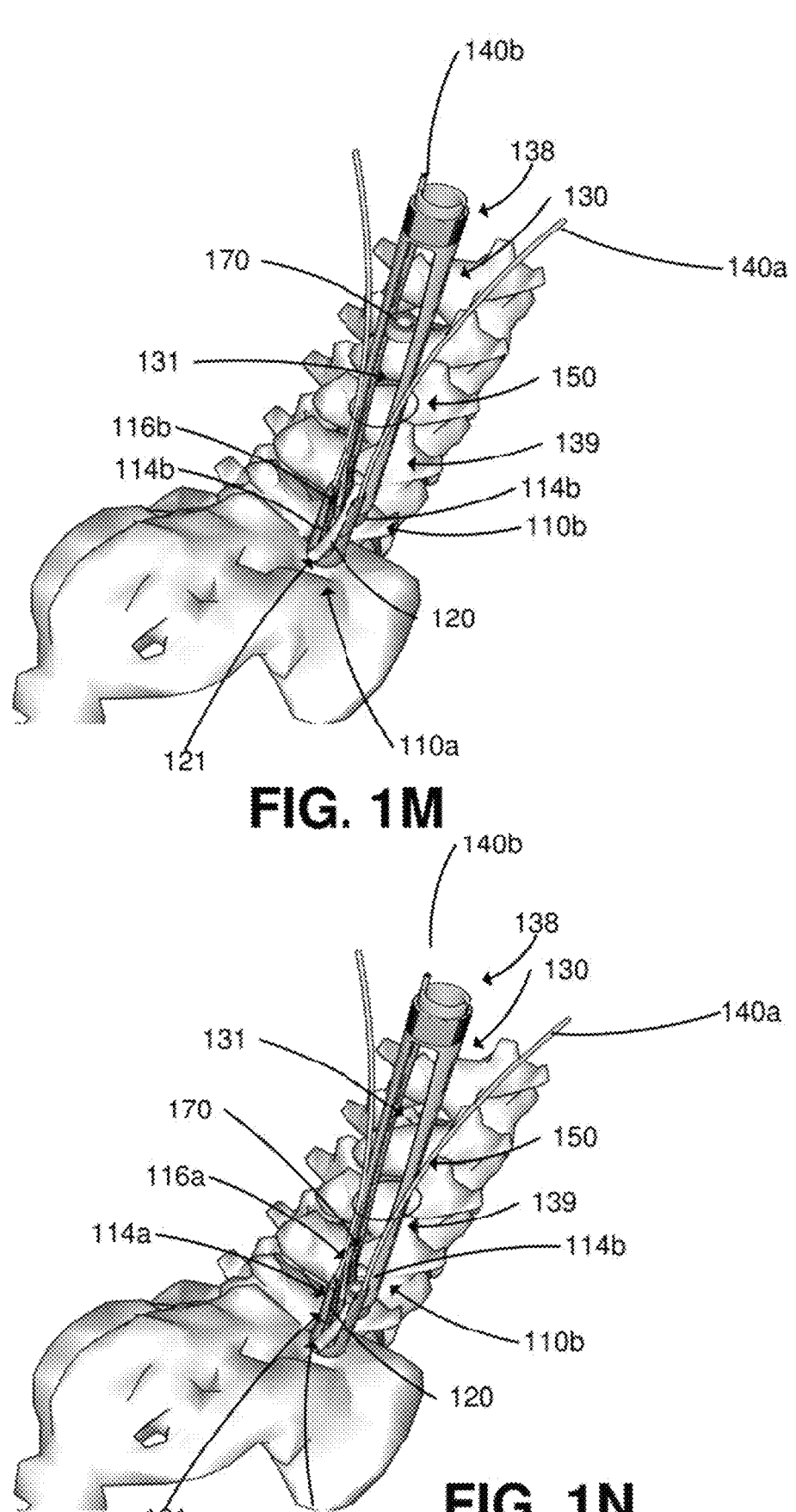

In some embodiments, in order to secure the rod 120 in the first screw 110a and second screw 110b, a locking assembly can be inserted over the rod 120. As discussed in more detail above, the locking assembly may be built into or attached onto the screw head or be a separate element. Locking assemblies that are separate elements include (but are not limited to) those reliant on caps and set screws. The locking assembly may be guided down to the screw before or after insertion of the rod depending upon the details of the locking mechanism used to secure the rod. In some embodiments, the locking assembly is already present on the screw head before the rod is received. In some examples, the rod is inserted into the screw head 114 first and the locking assembly follows. In some embodiments, as illustrated in FIGS. 1M and 1N, the locking assembly is a screw cap 170 that can be placed over the rod 120. As illustrated in FIG. 1M, the screw cap 170 can be placed into the opening 133 at the proximal end 138 of the tower 130. The tower 130 is configured to guide the tower 130 into the screw head 114b of the screw 110b (see FIG. 1N). In some embodiments, the upwardly extending arms of the screw head 114b can be internally threaded and the screw cap 170 can be externally threaded. To secure the screw cap 170, the externally threaded screw cap 170 can be rotated into the screw head 114b to apply a downward force to the rod 120 sitting in the insert 116b of the screw head 114b. This downward force can also then lock the second end 122 of the rod 120 such that the screw head 114b is secured relative to the rod 120.

Figure 1O:
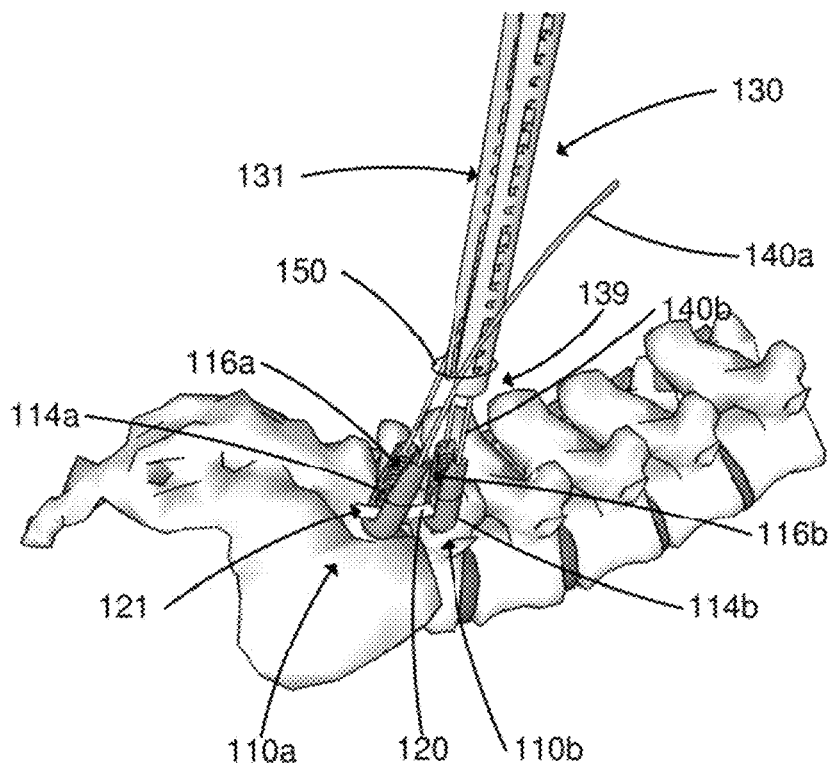
Figure 1P:
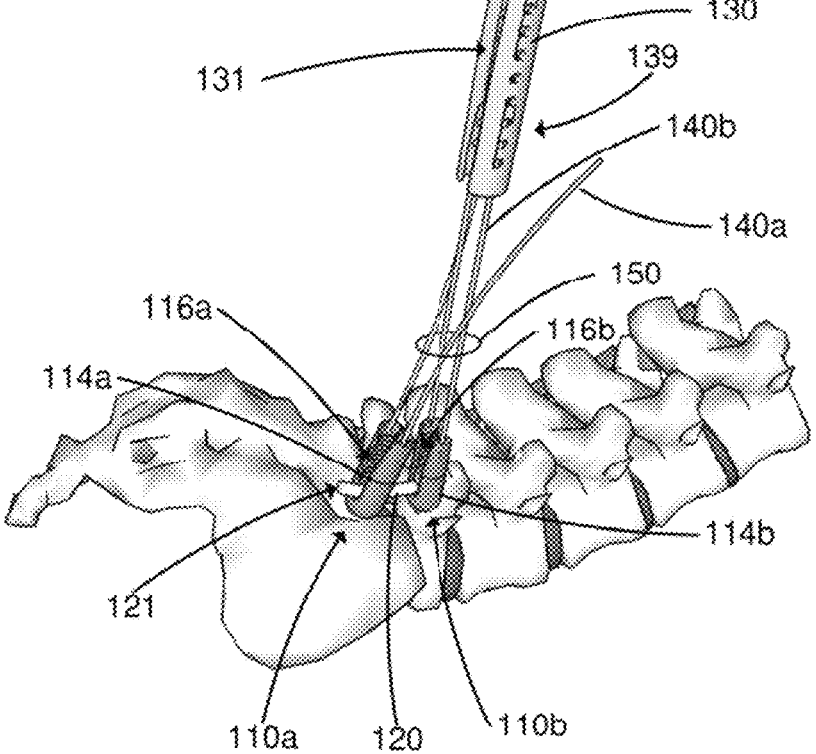
Figure 1Q:
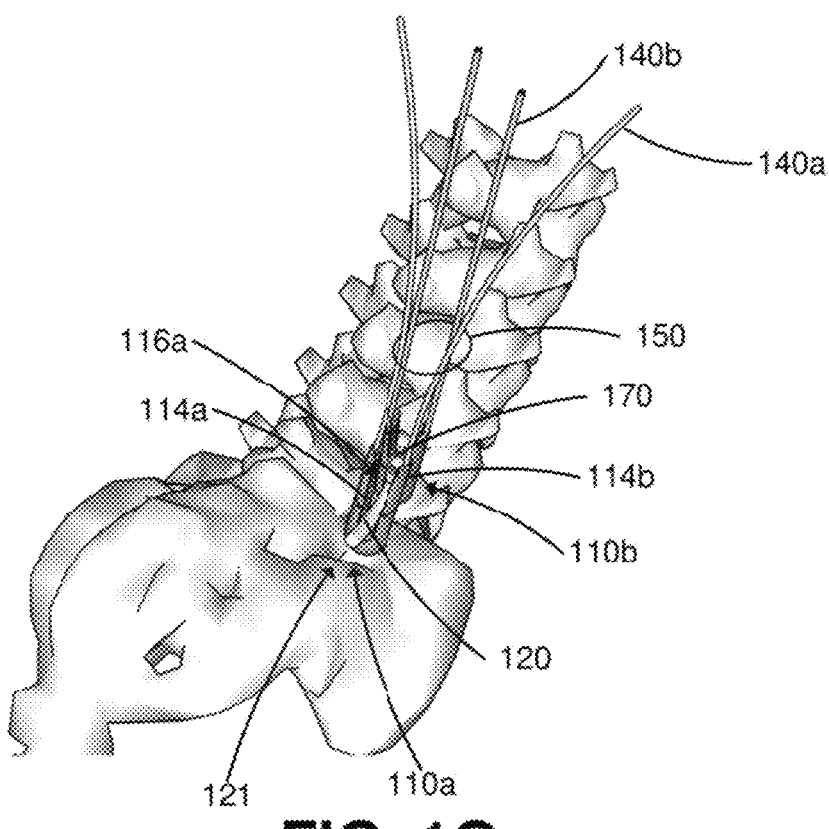
Figure 1R:
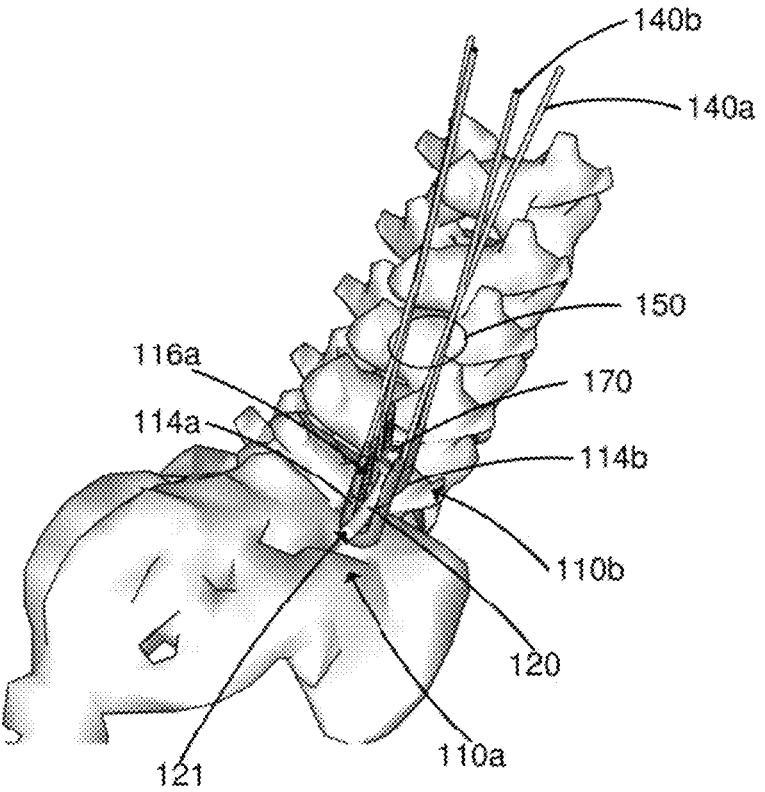
Figures 1S, 1T:
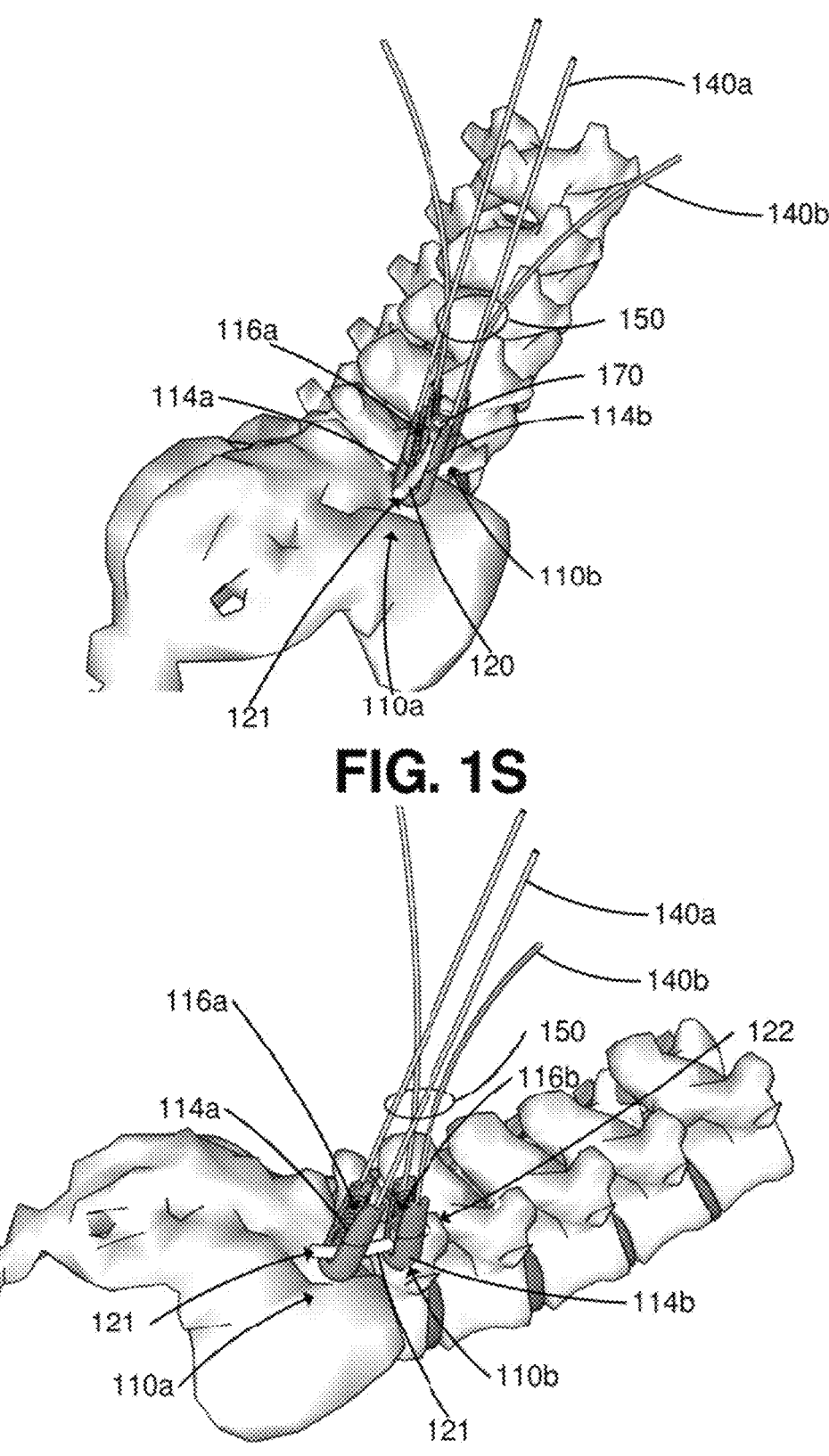

In some examples, the tower 130 can be moved from accessing one screw to another screw. FIGS. 1O-1V illustrate the tower 130 moved from accessing the second screw 110b to accessing the first screw 110a. As shown in FIG. 1O, the tower 130 can be withdrawn in a proximal direction such that the distal end 139 of the tower 130 is disengaged from the proximal end of the second screw head 114b. As the tower 130 is withdrawn, the tower 130 is pulled along the length of the wires 140b attached to the proximal end of the screw head 114b (see FIG. 1P). FIGS. 1Q-1S illustrates a perspective view of the implanted first screw 110a and the second screw 110b. In some embodiments, in order to allow the tower 130 to be disposed about the plurality of wires 140a of the first screw 110a, the wires 140a can be bent such that the pair of wires 140a are brought closer to each other (see FIG. 1R). In some examples, the plurality of wires 140b can be bent away from each other to provide additional room and access to the incision 150 (see FIG. 1S).

Figure 1U:
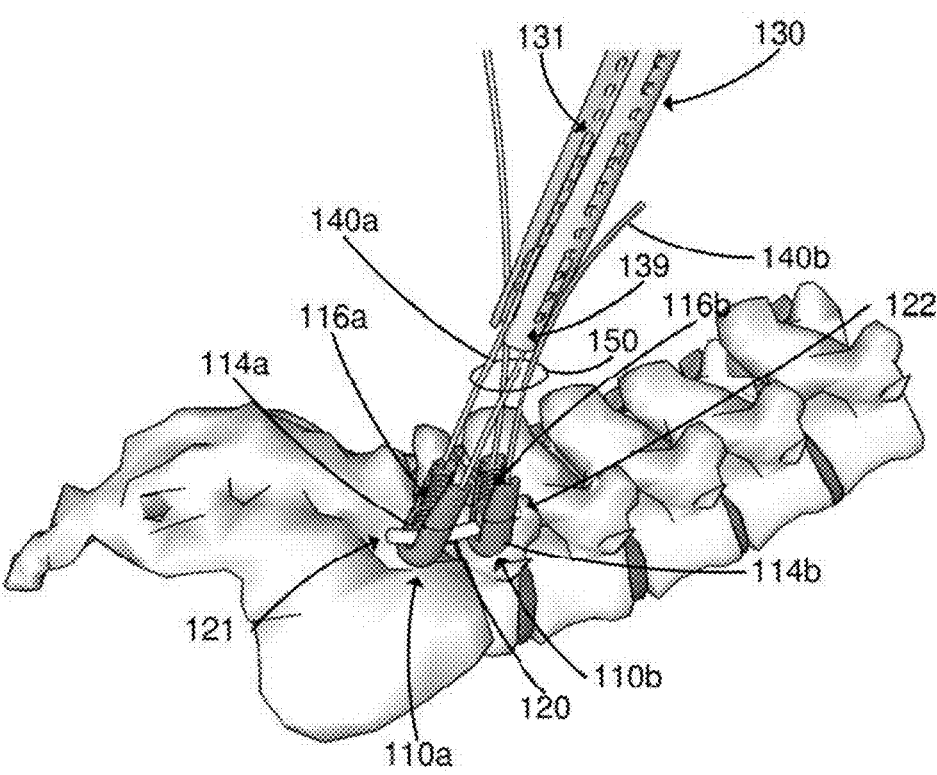
Figure 1V:
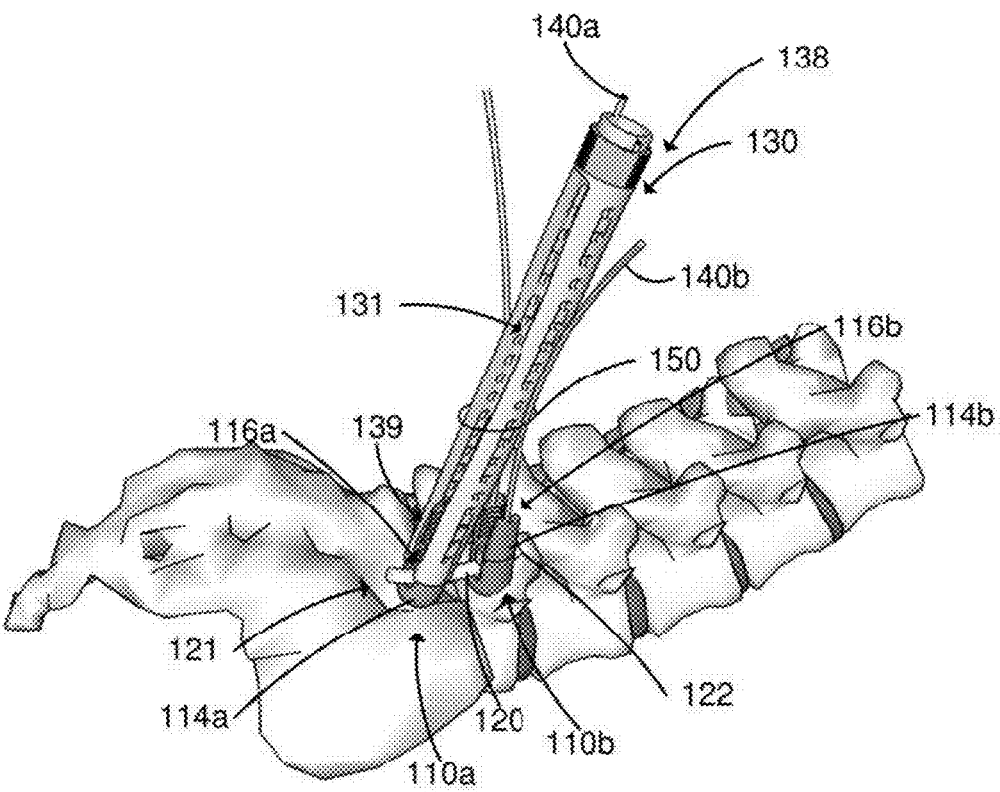

FIG. 1T illustrates a side view of the implanted first screw 110a and the second screw 110b. In some embodiments, once the wires 140a and wires 140b have been bent to accommodate the tower 130, the tower 130 can be disposed about the wires 140a of screw 110a. As shown in FIGS. 1U and 1V, the tower 130 can be inserted in a distal direction such that the distal end 139 of the tower 130 is disposed about the proximal end of the screw head 114a.

Figure 1W:
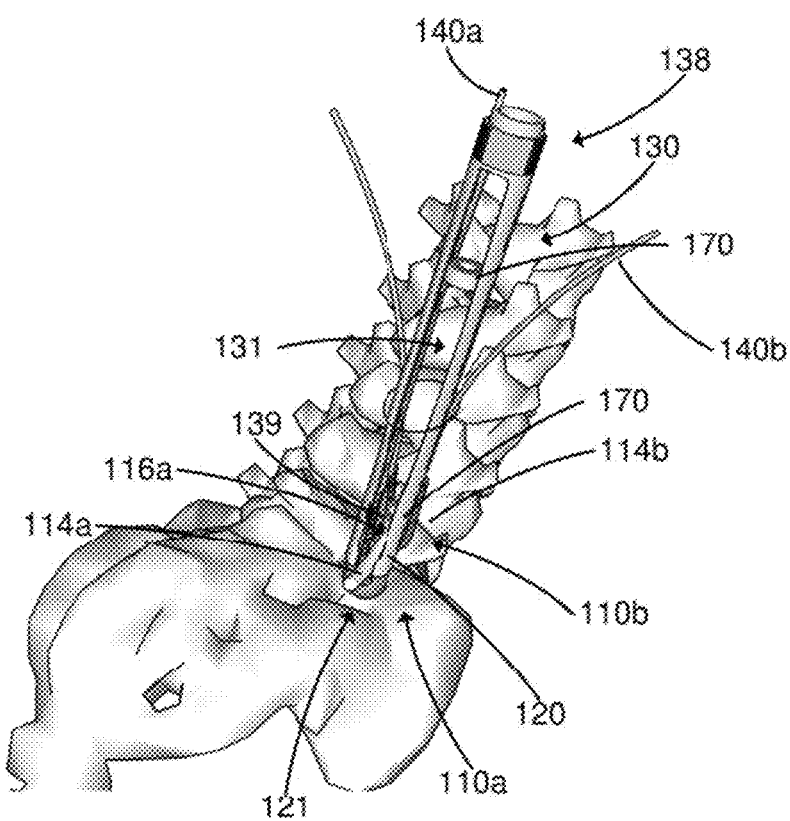
Figure 1X:
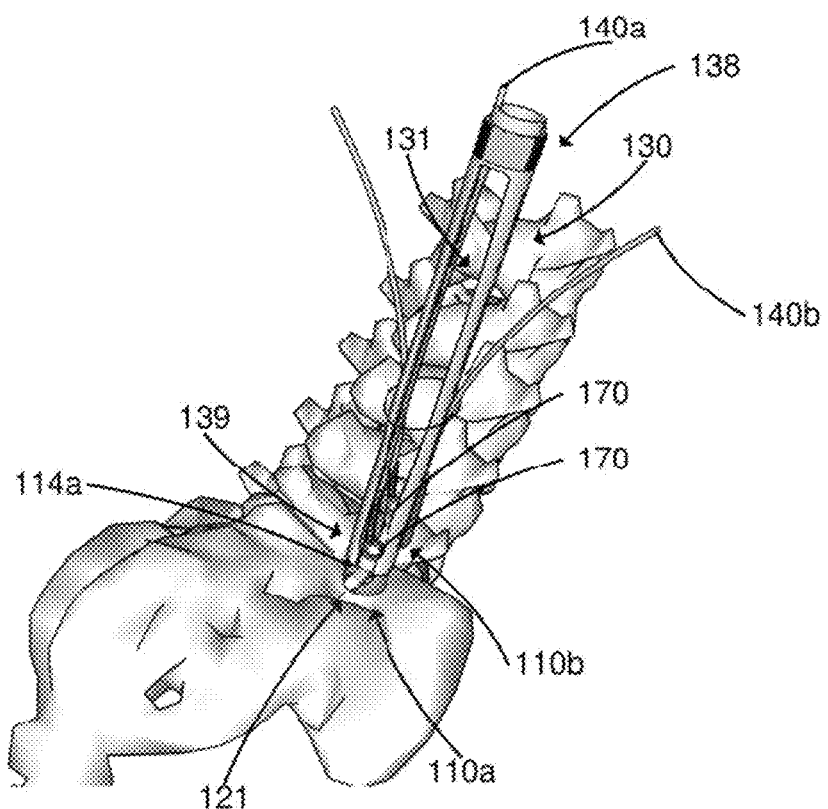
Figure 1Y:
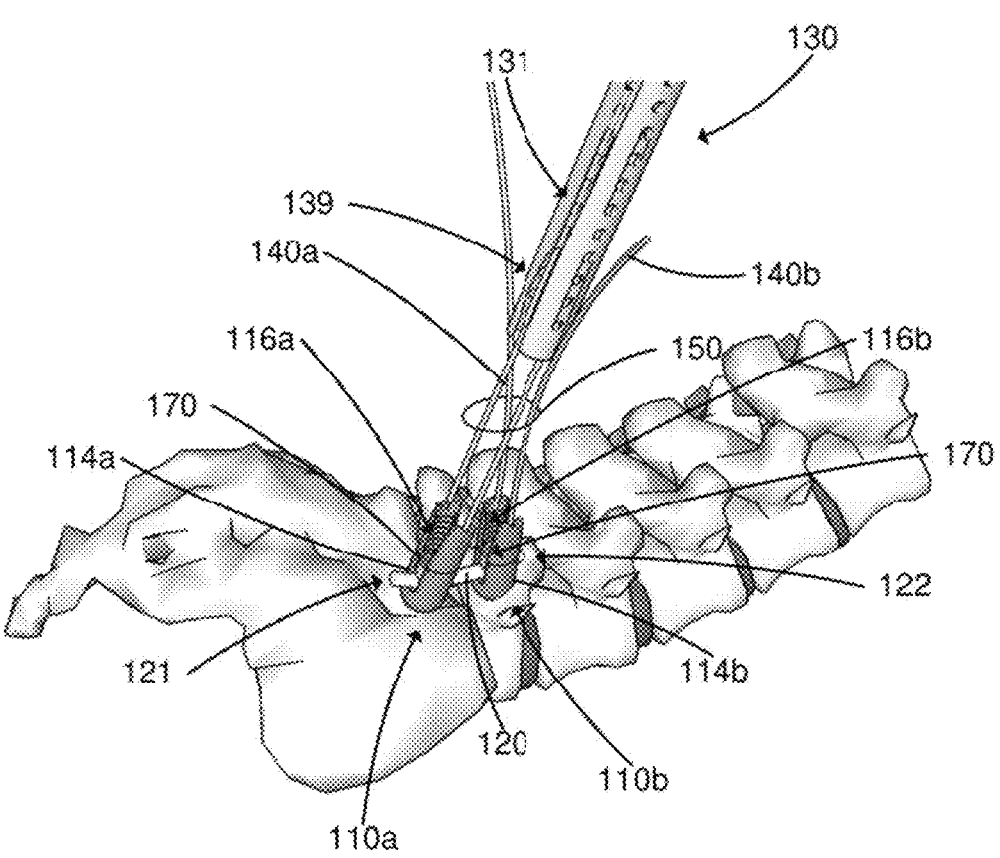
Figure 1Z:
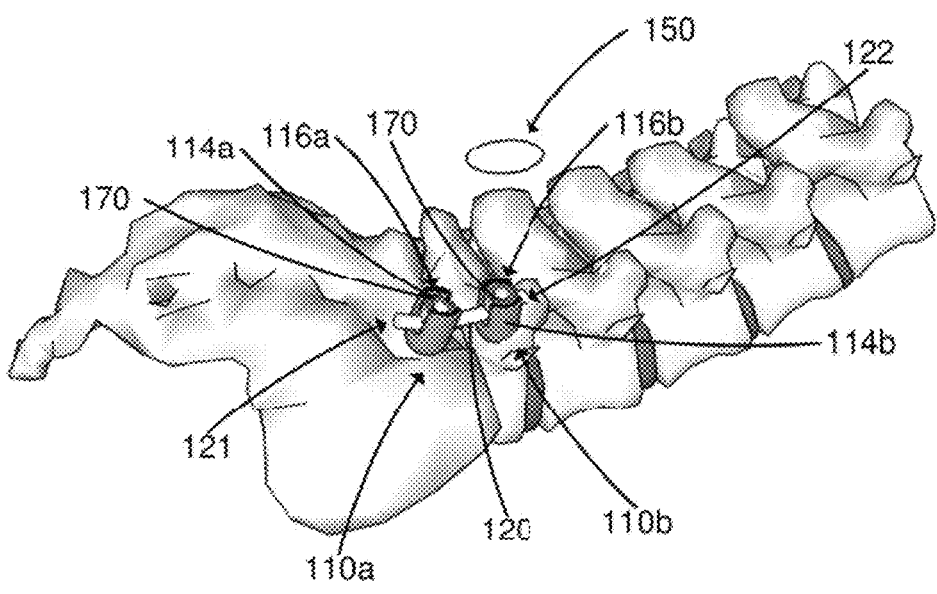

As discussed with regard to the insertion of the screw cap 170 into the screw head 114a of the screw 110a, a second screw cap 170 can be inserted through the opening 133 at the proximal end 138 of the tower 130. As shown in FIGS. 1W and 1X, the second screw cap 170 can be guided to the screw head 114a of the screw 110a. As discussed above with regard to the first screw cap 170, in some embodiments, the upwardly extending arms of the screw head 114a can be internally threaded and the second screw cap 170 can be externally threaded. To secure the second screw cap 170, the externally threaded screw cap 170 can be rotated into the screw head 114a to apply a downward force to the rod 120 sitting in the screw head 114a of the screw head 114a. This downward force can also then lock the first end 121 of the rod 120 such that the screw head 114a is secured relative to the rod 120.

Once the first screw 110a and the second screw 110b are implanted and the rod 120 is secured by the first screw cap 170 and the second screw cap 170, the tower 130 can be withdrawn from the incision 150. In some embodiments, as illustrated in FIG. 1Z, the first pair of wires 140a and the second pair of wires 140b can be removed from the implanted first screw 110a and second screw 110b. In some examples, the wires 140a, 140b are snapped off along with a proximal end of the screw head 114a, 114b. As shown in FIG. 1Z, in some embodiments, the first screw cap 170 and second screw cap 170 are adjacent to the proximal end of the screw head 114a, 114b.

Figure 2A:
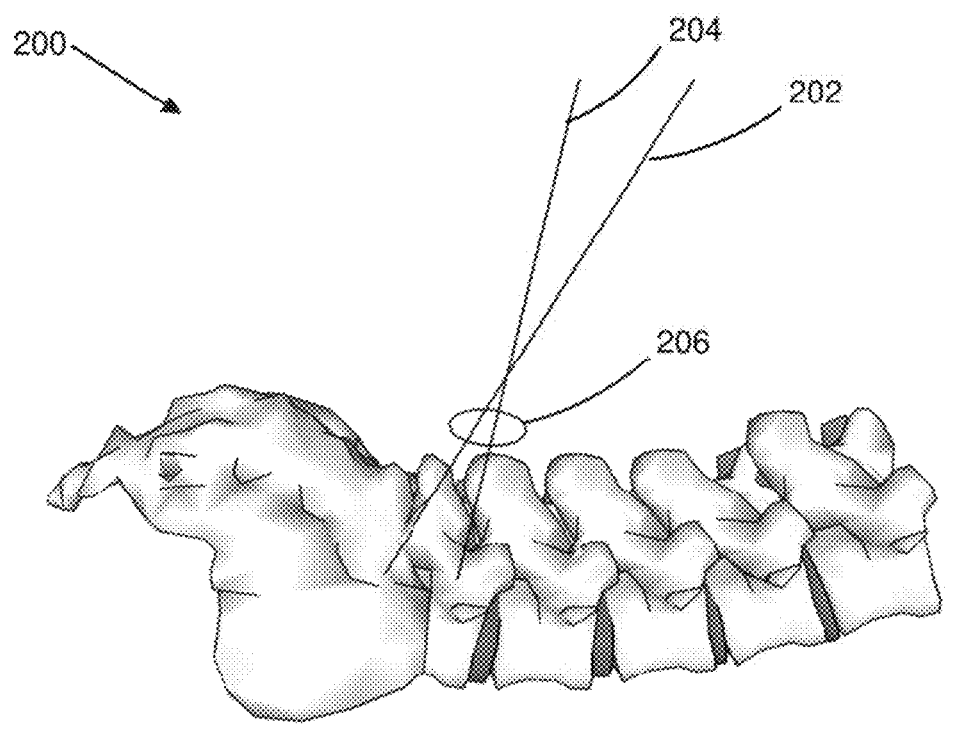
FIGS. 2A-2T illustrate another embodiment of a method and a system for stabilizing spinal vertebrae comprising spinal screws.

Systems, Devices and Methods of FIGS. 2A-2T

FIGS. 2A-2T show another embodiment of a method and a system 200 for stabilizing spinal vertebrae. Any of the embodiments of the system or systems disclosed herein can have any of the screws, extensions (also referred to as towers, extension towers, or guide elements), or other components, features, and/or other details of any of the other embodiments of the implant systems disclosed herein or which are disclosed in U.S. Pat. No. 8,721,691 or components thereof, which is incorporated by reference herein as if fully set forth herein, in place of or in any combination with any of the components, features, and/or other details disclosed herein for the embodiments of the system or systems disclosed below, including without limitation any of the embodiments of the system 200. Additionally, any of the steps, sequences of steps, or procedures described above with respect to any other system embodiments or which are disclosed in U.S. Pat. No. 8,721,691 can be used in place of or in any combination with any of the steps, sequences of steps, or procedures described below for any of the embodiments of the systems disclosed below (including, without limitation, the embodiments of the system 200) to form new steps, sequences of steps, and procedures for the embodiments of the system disclosed below (including, without limitation, the embodiments of the system 200).

Figure 2B:
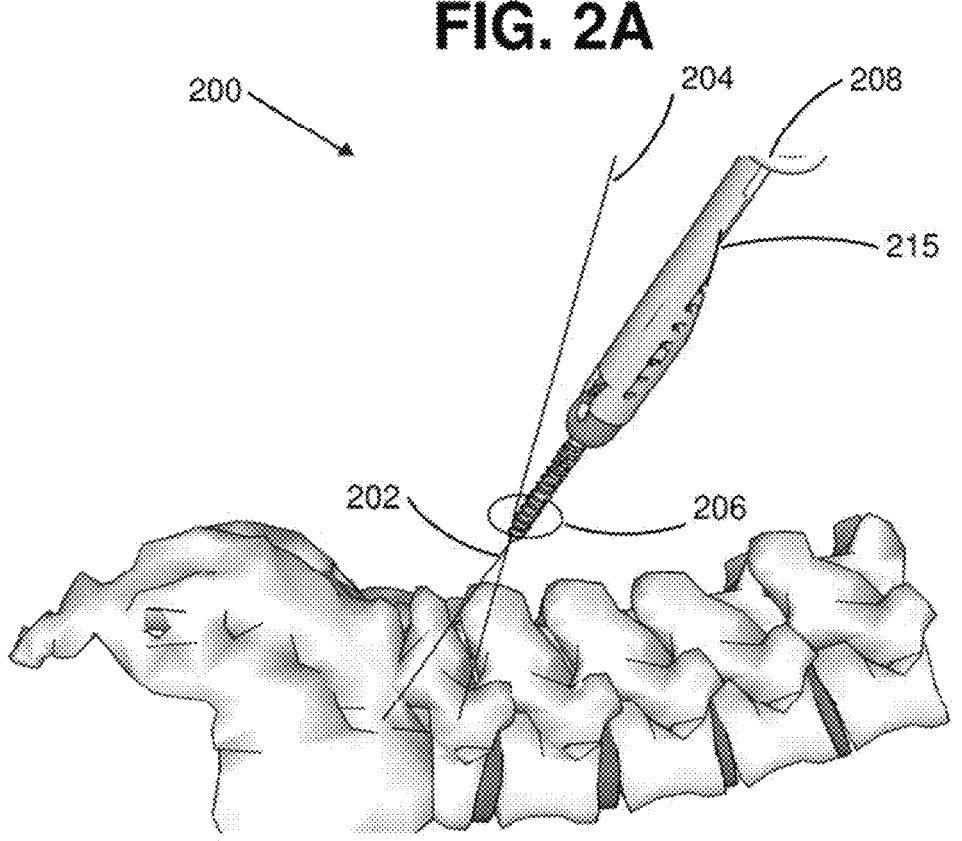

FIG. 2A shows a first guidewire 202 and a second guidewire 204 (which can be K wires) of the spinal stabilization system 200 advanced through an incision 206 and into the target locations in a patient's vertebra. In any embodiments, as illustrated the first and second guidewires can be advanced through a single incision. In other embodiments, three or more guidewires for three or more devices or implants can be advanced through a single incision. FIG. 2B shows a first extension 208 having a proximal end portion 208a and a distal end portion 208b that can be coupled with a first screw 210 advancing over the first guidewire 202 through the incision 206. The screw 210 can be selectively removable from the extension member 208, at a distal end portion 208b of the extension member 208.

The following is a description of some embodiments of the system 200 for stabilizing spinal vertebrae that can be performed through a single skin incision, such as incision 206. As shown in FIGS. 2A-2T, any embodiments of the system 200 can include a first screw 210 having a first screw head 210a, a second screw 230 having a second screw head 230a, a first extension 208 having a body portion 209, and a second extension 228 having a body portion 229. The first extension 208 can be configured to be removably coupled with the first screw 210 at a first end of the body portion 209 of the first extension 208 by any of the techniques or using any of the components known in the art or as disclosed herein, and the second extension can be configured to be removably coupled with the second screw at a first end of the body portion 229 of the second extension 228 by any of the techniques or using any of the components known in the art or as disclosed herein. The first extension 208 can further include a handle portion 214 (also referred to herein as a handle member) that can be coupled with a proximal end of the body portion of the first extension. The handle portion 214 can extend away from the proximal end of the body portion of the first extension 208 at an angle. Note that the terms guiding element or extension element can be used to describe the extension components described herein.

First Extension:

In any embodiments the first extension 208 can be shorter than the second extension. For example and without limitation, the first extension 208 can be sized such that a proximal end of the body portion 209 of the first extension 208 extends to a height just below the skin of a patient when the first screw 210 is implanted in a first vertebra 211, or wherein a proximal end 208a of the first extension 208 extends to a height just below the skin of a patient, or to a height level with the skin of a patient, when the first screw 210 is implanted in a vertebra. Alternatively, the first extension 208 can be sized such that only a proximal end portion 208a of the first extension 208 (for example and without limitation, 10% or approximately 10% or less of the entire length of the first extension 208, or from 5% or approximately 5% to 10% or approximately 10% of the entire length of the first extension 208) extends through the skin incision 206 when the first screw 210 is implanted in a vertebra, or such that no portion of the first extension 208 extends through the skin incision when the first screw 210 is implanted in a vertebra. Further, in any embodiments, the first extension 208 can be sized such that the entire body portion 209 of the first extension 208 is positionable below a skin surface of a patient, with only the handle portion 214 extending through the skin incision, when the first screw 210 is implanted in a vertebra.

For example and without limitation, a surgeon can measure a distance from the vertebra to the skin surface and select a first extension 208 having a suitable length to match, or approximately match, the distance from the vertebra to the skin surface. In some embodiments, the first extension 208 can have an adjustable length, such as a telescoping body that can be adjusted by a surgeon before and/or after the first screw 210 is implanted. In this configuration, a length of the first extension 208 can be, but is not required to be, adjusted so that the entire length of the first extension is at or below the skin surface of the patient, or substantially at or below (as described above) the skin surface of the patient.

Second Extension:

In any embodiments, the second extension 228 can be sized to extend completely through the skin incision 206 when the second screw 230 is implanted in a vertebra. In some embodiments, the body portion 209 of the first extension 208 can have an adjustable length. In some embodiments, each of the first extension 208 and the second extension 228 can have a fixed length. In some embodiments, the first and second body portions can be generally cylindrically shaped.

Handle Portion:

FIG. 4 shows the handle portion 214 (also referred to herein as a handle) that can be coupled with or integrally formed with the first extension 208. The handle portion 214 can have a proximal portion 214*a* and a distal portion 214*b*. In any embodiments, the handle portion 214 can be coupled with the first extension 208 at a proximal end portion 208*a* of the first extension 208. The handle portion 214 and the first extension 208 can be configured such that a surgeon or other user can rotate, move, torque, bend, or otherwise manipulate the first extension 208 when the first extension is inside the incision using the handle portion 214, when the handle portion is positioned outside of the body.

Figures 2C, 2D, 2E:
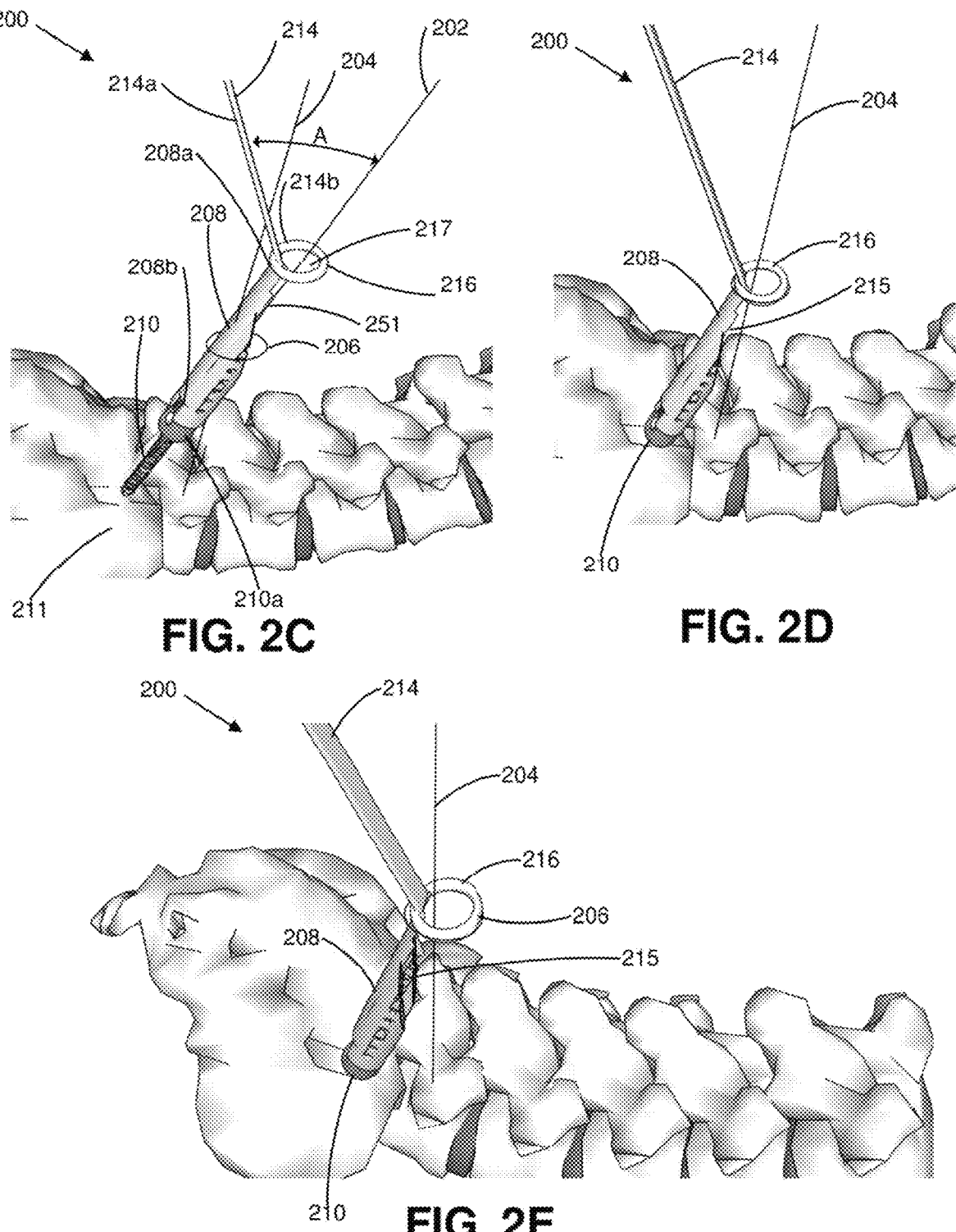

In any embodiments, the handle portion 214 can extend away from the first extension 208 at any desired angle. For example and without limitation, in some embodiments, the handle portion 214 can extend away from an axial centerline of the first extension 208 at an angle A (as shown in FIG. 2C) that is 45° or approximately 45° from the axial centerline of the first extension 208, or from 30° or approximately 30° to 50° or approximately 50°, or from 40° or approximately 40° to 45° or approximately 45° from the axial centerline of the first extension 208. Furthermore, in some embodiments, the angle of the handle portion 214 in relation to the first extension 208 may be variable through a joint attachment or adjustable angle connection between the handle portion 214 and the first extension 208. Additionally, the handle portion 214 can have any desired length. In some embodiments, the length of the handle portion can be varied such that a user can select the desired length of the handle portion from a kit of various sizes of handle portions, or the length of the handle portion can be adjustable. In some embodiments, the length of the handle portion 214 can be the same or approximately the same as the length of the first extension 208, or within 25% of the length of the first extension. The handle portion 214 or any other handle portion of any embodiment disclosed herein can optionally have any desired cross-sectional shape, including flat, curved, round, ovular, or otherwise. The handle portion 214 or any other handle portion of any embodiment disclosed herein can optionally can also have any desired longitudinal shape or curvature, including curved away from the skin, undulating curve to fit the grip of a surgeon's hand, or a curvature that couples with the handle portion of the second screw to provide a fulcrum thereby allowing compression of the screw heads when the two handles are squeezed.

The device 200 can be configured such that a handle portion 214 attached to the proximal end of the first extension 208 can be grasped by a surgeon to enable a surgeon to manipulate the first extension 208 and, hence, the first screw 210 and the first vertebra that the first screw 210 is anchored to or coupled with during the surgical procedures. In this configuration, a surgeon can, for example and without limitation, exert a compressive force on adjacent vertebra, or a decompressive force on adjacent vertebra, or rotate, torque (including a counter-torque force on the screw when a set screw is being installed to secure a rod between adjacent spinal screws), bend, or otherwise manipulate the first extension, first screw 210, and/or first vertebra. In some embodiments, the handle portion 214 can be used to exert a rotational force on the first extension 208 about at least a centerline axis of the first extension. For example and without limitation, the handle portion 214 can be configured to be grasped by a surgeon to enable a surgeon to manipulate the first extension, or to be grasped by a surgeon to enable a surgeon to exert a rotational force on the first extension 208 about the centerline axis of the first extension.

The handle portion 214 can be a separate component that is configured to be removably coupled with the body portion of the first extension. In some embodiments, the handle portion 214 can be removably coupled with the body portion of the first extension, the handle portion 214 having an end portion that can be receivable in a notch, groove, or other receptacle formed on a side of the body portion of the first extension. For example, the handle portion 214 can be separate from the extension and can be inserted into a notch, groove, or receptacle formed in one side of the first extension. In this configuration, the screw can be inserted with the first extension 208 using an inserter. During insertion, the inserter can be placed through the first extension 208 and inserted like a normal tower or extension configuration. But along the side of the inserter can be a groove or slots that lead to grooves or slots along the wall of the first extension. Thus, after the screw is inserted, but with the inserter still attached to the screw and first extension, then the handle portion 214 can be slid along the side of the inserter with a corresponding groove or configuration to accept the handle portion 214 and allow the handle portion 214 to slide down into the groove and slot in the wall of the first extension. The system can have locking mechanisms or features to selectively secure or lock the handle portion 214 in place in the wall of the first extension. In some embodiments, the handle portion 214 can be non-removably coupled with the body portion of the first extension, or integrally formed with the body portion of the first extension.

In any embodiments disclosed herein, the first extension 208 can have a recess or cutaway 215 formed therein at a mid-portion and/or the proximal end of the body portion 209 of the first extension 208 that can be configured to receive a portion of an outside surface of the body portion 229 of the second extension 228 therein in an operable state. The recess 215 can have a shape that generally complements a shape of an outside surface of the body portion 229 of the second extension 228. For example, in some embodiments wherein the body portion 229 of the second extension 228 has a round or circular cross-section, the recess 215 can have a curved profile or cross-section that accommodates the round or circular cross-section of the second extension 228. In some embodiments, the first extension 208 can have the recess 215 formed therein at least the middle portion and the proximal end 208*a* of the first extension 208, the recess being configured to receive a portion of an outside surface of the body portion 229 of the second extension 228 therein in an operable state. The handle portion 214 can extend away from the body portion 209 of the first extension 208 in a direction that is generally away from the recess. In this configuration, the second extension 228 can be positioned more closely to the first extension 208 and can be advanced through a smaller incision in the patient's skin. The recess 215 can result in a more compact system during operational procedures that can reduce the size of the incision, among other benefits.

In some embodiments, the first extension 208 can have a recess formed therein at the proximal end of the body portion of the first extension, the recess being configured to receive a portion of an outside surface of the body portion 229 of the second extension 228 therein in an operable state. The handle portion 214 can be coupled with a first side of the body portion 209 of the first extension 208 and the recess can be formed on a second side of the body portion 209 of the first extension 208 that can be opposite to the first side of the body portion of the first extension. In some embodiments, the handle portion 214 can attach to the body portion 209 of the first extension 208 adjacent to a recess formed in the body portion of the first extension. In some embodiments, some details of the recess can be similar to the recesses of the embodiments shown in FIGS. 39-45 of U.S. Pat. No. 8,721,691, the details of such embodiments shown in such figures and described therein being incorporated by reference as if fully set forth herein.

In some embodiments, the system can further include at least one handle portion (similar to the embodiments of the handle portion 214 disclosed herein) coupled with the body portion 229 of the second extension 228, or two handle portions coupled with the body portion 229 of the second extension 228, which can be used with the handle portion 214 that is coupled with the first extension 208.

Linking Member:

Any embodiments disclosed herein can further include a linking member 216 (which is also referred to herein as a restraint, such as with respect to restrain 650 described below, retention member, ring or ring member) that can be configured to couple the first extension 208 and the second extension 228 together, as shown in FIG. 21, among others. The linking member 216 can be rigid and can be formed integrally with or separately from the first extension 208 and welded, brazed, or otherwise coupled with the first extension. In this configuration, the linking member 216 can provide a selectable or reversible link or connection between the first extension 208 and the second extension 228. Any embodiments of the linking member 216 can be configured to improve the control and manipulation of the second extension 228 relative to the first extension 208, and/or the first extension 208 relative to the second extension 228. For example and without limitation, using the linking member 216 and the handle portion 214, the surgeon can exert a force on the first extension member 208 relative to the second extension member 228 to move the distal end 208b of the first extension member 208 toward the distal end 228b of the second extension member 228 to exert a contraction force on the first and second vertebra, or exert a force on the first extension member 208 relative to the second extension member 228 to spread the distal end 208b of the first extension member 208 away from the distal end 228b of the second extension member 228 to exert a traction force on the first and second vertebra.

In some embodiments, the linking member 216 can be coupled with and surround all or a portion of an outside surface of a proximal end 208a of the first extension 208 and the body portion 229 of the second extension 228 in an operable state. In other embodiments, the linking member 216 can be coupled with and extend away from an outside surface of the first extension 208. With reference to FIG. 21, in some embodiments, the linking member 216 can have an opening 217 therethrough that is aligned with the recess 215 formed in the first extension 208 that is sized and configured to receive the second extension 228 therethrough so that the second extension 208 can be advanced through the opening 217 and through the recess 215 as the second extension is advanced toward the patient's second vertebra.

Additionally, any embodiments can also have a linking member 216. In some embodiments, the linking member 216 can be coupled with or integrally formed with the first extension 208. In any embodiments, the linking member 216 can be coupled with the first extension 208 at a proximal end portion 208a of the first extension 208. In some embodiments, the linking member 216 can surround a portion of the first extension 208 and/or a portion of the handle portion 214, adjacent to a proximal end 208a of the first extension 208 and/or a distal portion 214b of the handle portion 214. In other embodiments, the linking member 216 can extend away from a side of the first extension 208 without surrounding any portion of the first extension 208. In some embodiments, the linking member 216 can be configured to provide a loose connection between the first extension 208 and the second extension 228.

Further, in any embodiments, the linking member 216 can be selectively openable so that a surgeon or other user can open the linking member 216 to facilitate advancing the second extension 228 through the linking member 216. For example and without limitation, the linking member can have a clasp that is selectively openable so that the second extension 228 or another extension can be advanced through an opening of the linking member 216 or otherwise coupled with the linking member 216. In some embodiments, the linking member 216 can have a deflectable arm and/or a clasp, for example and without limitation similar to that of a carabineer. In other embodiments, the linking member 216 can comprise a post such as a t-shaped post that can be received within a slot in the second extension 228 (for example, a lengthwise slot that extends along all or a portion of the length of the second extension) that can provide a selectively removable rigid connection between the first and second extensions.

Window in Extension Member:

The first extension 208, the second extension 228, or any other extension of any embodiments of the treatment system 200 or other treatment systems disclosed herein can have at least one window or slot 240 extending through a side thereof. With reference to FIG. 2L, the at least one slot 240 can be configured to receive a connecting element 244 that can be advanced through the slots 240 of the first and second extensions 208, 228 (and/or any other extensions) toward the first screw 210 and the second screw 230 and which can extend between and be used to connect the first screw 210 to the second screw 230 in an operable state.

Connecting Element:

As mentioned, any systems disclosed herein can further include a rigid connecting element 244 that can be coupled with the head 210a of the first screw 210 and the head 230a of the second screw 230. The first extension 208 and the second extension 228 can be configured to operably receive the connecting element 244 in the slots or windows 240 of the first and second extensions 208 thereof so that the connecting element 244 can be directed and advanced along the length of the first and second extensions 208, 228 toward the head 210a of the first screw 210 and the head 230a of the second screw 230. In an operable state, the connecting element 244 can extend between the first screw 210 and the second screw 230 when the first and second screws 210, 230 are implanted in a first and a second vertebra 211, 213, respectively. Other details regarding coupling of the connecting element 244 with the first and or second screws 210, 230 are set forth in U.S. Pat. No. 8,721,691, which details are incorporated by reference herein as if fully set forth herein such that any of the features, components, methods, or other details regarding any of the embodiments disclosed in U.S. Pat. No. 8,721,691 can be combined with any of the features, components, methods, or other details of any of the embodiments disclosed herein to form additional embodiments, all of which are part of the present disclosure. Any of the embodiments disclosed herein can be configured to include any of the details, components, methods or otherwise disclosed in U.S. Pat. No. 8,721,691, in combination with any of the details, components, or methods disclosed herein as if fully set forth herein.

An alternative embodiment regarding coupling of the connecting element of any embodiment disclosed herein with the first, second, and/or third second screws can be configured as a pendular mechanism to swing the connecting element from outside the skin through a separate skin incision. This pendular mechanism can be configured to then direct the connecting element from the separate skin incision through the heads of the first screw and then the second screw or vice versa in a sequential manner. This pendular method of inserting the connecting element was popularized by the Medtronic Sextant system for MIS fusion as discussed above. Any of the embodiments of the system and/or method of using the system can be configured for use with the pendular mechanism and can have any of the features of the Medtronic Sextant system for MIS fusion or similar systems or improved versions thereof.

In some embodiments, the screw head 210a of the first screw 210 can have a channel, recess, or other feature formed in the screw head 210a of the first screw 210 that is configured to receive the connecting element 244 and the screw head 230a of the second screw 230 can have a channel, recess, or other feature formed in the screw head 230a of the second screw 230 that is also configured to receive the connecting element 244. The first and second screw heads 210a, 230a can be configured to selectively secure or lock the connecting element 244 to the first and second screw heads 210a, 230a so that the connecting element 244 will remain in a fixed position after implantation. The connecting element 244 can, in this configuration, secure the first and second vertebra in the desired relative position.

Third Extension Member:

Any embodiments can further include a third screw (not shown) having a screw head and a third extension configured to be removably coupled with the third screw. The embodiments disclosed herein can further have a third screw having a screw head, a third extension configured to be removably coupled with the third screw, and a handle portion 214 coupled with a proximal end of the body portion of the third extension, the handle portion 214 extending away from the proximal end of the body portion of the third extension at an angle. The third extension can have a length that is approximately the same as a length of the first extension. The third extension can have a recess formed therein at the proximal end of the body portion of the third extension that can be configured to receive a portion of an outside surface of the body portion 229 of the second extension 228 therein in an operable state. Further, any embodiments of the third extension can also have an additional connecting element coupled with the third extension, the connecting element being configured to allow a removable connection between the third extension and the first extension 208 and/or the second extension 228.

Implantation Procedures:

Any of the embodiments disclosed herein can be implanted using any suitable procedures or steps, including any of the procedures or steps described with respect to any other embodiment disclosed herein, including without limitation as described in any of the embodiments disclosed in U.S. Pat. No. 8,721,691, which such procedures or steps are incorporated herein by reference as if fully set forth herein. For example and without limitation, any of the embodiments disclosed herein can be installed or implanted through a skin incision, the method including any combination of the following steps or actions: implanting a first screw 210 having a first extension 208 (also referred to as a first guiding element) coupled therewith through the incision and into a first vertebra, wherein the first extension 208 comprises a body portion extending only to a level of the skin incision or below the level of the skin incision when the first screw 210 is implanted in the first vertebra. The first extension 208 can have a handle portion 214 coupled with and extending away from a proximal end portion of the first extension 208. The method can further include implanting a second screw 230 having a second extension 228 coupled therewith through the incision and into a second vertebra, wherein the second extension 228 can have a body portion 229 extending through the skin incision when the second screw 230 is implanted in the second vertebra. The method can further include grasping the handle portion 214 coupled with the first extension 208 to manipulate the first extension 208, coupling a rigid connector (such as connecting element 244) with the first screw 210 and the second screw 230 to generally fix a position of the first screw 210 relative to the second screw 230. Thereafter, the first and second extensions 208, 228 can be removed from the first and second screws 210, 230 and from the body of the patient.

Some embodiments of the method can further include advancing the second extension 228 through a rigid linking member that can be positioned adjacent to the skin incision, advancing the second extension 228 through a rigid linking member (such as linking member 216) that can be coupled with a portion of the first extension 208, and/or positioning a rigid linking member around the first extension 208 adjacent to a distal end portion of the handle portion 214 where the distal end portion of the handle portion 214 couples with the first extension 208. In this configuration, implanting the second screw 230 having the second extension 228 coupled therewith through the incision and into a second vertebra can include advancing the second screw 230 and the second extension 228 through an opening (such as opening 217) in the linking member 216.

In some embodiments of the methods disclosed herein, the body portion of the first extension 208 can include a recess formed in proximal end portion thereof configured to receive a portion of an outside surface of the second extension 228 therein. Further, the first extension 208 and the second extension 228 can each have at least one window extending through a side thereof. Any of the methods disclosed herein can further include coupling a stabilizing element with the screw head 210a of the first screw 210 and the screw head 230a of the second screw 230.

FIG. 2E shows the first screw 210 implanted in a first vertebra 211. As shown in FIG. 2E and as mentioned above, the device 200 can be sized and configured such that, when the first screw is fully implanted within the first vertebra 211, the first extension 208 will be positioned fully within the incision 206 and, hence, fully within the skin of the patient so that substantially no portion of the first extension 208 extends out of the incision 206 away from the body of the patient. As shown, the handle portion 214 can extend away from the incision 206 so that all, or, in some embodiments, substantially all, of the handle portion 214 is outside of the body during the procedure. The first guidewire 202 can be removed thereafter, or can remain in its previous position for subsequent steps.

Figures 1, 2F:
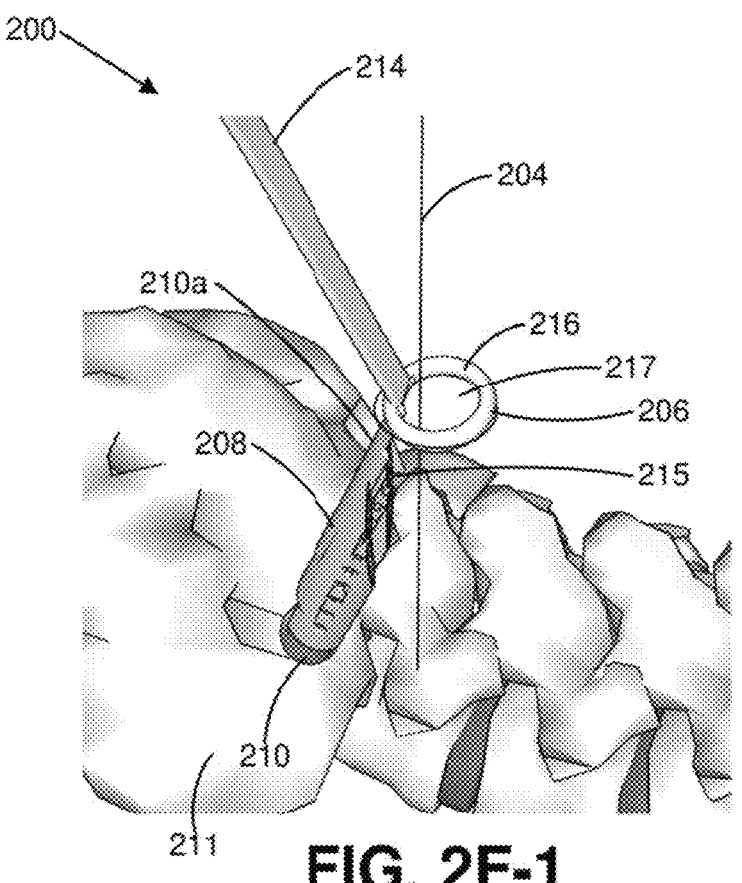
Figures 2, 2F:
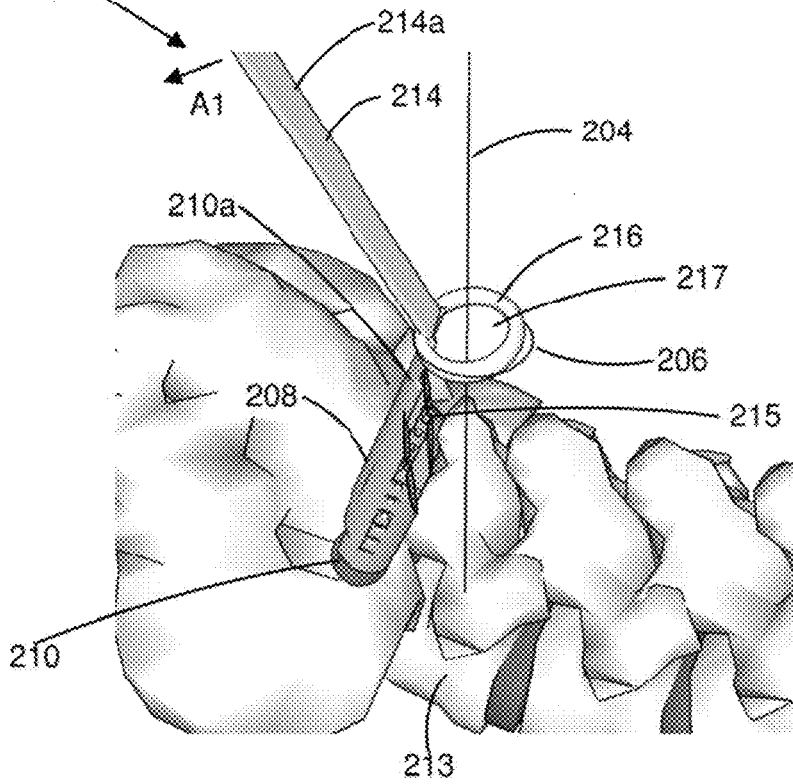

As shown in FIGS. 2F-1 and 2F-2 and as described above, the handle portion 214 can be used to exert forces on and to move or otherwise manipulate the first extension 208 and, consequently, the first vertebra 211 relative to the other vertebrae or otherwise. For example, as shown in FIG. 2F-2, a proximal portion 214a of the handle portion 214 can be forced and/or moved in any direction, including a first direction (represented by A1 in FIG. 2F-2) which can be in a direction away from second vertebrae 213 which would, in some embodiments and when all components of the system 200 are implanted, exert a compressive force on the first vertebra 211 relative to the second vertebra 213 and move the first vertebra 211 closer to the second vertebra 213. In other methods or procedures, the proximal portion 214a of the handle portion 214 can be forced and/or moved in a direction that is toward the second vertebrae 213, so as to, in some embodiments and when all components of the system 200 are implanted, exert a extension or traction force on the first vertebra 211 relative to the second vertebra 213 and move the first vertebra 211 further away from the second vertebra 213. As shown in FIGS. 2F-1 and 2F-2, the proximal end portion 214a of the handle portion 214 has been moved in the first direction A1 away from the second vertebra 213 so that a proximal portion 210a of the first extension 210 is moved in the first direction A1 away from the second vertebra 213.

Figures 1, 2, 2G:
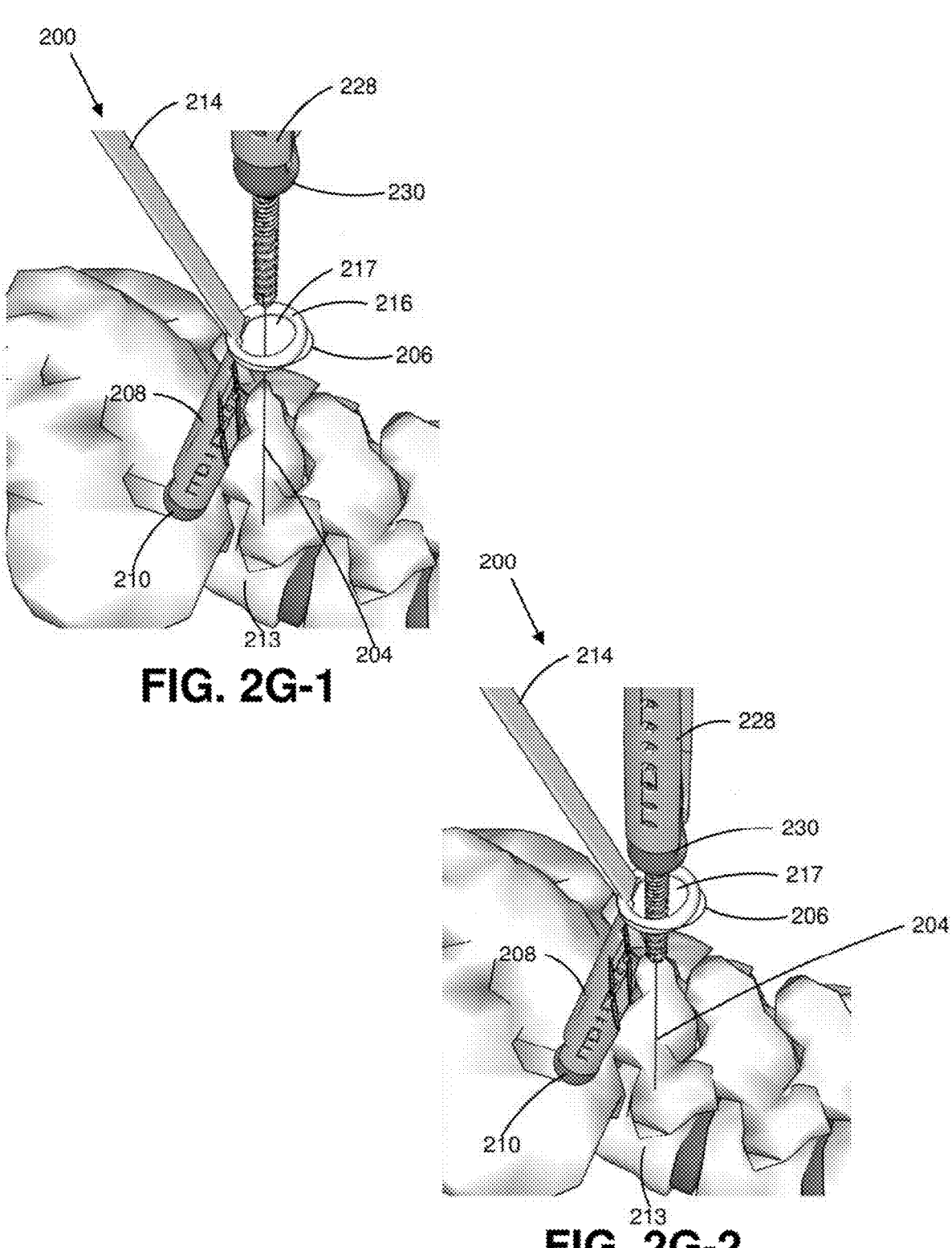
Figures 1, 2, 2H:
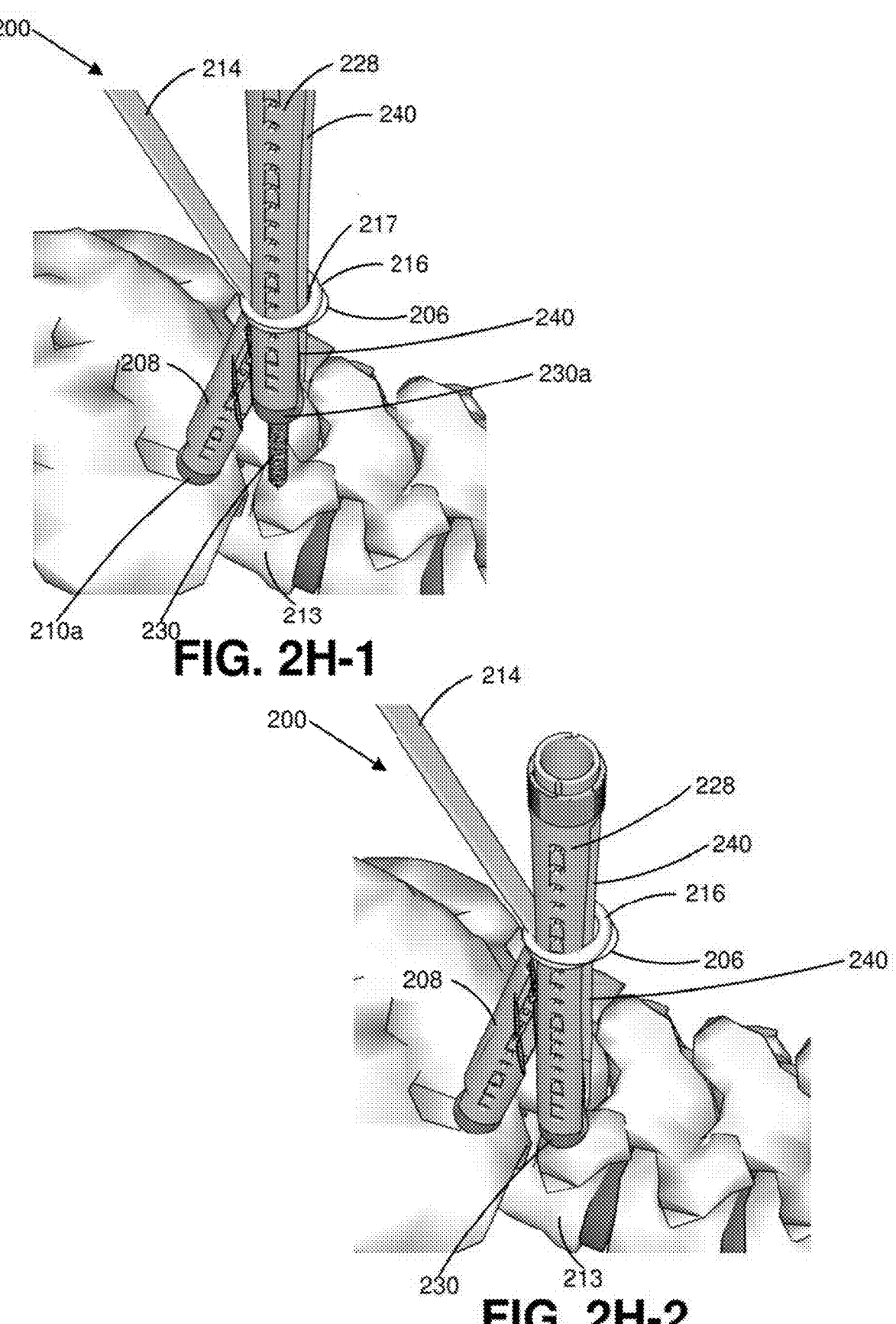
Figures 2I, 2J:
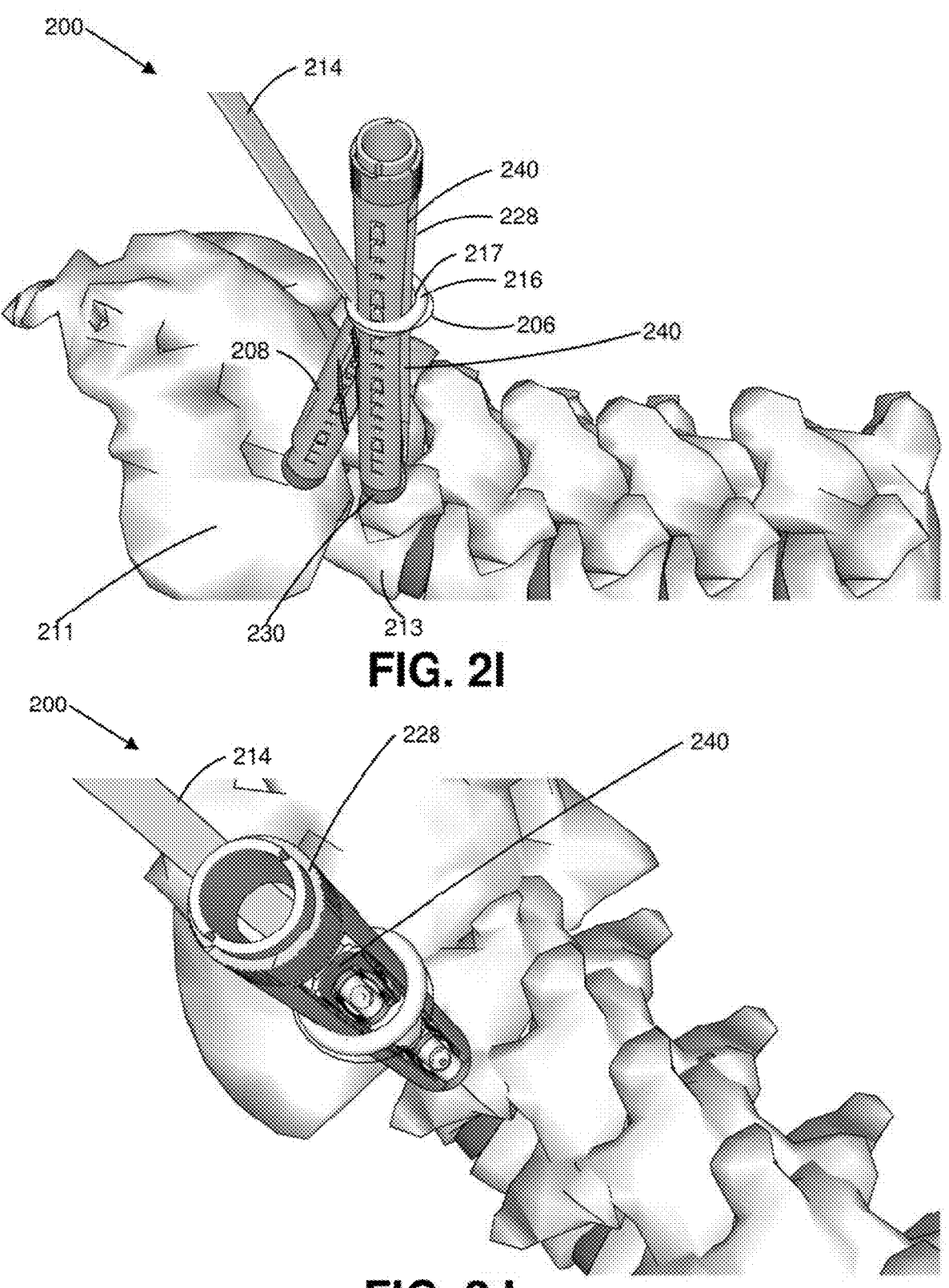
Figure 2K:
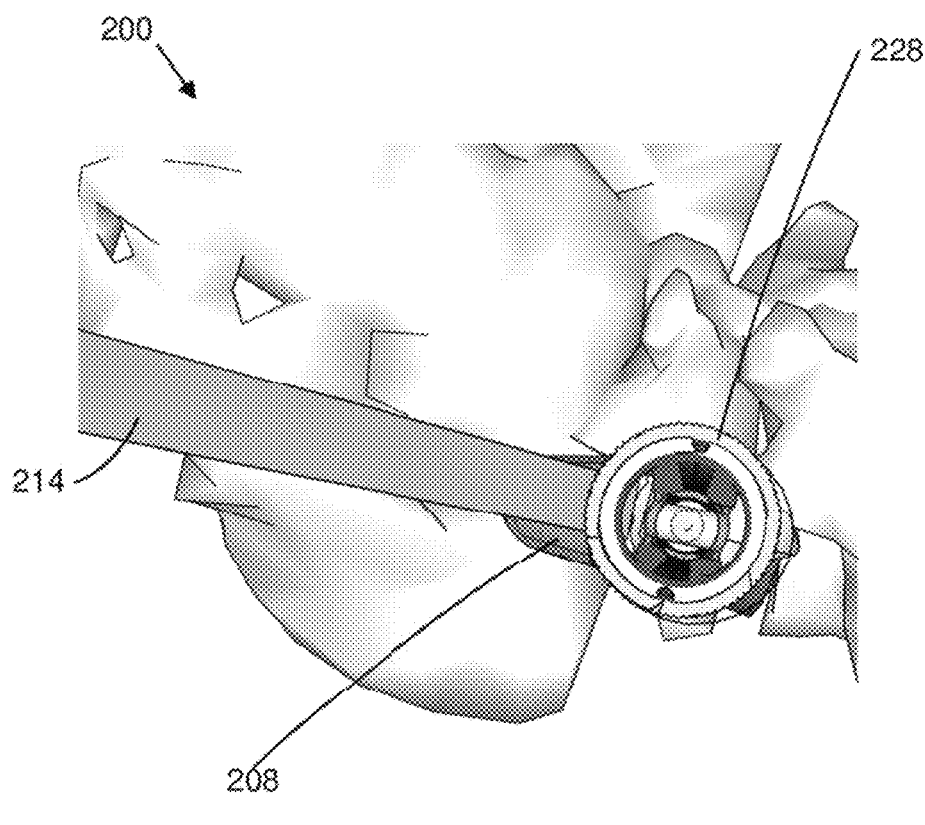
Figure 2L:
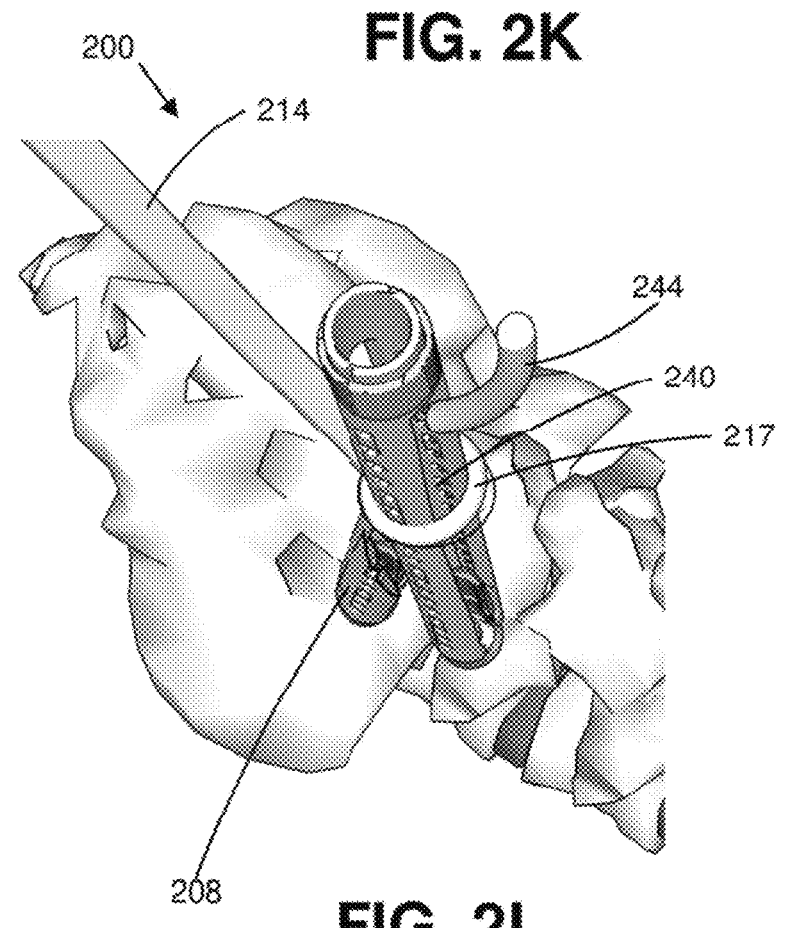
Figure 2M:
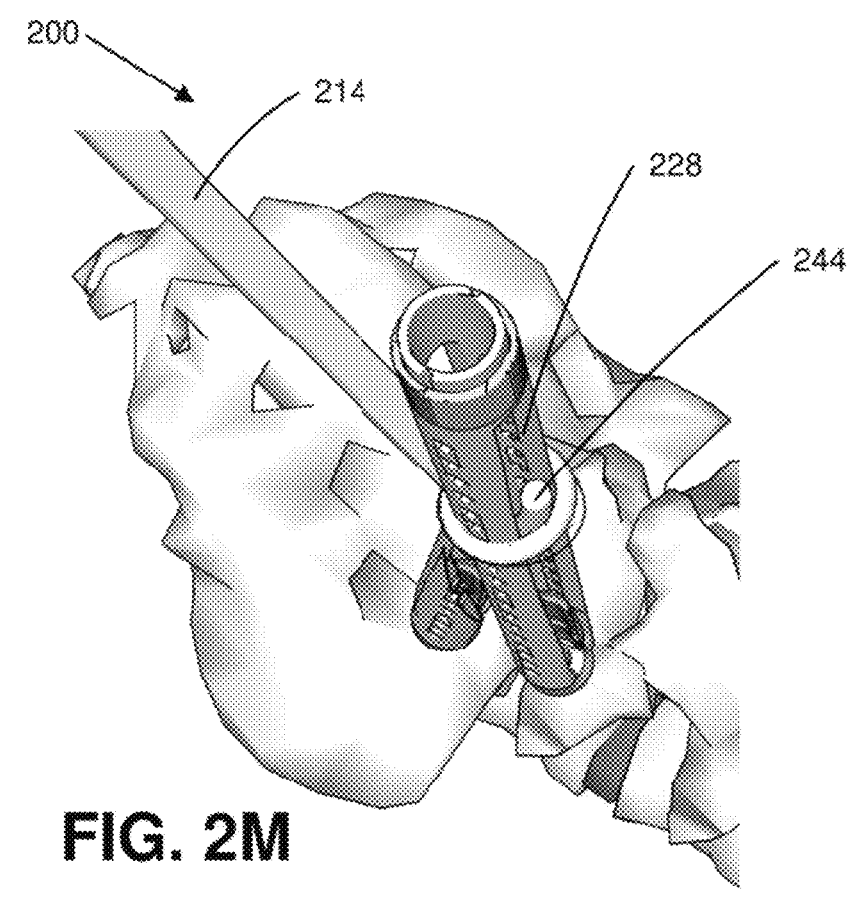
Figure 2N:
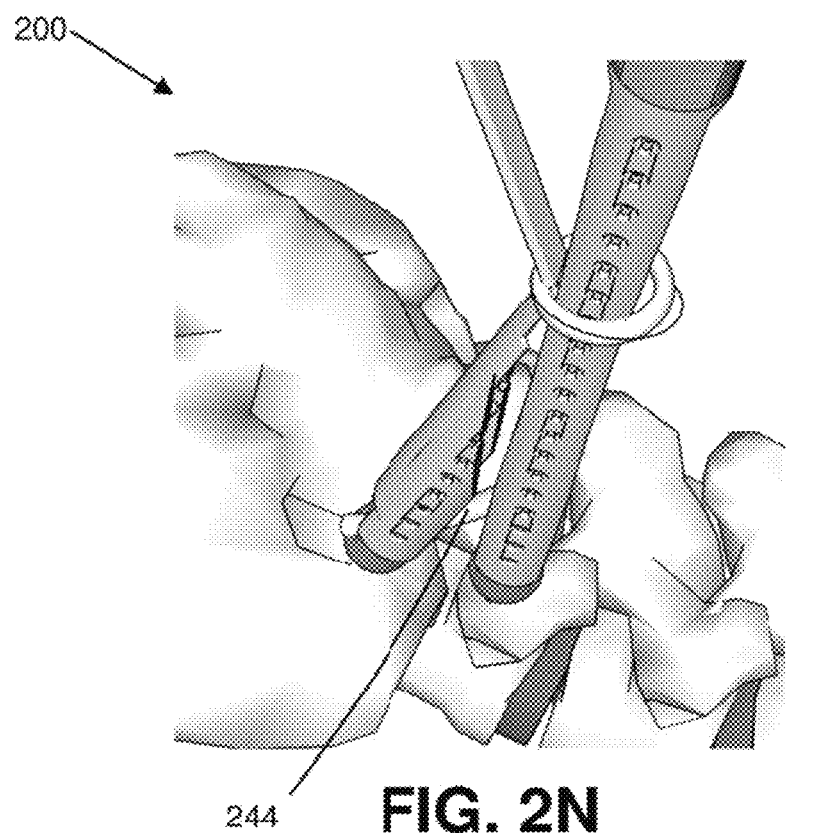
Figures 1, 20:
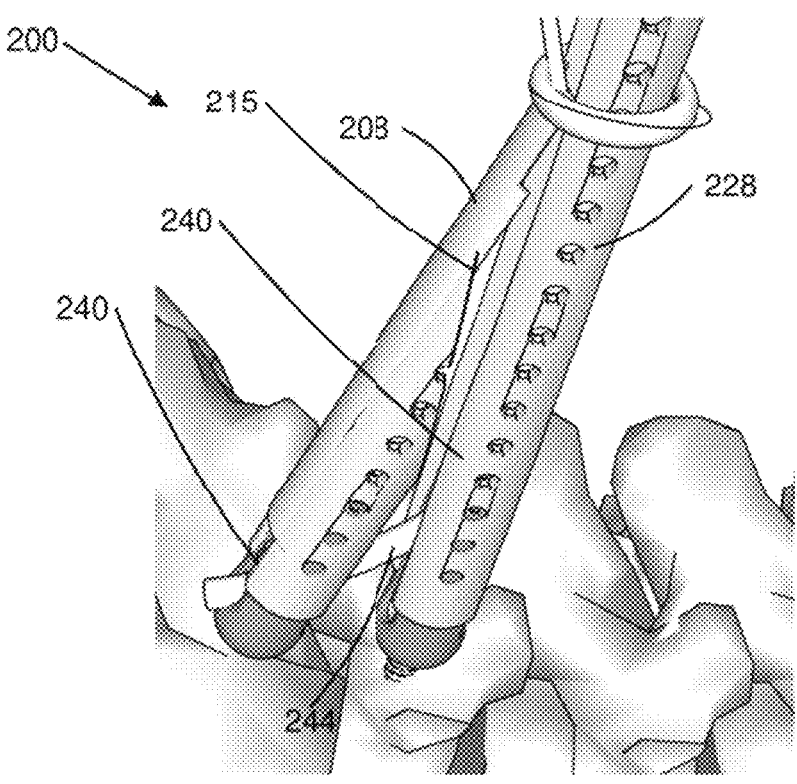
Figures 2, 20:
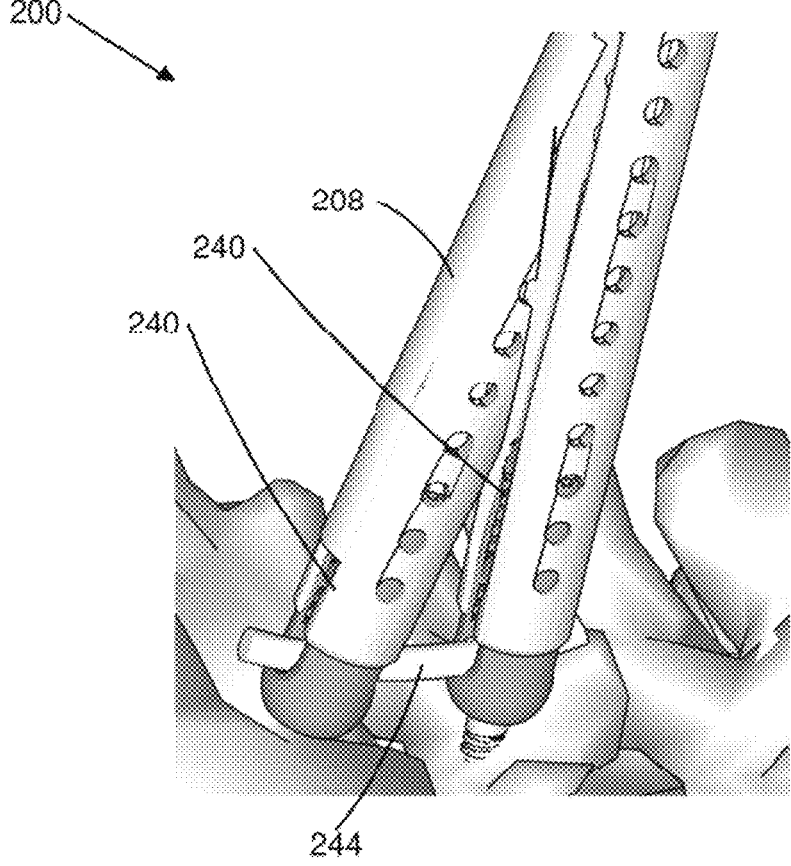
Figure 2P:
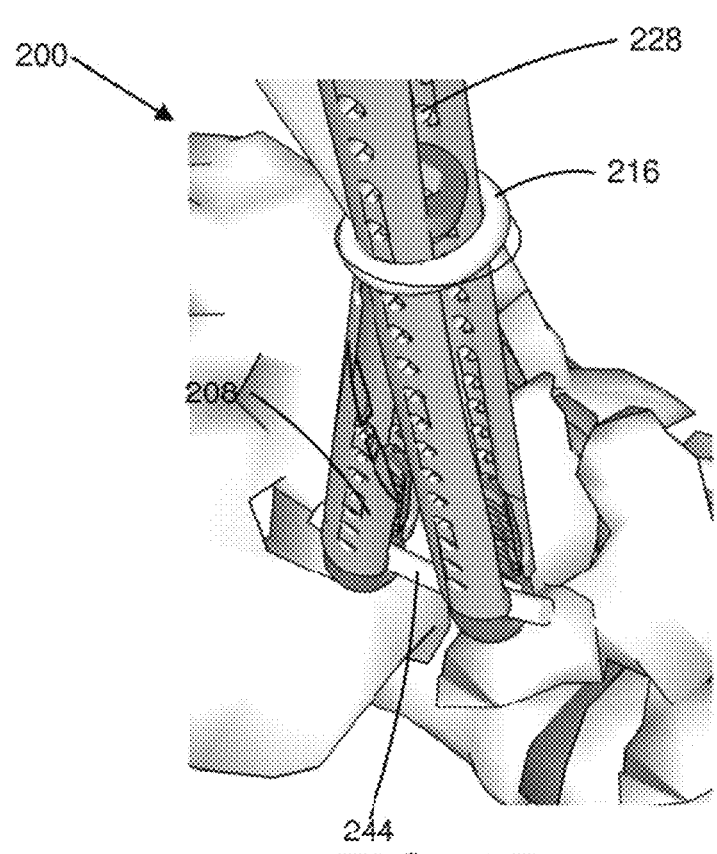
Figure 2Q:
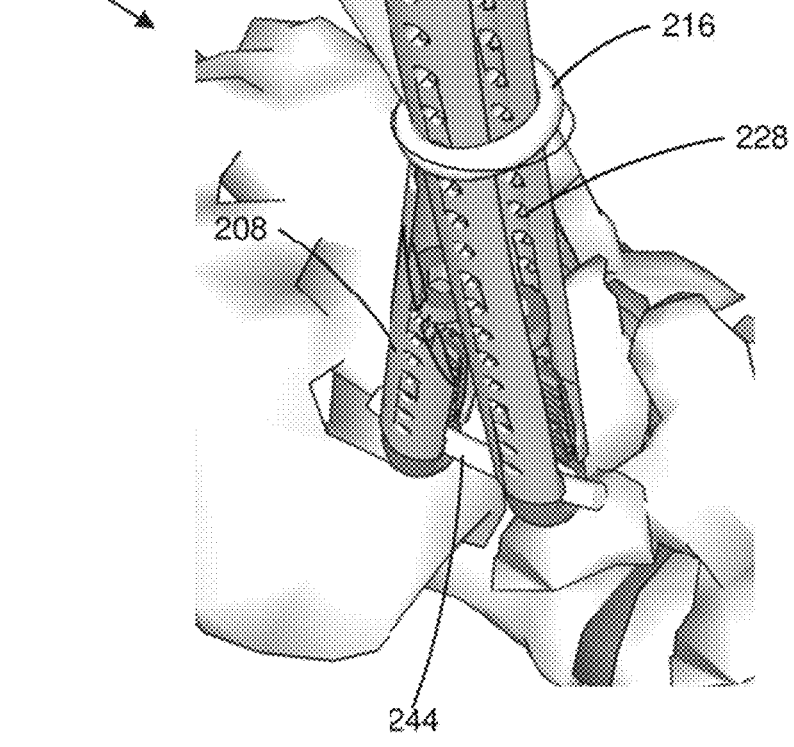

With reference to FIGS. 2G-1 and 2G-2, a second extension 228 that can be removably coupled with a second screw 230 can be then be advanced through the incision 206 over a second guidewire 204. Importantly, the linking member 216 can be implanted and positioned relative to the second guidewire 204 such that the second guidewire 204 extends through an opening or passageway 217 of the linking member 216. In this arrangement, when the second extension 228 is advanced along the second guidewire 204 through the incision 206, the second extension 228 will advance through the opening or passageway 217 of the linking member 216. The second spinal screw 230 can be implanted into the second vertebra 213 in this manner, as shown in FIGS. 2H-1 and 2H-2, and the second guidewire can thereafter be removed, as shown in FIG. 21, or remain in position for subsequent steps. Thereafter, the extensions, screws, and/or vertebra can be manipulated for compression, decompression, or otherwise, using the handle portion 214 and the second extension 228.

Incision:

In any embodiments disclosed herein, the incision can approximately be the diameter of a dime, or from approximately ½ to approximately an inch, or from approximately ½ inch to approximately ¾ of an inch. The system can be configured such that the first screw 210, the second screw, and a third screw are implanted through the skin incision.

Alternative Shapes of Extensions:

In some embodiments, the first extension 208 can have a first flat body and a second flat body (such as in some of the embodiments disclosed in U.S. Pat. No. 8,721,691), wherein the first flat body can be spaced apart from the second flat body so as to create a space between the first and second flat bodies.

Further, with reference to FIGS. 2L-2T, a rigid connecting element (also referred to as a connecting member or a rod) can be advanced through the extensions (such as, for example and without limitation, through the windows of such screws) and the incision and be secured to the first and second screws using any known or suitable techniques and/or components, such as by using set screws as shown in FIGS. 2P-2T. The extensions can thereafter be removed, as shown in FIG. 2T.

In addition to the hybrid systems discussed above, additional systems that combine any of the guiding elements discussed above are also possible. For example, a system for rod delivery can include a mixture of one blade and one or more wires on a single screw. Another system for rod delivery can include one tube or tower on a first screw and one or more wire or blade combinations on the second screw. Various combinations of guiding elements that can be used through a single incision are possible.

Certain aspects of the systems, devices, components and/or methods described above or as illustrated with respect to FIGS. 2A-2T are also encompassed by the following numbered embodiments. These numbered embodiments are considered to be directed to systems, devices, components and/or methods that include but are not limited to the embodiments of FIGS. 2A-2T, and thus these numbered embodiments may encompass other embodiments as described throughout this specification.

1. A system for stabilizing spinal vertebrae through a skin incision, comprising:
a first screw having a first screw head;
a second screw having a second screw head;
a first extension having a body portion that is configured to be removably coupled with the first screw at a distal end of the body portion of the first extension;
a second extension having a body portion that is configured to be removably coupled with the second screw at a distal end of the body portion of the second extension; and
a handle portion coupled with or configured to be coupled with a proximal end of the body portion of the first extension, the handle portion extending away from the proximal end of the body portion of the first extension at an angle;
wherein:
the handle portion is configured to be grasped by a surgeon to enable a surgeon to exert a rotational force on the first extension about at least a centerline axis of the first extension.

2. The system of Embodiment 1, wherein the first extension is sized such that a proximal end of the body portion of the first extension extends to a height just below the skin of a patient when the first screw is implanted in a first vertebra.

3. The system of Embodiment 1, wherein the first extension is sized such that a proximal end of the body portion of the first extension extends to a height just below the skin of a patient, or to a height level with the skin of a patient, when the first screw is implanted in a first vertebra.

4. The system of Embodiment 1, wherein the first extension is sized such that only a proximal end portion of the body portion of the first extension extends through the skin incision when the first screw is implanted in a first vertebra.

5. The system of Embodiment 1, wherein the first extension is sized such that no portion of the body portion of the first extension extends through the skin incision when the first screw is implanted in a first vertebra.

6. The system of Embodiment 1, wherein the first extension is sized such that the entire body portion of the first extension is positionable below a skin surface of a patient, with only the handle portion extending through the skin incision, when the first screw is implanted in a first vertebra.

7. The system of any of the previous Embodiments, wherein the second extension is sized to extend completely through the skin incision when the second screw is implanted in a second vertebra.

8. The system of any of the previous Embodiments, wherein the system is configured such that the first and second screws are implanted through the same skin incision.

9. The system of any of the previous Embodiments, wherein the system is configured such that the first screw, the second screw, and a third screw are implanted through the same skin incision.

10. The system of any of the previous Embodiments, wherein the handle portion is configured to be grasped by a surgeon to enable a surgeon to manipulate the first extension.

11. The system of any of the previous Embodiments, wherein the handle portion is configured to be grasped by a surgeon to enable a surgeon to exert a rotational force on the first extension about the centerline axis of the first extension.

12. The system of any of the previous Embodiments, wherein the handle portion is removably coupled with the body portion of the first extension.

13. The system of any of the previous Embodiments, wherein the handle portion is removably coupled with the body portion of the first extension, the handle portion having an end portion that is receivable in a notch, groove, or other receptacle formed on a side of the body portion of the first extension.

14. The system of any of the previous Embodiments, wherein the handle portion is non-removably coupled with the body portion of the first extension.

15. The system of any of the previous Embodiments, wherein the handle portion is integrally formed with the body portion of the first extension.

16. The system of any of the previous Embodiments, wherein the first extension has a recess formed therein at the proximal end of the body portion of the first extension that is configured to receive a portion of an outside surface of the body portion of the second extension therein in an operable state.

17. The system of Embodiment 16, wherein the recess has a shape that generally complements a shape of an outside surface of the body portion of the second extension.

18. The system of any of the previous Embodiments, wherein:

the first extension has a recess formed therein at the proximal end of the body portion of the first extension, the recess being configured to receive a portion of an outside surface of the body portion of the second extension therein in an operable state; and the handle portion extends away from the body portion of the first extension in a direction that is generally away from the recess.

19. The system of any of the previous Embodiments, wherein:

the first extension has a recess formed therein at the proximal end of the body portion of the first extension, the recess being configured to receive a portion of an outside surface of the body portion of the second extension therein in an operable state;

the handle portion is coupled with a first side of the body portion of the first extension; and the recess is formed on a second side of the body portion of the first extension that is opposite to the first side of the body portion of the first extension.

20. The system of any of the previous Embodiments, wherein the handle portion attaches to the body portion of the first extension adjacent to a recess formed in the body portion of the first extension.

21. The system of any of the previous Embodiments, wherein the body portion of the first extension has an adjustable length.

22. The system of any of the previous Embodiments, wherein each of the first and second extensions has a fixed length.

23. The system of any of the previous Embodiments, wherein the first and second body portions are cylindrically shaped.

24. The system of any of the previous Embodiments, wherein the first extension comprises a first flat body and a second flat body, wherein the first flat body is spaced apart from the second flat body so as to create a space between the first and second flat bodies.

25. The system of any of the previous Embodiments, further comprising a rigid linking member having an opening therein, the linking member being configured to surround a proximal end of the body portion of the first extension and the body portion of the second extension in an operable state and to couple the first and second extensions together.

26. The system of any of the previous Embodiments, further comprising a rigid linking member having an opening therein configured to surround a proximal end of the body portion of the first extension and the body portion of the second extension in an operable state, the linking member configured to provide a loose connection between the first and second extensions.

27. The system of either one of Embodiments 25-26, wherein the linking member is selectively openable.

28. The system of any of the previous Embodiments, further comprising:

a rigid connecting element;

a first receiving element coupled with the first screw head; and a second receiving element coupled with the second screw head;

wherein the first and second receiving elements are configured to operably receive the connecting element that, in an operable state, extends between the first and second receiving elements when the first and second screws are implanted in a first and a second vertebra, respectively.

29. The system of any of the previous Embodiments, wherein the first screw is configured to be implanted in a first vertebra and the second screw is configured to be implanted into a second vertebra.

30. The system of any of the previous Embodiments, wherein the first screw with the first extension and the second screw with the second extension are configured to be delivered into the first and second vertebra, respectively, through the skin incision, which is a minimally invasive skin incision.

31. The system of any of the previous Embodiments, comprising at least one handle portion coupled with the body portion of the second extension.

32. The system of any of the previous Embodiments, comprising at least one handle portion coupled with the body portion of the second extension.

33. The system of any of the previous Embodiments, further comprising a third screw having a screw head and a third extension configured to be removably coupled with the third screw.

34. The system of any of the previous Embodiments, further comprising:

a third screw having a screw head;

a third extension configured to be removably coupled with the third screw; and a handle portion coupled with a proximal end of the body portion of the third extension, the handle portion extending away from the proximal end of the body portion of the third extension at an angle.

35. The system of Embodiment 34, wherein the third extension has a length that is approximately the same as a length of the first extension.

36. The system of any of Embodiments 34-35, wherein the third extension has a recess formed therein at the proximal end of the body portion of the third extension that is configured to receive a portion of an outside surface of the body portion of the second extension therein in an operable state.

37. The system of any of the previous Embodiments, wherein the first extension has at least one window extending through a side of the body portion thereof, the at least one window configured to receive a connecting element that is configured to extend between the first and second screws in an operable state.

38. The system of any of the previous Embodiments, wherein the first extension is shorter than the second extension.

39. The system of any of the previous Embodiments, wherein the second extension has at least one window extending through a side of the body portion thereof, the at least one window of the second extension configured to receive a connecting element that is configured to extend between the first and second screws in an operable state.

40. A method of performing spinal stabilization through a skin incision, the method comprising:

implanting a first screw having a first guiding element coupled therewith through the incision and into a first vertebra, wherein the first guiding element comprises a body portion extending only to a level of the skin incision or below the level of the skin incision when the first screw is implanted in the first vertebra, wherein a handle portion is coupled with and extends away from a proximal end portion of the first guiding element either before or after the first screw is implanted in the first vertebra;

implanting a second screw having a second guiding element coupled therewith through the incision and into a second vertebra, wherein the second guiding element comprises a body portion extending through the skin incision when the second screw is implanted in the second vertebra;

grasping the handle portion coupled with the first guiding element to manipulate the first guiding element;

coupling a rigid connector with the first and second screws to generally fix a position of the first screw relative to the second screw; and removing the first and second guiding elements from the first and second screws, respectively.

41. The method of Embodiment 40, further comprising advancing the second guiding element through a rigid linking member that is positioned adjacent to the skin incision.

42. The method of Embodiment 40, further comprising advancing the second guiding element through a rigid linking member that also surrounds a portion of the first guiding element.

43. The method of Embodiment 40, further comprising positioning a rigid linking member around the first guiding element adjacent to a distal end portion of the handle portion, wherein implanting the second screw having the second guiding element coupled therewith through the incision and into a second vertebra comprises advancing the second screw and the second guiding element through an opening in the linking member.

44. The method of any one of Embodiments 40-43, wherein the linking member is a selectively openable linking member.

45. The method of Embodiment 44, wherein the linking member comprises a carabineer or is otherwise configured to be selectively openable.

46. The method of any one of Embodiments 40-45, wherein a distal portion of the handle portion extends through the skin incision to couple with the first guiding element when the first screw is implanted in the first vertebra.

47. The method of any one of Embodiments 40-46, wherein the body portion of the first guiding element comprises a recess formed in proximal end portion thereof configured to receive a portion of an outside surface of the second guiding element therein.

48. The method of any one of Embodiments 40-47, wherein the first guiding element has at least one window extending through a side of the first guiding element.

49. The method of Embodiment 48, wherein the second guiding element has at least one window extending through a side of the second guiding element.

50. The method of any one of Embodiments 40-49, further comprising coupling a stabilizing element a head portion of each of the first and second screws.

51. A guiding assembly for use in spinal surgery, comprising:

a guiding element comprising an elongate body portion, a distal end of the elongate body portion configured to be removably coupled with a screw and a proximal end of the body portion configured to be positioned at or below a level of a patient's skin; and a handle portion coupled with or configured to be coupled with a proximal end of the body portion, the handle portion extending away from the proximal end of the body portion of at an angle;

wherein the guiding element has a recess formed therein at the proximal end of the body portion that is configured to receive a portion of an outside surface of another guiding element; and wherein the handle portion extends away from the proximal end of the body portion in a direction away from the recess.

Figure 3A:
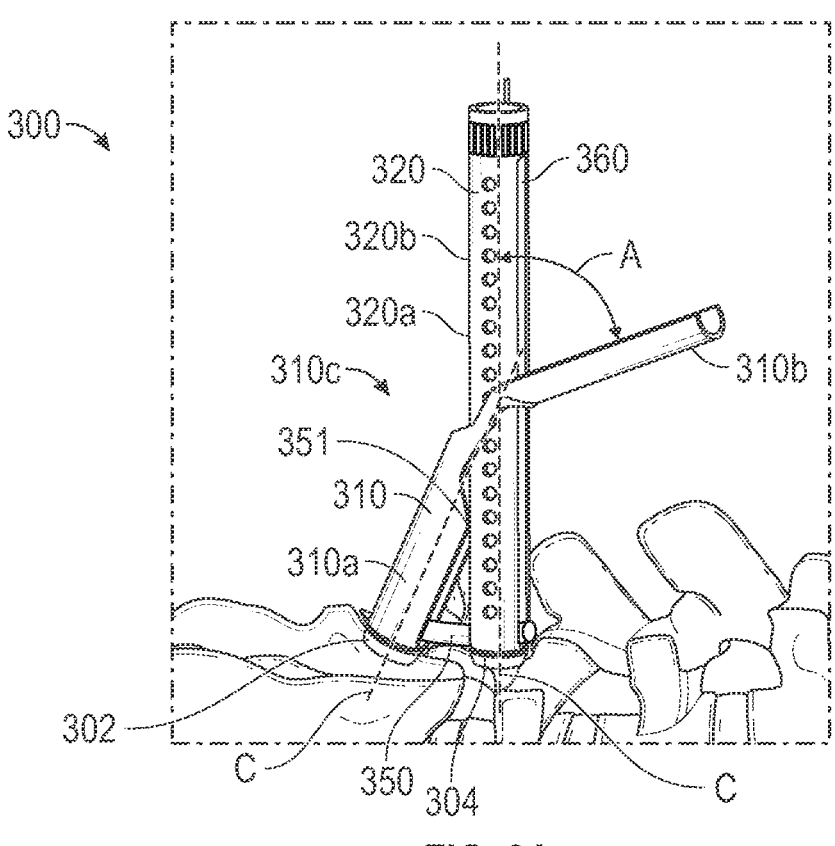
FIGS. 3A-3O illustrate another embodiment of a method and a system for stabilizing spinal vertebrae comprising spinal screws.
Figure 3B:
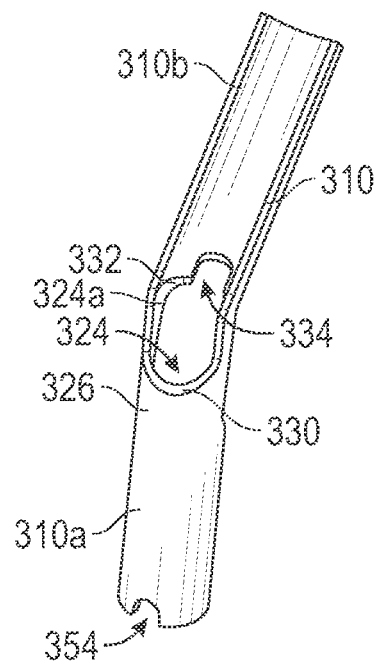
Figure 3C:
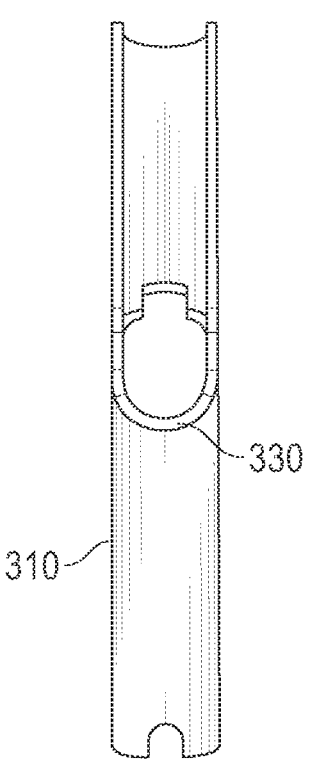
Figure 3D:
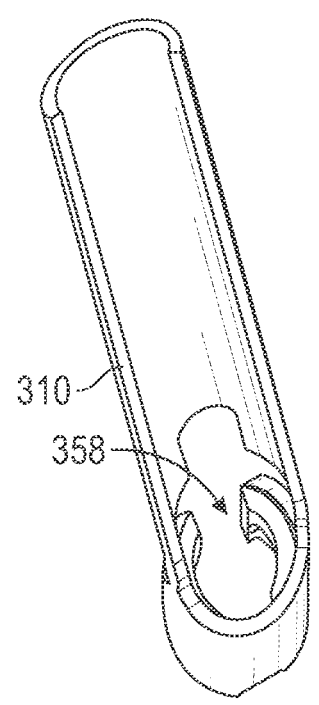
Figure 3E:
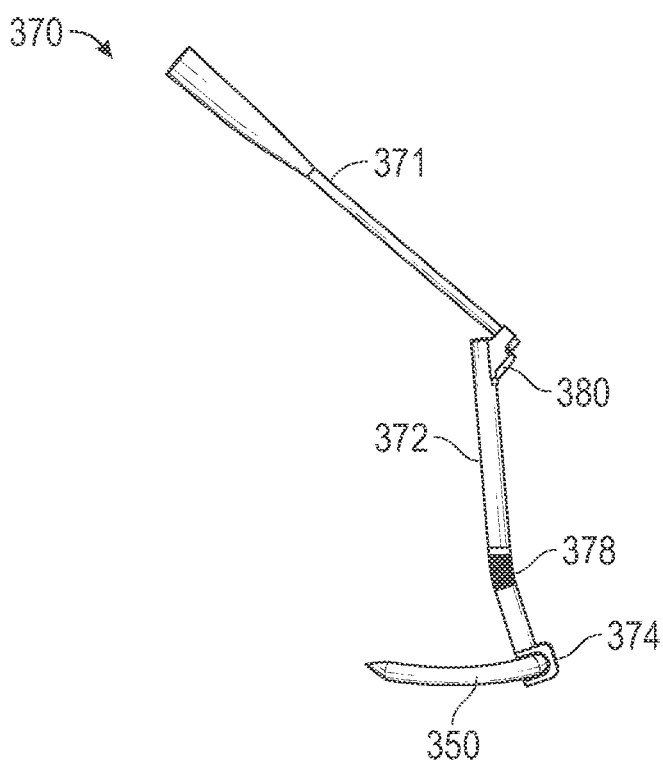
Figure 3F:
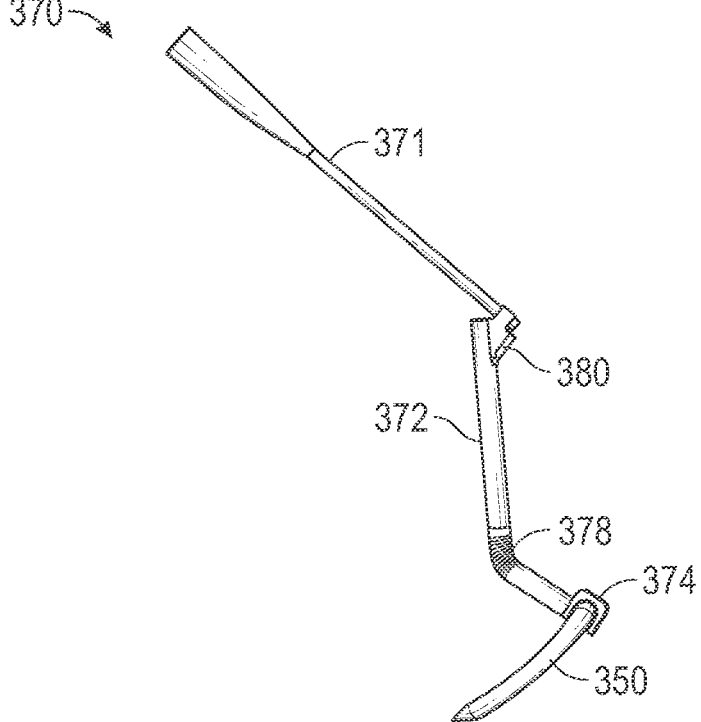
Figure 3G:
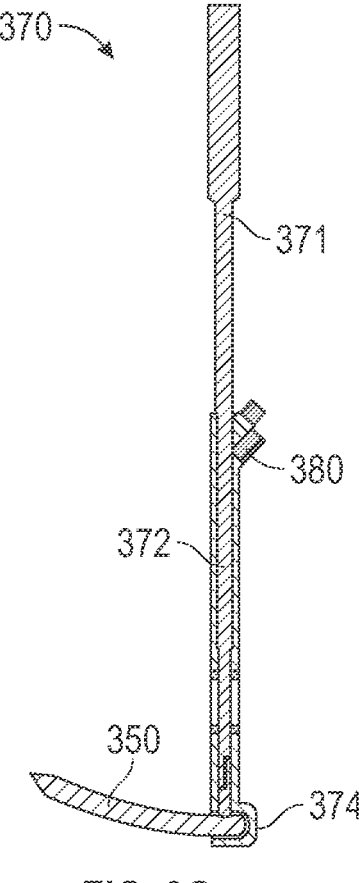
Figure 3H:
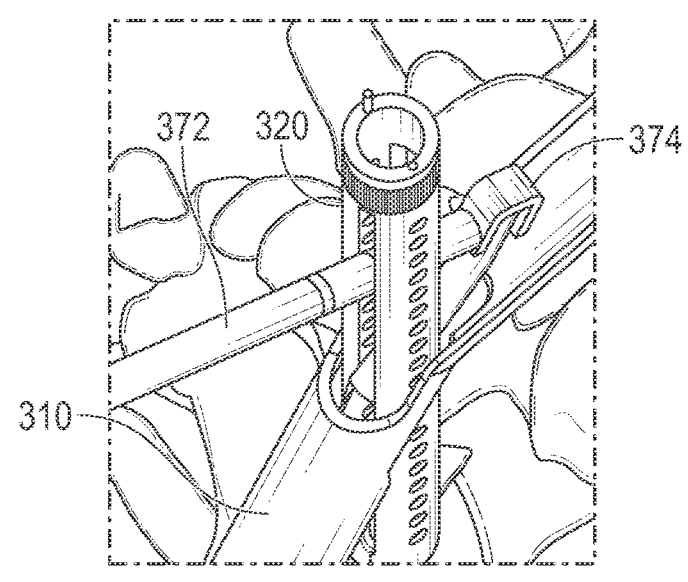
Figure 3I:
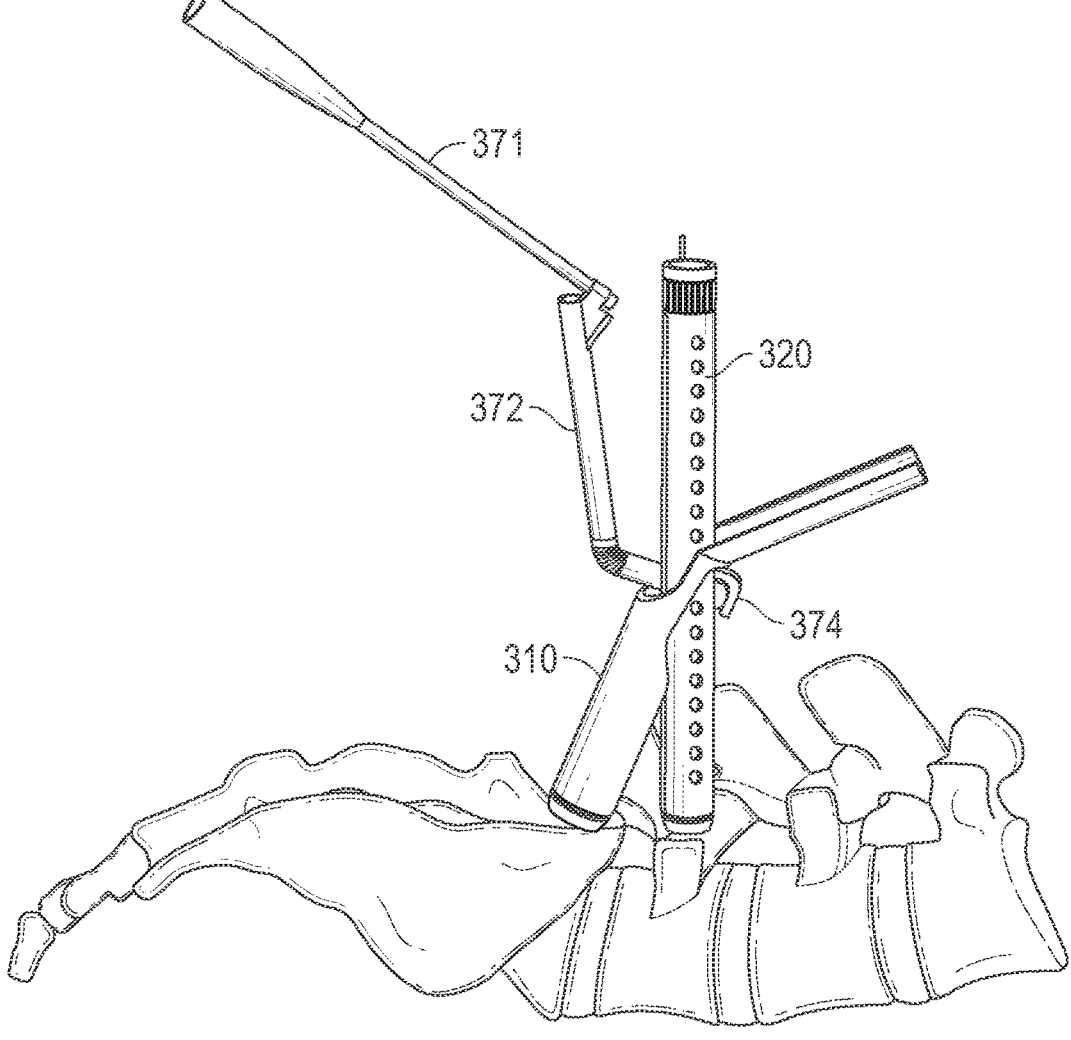
Figure 3J:
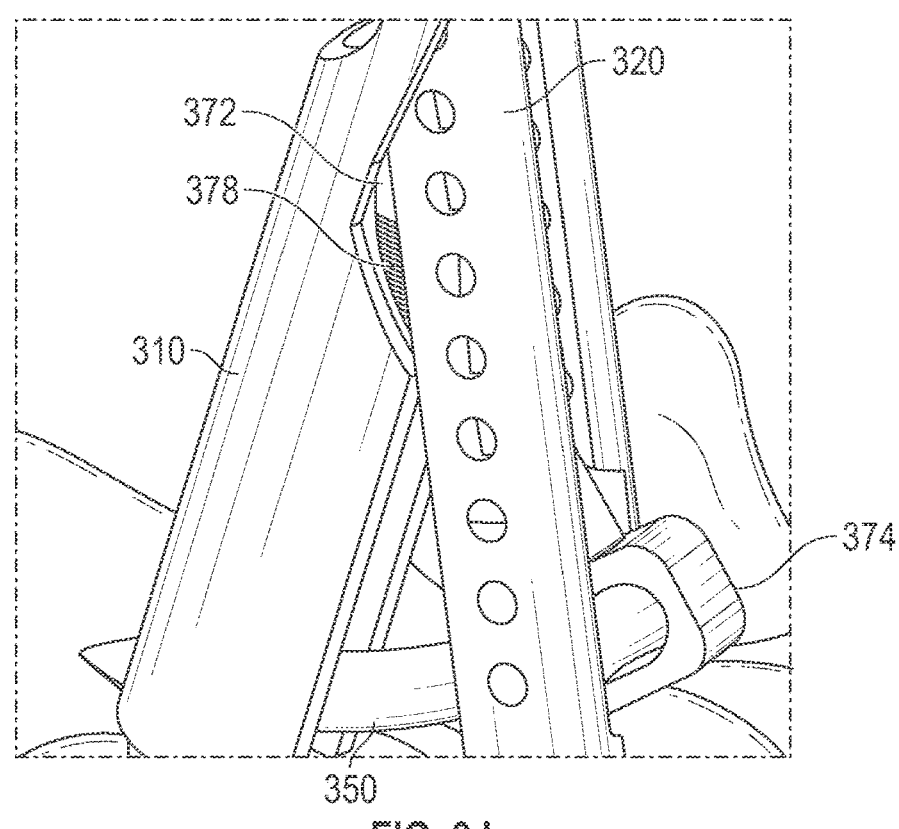
Figure 3K:
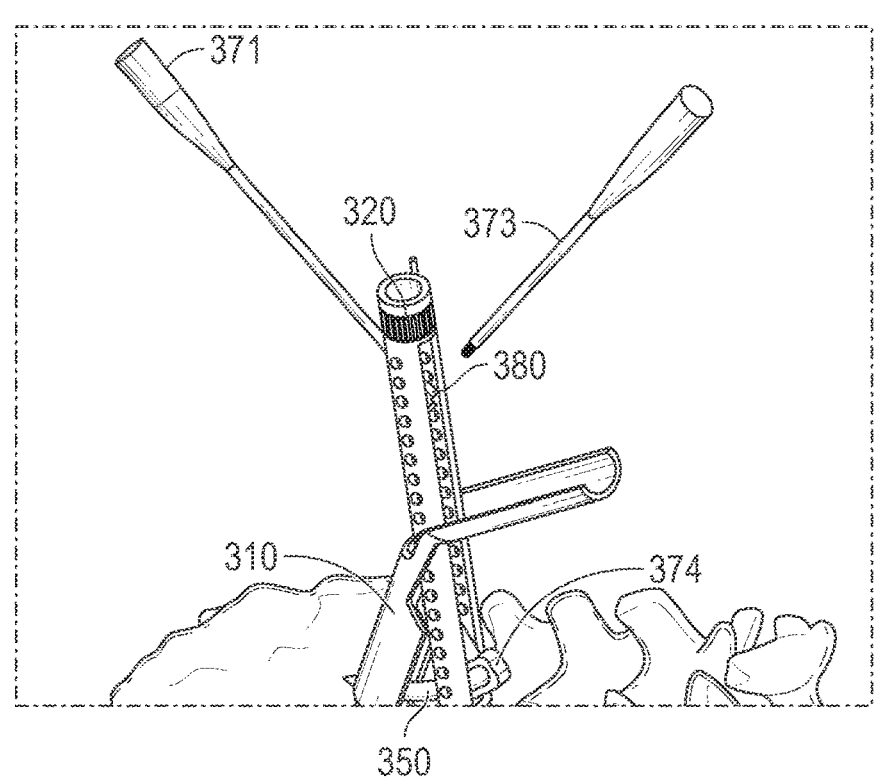
Figures 3L, 3M:
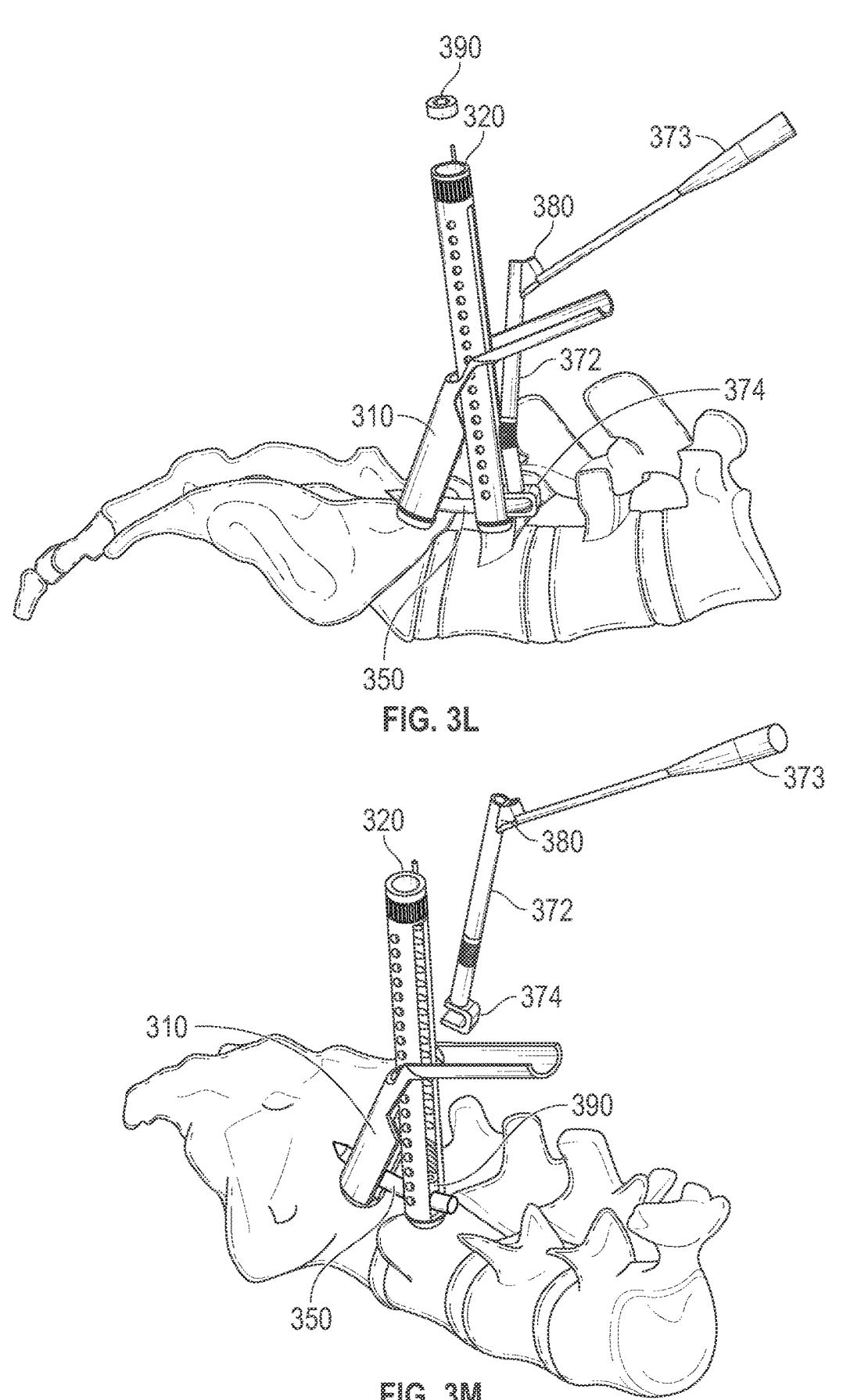
Figure 3N:
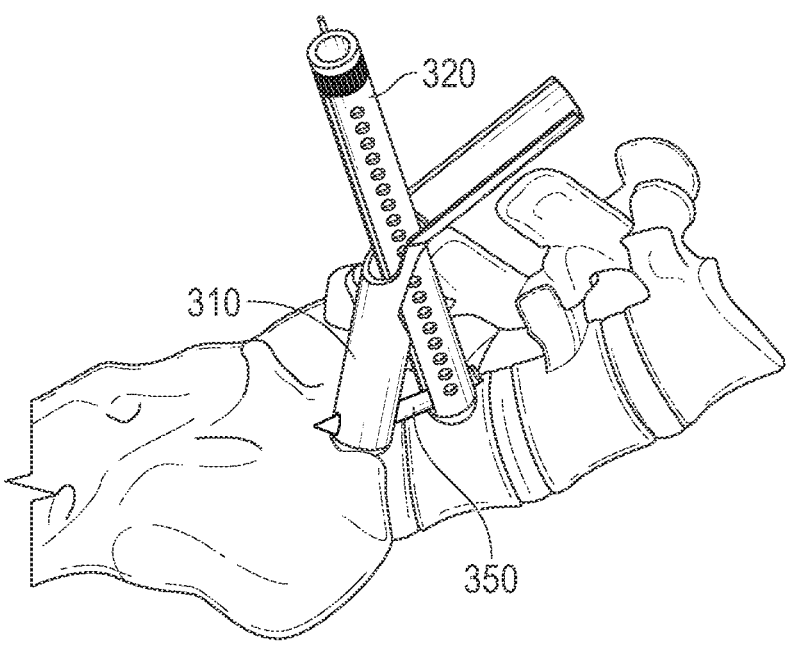
Figure 3O:
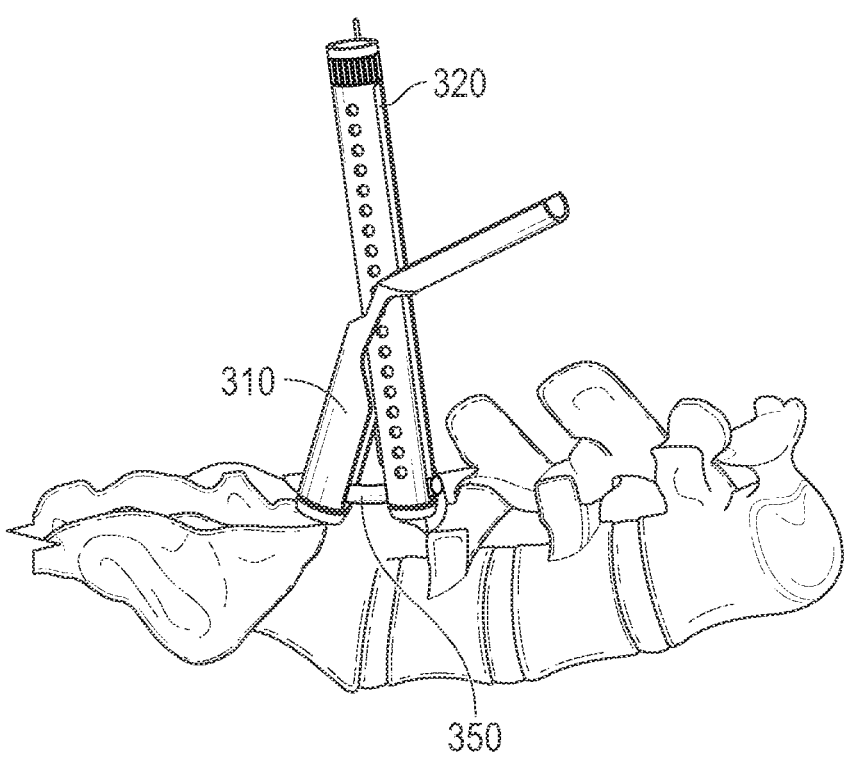

Systems, Devices and Methods of FIGS. 3A-3O

Additional embodiments of a system (e.g., system 300) that can be used for stabilizing or treating spinal vertebrae through a skin incision S are disclosed below. In any embodiments disclosed herein, any components, features, or other details of the system 300 can have any of the components, features, or other details of any other system embodiments disclosed herein or be used according to any of the steps of any other method embodiments disclosed herein, including without limitation any of the embodiments of the system 200 or methods of use thereof described above, in any combination with any of the components, features, or details of the system 300 or methods of use disclosed below. Similarly, any components, features, steps, or other details of any of the other system or method embodiments disclosed herein can have any of the components, features, steps, or other details of any embodiments of the system 300 or methods of use thereof disclosed herein in any combination with any of the components, features, or details of the system.

Some embodiments of the system 300 for stabilizing spinal vertebrae through a skin incision S can include a first screw 302 having a first screw head, a second screw 304 having a second screw head, a first extension 310 (also referred to herein as a first tower) having a distal portion 310*a* and a proximal portion 310*b*, the first extension 310 being configured to be removably coupled with the first screw 302 at a distal end of the first extension 310, and a second extension 320 (also referred to herein as a second tower) having at least one proximal portion 320*b*, the second extension 320 configured to be removably coupled with the second screw 304 at a distal end of the second extension 320. In any embodiments disclosed herein, the extension can be referred to as an extension, a guiding element, a tower, or using other similar terms.

In some embodiments, the first extension 310 can have a two or more proximal portions 310*b* extending away from the distal portion 310*a* of the first extension 310 at a variety of angles. In some embodiments, the first extension 310 can removably couple with the first screw 302 such that, when the first extension 310 is coupled with the first screw 302, an axial centerline C of the distal portion 310*a* of the first extension 310 is approximately collinear with an axial centerline C of the first screw 302. Further, the second extension 320 can removably couple with the second screw 304 such that, when the second extension 320 is coupled with the second screw 304, an axial centerline C of the distal portion 310*a* of the second extension 320 is approximately collinear with an axial centerline C of the second screw 304. In some embodiments, the first extension 310 can be shorter than the second extension 320, or longer than the second extension 320, or have approximately the same length as the second extension 320.

In some embodiments, the angle between the proximal portion 310*b* and distal portion 310*a* can be adjustable or the angle between the proximal portion 320*b* and distal portion 320*a* can be adjustable. A common mechanism for adjustability is a gear or ratchet mechanism. In this way, the proximal portion 310*b* or 320*b* can be angled away from the centerline of the distal portion of the respective screw. By adjusting the angle, there may be more room to place the rod and locking caps. Also, by adjusting the angle, it may be easier for a surgeon to grip both proximal portions of the towers in order to squeeze the two proximal portions of the two screws in order to compress the heads of screws when locking the caps onto the rod connecting the screw heads. In another embodiment, proximal portions 310*b* and 320*b* can be detachable from the distal portions 310*a* and 320*a*. In this manner, proximal portions with different angles in relation to centerline of the respective distal portions can be switched as needed and reconnected to the distal portions of the extensions.

Any embodiments of the system 300 disclosed herein can be configured such that the first screw 302 and the second screw 304 are implanted through the same skin incision S. Additionally, any embodiments of the system 300 can be configured such that the first screw 302, the second screw 304, and a third screw can be implanted through the same skin incision S.

In some embodiments, the proximal portion 310*b* of the first extension 310 can extend at an angle away from the axial centerline C of the distal portion 310*a* of the first extension 310 such that the proximal portion 310*b* of the first extension 310 is not approximately collinear with the distal portion 310*a* of the first extension 310. Further, the proximal portion 310*b* of the first extension 310 can be configured such that, in an operable state, the proximal portion 310*b* of the first extension 310 also can extend at an angle away from the axial centerline C of the distal portion of the second extension 320 so that the proximal portion 310*b* of the first extension 310 forms an acute angle A relative to the distal portion of the second extension 320, as shown in FIG. 3A. In some embodiments, the angle A can be 50° (or approximately) 50°, or from 40° (or approximately) 40° or less to 70° (or approximately) 70° or more.

In some embodiments, the first extension 310 can be sized and configured such that, in an operable state, the proximal portion 310*b* of the first extension 310 can extend away from the skin incision S toward the surgeon. In some embodiments, the distal portion 310*a* of the first extension 310 can extend away from the first screw 302 to a height just below the skin incision S, or to a height level with the skin of a patient, when the first screw 302 is fully implanted in a first vertebra. Further, the proximal portion 310*b* of the first extension 310 can be configured to be grasped by a surgeon to enable a surgeon to exert a rotational force on the first extension 310 about at least the axial centerline C of the distal portion 310*a* of the first extension 310 and/or a torque force on the first extension 310 so as to cause the first extension 310 to rotate about an axis that is perpendicular to an axial centerline C of the distal portion 310*a* of the first extension 310. In some embodiments, the first extension 310 can be sized such that only the proximal portion 310*b* of the first extension 310 is outside of the skin incision S when the first screw 302 is implanted in a first vertebra. In any embodiments, the second extension 320 can be sized to extend completely through the skin incision S when the second screw 304 is implanted in a second vertebra.

The proximal portion 310*b* of the first extension 310 can have a length that is approximately the same as a length of the distal portion 310*a* of the first extension 310, or can have a length that is at least 80% or less of a length of the distal portion 310*a* of the first extension 310. In some embodiments, the proximal portion 310*b* of the first extension 310 can be removably coupled with the distal portion 310*a* of the first extension 310. In other embodiments, the proximal portion 310*b* of the first extension 310 can be non-removably coupled with the distal portion 310*a* of the first extension 310. For example and without limitation, the proximal portion 310*b* of the first extension 310 can be integrally formed with the body portion of the first extension 310. In some embodiments, the proximal portion of the first extension 310*b* or second extension 320*b* can be coupled with the distal portion of the respective first or second extension 310*a* or 320*b* through an adjustable coupling that allows for adjustable angle between the proximal or distal portions of the respective extension. An example of such a coupling would be a hinge.

With reference to FIGS. 3A-3B, at least the distal portion 310*a*, the proximal portion 310*b* of the first extension 310, and/or the second extension 320 can have a tubular or half-tubular shape. Additionally, the first extension 310 can have a cutout 324 formed through a wall portion 326 of the first extension 310, the cutout 324 being configured to receive a portion of an outside surface 320*a* of the second extension 320 therein in an operable state, as shown in FIG. 3A, for example. In some embodiments, the cutout 324 can extend at least through a proximal end 310*c* of the distal portion 310*a* of the first extension 310. The cutout 324 can extend entirely through the first extension 310 such that, in an operable state, the second extension 320 and the screw coupled with the extension 320 can pass entirely through the cutout 324.

In some embodiments, the cutout 324 can extend entirely through the first extension 310 such that, in an operable state, the second extension 320 can pass entirely through the cutout 324 and such that the wall portion 326 of the first extension 310 completely and continuously surrounds an outside surface 320a of a portion of the second extension 320. Further, some embodiments of the cutout 324 can be shaped such that a distal edge 330 of the cutout 324 is configured to contact an outside surface 320a of the second extension 320 in an operable state so that the second extension 320 can be rotated about the distal edge 330 of the cutout 324 relative to the first extension 310. Some embodiments of the cutout 324 can have an ovular shape.

With reference to FIGS. 3B-3D, the cutout 324 can have a notch 334 at a proximal end 324a of the cutout 324, the notch 334 of the cutout 324 configured to permit a passage of at least a portion of a connecting element 350 to pass through the notch 334 during the deployment of the connecting element 350. In some embodiments, the cutout 324 can have a notch 334 at a proximal end thereof, the notch 334 of the cutout 324 configured to permit a passage of at least a portion of a connecting element 350 and a portion of a connecting element implantation device 370 to pass through the notch 334. A width of the notch 334 can be less than a width of an outside surface 320a of the second extension 320 so that the outside surface 320a of the second extension 320 is prevented from extending into the notch 334. A width of the notch 334 can be less than a width of the cutout 324 so that the cutout 324 defines a proximal edge 332 that is configured to contact an outside surface 320a of the second extension 320 so that the second extension 320 can be rotated about the proximal edge relative to the first extension 310 when at least a proximal portion 310b of the first extension 310 is moved toward a proximal portion 320b of the second extension 320. In some embodiments, the cutout 324 can be adjacent to a proximal end of the distal portion 310a of the first extension 310 and a distal end of the proximal portion 310b of the first extension 310. Further, some embodiments of the first extension 310 can have a distal notch 334 formed at a distal end of the first extension 310, the distal notch 334 configured to permit a passage of at least a portion of a connecting element 350 to pass through the distal notch 354 and into the heads of the screws.

In some embodiments, at least the distal portion 310a of the first extension 310 can have an adjustable length. Further, some embodiments of the first extension 310 and the second extension 320 can be cylindrically shaped. Other embodiments can have any other desired cross-sectional shape, including a generally square shape, a triangular cross-sectional shape, on ovular cross-sectional shape, a polygonal cross-sectional shape, or any combination of the foregoing. The proximal portion 310b of the first extension 310 can have a cross-sectional profile that can have a curved shape, as shown in the figures. Further, the proximal portion 310b of the first extension 310 can have a cross-sectional profile that can have a semi-circular tubular shape. In some embodiments, the proximal portion 310b of the first extension 310 can have a cross-sectional profile that is approximately the same as one-half of the distal portion 310a of the first extension 310. In some embodiments, the proximal portion 310b of the first extension 310 can have a planar shape.

As mentioned, any of the embodiments of the system 300 disclosed herein can have a rigid connecting element 350 (that can be implanted using any desired shape and configuration of a connecting element implantation device, such as the embodiment of the connecting element implantation device shown in FIGS. 3E-3F, a first receiving element coupled with the head of the first screw 302, and a second receiving element coupled with the head of the second screw 304. With reference to FIGS. 3L-3M, the first and second receiving elements can be configured to operably receive the connecting element 350 that, in an operable state, can extend between the first and second receiving elements when the first screw 302 and the second screw 304 are implanted in a first and a second vertebra, respectively. The first screw 302 can be configured to be implanted in a first vertebra and the second screw 304 is configured to be implanted into a second vertebra.

In some embodiments, the first extension 310 can have at least one window or slot 358 extending through a side of the body portion thereof, the at least one slot 358 configured to receive a connecting element 350 or configured to permit a passage of a connecting element 350 therethrough, the connecting element 350 being configured to extend between the first screw 302 and the second screw 304 in an operable state. Further, the second extension 320 can have at least one slot or window 360 extending through a side of the body portion of the second extension 320, the at least one slot 360 of the second extension 320 configured to receive a connecting element 350 that is configured to extend between the first screw 302 and the second screw 304 in an operable state.

Some embodiments of methods for treating a spinal defect include implanting the first screw 302 that is coupled with the first extension 310 through the incision into a first vertebra, advancing the second extension 320 that is coupled with the second screw 304 through the cutout 324 formed in the first extension 310 and implanting the second screw 304 into a second vertebra, and moving a proximal end of the proximal portion 310b of the first extension 310 toward a proximal end of the second extension 320 to cause the outside surface 320a of the second extension 320 to contact at least proximal edge 332 of the cutout 324 or a distal edge 351 (shown in FIG. 3A) or other portion of the surface of the cutout 324. In some embodiments, further moving the proximal end of the proximal portion 310b of the first extension 310 toward a proximal end of the second extension 320 can cause the outside surface 320a of the second extension 320 to rotate about at least the distal edge 330 of the cutout 324 and cause the distal end of the first extension 310 to move toward the distal end of the second extension 320, thereby moving the first vertebra toward the second vertebra. In some embodiments, the method can further include coupling a rigid connector 350 with the first screw 302 and the second screw 304 to generally fix a position of the first screw 302 relative to the second screw 304.

With reference to FIGS. 3E-3G, an embodiment of a connecting element insertion device 370 is shown. In any embodiments disclosed herein, the connecting element insertion device 370 can have a handle 371, a main stem or arm 372 coupled with the handle 371, and a head portion 374 coupled with the main stem 372. In some embodiments, the main stem can have a flexible joint 378 in a middle portion thereof. With reference to FIGS. 3E and 3F, the joint 378 can be configured to flex or bend so that a distal portion of the stem 372 can rotate relative to a proximal portion of the main stem 372. In some embodiments, the joint 378 can permit the connecting element 350 to rotate. The joint 378 can be a separate flexible joint or element (such as a component comprising plastic, rubber, and/or nitinol) that is added to the shaft 372, or can be formed by other methods such as a flexible cut outs in the tube of the shaft 372. The flexibility of the joint 378 can permit the tip of the connecting element 350 to enter approximately vertically in the axis of the first extension with the solid wall. Then the tip of the connecting element 150 can be slid down the wall on the way to the screw head towards passage 354, as shown in FIGS. 3H-3L.

In some embodiments, the connecting element insertion device 370 can be shorter than conventional rod inserters or devices for inserting connecting elements. The connecting element insertion device 370 can be shorter so that the main stem 372 of the connecting element insertion device 370 can pass through a standard extensions or towers. Conventional rod inserters were too long and could not pass within standard extensions or towers. In order to do this, a connection member 380 at the top of the main shaft 372 connecting element insertion device 370 can have two, three, or more holes or connection interfaces that a handle such as handle 371 can connect with. Each of the holes can be configured to permit the handle to extend away from the connection member 380 at a different orientation.

In some embodiments, the center hole that can pass down the center of the shaft 372 of the connecting element insertion device 370 can be for a screw driver that can tighten or loosen a screw that secures the connecting element 350 (also referred to herein as a rod) in a head portion 374 of the connecting element insertion device 370. The other two holes can be threaded holes for handles such as handle 371 that can attach to the connecting member 380 from the front side and/or the back side. The front side handle 371 can be inserted first and can be used to lower the connecting element 350 into the extension or tower as the connecting element 350 passes from a vertical orientation down to the head of the first screw. As the connecting element 350 starts to turn horizontally into the seat of the heads of both screws, the main shaft 372 of the connecting element insertion device 370 can rotate through the extension or tower and end up on the other side of the extension or tower. On the other side, the last handle can be inserted into the threaded hole so that the connecting element insertion device 370 can be held and stabilized on the other side of the extension or tower. Lastly, in some embodiments, though not required, the main shaft 372 of the connecting element insertion device 370 shaft can be flexible. This flexibility can be either a hinge or flexible as shown here as cutouts in the wall of the shaft 372. Any suitable methods or materials to make the shaft 372 flexible can be used, including without limitation using flexible materials such as plastic, rubber, or metals such as nitinol.

With reference to FIG. 3J, this figure shows the connecting element 350 being inserted into the seat of the heads of both screws. The connecting element 350 is transitioning from vertical orientation to the horizontal orientation. The flexible portion 378 of the shaft 372 can be bent as shown in FIG. 3J. One beneficial way to insert the connecting element 350 is to keep the tip of the connecting element 350 in contact with the midline wall of the first extension or tower. By keeping the tip of the connecting element 350 in contact with the wall, the surgeon can feel the position of the connecting element 350 until it hits the bottom of the tower and enters the seat of the head of the screw. The insertion device 370 can then be rotated to the other side of the extension or tower to allow the connecting element 350 to sit into the heads of both screws. The insertion device 370 can then be moved to the other side of the extension or tower so that the cap (such as cap 390) can be placed through the extension or tower to secure the connecting element 350 to the screw attached to the screw.

Some embodiments of the connecting element insertion device 370 can have a second property. The connecting element insertion device 370 can be short enough to pass under the top part of the tower of the second screw that holds the two "blades" or sides of the tower or extension together. A second handle 371 can screw into the connection member 380 from the other side of the extension (such as is shown in FIG. 3K) after the connecting element insertion device 370 passes through between the blades of the extension or through a slot in the extension. At this point, the first handle 371 of the rod holder can be removed. In any embodiments, as has been described, the handle 371 of the insertion device 370 can move from one side of the extension or tower to the other side. Alternatively, in some embodiments, a second screw can be open at the top (distal end) like open blades. Then the handle 371 can pass easily. The blades can be locked together after that by a cap or screw cap. After the connecting element 350 has been coupled with the screws or screw heads, in any embodiments, disclosed herein, a fastener such as the insert screw or cap 390 shown in FIGS. 3L-3M can be advanced through the extension and coupled with the insert or the seat that supports the connecting element 350.

With reference to FIG. 3L, the insertion device 370 is now positioned at the other side of the extension or tower with the second handle 373 inserted and the first handle 371 removed. The cap 390 can be inserted through the tower and be secured onto the L5 screw, which can be connected to the extension or tower. The screw can be final tightened to the final torque. It is during the final tightening process which cap 390 can be tightened to a final torque. This final torque tightening requires a counter torque mechanism for the screw head while the cap is being tightened to the final torque so that the whole construct does not rotate during final tightening. The angled proximal portion of the first extension of the first screw 310b serves as a handle for counter torque. Thus the extension 310 and 302 serves as tower for screw head alignment, for creating a path for connecting element (rod) 350 insertion, for the conduit for locking cap 390 insertion, for compression of the screw heads when the tightening caps 390 are final tightened onto the connecting element 350, and as counter torque when the caps 390 are final tightened. All of these steps usually entail separate tools to be inserted and removed at the appropriate step of the process. However in the present invention, all these steps are incorporated and performed by the same extensions 310 and 320. In this way the surgery is simplified, shortened, and streamlined. Finally the insertion device 370 can be disconnected from the connecting element 350 by unscrewing the internal screw that secures the connecting element 350 to the head of the insertion device 370.

In any embodiments disclosed herein, the system can include generally nonflexible structures (e.g., the extensions) attached to the screws which pass through each other and then interact so that the extensions can allow compression and reduction without additional tools being inserted into the patient. This saves time and still maintains a small incision for faster recovery. Additionally, any of the embodiments disclosed herein, the components of the system can be configured for use in robotic surgery. Because the extensions are generally rigid, these extensions can be secured and held or attached to robotic arms that then can know the exact position and orientation of the heads of each screw. Knowing this information allows for the robotic insertion of a connecting element into the seat of the screw heads.

In any embodiments disclosed herein, the one or more screws can be implanted using other means, and the extensions or guide elements can be coupled with the screw heads or other components coupled with the screws after the screws have been implanted. In any embodiments disclosed herein, the extensions, guide elements, and/or towers can be used with any of the devices or components shown and described in relation to FIGS. 1A-1Z, including without limitation the wires 140*a*, 140*b*, the screws 110, the inserts 116*a*, and/or the screw heads 114. For example and without limitation, in any embodiments, the first and second extensions 310, 320 can be passed over any of the wires 140*a*, 140*b* and secured to the screws 110 or screw heads 114 so that the first and second extensions 310, 320 are coupled with the screws 110 for further procedures as disclosed herein or otherwise.

Certain aspects of the systems, devices, components and/or methods described above or as illustrated with respect to FIGS. 3A-3O are also encompassed by the following numbered embodiments. These numbered embodiments are considered to be directed to systems, devices, components and/or methods that include but are not limited to the embodiments of FIGS. 3A-3O, and thus these numbered embodiments may encompass other embodiments as described throughout this specification.

1. A system for stabilizing spinal vertebrae through a skin incision, comprising:

a first screw having a first screw head;

a second screw having a second screw head;

a first extension having a distal portion and a proximal portion, the first extension being configured to be removably coupled with the first screw at a distal end of the first extension; and a second extension having at least a proximal portion, the second extension configured to be removably coupled with the second screw at a distal end of the second extension;

wherein:

the first extension is configured to removably couple with the first screw such that, when the first extension is coupled with the first screw, an axial centerline of the distal portion of the first extension is approximately collinear with an axial centerline of the first screw;

the second extension is configured to removably couple with the second screw such that, when the second extension is coupled with the second screw, an axial centerline of the distal portion of the second extension is approximately collinear with an axial centerline of the second screw;

the proximal portion of the first extension extends at an angle away from the axial centerline of the distal portion of the first extension such that the proximal portion of the first extension is not approximately collinear with the distal portion of the first extension; and the proximal portion of the first extension is configured such that, in an operable state, the proximal portion of the first extension also extends at an angle away from the axial centerline of the proximal portion of the second extension so that the proximal portion of the first extension forms an acute angle relative to the proximal portion of the second extension.

2. The system of Embodiment 1, wherein the first extension is sized and configured such that, in an operable state, the proximal portion of the first extension extends away from a skin incision toward a surgeon.

3. The system of Embodiment 1 or 2, wherein the distal portion of the first extension extends away from the first screw to a height just below the skin incision, or to a height level with the skin of a patient, when the first screw is fully implanted in a first vertebra.

4. The system of any one of the previous Embodiments, wherein the proximal portion of the first extension is configured to be grasped by a surgeon to enable a surgeon to exert a rotational force on the first extension about at least the axial centerline of the distal portion of the first extension and/or a torque force on the first extension so as to cause the first extension to rotate about an axis that is perpendicular to an axial centerline of the distal portion of the first extension.

5. The system of any one of the previous Embodiments, wherein the first extension is sized such that only the proximal portion of the first extension is outside of a skin incision when the first screw is implanted in a first vertebra.

6. The system of any one of the previous Embodiments, wherein the second extension is sized to extend completely through a skin incision when the second screw is implanted in a second vertebra.

7. The system of any one of the previous Embodiments, wherein the system is configured such that the first and second screws are implanted through the same skin incision.

8. The system of any one of the previous Embodiments, wherein the system is configured such that the first screw, the second screw, and a third screw are implanted through the same skin incision.

9. The system of any one of the previous Embodiments, wherein the proximal portion of the first extension has a length that is approximately the same as a length of the distal portion of the first extension.

10. The system of any one of the previous Embodiments, wherein the proximal portion of the first extension has a length that is at least 80% of a length of the distal portion of the first extension.

11. The system of any one of the previous Embodiments, wherein the proximal portion of the first extension is removably coupled with the distal portion of the first extension.

12. The system of any one of the previous Embodiments, wherein the proximal portion of the first extension is non-removably coupled with the distal portion of the first extension.

13. The system of any one of the previous Embodiments, wherein the proximal portion of the first extension is integrally formed with the body portion of the first extension.

14. The system of any one of the previous Embodiments, wherein at least the proximal portions of the first extension and the second extensions have a tubular shape.

15. The system of any one of the previous Embodiments, wherein the first extension has a cutout formed through a wall portion of the first extension, the cutout being configured to receive a portion of an outside surface of the second extension therein in an operable state.

16. The system of Embodiment 15, wherein the cutout extends at least through a proximal end of the distal portion of the first extension.

17. The system of Embodiment 15, wherein the cutout extends entirely through the first extension such that, in an operable state, the second extension can pass entirely through the cutout.

18. The system of Embodiment 15, wherein the cutout extends entirely through the first extension such that, in an operable state, the second extension can pass entirely through the cutout and such that the wall portion of the first extension surrounds an outside surface of a portion of the second extension.

19. The system of any one of Embodiments 15-18, wherein the cutout is shaped such that a distal edge of the cutout is configured to contact an outside surface of the second extension in an operable state so that the second extension can be rotated about the distal edge of the cutout relative to the first extension.

20. The system of any one of Embodiments 15-19, wherein the cutout has an ovular shape.

21. The system of any one of Embodiments 15-20, wherein the cutout has a notch at a proximal end of the cutout, the notch of the cutout configured to permit a passage of at least a portion of a connecting element to pass through the notch.

22. The system of any one of Embodiments 15-21, wherein the cutout has a notch at a proximal end thereof, the notch of the cutout configured to permit a passage of at least a portion of a connecting element and a portion of a connecting element implantation device to pass through the notch.

23. The system of Embodiment 22, wherein a width of the notch is less than a width of an outside surface of the second extension so that the outside surface of the second extension is prevented from extending into the notch.

24. The system of Embodiment 22, wherein a width of the notch is less than a width of the cutout so that the cutout defines a proximal edge that is configured to contact an outside surface of the second extension so that the second extension can be rotated about the proximal edge relative to the first extension when at least a proximal end of the first extension is moved toward a proximal end of the second extension.

25. The system of any one of Embodiments 15-24, wherein the cutout is adjacent to a proximal end of the distal portion of the first extension and a distal end of the proximal portion of the first extension.

26. The system of any one of the previous Embodiments, wherein the first extension has a distal notch formed at a distal end of the first extension, the distal notch configured to permit a passage of at least a portion of a connecting element to pass through the distal notch.

27. The system of any one of the previous Embodiments, wherein at least the distal portion of the first extension has an adjustable length.

28. The system of any one of the previous Embodiments, wherein the first extension and the second extension are cylindrically shaped.

29. The system of any one of the previous Embodiments, wherein the proximal portion of the first extension has a cross-sectional profile that has a curved shape.

30. The system of any one of the previous Embodiments, wherein the proximal portion of the first extension has a cross-sectional profile that has a semi-circular tubular shape.

31. The system of any one of the previous Embodiments, wherein the proximal portion of the first extension has a cross-sectional profile that is approximately the same as one-half of the distal portion of the first extension.

32. The system of any one of the previous Embodiments, wherein the proximal portion of the first extension has a planar shape.

33. The system of any one of the previous Embodiments, further comprising:
a rigid connecting element;
a first receiving element coupled with the first screw head; and
a second receiving element coupled with the second screw head;
wherein the first and second receiving elements are configured to operably receive the connecting element that, in an operable state, extends between the first and second receiving elements when the first and second screws are implanted in a first and a second vertebra, respectively.

34. The system of any one of the previous Embodiments, wherein the first screw is configured to be implanted in a first vertebra and the second screw is configured to be implanted into a second vertebra.

35. The system of any one of the previous Embodiments, comprising more than one discrete proximal portions extending away from the distal portion of the first extension.

36. The system of any one of the previous Embodiments, wherein the first extension has at least one window extending through a side of the body portion thereof, the at least one window configured to receive a connecting element that is configured to extend between the first and second screws in an operable state.

37. The system of any one of the previous Embodiments, wherein the first extension is shorter than the second extension.

38. The system of any one of the previous Embodiments, wherein the second extension has at least one window extending through a side of the body portion thereof, the at least one window of the second extension configured to receive a connecting element that is configured to extend between the first and second screws in an operable state.

39. A method of stabilizing spinal vertebrae, comprising:
implanting a first screw that is coupled with a first extension through an incision into a first vertebra;
advancing a second extension that is coupled with a second screw through a cutout formed in the first extension and implanting the second screw into a second vertebra;
moving a proximal end of a proximal portion of the first extension toward a proximal end of the second extension to cause an outside surface of the second extension to contact at least a distal edge of the cutout; and
further moving the proximal end of the proximal portion of the first extension toward a proximal end of the second extension to cause the outside surface of the second extension to rotate about at least a distal edge of the cutout and to cause a distal end of the first extension to move toward a distal end of the second extension, thereby moving the first vertebra toward the second vertebra.

40. The method of Embodiment 39, further comprising coupling a rigid connector with the first screw and the second screw to generally fix a position of the first screw relative to the second screw.

Figure 4A:
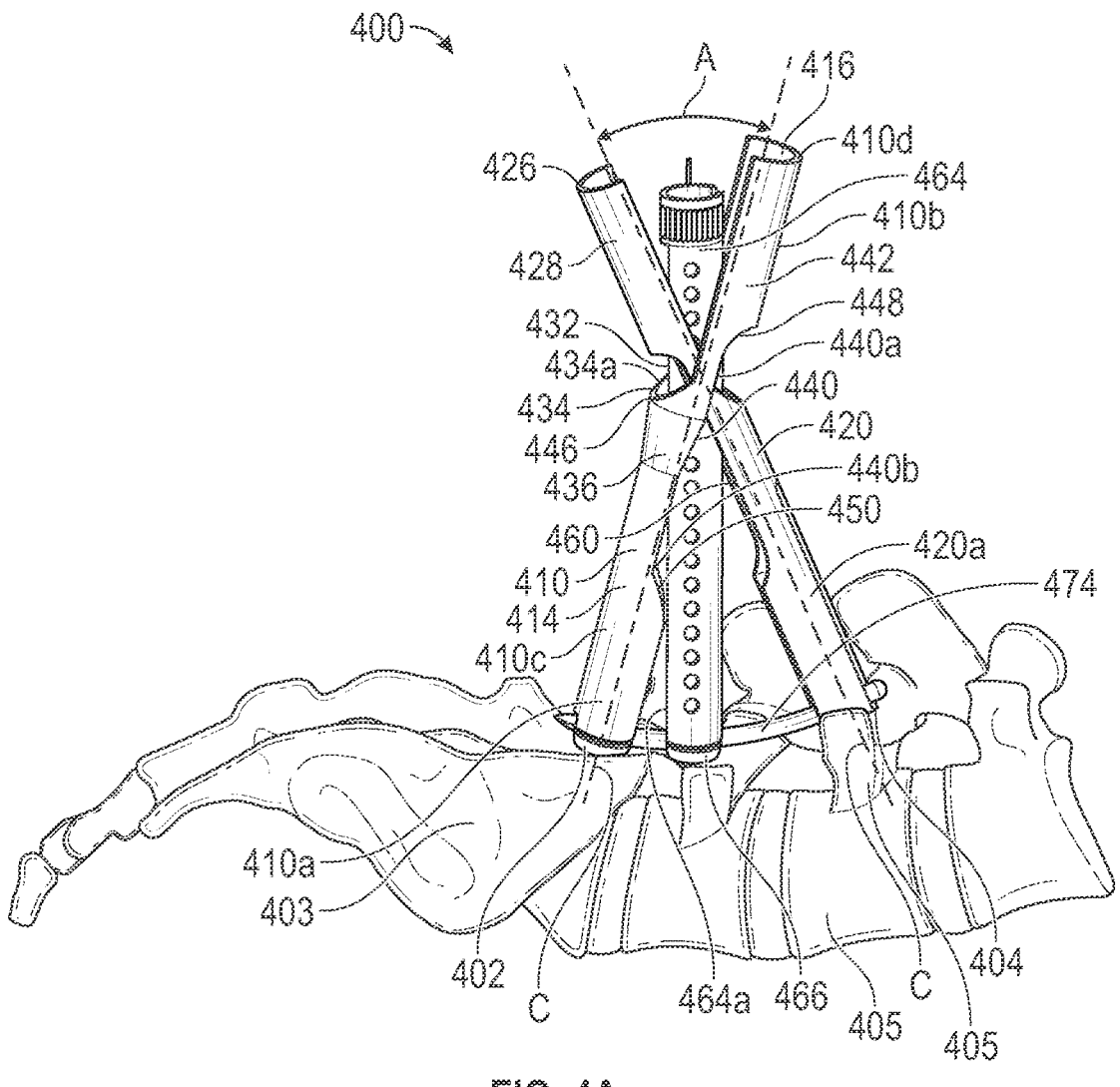
FIGS. 4A-4T illustrate another embodiment of a method and a system for stabilizing spinal vertebrae comprising spinal screws.
Figure 4B:
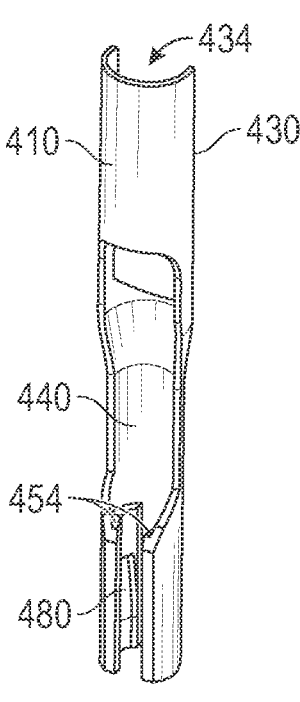
Figure 4C:
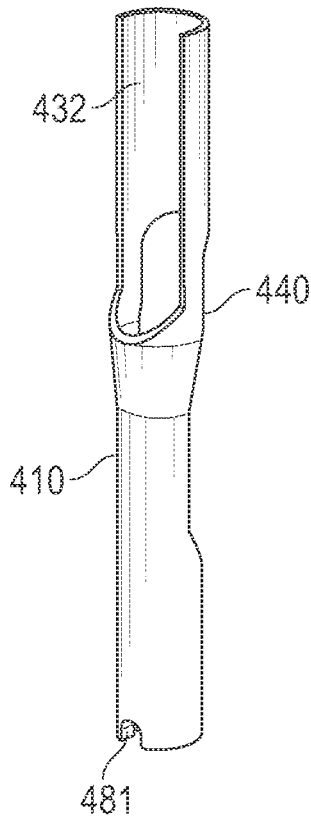
Figure 4D:
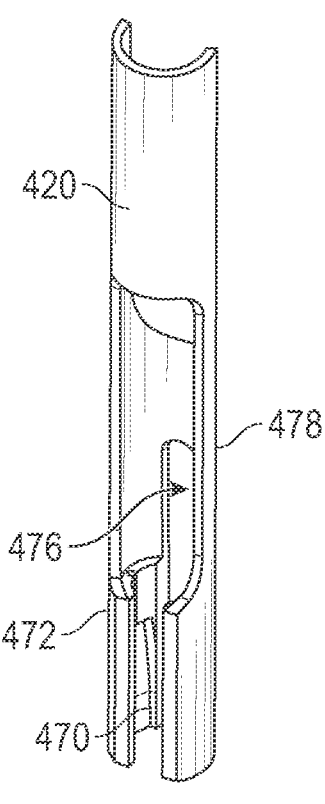
Figure 4E:
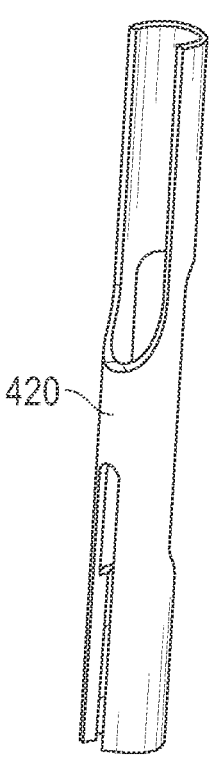
Figure 4F:
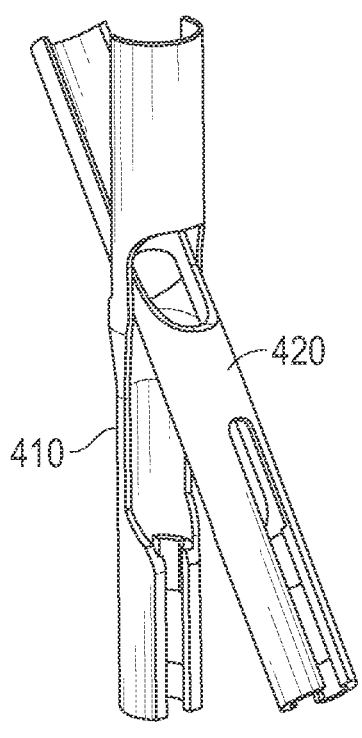
Figure 4G:
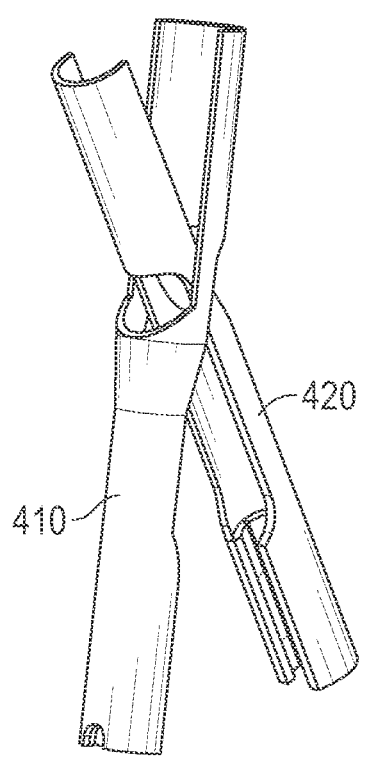
Figure 4H:
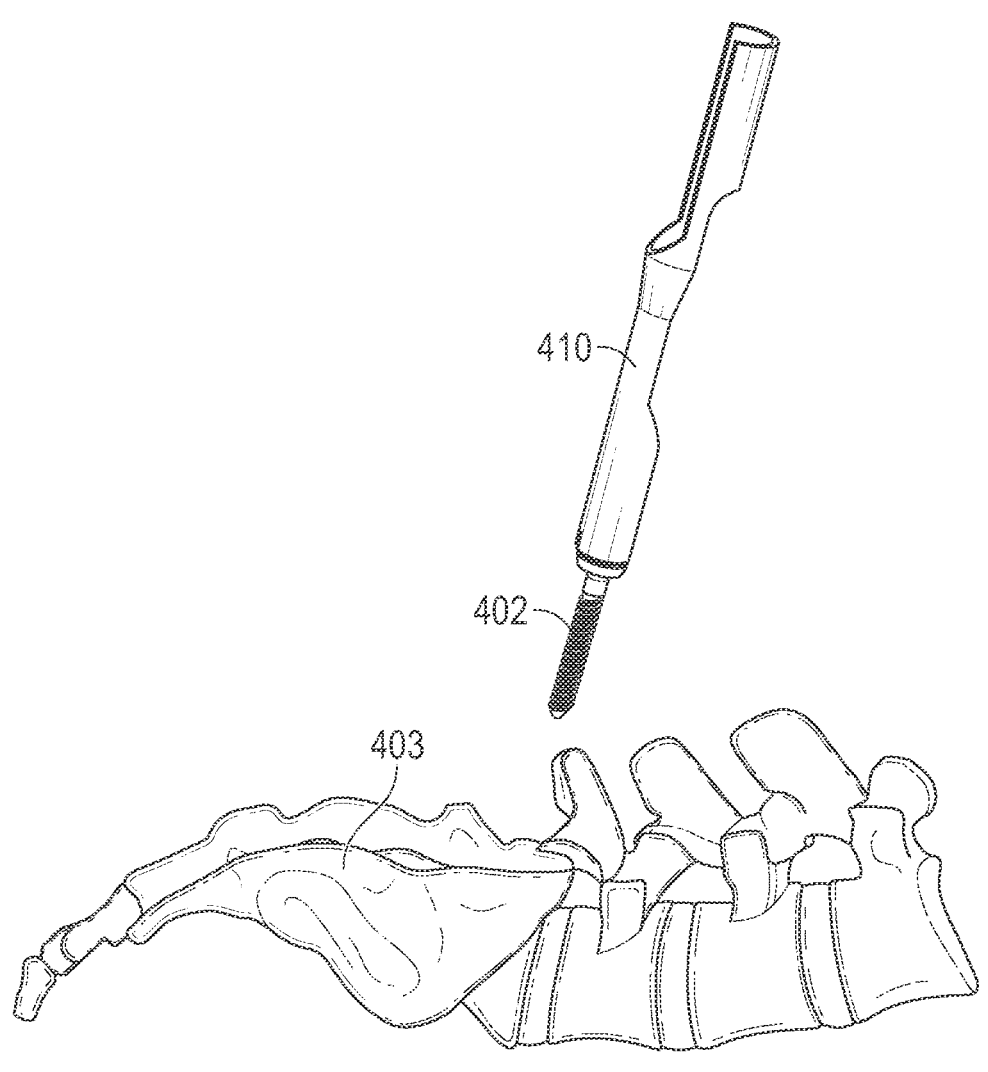
Figure 4I:
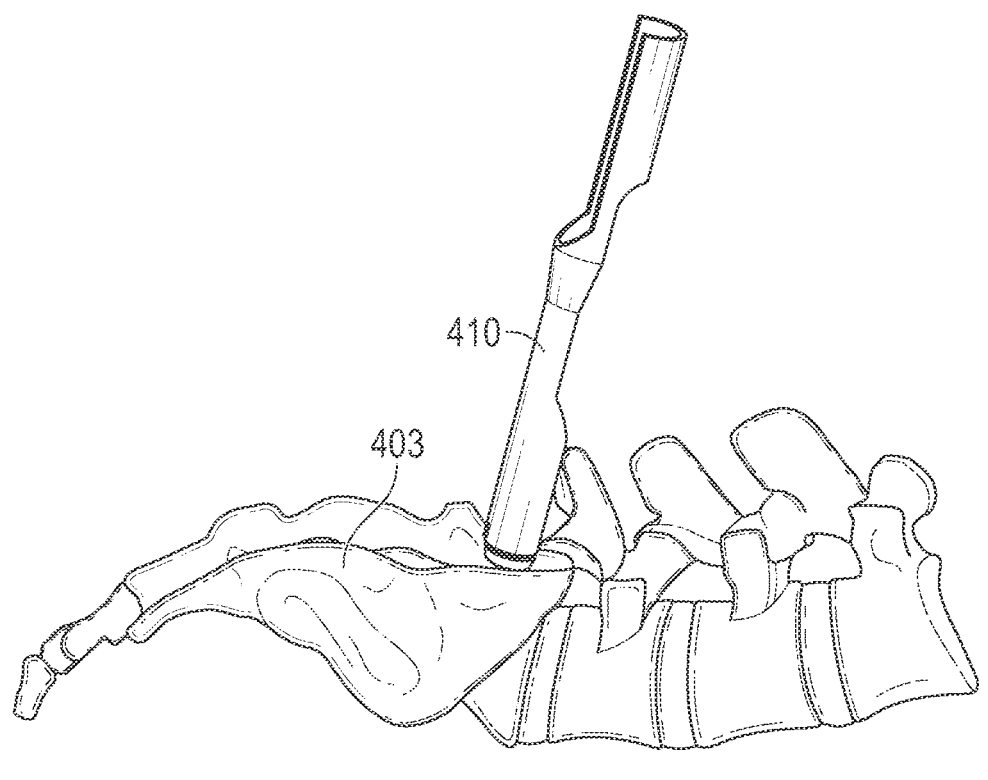
Figure 4J:
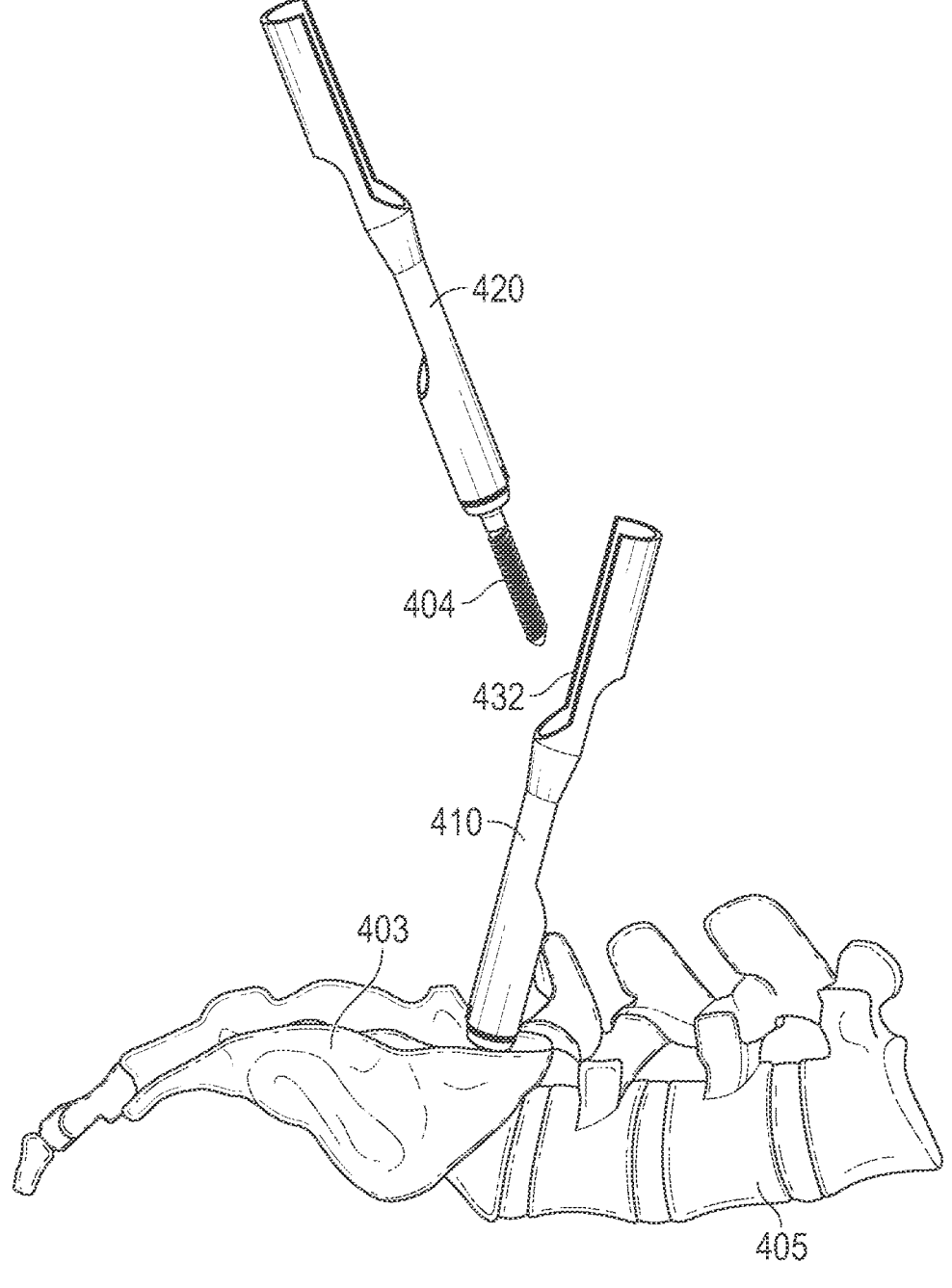
Figure 4K:
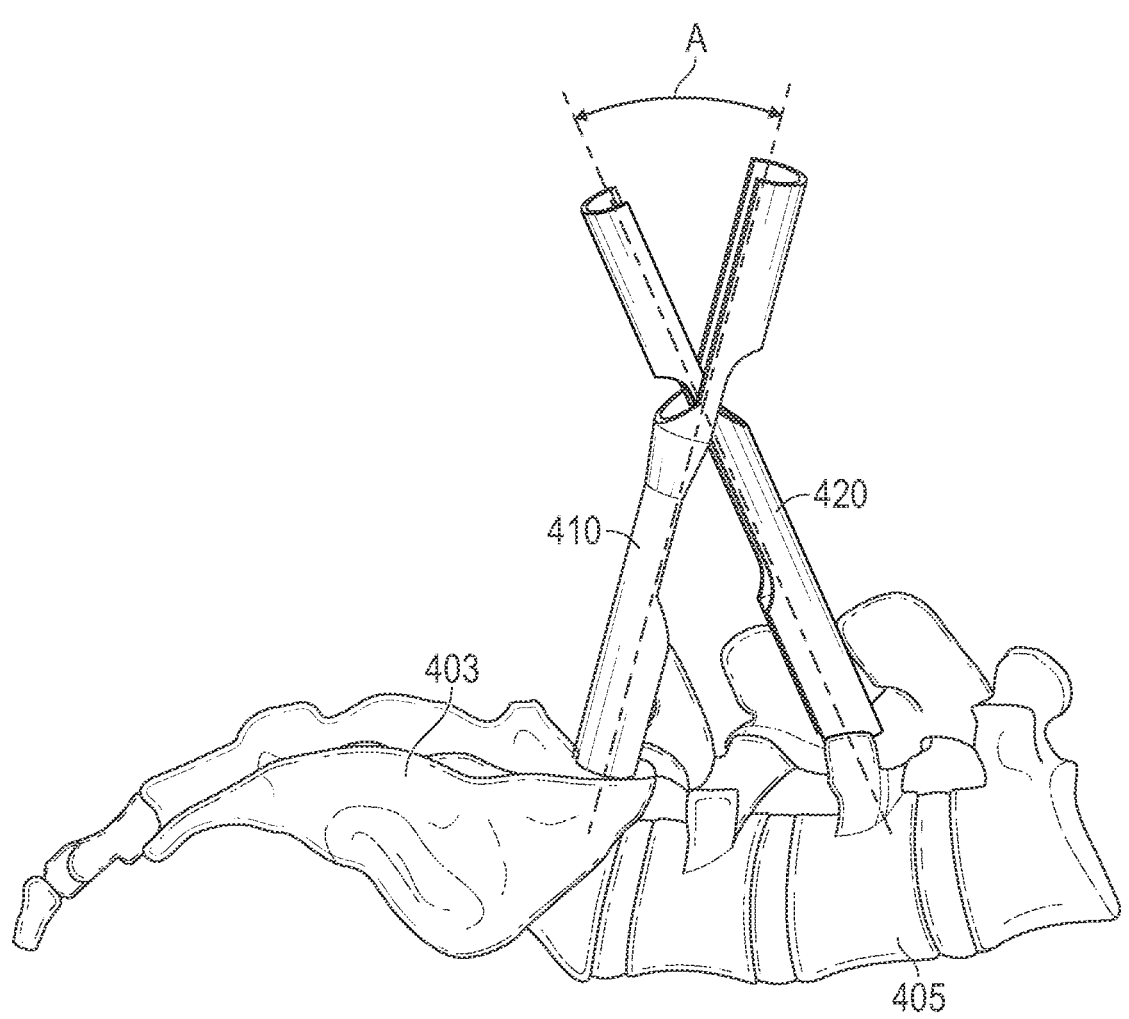
Figure 4L:
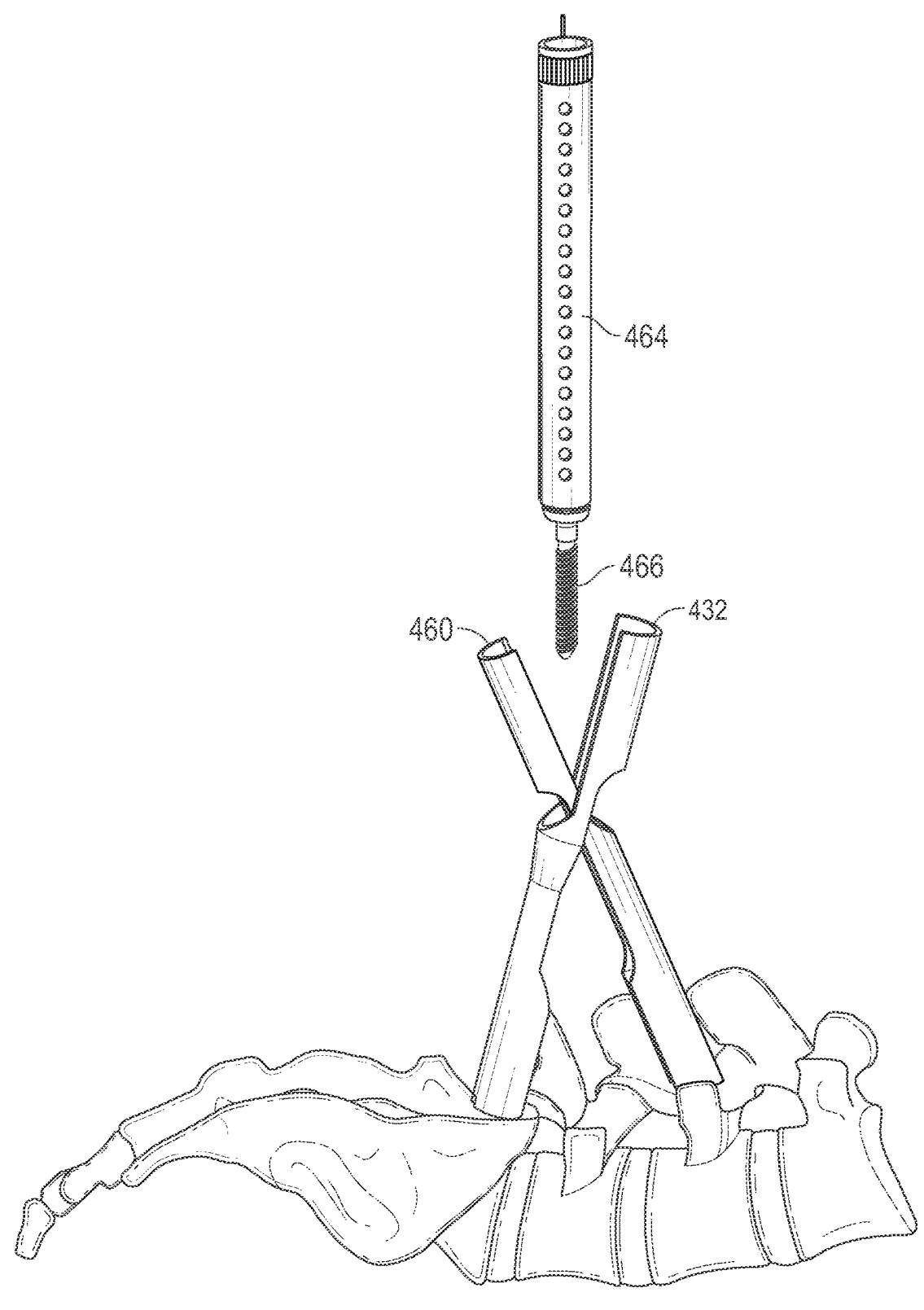
Figure 4M:
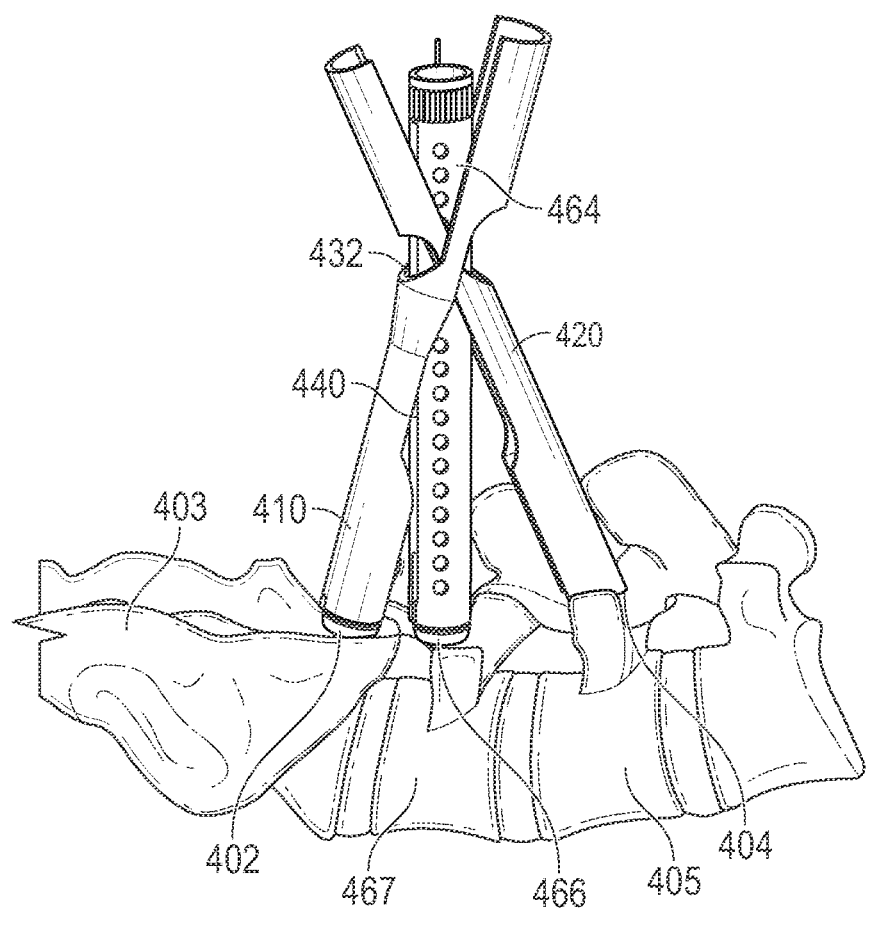
Figure 4N:
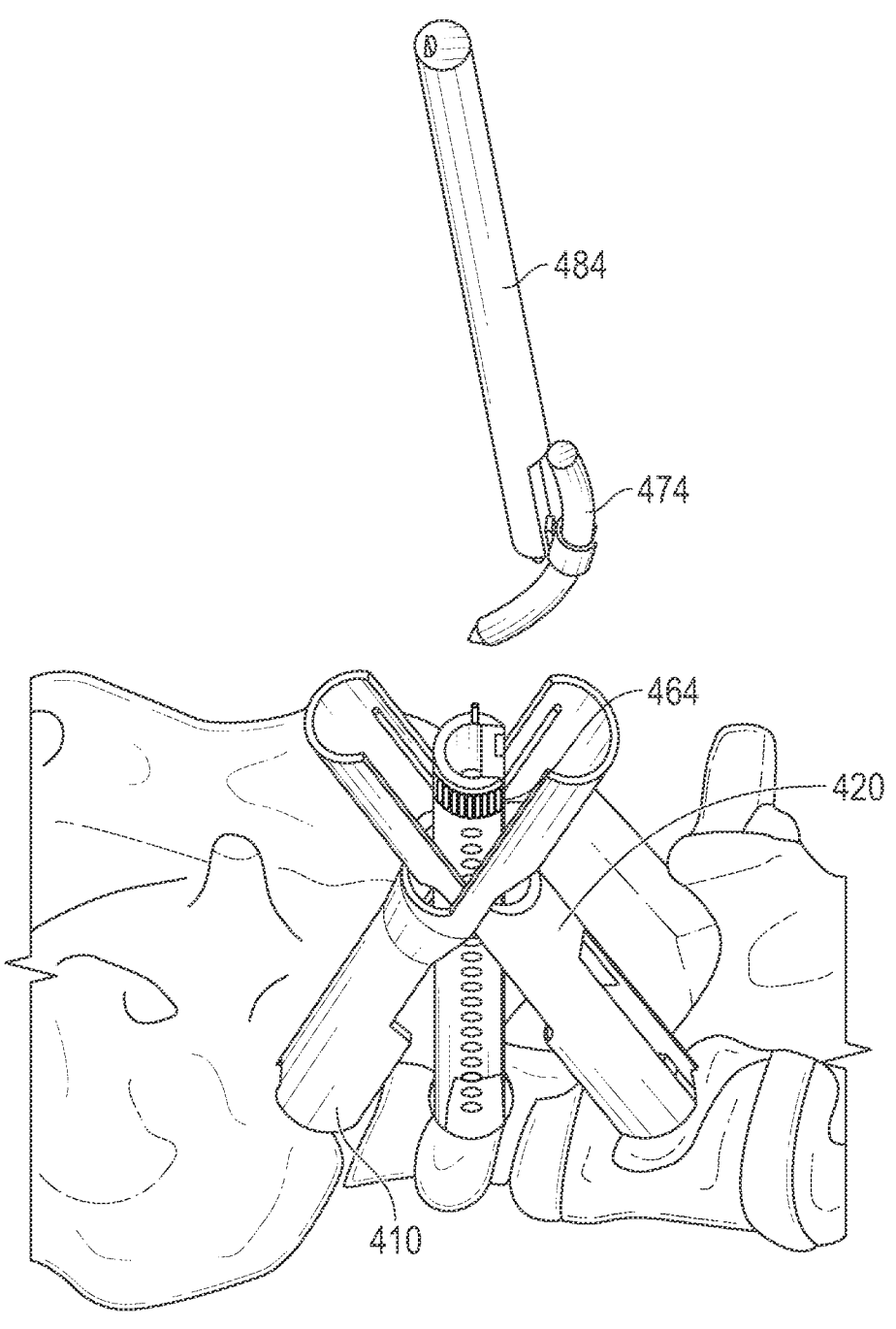
Figures 4O, 4P:
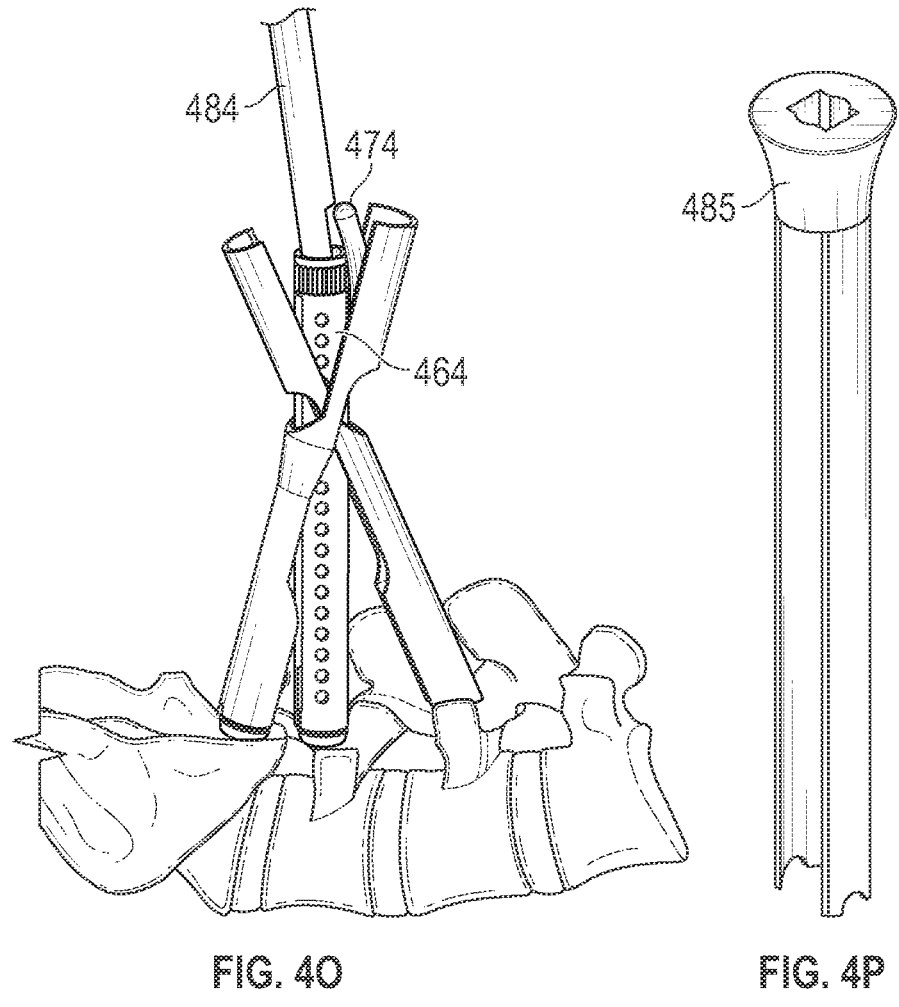
Figure 4Q:
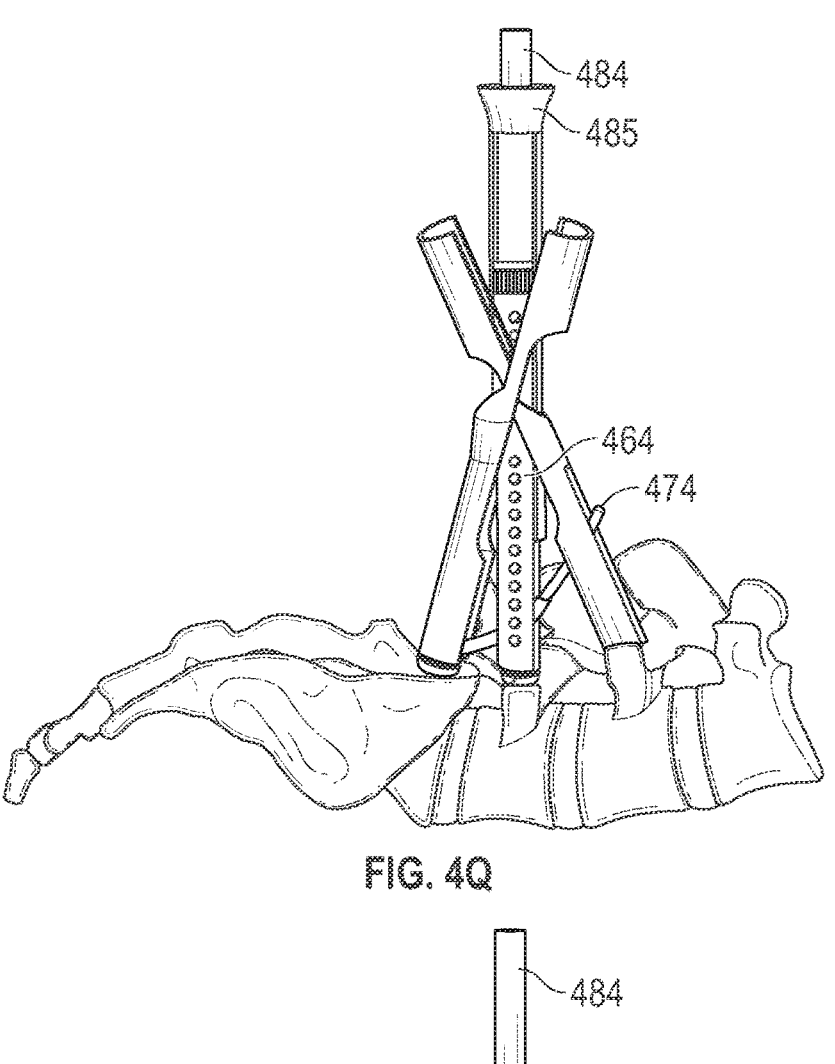
Figure 4R:
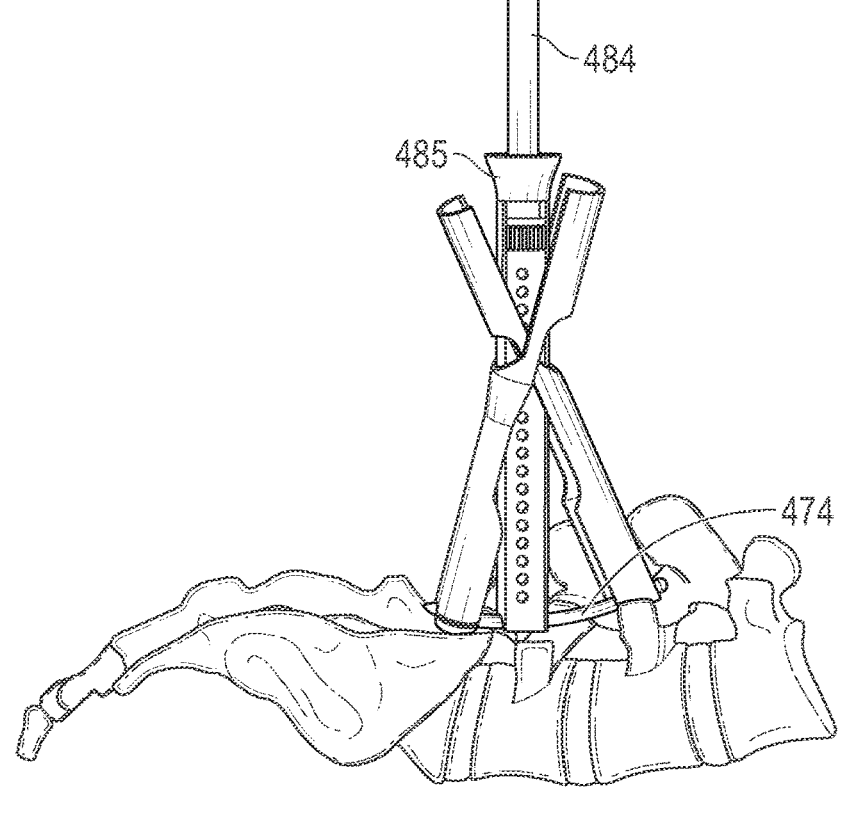
Figure 4S:
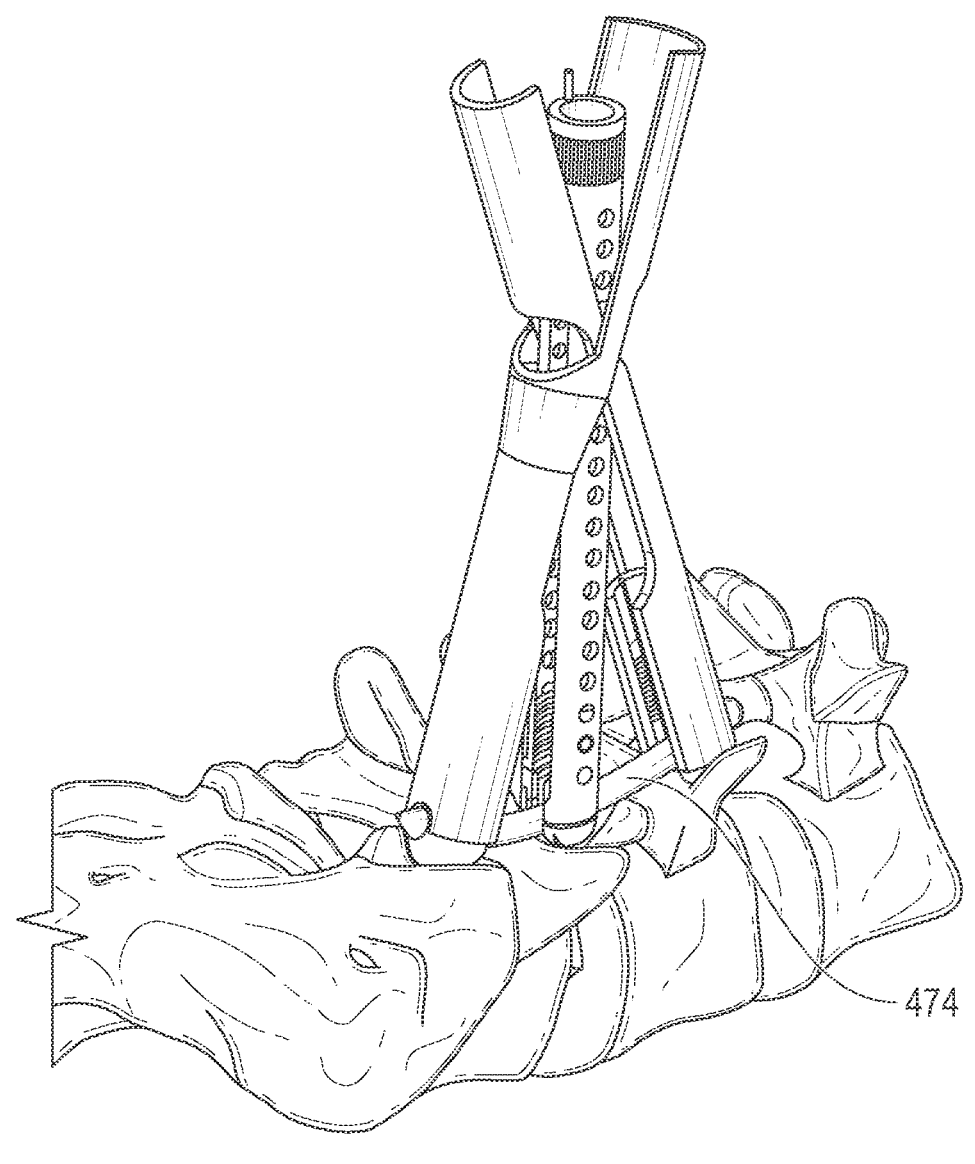
Figure 4T:
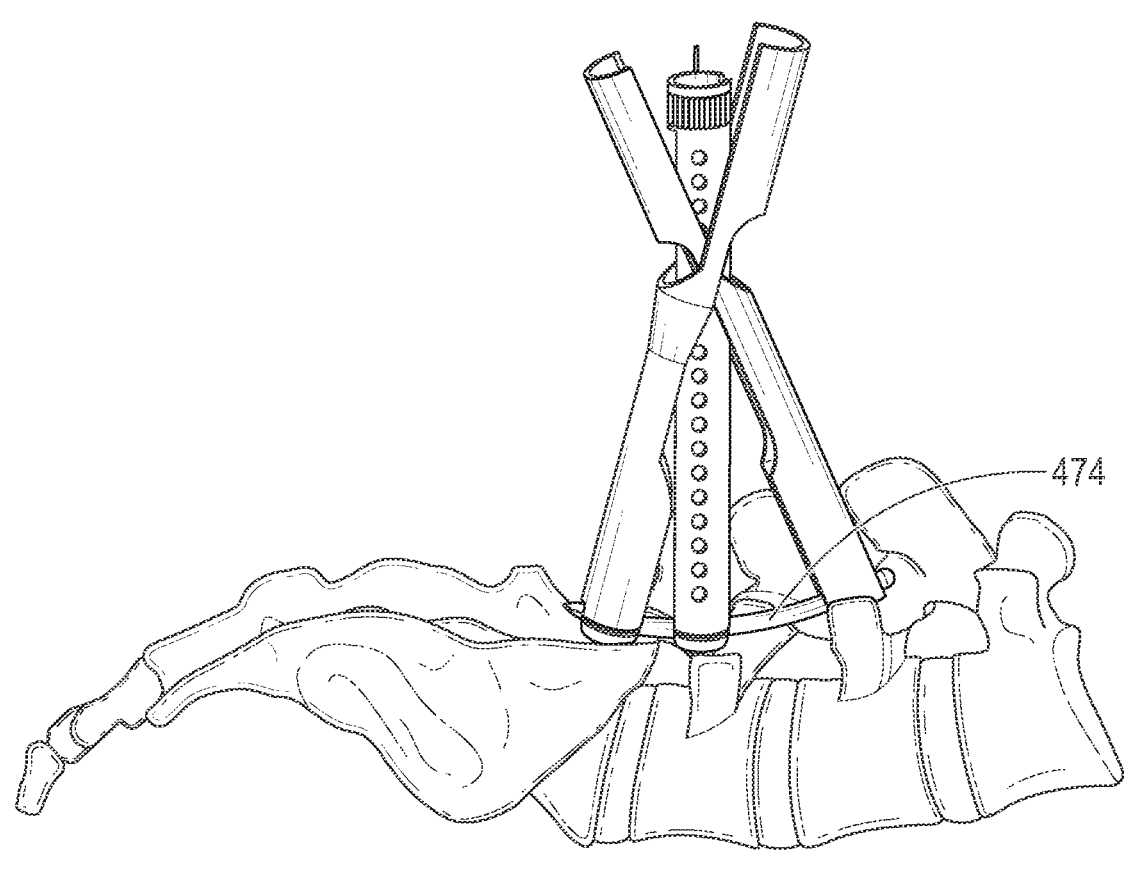

Systems, Devices and Methods of FIGS. 4A-4T

Additional embodiments of a system 400 for stabilizing spinal vertebrae through a skin incision S will now be described. In any embodiments disclosed herein, any components, features, or other details of the system 400 can have any of the components, features, or other details of any other system embodiments disclosed herein or be used according to any of the steps of any other method embodiments disclosed herein, including without limitation any of the embodiments of the system 200 or 300 or methods of use thereof described above, in any combination with any of the components, features, or details of the system 400 or methods of use disclosed below. Similarly, any components, features, steps, or other details of any of the other system or method embodiments disclosed herein can have any of the components, features, steps, or other details of any embodiments of the system 400 or methods of use thereof disclosed herein in any combination with any of the components, features, or details of the system.

In some embodiments, the system 400 can include a first screw 402 having a first screw head, a second screw 404 having a second screw head, a first extension 410 configured to be removably coupled with the first screw 402 at a distal end 410a of the first extension 410, the first extension 410 having a first wall 414 and a first passageway 416 extending through the first extension 410 along an axial centerline C of the first extension 410 such that the first wall 414 of the first extension 410 at least partially surrounds the first passageway 416. In some embodiments, the first screw 402 can be configured to be implanted in a first vertebra 403 and the second screw 404 can be configured to be implanted into a second vertebra 405. The system 400 can further have a second extension 420 configured to be removably coupled with the second screw 404 at a distal end 420a of the second extension 420, the second extension 420 having a second wall 428 (also referred to herein as a wall) and a second passageway 426 extending through the second extension 420 along an axial centerline C of the second extension 420 such that the second wall 428 of the second extension 420 at least partially surrounds the second passageway 426.

The first extension can further have an opening 432 (also referred to herein as a first opening) extending through the first wall 414 of the first extension 410. The opening 432 and the first wall 414 of the first extension 410 adjacent to the opening 432 can be sized and configured such that the second extension 420 can be advanced through the opening 432 in an operable state so that the second extension 420 or an axial centerline thereof is restrained or supported at an acute angle A (as shown in FIG. 4A) relative to an axial centerline C of the first extension 410.

In some embodiments, the first extension 410 can be removably coupleable with the first screw 402 such that, when the first extension 410 is coupled with the first screw 402, the axial centerline C of the first extension 410 is approximately collinear with an axial centerline C of the first screw 402 and wherein the second extension 420 is removably coupleable with the second screw 404 such that, when the second extension 420 is coupled with the second screw 404, an axial centerline C of the second extension 420 is approximately collinear with an axial centerline C of the second screw 404. In any embodiments disclosed herein, the first extension 410 and the second extension 420 can be generally cylindrically shaped and/or have a generally tubular shape. Other embodiments can have any other desired cross-sectional shape, including a generally square shape, a triangular cross-sectional shape, on ovular cross-sectional shape, a polygonal cross-sectional shape, or any combination of the foregoing. Further, some embodiments of the first extension 410 and/or the second extension 420 can be generally rigid.

Further, in some embodiments, at least a distal portion 410c of the first extension 410 and/or the second extension 420 can have an adjustable length. As with other embodiments, the first extension 410 can be sized and configured such that, in an operable state, a proximal portion 410b of the first extension 410 can extend away from the skin incision S toward the surgeon.

In some embodiments, an inside size of the first wall 414 of the first extension 410 adjacent to the opening 432 in the first extension 410 can be greater than an outside size of at least a portion of the second wall 428 of the second extension 420 such that at least a portion of the second extension 420 can be passed through the opening 432 of the first extension 410 at an acute angle A relative to the axial centerline C of the first extension 410 and be at least partially surrounded by the first wall 414 of the first extension 410. Further, a proximal portion 410b of the first extension 410 can have an inside cross-sectional size that is greater than an inside cross-sectional size of a distal portion 410c of the first extension 410. Further, in some embodiments, the inside cross-sectional size of the proximal portion 410b of the first extension 410 can also be greater than an outside cross-sectional size of at least a distal portion of the second extension 420 so that at least the distal portion of the second extension 420 can be advanced completely through the opening 432 of the first extension 410.

In some embodiments, the opening 432 in the first extension 410 can pass through the first wall 414 of the first extension 410 at an angle that is acute relative to the axial centerline C of the first extension 410. In some embodiments, the opening 432 can include a first cutout 434 in a first side 436 of the first wall 414 and a second cutout 440 in a second side 442 of the first wall 414, wherein the second side 442 of the first wall 414 is opposite to the first side 436 of the first wall 414. The second cutout 440 can be separate from the first cutout 434 such that the first cutout 434 and the second cutout 440 are not overlapping or connected. Further, the second cutout 440 can be positioned closer to a distal end 410a of the first extension 410 than the first cutout 434.

In some embodiments, the first cutout 434 can extend in a distal direction from a proximal end 410d of the first extension 410 such that the first wall 414 of the first extension 410 does not form a complete or continuous enclosure around the first passageway 416 at the proximal end 410d of the first extension 410. In some embodiments, the first cutout 434 can remove at least approximately 40% of the first wall 414 of the first extension 410 at least the proximal end 410d of the first extension 410. Some embodiments of the first cutout 434 can extend along a length of the first extension 410 that is at least approximately 30% of a total length of the first extension 410, or that is at least approximately 40% of a total length of the first extension 410. Further, in some embodiments, a distal edge 446 of the first cutout 434 can be planar and can be angled downwardly toward the distal end 410a of the first extension 410.

In some embodiments, a proximal portion 440a of the second cutout 440 can overlap a distal portion 434a of the first cutout 434 in an axial direction. Further, the second cutout 440 can be positioned between a proximal end 410d and the distal end 410a of the first extension 410 such that a proximal portion 440a of the second cutout 440 is spaced apart from the proximal end 410d of the first extension 410 and a distal portion 440b of the second cutout 440 is spaced apart from the distal end 410a of the first extension 410. In some embodiments, the second cutout 440 can remove at least approximately 40% of the first wall 414 of the first extension 410 in at least a middle portion of the first extension 410. Further, the second cutout 440 can extend along a length of the first extension 410 that is at least approximately 30% of a total length of the first extension 410.

The second cutout 440 can extend along a length of the first extension 410 that is at least approximately 40% of a total length of the first extension 410. Further, in some embodiments, a proximal edge 448 of the second cutout 440 can be curved or planar. In some embodiments, a distal edge 450 of the second cutout 440 can be planar and can be angled downwardly toward the distal end 410a of the first extension 410. Further, in some embodiments, one or more projections 454 adjacent to the distal edge 450 of the second cutout 440 can provide a surface or a shoulder against which the second extension 420 can contact to limit a range of rotation of the second extension 420 relative to the first extension 410. In some embodiments the projection 454 is a sloped cutout instead of a projection and allows closer approximation between the two screws and two extension, for instance in the case that there is severe lordosis and the angle A between neighboring screws is severe.

In some embodiments, the first extension 410 and the second extension 420 can be configured such that, in an operable state wherein the second extension 420 is advanced through the opening 432 in the first extension 410, moving a proximal end of the first extension 410 either toward or away from a proximal end of the second extension 420 can cause the second extension 420 to hinge and/or rotate relative to first extension 410 so as to cause the distal end of the second extension 420 to move toward or away from the distal end 410a of the first extension 410, respectively. For example and without limitation, moving a proximal end of the first extension 410 either toward or away from a proximal end of the second extension 420 can cause the second extension 420 to hinge and/or rotate about an edge of the opening 432 in the first extension 410 so as to cause the distal end of the second extension 420 to move toward or away from the distal end 410a of the first extension 410, respectively.

The hinge effect can be created in some embodiments due to the physical barrier of having extension 410 passing through an opening 434 within the other extension 430. In essence extension 410 can be trapped within the hole (topologically defined) created by the opening or cutouts in extension 430. Alternatively, an actual hinge can exist between the extensions 430 and 410 by having complementary protrusions near the point of contact to make the such as a ball and socket hinge. Some embodiments of the system 400 can be configured to generate a hinge effect by imposing a constraint imposed on the movement between extension 410 and 430. An external ring or restraint such as is shown in FIG. 6F and in other embodiments disclosed herein and external blockers to movement such as those shown in FIGS. 6O, 6P, and/or 6R can all be used to restrain movement in order to maintain a hinge effect that allows compression of the screws during final locking as well as reduction and counter-torque using an all in one system show in 400. In contrast to prior art in which towers and extensions are designed to be parallel and do not interact, the constraint for movement during compression comes from external tools. In the present invention, because towers and blades crisscross and intermingle and interact directly, the extensions themselves create the hinge effect by direct limiting and constraining movement of one extension relative to another. This reduces the need for additional tools and saves time and space during surgery.

In some embodiments, the first extension 410 and the second extension 420 can be configured such that, in an operable state wherein the second extension 420 is advanced through the opening 432 in the first extension 410, a contact between an outside surface of the second wall 428 of the second extension 420 and the first wall 414 of the first extension 410 surrounding the opening 432 will result in a hinge that the second extension 420 can rotate about relative to the first extension 410. Further, the first extension 410 can be configured such that, in an operable state, when the second extension 420 is advanced through the opening 432 in the first extension 410, the first wall 414 of the first extension 410 surrounding the opening 432 can be configured to prevent or inhibit the second extension 420 from rotating relative to the first extension 410 beyond a predetermined amount.

Further, in some embodiments, the first extension 410 can be configured such that, in an operable state, when the second extension 420 is advanced through the opening 432 in the first extension 410 and rotated so as to be in contact with the first wall 414 of the first extension 410 adjacent to the opening 432, the first wall 414 of the first extension 410 surrounding the opening 432 can restrain a rotation of the second extension 420 relative to the first extension 410 so that moving a proximal end of the first extension 410 either toward or away from a proximal end of the second extension 420 will cause the distal end of the second extension 420 to move toward or away from the distal end 410a of the first extension 410, respectively. As with other embodiments, a proximal portion 410b of the first extension 410 can be configured to be grasped by a surgeon to enable a surgeon to exert a rotational force on the first extension 410 about at least the axial centerline C of the distal portion 410c of the first extension 410 and/or a torque force on the first extension 410 so as to cause the first extension 410 to rotate about an axis that is perpendicular to an axial centerline C of the distal portion 410c of the first extension 410.

Some embodiments of the second extension 420 can have any of the same features or details of any embodiments of the first extension 410 disclosed herein, including without limitation any of the details related to the opening, the cutouts, and/or the slots formed in the first extension 410. In some embodiments, the second extension 420 can include an opening 460 (also referred to as a second opening) extending through the second wall 428 of the second extension 420, wherein the opening 460 and the second extension 420 adjacent to the opening 460 can be sized and configured such that a third extension 464 can be advanced through the opening 460 in the second extension 420 in an operable state so that the third extension 464 is angled at an acute angle relative to an axial centerline C of the second extension 420. In any embodiments disclosed herein, the third extension 464 can be a standard, straight, tubular extension configured to facilitate an implantation of a third screw 466 into a third vertebra.

In some embodiments, the first extension 410 and the second extension 420 can be configured such that the third extension 464 can be advanced through the opening 432 in in the first extension 410 and through the opening 460 in the second extension 420 in an operable state so that the third extension 464 is angled at an acute angle relative to the axial centerline C of the first extension 410 and the axial centerline C of the second extension 420. In some embodiments, as in the illustrated embodiment, the third extension 464 can be configured to implant a screw generally perpendicularly into the third vertebra. In some embodiments, a distal end 464a of the third extension 464 can be positioned between the distal end 410a of first extension 410 and a distal end 420a of the second extension 420 in an operable state.

In any embodiments disclosed herein, the second extension 420 can include at least one slot or window 470 extending through a first side 472 of the second extension 420, the at least one slot 470 of the second extension 420 configured to receive a connecting element 474 (also referred to herein as a rod or connector) that is configured to extend between the first screw 402 and the second screw 404 in an operable state and/or to permit the connecting element 474 to pass therethrough. Further, in any embodiments disclosed herein, the second extension 420 can include a second slot 476 extending through a second side 478 of the second extension 420 (opposite to the first side 472 of the second extension), the second slot 476 also being configured to permit a connecting element 474 that is configured to extend between the first screw 402 and the second screw 404 in an operable state to pass through the second slot 476.

Any embodiments of the system 400 disclosed herein can further include a rigid connecting element 474, a first receiving element coupled with the screw head of the first screw 402, and a second receiving element coupled with the screw head of the second screw 404, wherein the first and second receiving elements can be configured to operably receive the connecting element 474 that, in an operable state, can extend between the first and second receiving elements when the first screw 402 and the second screw 404 are implanted in a first and a second vertebra 405, respectively. In some embodiments, the first extension 410 can include a first slot 480 extending through the first wall thereof, the first slot 480 of the first extension 410 configured to permit a connecting element 474 configured to extend between the first screw 402 and the second screw 404 in an operable state to be advanced through the first slot 480. With reference to FIG. 4C, the first extension 410 can also have a second slot 481 configured to receive a connecting element 474 that is configured to extend between the first screw 402 and the second screw 404 in an operable state and/or to permit the connecting element 474 to pass therethrough.

In some embodiments, the first slot 480 of the first extension 410 can extend in a proximal direction from the distal end 410a of the first extension 410 to the second cutout 440 of the first extension 410. The first slot 480 of the first extension 410 can have a width that is less than 50% of a width of an outside surface of the first extension 410.

As mentioned, the second extension 420 can include a first slot 470 extending through the second wall 428 of the second extension 420, the first slot 470 of the second extension 420 configured to permit a connecting element 474 configured to extend between the first screw 402 and the second screw 404 in an operable state to be advanced through the first slot 470 of the second extension 420. In some embodiments, the first slot 470 of the second extension 420 can extend in a proximal direction from the distal end 420a of the second extension 420 to the second cutout 440 of the second extension 420. Further, the first slot 470 of the second extension 420 can have a width that is less than 50% of a width of an outside surface of the second extension 420.

In some embodiments, the first slot 470 of the second extension 420 can be in a first side 472 of the second wall 428 of the second extension 420, and the second extension 420 can further include a second slot 476 extending through a second side 478 of the second wall 428 of the second extension 420, the second side 478 of the second wall 428 being opposite to the first side 472 of the second wall 428. The second slot 476 of the second extension 420 can be configured to permit a connecting element 474 configured to extend between the first screw 402 and the second screw 404 in an operable state to be advanced through the second slot 476 of the second extension 420. In some embodiments, the second slot of the second extension 420 can extend in a proximal direction from the distal end of the second extension 420 and can have a length that is 40% (or approximately 40%) or greater of a length of the second extension 420, or that is 30% (or approximately 30%) or greater of the length of the second extension 420.

Some embodiments of methods for treating a spinal defect include implanting the first screw 402 that can be coupled with the first extension 410 through the incision into a first vertebra 403 (as shown in FIGS. 4H-4I). Note that, in some embodiments, a tool removably coupled with any of the screws disclosed herein can be advanced through any of the guiding elements or extensions and removably engage with the screw head of the screw to implant the screw. Further, with reference to FIGS. 4J-4K, the second extension 420 that can be coupled with the second screw 404 can be advanced through the incision and through the opening 432 formed in the first extension 410 so that the axial centerline C of the second extension 420 can be at an acute angle A relative to the axial centerline C of the first extension 410 and so that the second screw 404 can be implanted into a second vertebra 405. Further, as described above, with reference to FIGS. 4L-4M, if a two level fusion is desired, the third extension 464 can be advanced through the opening 432 in the first extension and the opening 460 in the second extension 420 so that the third screw 466 can be implanted in the third vertebra 467. With reference to FIG. 4L-4M, a third screw 466 can be implanted into a third vertebra 467 that is between the first and second vertebra 403, 405 by advancing the third extension 464 through the first and second cutouts 434, 440 of the first extension 410 and through the first and second cutouts 434, 440 of the second extension 410. If only a two level fusion is desired, the first extension 410 and the second extension 420 can be coupled with screws that are positioned in adjacent vertebra or, in other embodiments, are not positioned in adjacent vertebra.

In any embodiments disclosed herein, the screw can be implanted using other means, and the extensions or guide elements can be coupled with the screw heads or other components coupled with the screws after the screws have been implanted. In any embodiments disclosed herein, the extensions, guide elements, and/or towers can be used with any of the devices or components shown and described in relation to FIGS. 1A-1Z, including without limitation the wires 140a, 140b, the screws 110, the inserts 116a, and/or the screw heads 114. For example and without limitation, in any embodiments, the first and second extensions 410, 420 can be passed over any of the wires 140a, 140b and secured to the screws 110 or screw heads 114 so that the first and second extensions 410, 420 are coupled with the screws 110 for further procedures as disclosed herein or otherwise.

The third extension 464 in some embodiments can be supported within the opening 432 of the first extension 410 and the opening 460 of the second extension 420 so that the third extension 464 is restricted to a position in which the third extension 464 is at an acute angle relative to an axial centerline C of the second extension 420 and/or the first extension 410. The method or procedure can also include moving a proximal portion 410b of the first extension 410 toward a proximal portion of the second extension 420 to cause an outside surface of the second extension 420 to hinge relative to the second extension 420, for example and without limitation, by contacting at least a distal edge 446 of the opening 432 in the first extension 410 or other contact surface of the first extension 410. In this arrangement, further movement of the proximal portion 410b of the first extension 410 toward the proximal portion of the second extension 420 can cause a rotation of the second extension 420 about the hinge point which, again, can be the distal edge 446 of the opening 432 or other contact surface of the first extension 410, to move the distal end portion of the first extension 410 toward the distal end portion of the second extension 420. This method or procedure can be used to move the first vertebra 403 that the first screw 402 is implanted into toward the second vertebra 405 that the second screw 404 is implanted into, and/or move the first vertebra 403 that the first screw 402 is implanted into and the second vertebra 405 that the second screw 404 is implanted into toward the third vertebra 467 that the third screw 466 is implanted into.

With reference to FIGS. 4N-4T, to secure the first and second vertebra 405 in the desired positions, the surgeon can couple a rigid connecting element 474 with the first screw 402, the second screw 404, and/or the third screw 466 to generally fix a position of the first screw 402 relative to the second screw 404 and/or the third screw 466. A connecting element insertion device 484 can be used to advance the connecting element 464 through the openings, channels, and/or slots of the first extension 410, the second extension 420, and/or the third extension 466 and into the channels or tulips coupled with the first screw 402, second screw 404, and/or the third screw 466. A second connecting element insertion device 485 can also be used with the connecting element insertion device 484 to advance the connecting element 464 through the openings, channels, and/or slots of the first extension 410, the second extension 420, and/or the third extension 466 and into the channels or tulips coupled with the first screw 402, second screw 404, and/or the third screw 466.

For example and without limitation, the second connecting element insertion device 485 can push the connecting element 464 out from the connecting element insertion device 484 and hold the connecting element 464 in a desired position when the connecting element insertion device 484 is removed. The second connecting element insertion device 485 can then allow for a cap to be placed through the third extension 464 to lock and also reduce the connecting element 464 down to the third screw. At this point, in some embodiments, the third screw 466 can be final tightened (i.e., to the final torque tightness).

In some embodiments, the second connecting element insertion device 485 can have variable length blades so that both blades can contact the connecting element 464 on either side of the third tower 464 even when the connecting element 464 is more vertical in orientation. The variable blade lengths of some embodiments of the second connecting element insertion device 485 can then be used to push the connecting element 464 down until the connecting element 464 is horizontal and sitting in the seat or receiving element of all three of the first, second, and third screws. Once the connecting element 464 is down into the seat of the screws, the second connecting element insertion device 485 can be used to hold the connecting element 464 down as the connecting element insertion device 484 is removed, allowing a cap to be placed into the third tower to secure the connecting element 464 in place and even reducing the connecting element 464 into the third tower if there is spondylolisthesis.

It is again important to note that, in any embodiments, the first, second, and third extensions 410, 420, 464 coupled with the screws extend outside the body through the incision, and the proximal ends thereof can provide "handles" to allow the surgeon to know the position and orientation of the three screw heads constantly. This arrangement can also permit a robotic system to "know" the orientation and position of all screw heads so that a robotic system would be able to lower the connecting element 464 directly into the screw heads, including with rotating the connecting element 464 from vertical to horizontal into the seat of the heads of the screws. Any of the extensions can have additional components added thereto or otherwise be configured to integration into a robotic system. Thereafter, the extensions can be removed and withdrawn from the body.

Additionally, stereotactic intraoperative navigation and robotic assistance have been implemented in spinal fusion surgery. Both navigation and robotic guidance have been used to guide the trajectories of pedicle screws either using guidewires or direct placement of screws into the vertebrae. However, thus far, stereotactic navigation nor robotics have been used to assist in lining up the screw heads or assisted in the placement of the rod or connecting element into the seat of the screw heads. Lastly, with the natural lordotic curve of the lumbar spine, especially at L4, L5, and S1 (where 80% of all fusions occur), the traditional towers or extensions connected to the pedicle screws typically cross paths and interfere with each other during minimally invasive screw placement. Typically, the towers end up crossing at the incision but next to one another. In the embodiments disclosed herein, the towers are designed to criss-cross within each other. Thus there is no interference to the crossed trajectories of the screw extension elements and towers. Furthermore, by having attachments to the proximal ends of the extensions by which robotic arms can attach and thus "know" the 3-dimensional special orientation of each tower or extension relative to each other.

By computer modeling and "knowing" the 3-D spatial composition of each part, a robotic system is able to implant screw 402 with extension 410 and then implant screw 404 with extension 440. The robotic system is able to adjust the two extensions and thereby the screws attached to them to align the screw heads. The robotic system is then able to insert a third screw for a two level fusion. Because the screw heads are aligned and the channel is created between the towers by the cutouts and openings, there is a natural space for the rod or extension element to be inserted by another robotic arm. In this manner, then entire process from pedicle screw trajectory localization to screw insertion to alignment of the screw heads to insertion of the rod and then insertion of the locking caps. The final locking step with compression of the towers can also be performed by the same robotic arms by squeezing the proximal ends of the extension towers together and final locking the connecting element or rod using the locking caps. The entire process can be performed by a streamlined process without fear of interference of the paths of the different screws due to the lumbar lordosis.

Certain aspects of the systems, devices, components and/or methods described above or as illustrated with respect to FIGS. 4A-4T are also encompassed by the following numbered embodiments. These numbered embodiments are considered to be directed to systems, devices, components and/or methods that include but are not limited to the embodiments of FIGS. 4A-4T, and thus these numbered embodiments may encompass other embodiments as described throughout this specification.

1. A system for stabilizing spinal vertebrae through a skin incision, comprising:

a first screw having a first screw head;

a second screw having a second screw head;

a first extension configured to be removably coupled with the first screw at a distal end of the first extension, the first extension having a wall and a first passageway extending through the first extension along an axial centerline of the first extension such that the wall of the first extension at least partially surrounds the first passageway; and a second extension configured to be removably coupled with the second screw at a distal end of the second extension, the second extension having a wall and a second passageway extending through the second extension along an axial centerline of the second extension such that the wall of the second extension at least partially surrounds the second passageway; and a first opening extending through the wall of the first extension;

wherein:

the first opening and the wall of the first extension adjacent to the first opening are sized and configured such that the second extension can be advanced through the first opening so that the second extension is restrained within the first opening and positionable at an acute angle relative to an axial centerline of the first extension.

2. The system of Embodiment 1, wherein the first extension is removably coupleable with the first screw such that, when the first extension is coupled with the first screw, the axial centerline of the first extension is approximately collinear with an axial centerline of the first screw and wherein the second extension is removably coupleable with the second screw such that, when the second extension is coupled with the second screw, an axial centerline of the second extension is approximately collinear with an axial centerline of the second screw.

3. The system of Embodiment 1 or 2, wherein the first extension and the second extension are generally cylindrically shaped.

4. The system of any one of the previous Embodiments, wherein the first extension and the second extension are generally rigid.

5. The system of any one of the previous Embodiments, wherein the first extension and the second extensions have a tubular shape.

6. The system of any one of the previous Embodiments, wherein at least a distal portion of the first extension has an adjustable length.

7. The system of any one of the previous Embodiments, wherein the first screw is configured to be implanted in a first vertebra and the second screw is configured to be implanted into a second vertebra.

8. The system of any one of the previous Embodiments, wherein the first extension is sized and configured such that, in an operable state, a proximal portion of the first extension extends away from a skin incision toward a surgeon.

9. The system of any one of the previous Embodiments, wherein an inside size of the wall of the first extension adjacent to the first opening in the first extension is greater than an outside size of at least a portion of the wall of the second extension such that at least a portion of the second extension can be passed through the first opening of the first extension at an acute angle relative to the axial centerline of the first extension and be at least partially surrounded by the wall of the first extension.

10. The system of any one of the previous Embodiments, wherein:

a proximal portion of the first extension has an inside cross-sectional size that is greater than an inside cross-sectional size of a distal portion of the first extension; and the inside cross-sectional size of the proximal portion of the first extension is also greater than an outside cross-sectional size of at least a distal portion of the second extension so that at least the distal portion of the second extension can be advanced completely through the first opening of the first extension.

11. The system of any one of the previous Embodiments, wherein the first opening in the first extension passes through the wall of the first extension at an angle that is acute to the axial centerline of the first extension.

12. The system of any one of the previous Embodiments, wherein the first opening comprises a first cutout in a first side of the wall and a second cutout in a second side of the wall of the first extension, wherein: the second side of the wall is opposite to the first side of the wall; the second cutout is separate from the first cutout such that the first and second cutouts are not overlapping or connected; and the second cutout is positioned closer to a distal end of the first extension than the first cutout.

13. The system of Embodiment 12, wherein the first cutout extends in a distal direction from a proximal end of the first extension such that the wall of the first extension does not form a complete or continuous enclosure around the first passageway at the proximal end of the first extension.

14. The system of Embodiment 12 or 13, wherein the first cutout removes at least approximately 40% of the wall of the first extension at least the proximal end of the first extension.

15. The system of any one of Embodiments 12-14, wherein the first cutout extends along a length of the first extension that is at least approximately 30% of a total length of the first extension.

16. The system of any one of Embodiments 12-15, wherein the first cutout extends along a length of the first extension that is at least approximately 40% of a total length of the first extension.

17. The system of any one of Embodiments 12-16, wherein a distal edge of the first cutout is planar and is angled downwardly toward the distal end of the first extension.

18. The system of any one of Embodiments 12-17, wherein a proximal portion of the second cutout overlaps a distal portion of the first cutout in an axial direction.

19. The system of any one of Embodiments 12-18, wherein the second cutout is positioned between a proximal end and the distal end of the first extension such that a proximal end of the second cutout is spaced apart from the proximal end of the first extension and a distal end of the second cutout is spaced apart from the distal end of the first extension.

20. The system of any one of Embodiments 12-19, wherein the second cutout removes at least approximately 40% of the wall of the first extension in at least a middle portion of the first extension.

21. The system of any one of Embodiments 12-20, wherein the second cutout extends along a length of the first extension that is at least approximately 30% of a total length of the first extension.

22. The system of any one of Embodiments 12-21, wherein the second cutout extends along a length of the first extension that is at least approximately 40% of a total length of the first extension.

23. The system of any one of Embodiments 12-22, wherein a proximal edge of the second cutout is curved.

24. The system of any one of Embodiments 12-23, wherein a distal edge of the second cutout is planar and is angled downwardly toward the distal end of the first extension.

25. The system of any one of the previous Embodiments, wherein the first extension and the second extension are configured such that, in an operable state wherein the second extension is advanced through the first opening in the first extension, moving a proximal end of the first extension either toward or away from a proximal end of the second extension will cause the second extension to hinge about an edge of the first opening and rotate relative to first extension about the edge of the first opening in the first extension so as to cause the distal end of the second extension to move toward or away from the distal end of the first extension, respectively.

26. The system of any one of the previous Embodiments, wherein the first extension and the second extension are configured such that, in an operable state wherein the second extension is advanced through the first opening in the first extension, a contact between an outside surface of the wall of the second extension and the wall of the first extension surrounding the first opening will result in a hinge that the second extension can rotate about relative to the first extension.

27. The system of any one of the previous Embodiments, wherein the first extension is configured such that, in an operable state, when the second extension is advanced through the first opening in the first extension, the wall of the first extension surrounding the first opening prevents the second extension from rotating relative to the first extension beyond a predetermined amount.

28. The system of any one of the previous Embodiments, wherein the first extension is configured such that, in an operable state, when the second extension is advanced through the first opening in the first extension and rotated so as to be in contact with the wall of the first extension adjacent to the first opening, the wall of the first extension surrounding the first opening restrains a rotation of the second extension relative to the first extension so that moving a proximal end of the first extension either toward or away from a proximal end of the second extension will cause the distal end of the second extension to move toward or away from the distal end of the first extension, respectively.

29. The system of any one of the previous Embodiments, wherein a proximal portion of the first extension is configured to be grasped by a surgeon to enable a surgeon to exert a rotational force on the first extension about at least the axial centerline of the distal portion of the first extension and/or a torque force on the first extension so as to cause the first extension to rotate about an axis that is perpendicular to an axial centerline of the distal portion of the first extension.

30. The system of any one of the previous Embodiments, wherein the second extension comprises a second opening extending through the wall of the second extension, and wherein the second opening and the second extension adjacent to the second opening are sized and configured such that a third extension can be advanced through the second opening in an operable state so that the third extension is angled at an acute angle relative to an axial centerline of the second extension.

31. The system of Embodiment 30, wherein the first extension and the second extension are configured such that the third extension can be advanced through the first opening in in the first extension and through the second opening in the second extension in an operable state so that the third extension is angled at an acute angle relative to the axial centerline of the first extension and the axial centerline of the second extension.

32. The system of Embodiment 30 or 31, wherein a distal end of the third extension is positioned between the distal end of first extension and a distal end of the second extension in an operable state.

33. The system of any one of Embodiments 30-32, wherein the third extension has a tubular shape.

34. The system of any one of the previous Embodiments, wherein the second extension comprises at least one slot extending through the wall of the second extension, the at least one slot of the second extension being configured to receive a connecting element that is configured to extend between the first and second screws in an operable state.

35. The system of any one of the previous Embodiments, further comprising:
  a rigid connecting element;
  a first receiving element coupled with the first screw head; and a second receiving element coupled with the second screw head;
  wherein the first and second receiving elements are configured to operably receive the connecting element that, in an operable state, extends between the first and second receiving elements when the first and second screws are implanted in a first and a second vertebra, respectively.

36. The system of any one of the previous Embodiments, wherein the first extension comprises a first slot extending through the wall thereof, the first slot of the first extension configured to permit a connecting element configured to extend between the first screw and the second screw in an operable state to be advanced through the first slot.

37. The system of Embodiment 36, wherein the first slot of the first extension extends in a proximal direction from the distal end of the first extension to the second cutout of the first extension.

38. The system of Embodiment 36, wherein the first slot of the first extension has a width that is less than 50% of a width of an outside surface of the first extension.

39. The system of any one of the previous Embodiments, wherein the second extension comprises a first slot extending through the wall of the second extension, the first slot of the second extension configured to permit a connecting element configured to extend between the first screw and the second screw in an operable state to be advanced through the first slot of the second extension.

40. The system of Embodiment 39, wherein the first slot of the second extension extends in a proximal direction from the distal end of the second extension to the second cutout of the second extension.

41. The system of Embodiment 39, wherein the first slot of the second extension has a width that is less than 50% of a width of an outside surface of the second extension.

42. The system of Embodiment 39, wherein the first slot of the second extension is in a first side of the wall of the second extension, and wherein the second extension further comprises a second slot extending through a second side of the wall of the second extension, the second side of the wall of the second extension being opposite to the first side of the wall of the second extension, the second slot of the second extension configured to permit a connecting element configured to extend between the first screw and the second screw in an operable state to be advanced through the second slot of the second extension.

43. The system of Embodiment 42, wherein the second slot of the second extension extends in a proximal direction from the distal end of the second extension and has a length that is approximately 40% or greater of a length of the second extension.

44. A method of stabilizing spinal vertebrae comprising:
  implanting a first screw that is coupled with a first extension through an incision into a first vertebra;
  advancing a second extension that is coupled with a second screw through the incision and through a first opening formed in the first extension so that an axial centerline of the second extension is at an acute angle relative to an axial centerline of the first extension;
  implanting the second screw into a second vertebra;
  moving a proximal portion of the first extension toward a proximal portion of the second extension to cause an outside surface of the second extension to contact at least a distal edge of the first opening in the first extension; and
  further moving the proximal portion of the first extension toward the proximal portion of the second extension to rotate the second extension about at least the distal edge of the first opening to move the distal end portion of the first extension toward the distal end portion of the second extension, thereby moving the first vertebra toward the second vertebra.

45. The method of Embodiment 44, further comprising coupling a rigid connector with the first screw and the second screw to generally fix a position of the first screw relative to the second screw.

46. A system for bone stabilization, comprising:

a first screw comprising a first screw head; and a first guiding element configured to extend away from the first screw, wherein the first guiding element comprises:

a partially enclosed tubular body extending along a first longitudinal axis between a proximal end and a distal end, wherein the distal end of the partially enclosed tubular body is configured to engage with the first screw head; and an opening extending through an intermediate section of the partially enclosed tubular body, the opening oriented at an angle to the first longitudinal axis.

47. The system of Embodiment 46, wherein the partially enclosed tubular body comprises:

a proximal portion proximal to the intermediate section comprising a partially enclosed tubular section having an inner concave surface facing in a first direction and an outer convex surface facing in a second direction opposite to the first direction;

a distal portion distal to the intermediate section comprising a partially enclosed tubular section having an inner concave surface facing in the second direction and an outer convex surface facing in the first direction.

48. The system of Embodiment 47, wherein the proximal portion circumscribes a surface of at least 180°.

49. The system of Embodiment 47 or 48, wherein the distal portion circumscribes a surface of at least 180°.

50. The system of any one of Embodiments 47-49, wherein the distal portion comprises a longitudinal slot extending to the distal end of the partially enclosed tubular body.

51. The system of any one of Embodiments 47-50, further comprising a second screw comprising a second screw head; and a second guiding element configured to extend away from the second screw;

wherein the second guiding element is configured to pass through the opening of the first guiding element.

52. The system of Embodiment 51, wherein the second guiding element comprises:

a partially enclosed tubular body extending along a second longitudinal axis between a proximal end and a distal end, wherein the distal end of the partially enclosed tubular body is configured to engage with the second screw head, and an opening extending through an intermediate section of the partially enclosed tubular body, the opening extending at an angle to the second longitudinal axis.

53. The system of Embodiment 52, wherein the partially enclosed tubular body of the second guiding element comprises:

a proximal portion proximal to the intermediate section comprising a partially enclosed tubular section having an inner concave surface facing in a third direction and an outer convex surface facing in a fourth direction opposite to the third direction; and a distal portion distal to the intermediate section comprising a partially enclosed tubular section having an inner concave surface facing in the fourth direction and an outer convex surface facing in the third direction.

54. The system of Embodiment 53, further comprising a third screw comprising a third screw head; and a third guiding element configured to extend away from the third screw;

wherein the third guiding element is configured to pass through the openings of the first guiding element and the second guiding element.

55. The system of Embodiment 54, wherein the third guiding element comprises a tubular body.

56. The system of Embodiment 55, wherein the third guiding element comprises a longitudinal slot to facilitate passage of a rod.

57. The system of any one of Embodiments 46-56, further comprising a rod inserter configured to deliver a rod.

58. The system of Embodiment 57, further comprising a rod trapper configured to release the rod from the rod inserter.

59. A system for bone stabilization, comprising:

a plurality of guiding elements, wherein each of the plurality of guiding elements comprises:

a partially enclosed tubular body extending between a proximal end and a distal end, wherein the distal end of the partially enclosed tubular body is configured to engage with a screw head; and an opening extending through an intermediate section of the partially enclosed tubular body, the opening oriented at an angle to a longitudinal axis of the guiding element;

wherein the opening of each of the plurality of guiding elements is sized and configured to allow for passage of another guiding element therethrough.

60. The system of Embodiment 59, wherein the plurality of guiding elements comprises a first guiding element and a second guiding element each comprising:

a proximal portion proximal to the intermediate section comprising a partially enclosed tubular section having an inner concave surface facing in a first direction and an outer convex surface facing in a second direction opposite to the first direction; and a distal portion distal to the intermediate section comprising a partially enclosed tubular section having an inner concave surface facing in the second direction and an outer convex surface facing in the first direction;

wherein the second guiding element is configured to pass through the opening in the first guiding element, and wherein the inner concave surfaces of the proximal portions of the first and second guiding elements face each when the second guiding element passes through the opening in the first guiding element.

61. The system of Embodiment 59 or 60, wherein the plurality of guiding elements comprises a first guiding element, a second guiding element, and a third guiding element, wherein the opening extending through the intermediate section of the first guiding element is sized and configured to allow for passage of the second guiding element therethrough, and wherein the opening extending through the intermediate section of the third guiding element is sized and configured to allow for passage of the first and the second guiding elements therethrough when the second guiding element is passed through the opening of the first guiding element.

Systems, Devices and Methods of FIGS. 5A-5K

Described below are embodiments directed to a system 500 for stabilizing spinal vertebrae through a skin incision S. In any embodiments disclosed herein, any components, features, or other details of the system 500 can have any of the components, features, or other details of any other system embodiments disclosed herein or be used according to any of the steps of any other method embodiments disclosed herein, including without limitation any of the embodiments of the system 200, 300, and/or 400 or methods of use thereof described above, in any combination with any of the components, features, or details of the system 500 or methods of use disclosed below. Similarly, any components, features, steps, or other details of any of the other system or method embodiments disclosed herein can have any of the components, features, steps, or other details of any embodiments of the system 500 or methods of use thereof disclosed herein in any combination with any of the components, features, or details of the system.

In any embodiments disclosed herein, the system 500 can have blades that have openings that can be positioned at various lengths relative to the screw head, for example. The openings can be sized and configured to allow other screws and towers or other guiding elements or extensions to pass through the openings.

In any embodiments disclosed herein, the blades can then be attached to or coupled with the screw by any appropriate attachment mechanisms. In some embodiments, one or more wires including, without limitation, wires 140a, 140b, can be used to couple the blades with the screw heads. Then, when the desired number of towers are engaged with the screw heads, in any embodiments disclosed herein, one or more connectors or caps can couple each pair of blades together to close the towers and also increase the rigidity of the blades and towers. Additionally, in any embodiments disclosed herein, the blades can have one or more stiffeners or reinforcements proximal to or distal to the openings to increase the bending stiffness of the blades or the proximal and distal portions of the blades can have an increased stiffness to reduce the flexibility of the towers during use.

In some embodiments, the system 500 can include a first screw 502 that can include a first screw head 504, the first screw head 504 including a first side 506 and a second side 508, the first side 506 and the second side 508 being opposite each other, and a first guiding element 510 configured to extend away from the first screw 502. In any embodiments disclosed herein, the first guiding element 510 can include a first blade 520 extending along a first longitudinal axis A1 between a proximal end 520a and a distal end 520a of the first blade 520. The first blade 520 can include a curved intermediate section 524 between the proximal and distal ends 520a, 520b. The distal end 520b of the first blade 520 can be configured to engage with or couple with the first side 506 of the first screw head 504.

The first guiding element 510 can further include a second blade 530 extending along a second longitudinal axis A2 between a proximal end 530a and a distal end 530b. The second blade 530 can include a curved intermediate section 534 between the proximal and distal ends 530a, 530b. The distal end 530b of the second blade 530 can be configured to engage with the second side 508 of the first screw head 504. The first guiding element 510 can be configured such that, when the distal end 520b of the first blade 520 and the distal end 530b of the second blade 530 are engaged with the first screw head 504, an inner surface 520c of the first blade 520 faces an inner surface 530c of the second blade 530 and is spaced therefrom. Further, in some embodiments, the curved intermediate sections 524, 534 of the first and second blades 520, 530 can form an enlarged opening 540 with an increased spacing between the inner surfaces 520c, 530c of the first and second blades 520, 530 relative to a spacing between the inner surfaces of the first blade 520 and the second blade 530 proximal and distal to the intermediate sections 524, 534.

In any embodiments, the first and second longitudinal axes A1, A2 can be parallel to one another when the distal ends 520b, 530b of the first blade 520 and the second blade 530 are engaged with the first screw head 504. Further, in some embodiments, the curved intermediate sections of each of the first blade 520 and the second blade 530 can be bowed outwardly and can have a curved or rounded shape. In any other embodiments, the intermediate sections of each of the first blade 520 and the second blade 530 can be bend bowed outwardly to a midpoint of the intermediate sections and can have an angled or a tapered shape. The first blade 520 and the second blade 530 can bend inwardly proximal to the midpoint of the intermediate sections.

In some embodiments, the enlarged opening 540 of the first guiding element 510 can be oriented parallel or substantially parallel to the inner surfaces of the first and second blades 520, 530. Further, in any embodiments disclosed herein, each of the first blade 520 and the second blade 530, and/or any blade of any guiding element disclosed herein, can have a substantially uniform cross-sectional thickness from the proximal end to the distal end.

In some embodiments, the enlarged opening 540 of the first guiding element 510 can be configured to allow passage of a subsequently advanced guiding element or a plurality of subsequently advanced guiding elements therethrough, including without limitation an enlarged intermediate portion of a subsequently advanced guiding element or subsequently advanced guiding elements. For example and without limitation, in some embodiments, the enlarged opening 540 between the first blade 520 and the second blade 530 can be sized and configured to allow for passage of the second screw and the second guiding element 510 therethrough, including the enlarged intermediate section of the second guiding element.

Figures 5A, 5B:
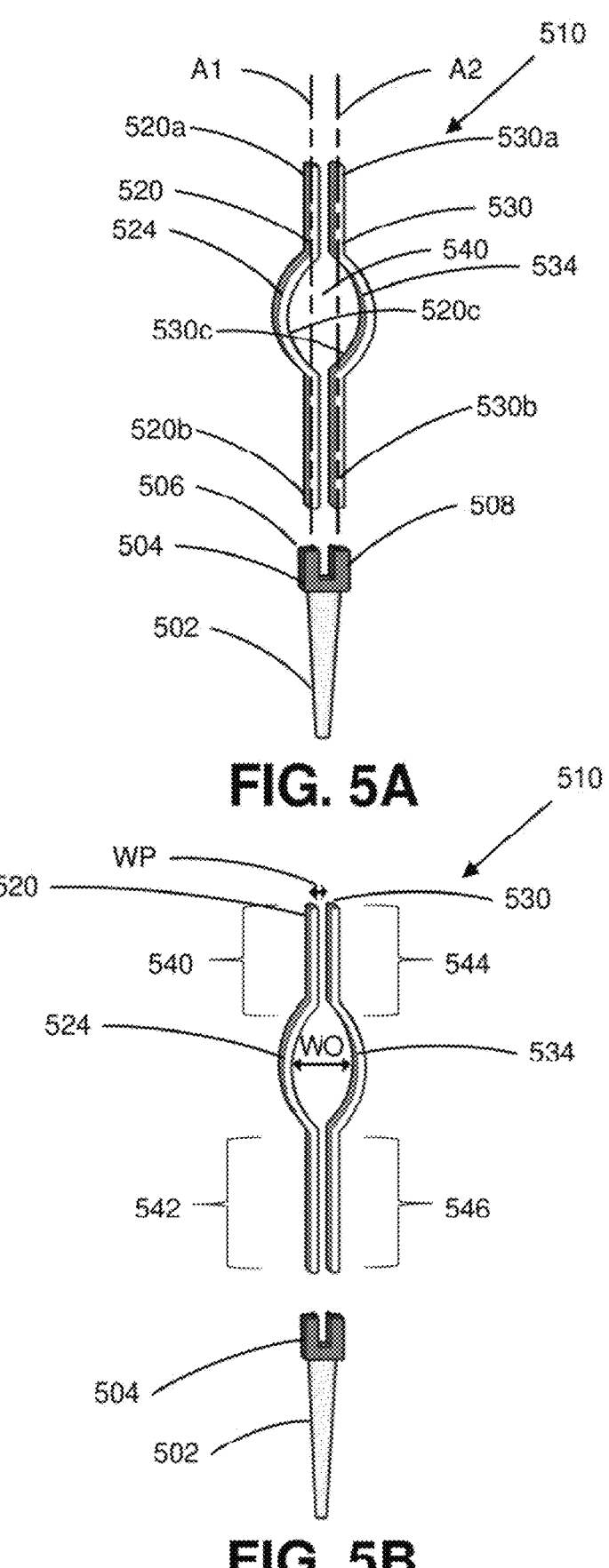

With reference to FIG. 5B, some embodiments of the guiding element 510 can be configured such that the first blade 520 has a proximal section 540 and a distal section 542 and the second blade 530 has a proximal section 544 and a distal section 546, wherein the intermediate section 524 of the first blade 520 is between the proximal and distal sections 540, 542 of the first blade 520, and wherein the intermediate section 534 of the second blade 530 is between the proximal and distal sections 540, 542 of the second blade 530. In any embodiments disclosed herein, the proximal sections 540, 544 of the first and second blades 520, 530 and/or the distal sections 542, 546 of the first and second blades 520, 530 can be planar or substantially planar and parallel to each other.

In some embodiments, a distance of the increased spacing (e.g., at the enlarged opening 540) between the inner surfaces of the third and fourth blades 560, 564 of a second guiding element 550 can be less than a distance of the increased spacing (e.g., the enlarged opening 540) between the inner surfaces of the first blade 520 and the second blade 530. For example and without limitation, in any embodiments disclosed herein, a width WO of the guiding element from the inside surface of the first blade to the inside surface of the second blade at the widest point of the opening (as shown in FIG. 5B) can be approximately 100% greater than (i.e., twice as wide as) a width WP from the inside surface of the first blade to the inside surface of the second blade in the proximal portion (e.g., proximal portion 540, 544 of the first and second blades 520, 530), or from 80% (or approximately 80%) greater to 400% (or approximately 400%) or more greater than the width WP from the inside surface of the first blade to the inside surface of the second blade in the proximal portion. In any embodiments disclosed herein, the proximal portion and the distal portion of the guiding elements can have approximately the same width, or can have a different width.

In any embodiments disclosed herein, the guiding elements can have any of a range of lengths suitable for a range of differently sized anatomies, thereby permitting a surgeon to choose the desired length or lengths of the blades and positions of the enlarged openings after measurement of the depth of the tissue, for example. With reference to FIG. 5D, the guiding elements 510 can be provided in varying lengths where the length of the distal portion LD to the distal edge of the enlarged opening 540 can vary. For example and without limitation, kits can be provided wherein the system has a range of guiding elements 510 having a range of overall lengths and a range of lengths LD of the distal portion of the guiding element. As shown in FIG. 5D, some embodiments of the guiding element 510 can have a distal portion having a length LD1 that is less than a second guiding element 510 that has a distal portion having a length LD2. LD2 can also be less than that of a third guiding element 510 that has a distal portion having a length LD3, which can be less than a fourth guiding element 510 that has a distal portion having a length LD4. LD4 can be less than that of a fifth guiding element 510 that has a distal portion having a length LD5. In any embodiments, the overall length and/or the length of the distal portion LD can be 10% (or approximately 10% or less) greater between each of the successive sizes, or 15% (or approximately 15%) greater between each of the successive sizes, or 20% (or approximately 20% more) greater between each of the successive sizes.

For example and without limitation, the enlarged opening of any of the embodiments of the guiding elements disclosed herein can be oriented at any desired angle (for example, a perpendicular angle, or any acute or non-perpendicular angle) relative to a longitudinal axis of the guiding element so that the enlarged opening in the guiding element can be at any desired angle when the distal ends of the first blade and the second blade are engaged with the first screw head.

In some embodiments, with reference to FIGS. 5E-5G, the enlarged opening 540 of the first guiding element 510 can be oriented at an angle relative to an axial centerline axis C (also referred to as a longitudinal axis), for example and without limitation, when the distal ends of the first blade 520 and the second blade 530 are engaged with the first screw head 504. For example, as shown in FIG. 5E, the first opening 540 of the first guiding element 510 (or any other guiding element, including the second guiding element, third guiding element, etc.) can be at an angle A1 relative to the centerline axis C that can be 90° (or approximately) 90°. As shown in FIG. 5F, the first opening 540 of the first guiding element 510 (or any other guiding element, including the second guiding element, third guiding element, etc.) can be at an angle A2 relative to the centerline axis C that can be less than 90°, such as, for example, 70° (or approximately) 70° relative to the centerline axis C, or from 50° (or approximately) 75° relative to the centerline axis C. As shown in FIG. 5G, the first opening 540 of the first guiding element 510 (or any other guiding element, including the second guiding element, third guiding element, etc.) can be at an angle A3 relative to the centerline axis C that can be less than A2, such as, for example, 45° (or approximately) 45° relative to the centerline axis C, or from 30° (or approximately) 30° to 50° (or approximately) 50° relative to the centerline axis C.

In this arrangement, with reference to FIG. 5H, the first guiding element 510 can have an enlarged opening 540 at an angle A relative to the centerline axis C of the first guiding element 510 that can permit the second guiding element 550 to pass therethrough so that the second guiding element 550, in an operable state as shown in FIG. 5H, can be oriented so that a centerline axis C of the second guiding element 550 is also angled at the same angle A relative to the centerline axis as the enlarged opening 540 of the first guiding element. Again, the angle A of the first guiding element can be any desired angle. In any embodiments, the angle of the enlarged opening can be an acute or non-perpendicular angle, such as angle A2 or angle A3 shown in FIGS. 5E, 5F. The angle can range from 20° (or approximately) 20° or less to 70 (or approximately) 70° or more, or from 40° (or approximately) 40° to 60 (or approximately) 60°, within a kit. In any embodiments disclosed herein, the second guiding element 550 or a third guiding element 582 can have generally planar blades as shown, or can also have an enlarged opening configured to permit the passage of a third guiding element therethrough.

Figure 5C:
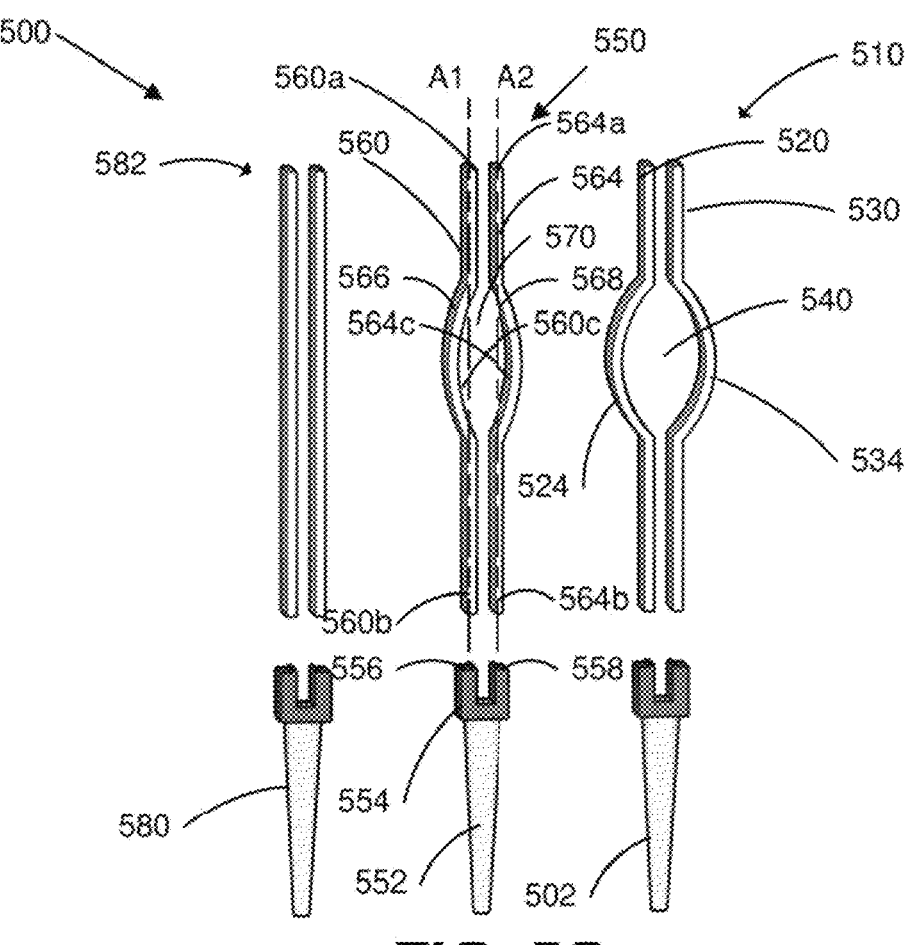
Figure 5D:
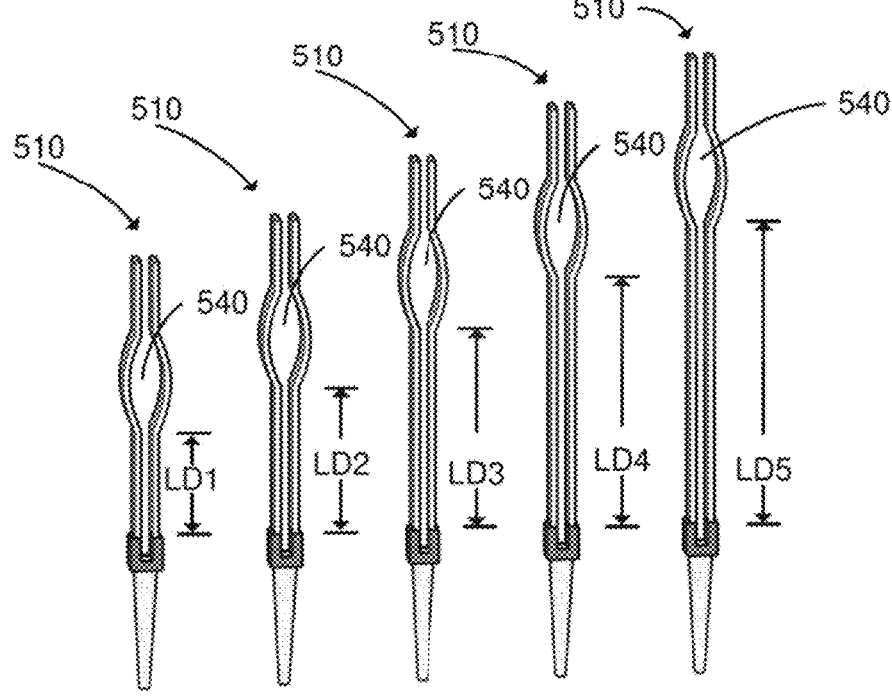
Figure 5I:
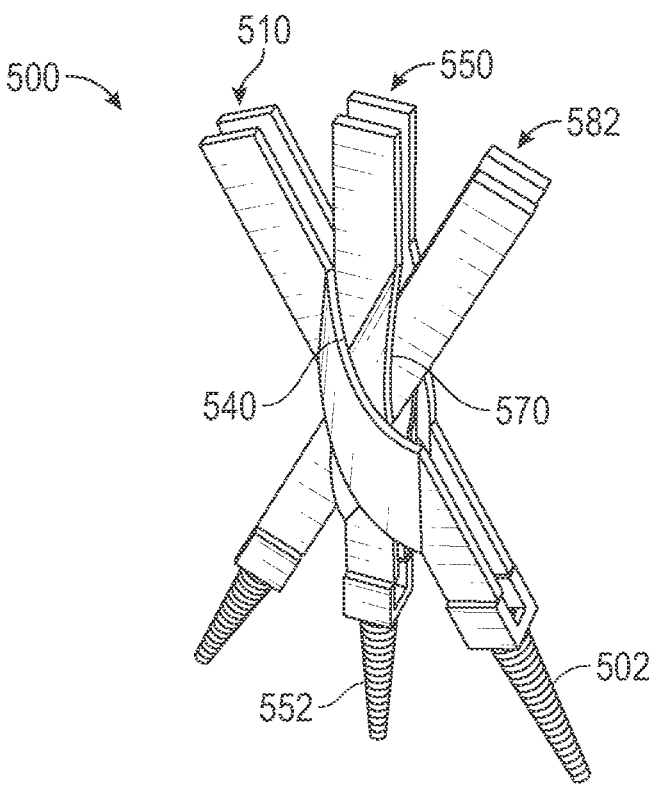
Figure 5J:
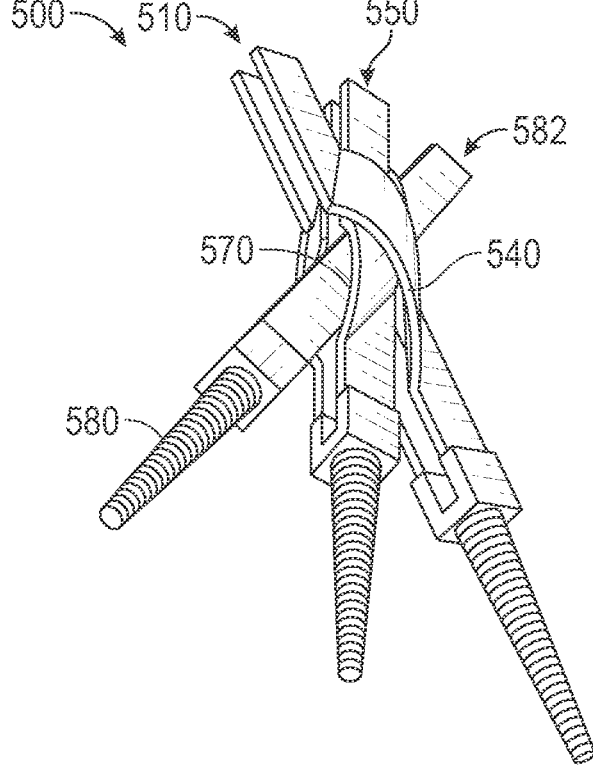

In any embodiments disclosed herein, as shown in FIG. 5C, the system 500 can further include a second guiding element 550 that can have any of the same features, components, and/or other details of any of the embodiments of the first guiding element 510 disclosed herein, including an enlarged opening at any desired angle. The second guiding element 550 can include a second screw 552 that can include a second screw head 554 having a first side 556 and a second side 558 wherein the first side 556 and the second side 558 are opposite each other. The second guiding element 550 can be configured to extend away from the second screw 552 and can include a third blade 560 extending along a third longitudinal axis between a proximal end 560a and a distal end 560b, wherein the distal end 560b of the third blade 560 is configured to engage with the first side 556 of the second screw head 554. The second guiding element 510 can also include a fourth blade 564 extending along a fourth longitudinal axis A4 between a proximal end 564a and a distal end 564b, wherein the distal end 564b of the fourth blade 564 is configured to engage with the second side 558 of the second screw head 554.

Similar to the first blade 520, the third blade 560 can include a curved intermediate section 566 between the proximal and distal ends 560a, 560b and the fourth blade 564 can include a curved intermediate section 568 between the proximal and distal ends 564a, 564b. Further, in some embodiments, the curved intermediate sections 566, 568 of the third and fourth blades 560, 564 can form an enlarged opening 570 with an increased spacing between the inner surfaces 560c, 564c of the third and fourth blades 560, 564 relative to a spacing between the inner surfaces of the first blade 560 and the second blade 564 proximal and distal to the intermediate sections 566, 568.

In some embodiments, the distal ends 560b, 564b of the third and fourth blades can be engaged with the second screw head 554. Further, an inner surface 560c of the third blade 560 can face an inner surface 564c of the fourth blade 564 and can be spaced therefrom.

In some embodiments, with reference to FIGS. 5C and 5I-5K, the enlarged opening 570 of the second guiding element 550 can be configured to allow passage of a subsequently advanced guiding element or a plurality of subsequently advanced guiding elements therethrough, including without limitation an enlarged intermediate portion of a subsequently advanced guiding element or subsequently advanced guiding elements, or a subsequently advanced guiding element having generally straight or planar blades. For example and without limitation, in some embodiments, the enlarged opening 570 between the third blade 560 and the fourth blade 564 can be sized and configured to allow for passage of the third screw 580 and a third guiding element 582 therethrough, wherein the third guiding element 582 has generally planar blades, or guiding elements having enlarged intermediate sections.

Figure 5K:
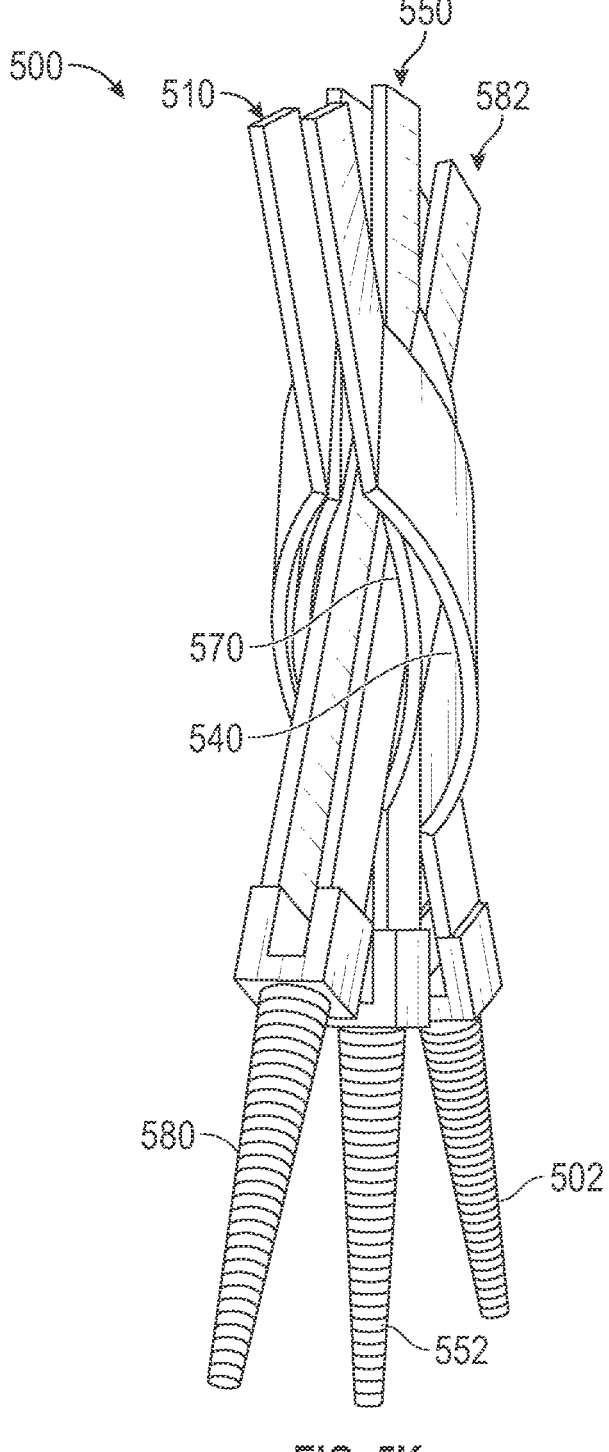

In any embodiments, as shown in FIGS. 51-5K, a size and/or an orientation of the enlarged opening 570 between the third and fourth blades of the second guiding element 550 can be different than the orientation of the enlarged opening 540 between the first blade 520 and the second blade 530 of the first guiding element 540. Further, in any embodiments disclosed herein, a longitudinal position of the enlarged opening of the second guiding element can be different than a longitudinal position of the enlarged opening of the second guiding element.

In some embodiments, the third guiding element can have an enlarged opening that is configured to permit the passage of a first guiding element and a second guiding element therethrough. In some embodiments, the third guiding element can have an enlarged opening having any of the features or details of any of the embodiments disclosed herein and the first guiding element can have an enlarged opening having any of the features or details of any of the embodiments disclosed herein. The second guiding element can have an enlarged opening therein or can have generally planar blades. In some embodiments, the enlarged opening of the third guiding element can be sized and configured to permit the passage of the first and the second guiding elements, and the first guiding element can be sized and configured to permit the passage of the second guiding element.

In some embodiments, the third guiding element can include a fifth blade extending along a fifth longitudinal axis between a proximal end and a distal end, the fifth blade including either a straight or a curved intermediate section between the proximal and distal ends, wherein the distal end of the fifth blade is configured to engage with a first side of a third screw head. In some embodiments, the third guiding element can have a sixth blade extending along a second longitudinal axis between a proximal end and a distal end, the sixth blade that can include a straight or a curved intermediate section between the proximal and distal ends, wherein the distal end of the sixth blade is configured to engage with a second side of the third screw head. An inner surface of the fifth blade can face an inner surface of the sixth blade and can be spaced therefrom, as shown in the figures. In some embodiments, the curved intermediate sections of the fifth and sixth blades can form an enlarged opening with an increased spacing between the inner surfaces of the fifth and sixth blades relative to a spacing between the inner surfaces of the fifth and sixth blades proximal and distal to the intermediate sections.

Further, in some embodiments, a distance of the increased spacing at the enlarged opening, if any, between the inner surfaces of the fifth and sixth blades can be greater than a distance of the increased spacing between the inner surfaces of the first blade 520 and the second blade 530, such that the enlarged opening between the fifth and sixth blades can be sized and configured to allow for passage of the second screw and the second guiding element 510 therethrough and to allow for passage of the first screw 502 and the first guiding element 510 therethrough.

Some embodiments of the system 500 for bone stabilization can include a plurality of guiding elements, wherein each of the plurality of guiding elements can include a first blade 520 that can include a proximal end 520a and a distal end 520b, the first blade 520 including a curved intermediate section 524 between the proximal and distal ends 520a, 520b, and a second blade 530 that can include proximal end 530a and a distal end 530b, the second blade including a curved intermediate section 534 between the proximal and distal ends 530a, 530b. In some embodiments, the distal ends 520b, 530b of the first blade 520 and the second blade 530 can be configured to engage with a bone screw 502 such that, when engaged with the bone screw 502 an inner surface 520c of the first blade 520 faces an inner surface 530c of the second blade 530 and is spaced therefrom. Further, the curved intermediate sections 524, 534 of the first blade 520 and the second blade 530 can form an enlarged opening 540 with an increased spacing between the inner surfaces 520c, 530c of the first blade 520 and the second blade 530 relative to a spacing between the inner surfaces 520c, 530c of the first blade 520 and the second blade 530 proximal and distal to the intermediate sections 524, 534. Further, in some embodiments, the first blade 520 and the second blade 530 of a first guiding element 510 of the plurality of guiding elements can form an enlarged opening 540 having a different longitudinal position, a different spacing between the inner surfaces of the first blade 520 and the second blade 530, and/or a different orientation as compared to the enlarged opening formed by the first blade 560 and the second blade 564 of a second guiding element 550 of the plurality of guiding elements.

Further, in some embodiments, wherein the system 500 includes a third guiding element having an enlarged opening, a first blade and a second blade of the third guiding element of the plurality of guiding elements can form an enlarged opening having a different longitudinal position, a different spacing between the inner surfaces of the first and second blades, and/or a different orientation as compared to the enlarged opening formed by the first and second blades of the second of the plurality of guiding elements and as compared to the enlarged opening formed by the first and second blades of the first of the plurality of guiding elements. The third guiding element can be coupled with a screw head of a third screw.

Further, in some embodiments, wherein the system 500 includes a fourth guiding element having an enlarged opening, the first and second blades of the fourth guiding element of the plurality of guiding elements can form an enlarged opening having a different longitudinal position, a different spacing between the inner surfaces of the first and second blades, and/or a different orientation as compared to the enlarged opening formed by the first and second blades of the third of the plurality of guiding elements, as compared to the enlarged opening formed by the first and second blades of the second of the plurality of guiding elements, and as compared to the enlarged opening formed by the first and second blades of the first of the plurality of guiding elements. The fourth guiding element can be coupled with a screw head of a fourth screw.

Further, in some embodiments, wherein the system 500 includes a fifth guiding element having an enlarged opening, the first and second blades of the fifth guiding element can form an enlarged opening having a different longitudinal position, a different spacing between the inner surfaces of the first and second blades, and/or a different orientation as compared to the enlarged opening formed by the first and second blades of the fourth of the plurality of guiding elements, as compared to the enlarged opening formed by the first and second blades of the third of the plurality of guiding elements, as compared to the enlarged opening formed by the first and second blades of the second of the plurality of guiding elements, and as compared to the enlarged opening formed by the first and second blades of the first of the plurality of guiding elements. The fifth guiding element can be coupled with a screw head of a fifth screw.

Certain aspects of the systems, devices, components and/or methods described above or as illustrated with respect to FIGS. 5A-5K are also encompassed by the following numbered embodiments. These numbered embodiments are considered to be directed to systems, devices, components and/or methods that include but are not limited to the embodiments of FIGS. 5A-5K, and thus these numbered embodiments may encompass other embodiments as described throughout this specification.

1. A system for bone stabilization, comprising:
a first screw comprising a first screw head, the first screw head comprising a first side and a second side, the first side and the second side being opposite each other; and
a first guiding element configured to extend away from the first screw, wherein the first guiding element comprises:
a first blade extending along a first longitudinal axis between a proximal end and a distal end, the first blade comprising a curved intermediate section between the proximal and distal ends, wherein the distal end of the first blade is configured to engage with the first side of the first screw head, and
a second blade extending along a second longitudinal axis between a proximal end and a distal end, the second blade comprising a curved intermediate section between the proximal and distal ends, wherein the distal end of the second blade is configured to engage with the second side of the first screw head;
wherein when the distal ends of the first and second blades are engaged with the first screw head:
an inner surface of the first blade faces an inner surface of the second blade and is spaced therefrom; and
the curved intermediate sections of the first and second blades form an enlarged opening with an increased spacing between the inner surfaces of the first and second blades relative to a spacing between the inner surfaces of the first and second blades proximal and distal to the intermediate sections.

2. The system of Embodiment 1, wherein each of the first blade and the second blade comprises a proximal section and a distal section, wherein the intermediate section is between the proximal and distal sections, and the proximal and distal sections are planar or substantially planar and parallel to each other.

3. The system of any one of the preceding Embodiments, wherein the enlarged opening is oriented at an angle relative to the first and second longitudinal axes when the distal ends of the first and second blades are engaged with the first screw head.

4. The system of any one of the preceding Embodiments, wherein the enlarged opening is oriented parallel or substantially parallel to the inner surfaces of the first and second blades.

5. The system of any one of the preceding Embodiments, wherein the first and second longitudinal axes are parallel to one another when the distal ends of the first and second blades are engaged with the first screw head.

6. The system of any one of the preceding Embodiments, wherein each of the curved intermediate sections of the first and second blades is bowed outward.

7. The system of any one of the preceding Embodiments, wherein each of the first and second blades has a substantially uniform cross-sectional thickness from the proximal end to the distal end.

8. The system of any one of the preceding Embodiments, further comprising:
a second screw comprising a second screw head, the second screw head comprising a first side and a second side, the first side and the second side opposite each other;
a second guiding element configured to extend away from the second screw, wherein the second guiding element comprises:
a third blade extending along a third longitudinal axis between a proximal end and a distal end, wherein the distal end of the third blade is configured to engage with the first side of the second screw head, and
a fourth blade extending along a fourth longitudinal axis between a proximal end and a distal end, wherein the distal end of the fourth blade is configured to engage with the second side of the second screw head;
wherein the enlarged opening between the first and second blades is sized and configured to allow for passage of the second screw and the second guiding element therethrough.

9. The system of Embodiment 8, wherein the third blade of the second guiding element comprises a curved intermediate section between the proximal and distal ends, and the fourth blade of the second guiding element comprises a curved intermediate section between the proximal and distal ends, and wherein when the distal ends of the third and fourth blades are engaged with the second screw head:
an inner surface of the third blade faces an inner surface of the fourth blade and is spaced therefrom; and
the curved intermediate sections of the third and fourth blades form an enlarged opening with an increased spacing between the inner surfaces of the third and fourth blades relative to a spacing between the inner surfaces of the third and fourth blades proximal and distal to the intermediate sections.

10. The system of Embodiment 9, wherein a distance of the increased spacing between the inner surfaces of the third and fourth blades is less than a distance of the increased spacing between the inner surfaces of the first and second blades.

11. The system of Embodiment 9 or 10, wherein an orientation of the enlarged opening between the third and fourth blades is different from the orientation of the enlarged opening between the first and second blades.

12. The system of any one of Embodiment 9-11, wherein a longitudinal position of the enlarged opening between the third and fourth blades is different from a longitudinal position of the enlarged opening between the first and second blades.

13. The system of Embodiment 8, wherein each of the third and fourth blades of the second guiding element are entirely planar or entirely substantially planar from the proximal end to the distal end.

14. The system of any one of Embodiments 8-13, further comprising:

a third screw comprising a third screw head, the third screw head comprising a first side and a second side, the first side and the second side opposite each other;

a third guiding element configured to extend away from the third screw, wherein the third guiding element comprises:

a fifth blade extending along a fifth longitudinal axis between a proximal end and a distal end, the fifth blade comprising a curved intermediate section between the proximal and distal ends, and wherein the distal end of the fifth blade is configured to engage with the first side of the third screw head, a sixth blade extending along a second longitudinal axis between a proximal end and a distal end, the sixth blade comprising a curved intermediate section between the proximal and distal ends, wherein the distal end of the sixth blade is configured to engage with the second side of the third screw head;

wherein when the distal ends of the fifth and sixth blades are engaged with the third screw head:

an inner surface of the fifth blade faces an inner surface of the sixth blade and is spaced therefrom;

the curved intermediate sections of the fifth and sixth blades form an enlarged opening with an increased spacing between the inner surfaces of the fifth and sixth blades relative to a spacing between the inner surfaces of the fifth and sixth blades proximal and distal to the intermediate sections; and a distance of the increased spacing between the inner surfaces of the fifth and sixth blades is greater than a distance of the increased spacing between the inner surfaces of the first and second blades, such that the enlarged opening between the fifth and sixth blades is sized and configured to allow for passage of the second screw and the second guiding element therethrough and to allow for passage of the first screw and the first guiding element therethrough.

15. A system for bone stabilization, comprising:

a plurality of guiding elements, wherein each of the plurality of guiding elements comprises:

a first blade comprising a proximal end and a distal end, the first blade comprising a curved intermediate section between the proximal and distal ends; and a second blade comprising proximal end and a distal end, the second blade comprising a curved intermediate section between the proximal and distal ends;

wherein the distal ends of the first and second blades are configured to engage with a bone screw such that, when engaged with the bone screw:

an inner surface of the first blade faces an inner surface of the second blade and is spaced therefrom; and the curved intermediate sections of the first and second blades form an enlarged opening with an increased spacing between the inner surfaces of the first and second blades relative to a spacing between the inner surfaces of the first and second blades proximal and distal to the intermediate sections;

wherein the first and second blades of a first of the plurality of guiding elements form an enlarged opening having a different longitudinal position, a different spacing between the inner surfaces of the first and second blades, and/or a different orientation as compared to the enlarged opening formed by the first and second blades of a second of the plurality of guiding elements.

16. The system of Embodiment 15, wherein the first and second blades of a third of the plurality of guiding elements form an enlarged opening having a different longitudinal position, a different spacing between the inner surfaces of the first and second blades, and/or a different orientation as compared to the enlarged opening formed by the first and second blades of the second of the plurality of guiding elements and as compared to the enlarged opening formed by the first and second blades of the first of the plurality of guiding elements.

17. The system of Embodiment 16, wherein the first and second blades of a fourth of the plurality of guiding elements form an enlarged opening having a different longitudinal position, a different spacing between the inner surfaces of the first and second blades, and/or a different orientation as compared to the enlarged opening formed by the first and second blades of the third of the plurality of guiding elements, as compared to the enlarged opening formed by the first and second blades of the second of the plurality of guiding elements, and as compared to the enlarged opening formed by the first and second blades of the first of the plurality of guiding elements.

18. The system of Embodiment 17, wherein the first and second blades of a fifth of the plurality of guiding elements form an enlarged opening having a different longitudinal position, a different spacing between the inner surfaces of the first and second blades, and/or a different orientation as compared to the enlarged opening formed by the first and second blades of the fourth of the plurality of guiding elements, as compared to the enlarged opening formed by the first and second blades of the third of the plurality of guiding elements, as compared to the enlarged opening formed by the first and second blades of the second of the plurality of guiding elements, and as compared to the enlarged opening formed by the first and second blades of the first of the plurality of guiding elements.

Figure 6A:
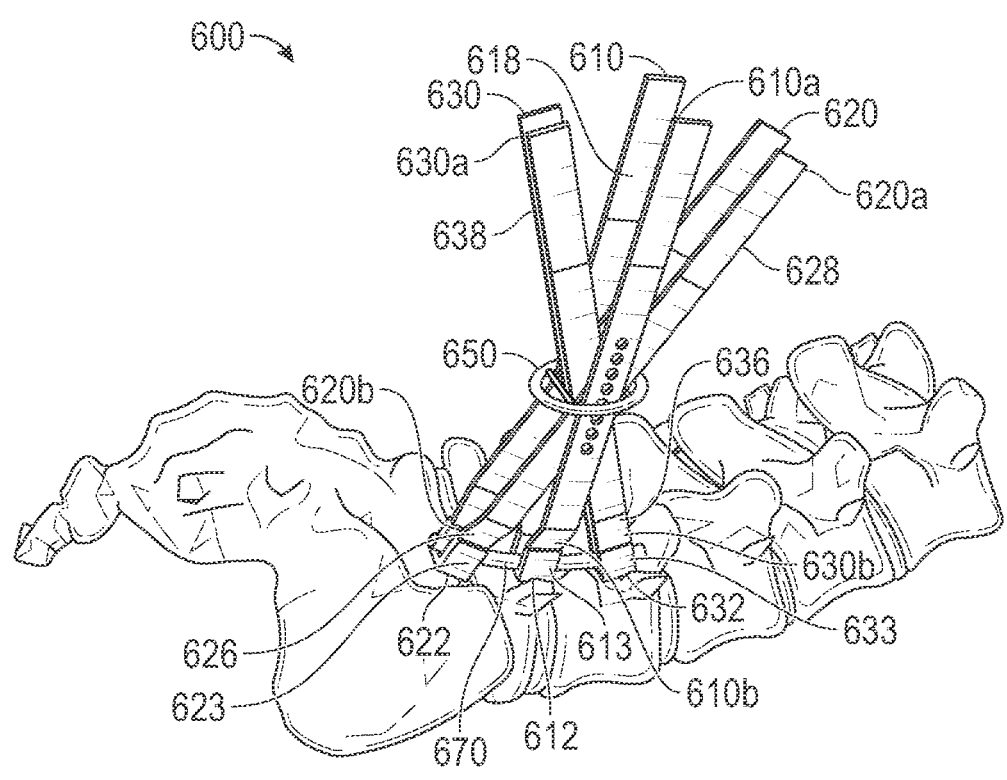
FIGS. 6A-6V illustrate another embodiment of a method and a system for stabilizing spinal vertebrae comprising spinal screws.
Figure 6B:
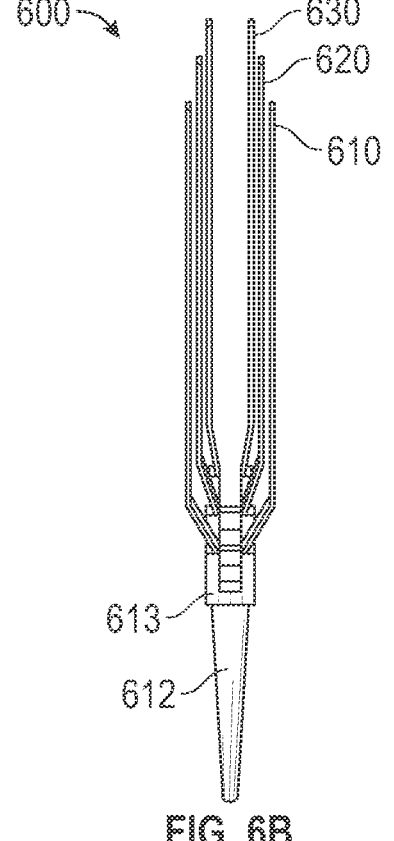
Figure 6G:
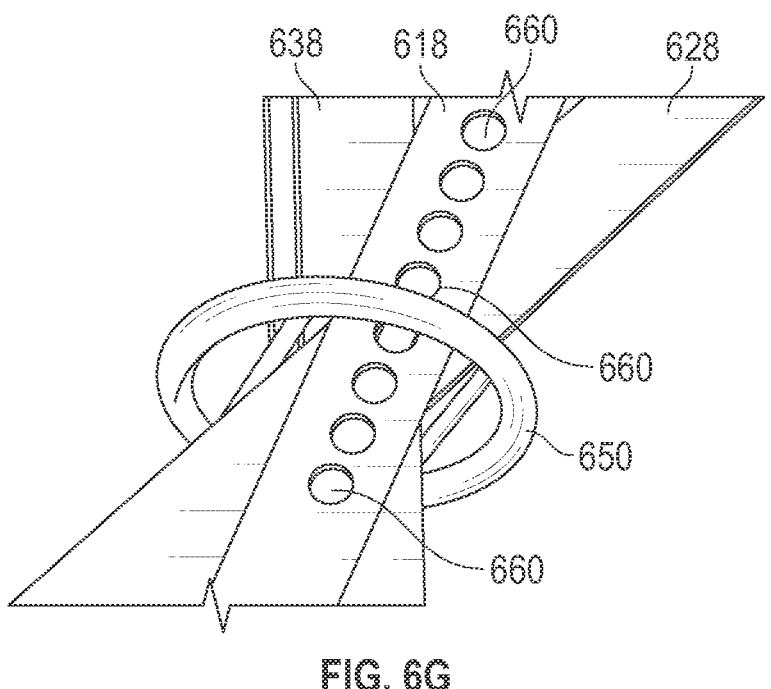
Figure 6H:
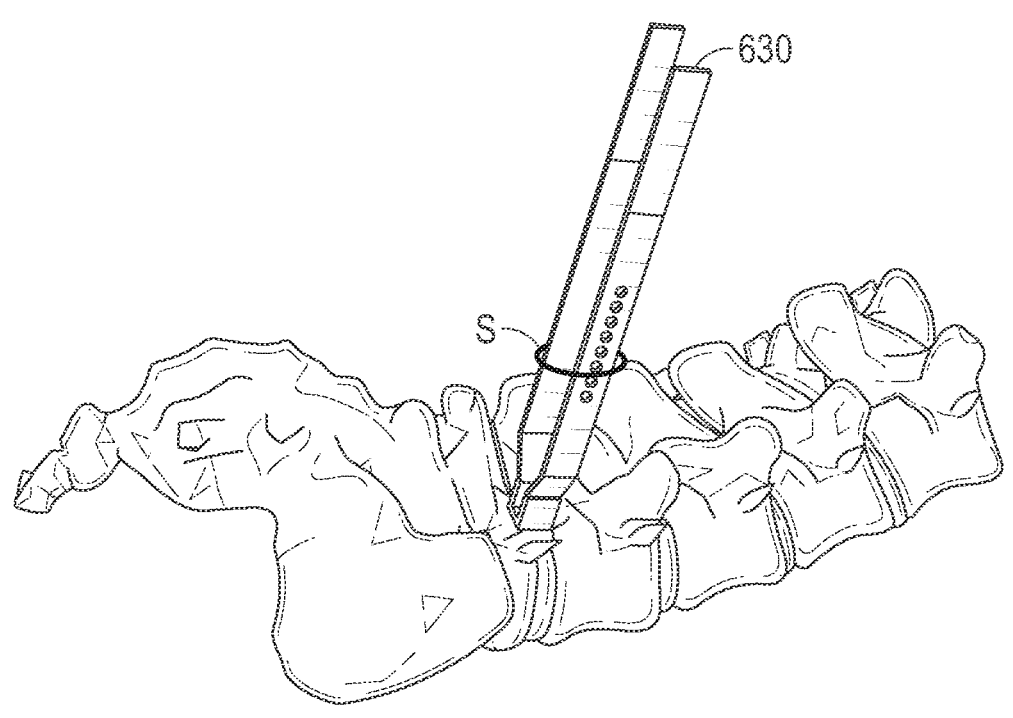
Figure 6I:
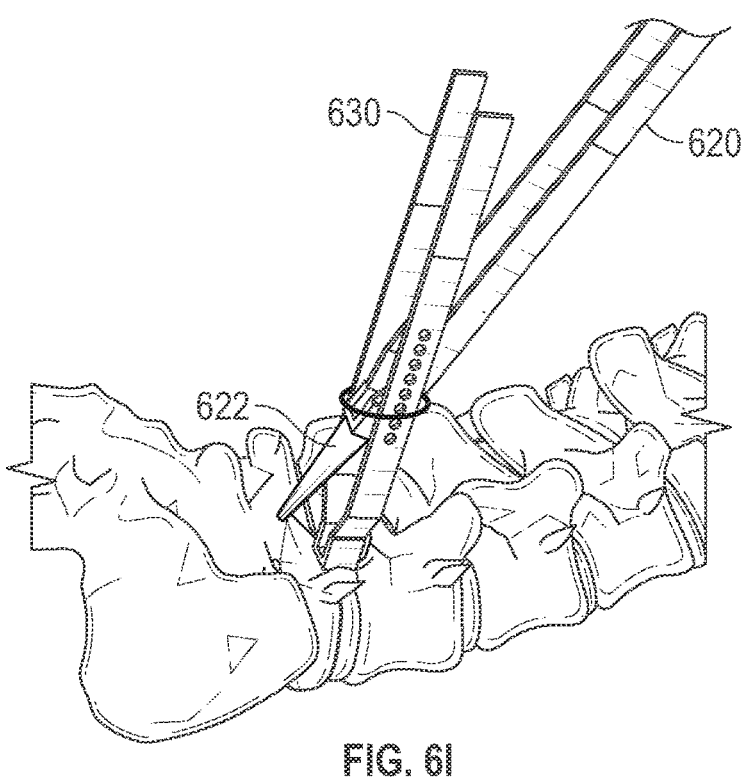
Figure 6J:
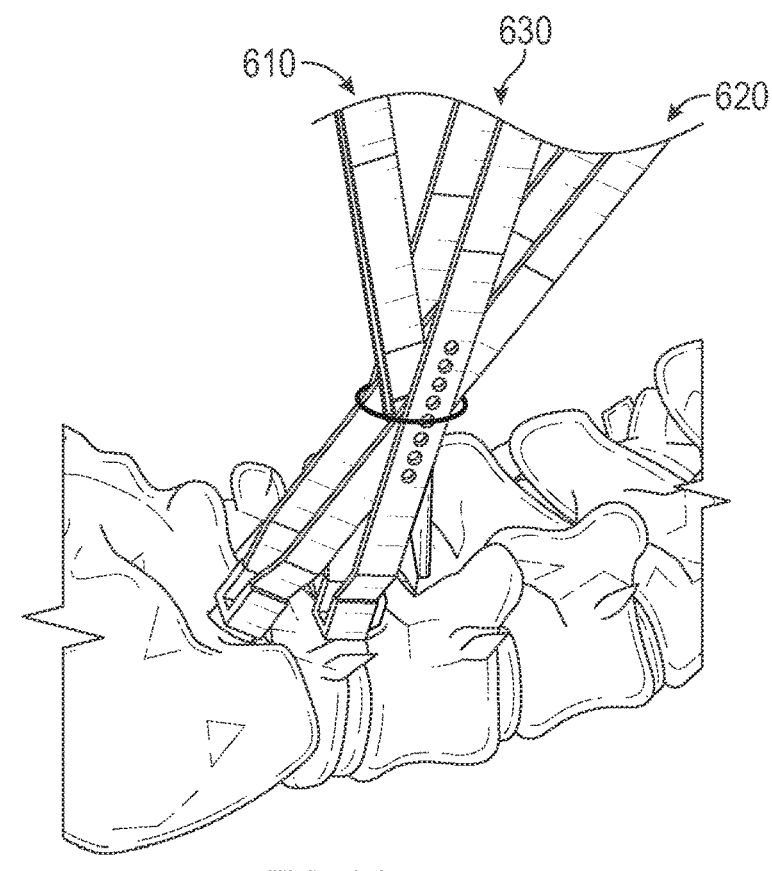
Figure 6K:
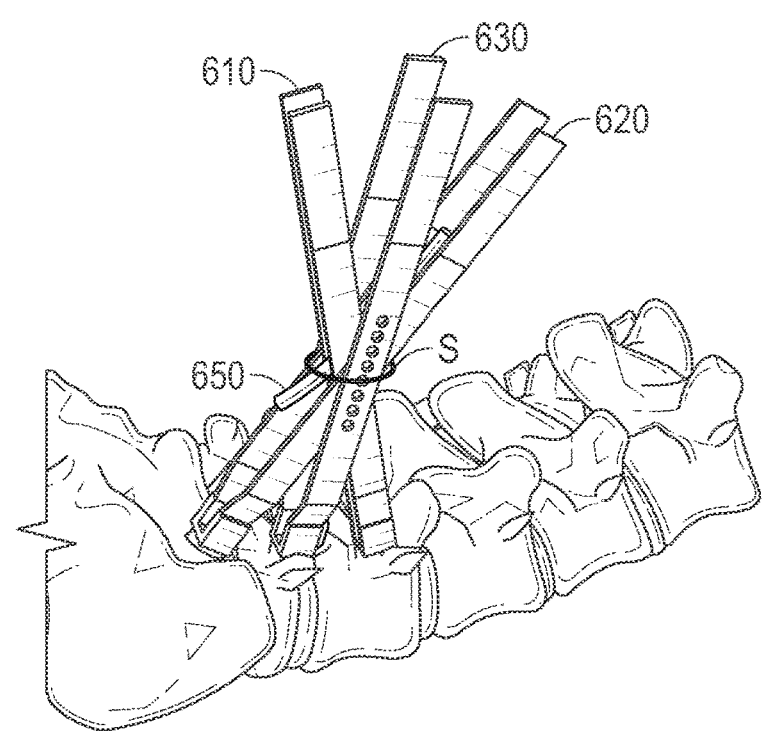
Figure 6L:
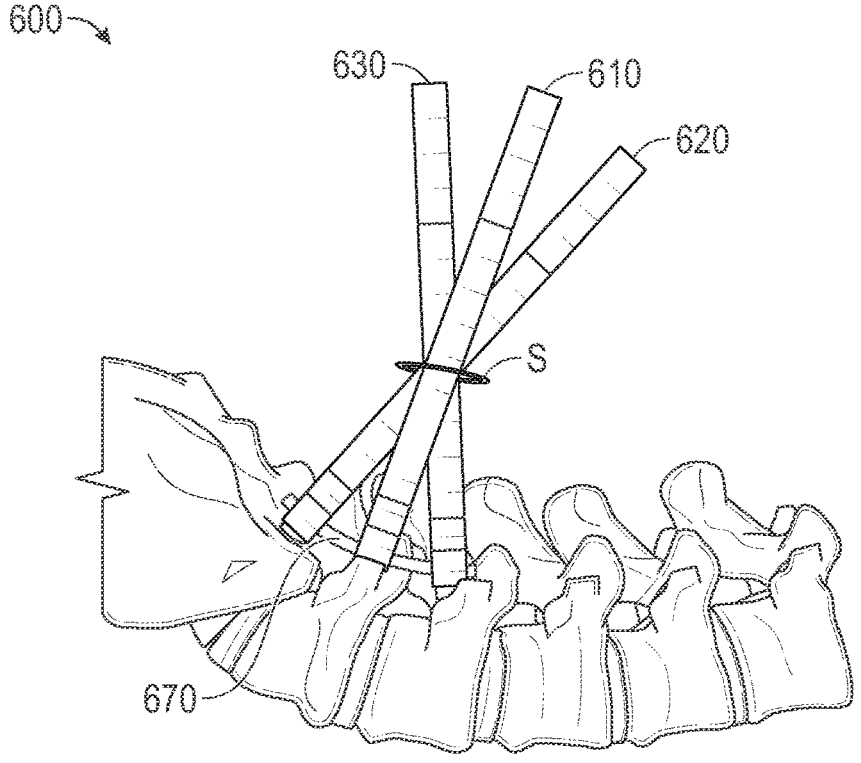
Figure 6M:
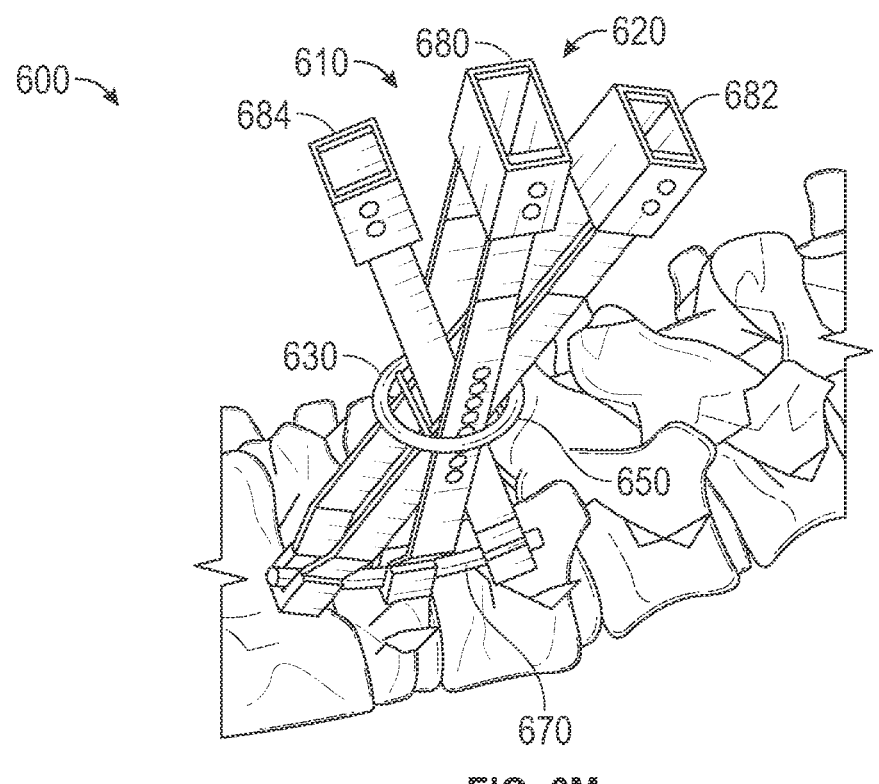
Figure 6N:
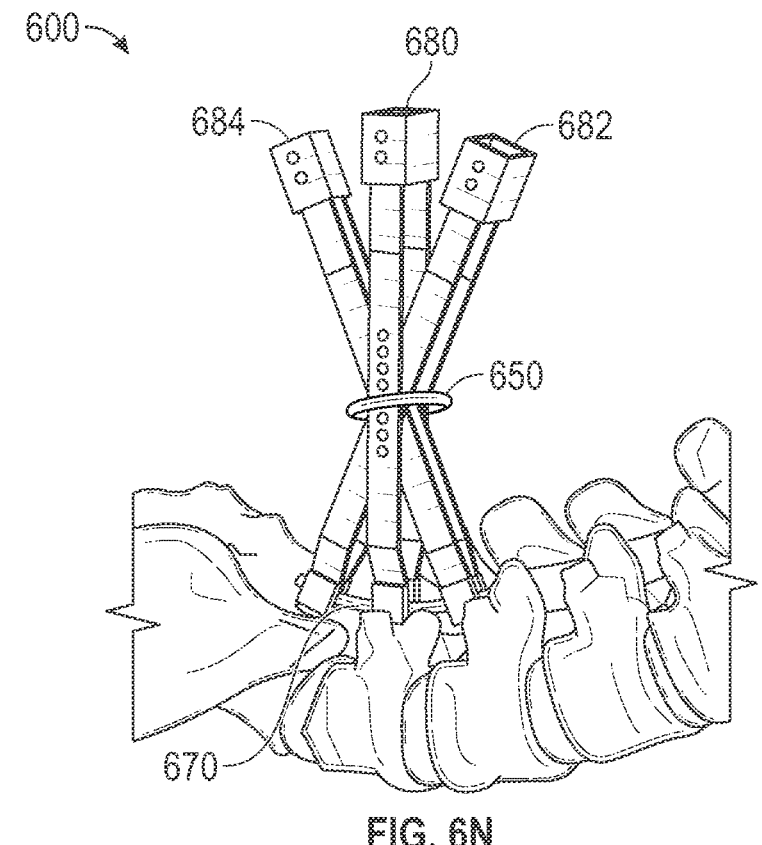
Figure 6O:
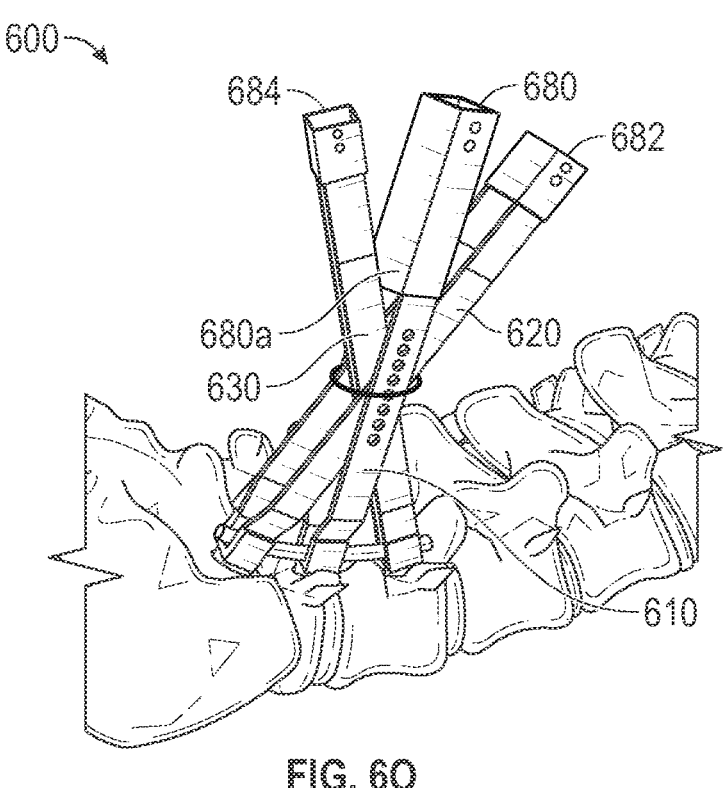
Figure 6P:
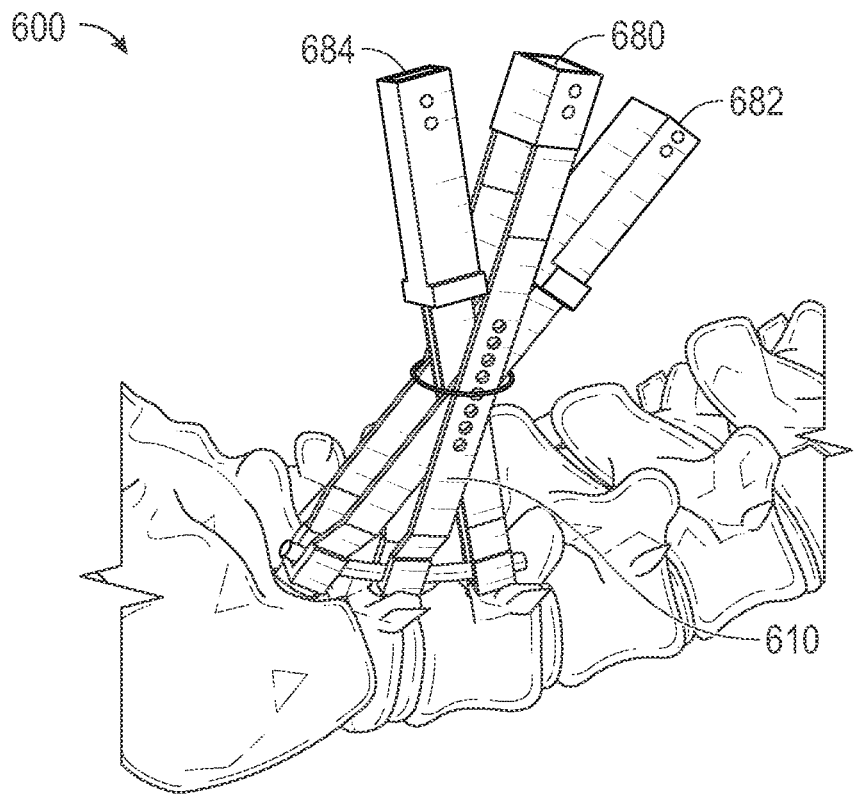
Figure 6Q:
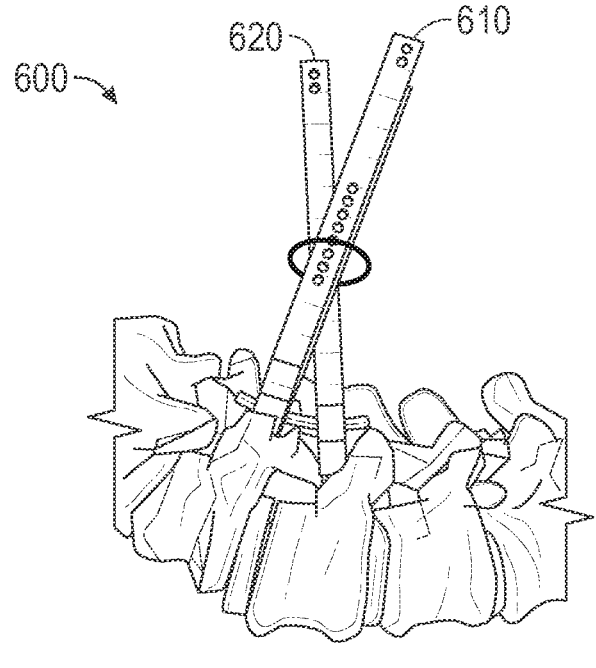
Figure 6R:
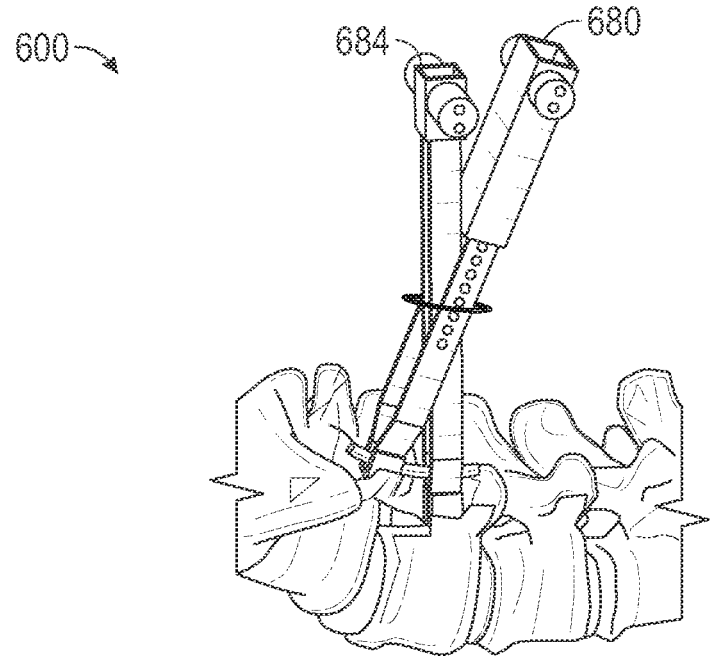
Figure 6U:
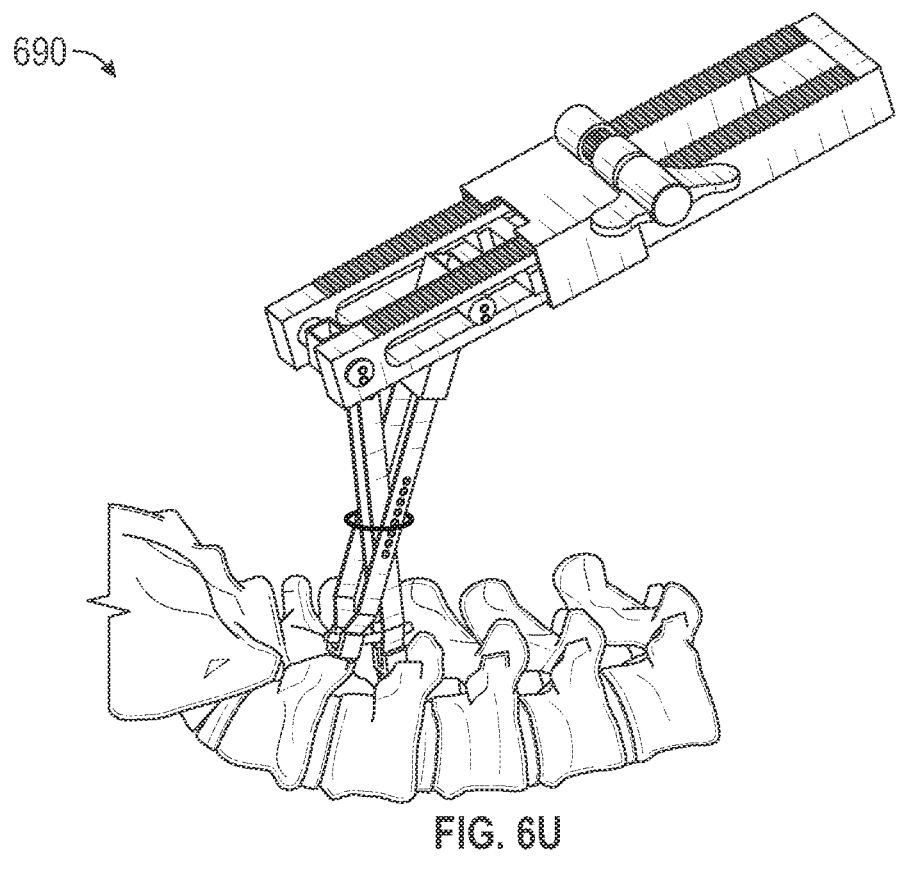
Figure 6V:
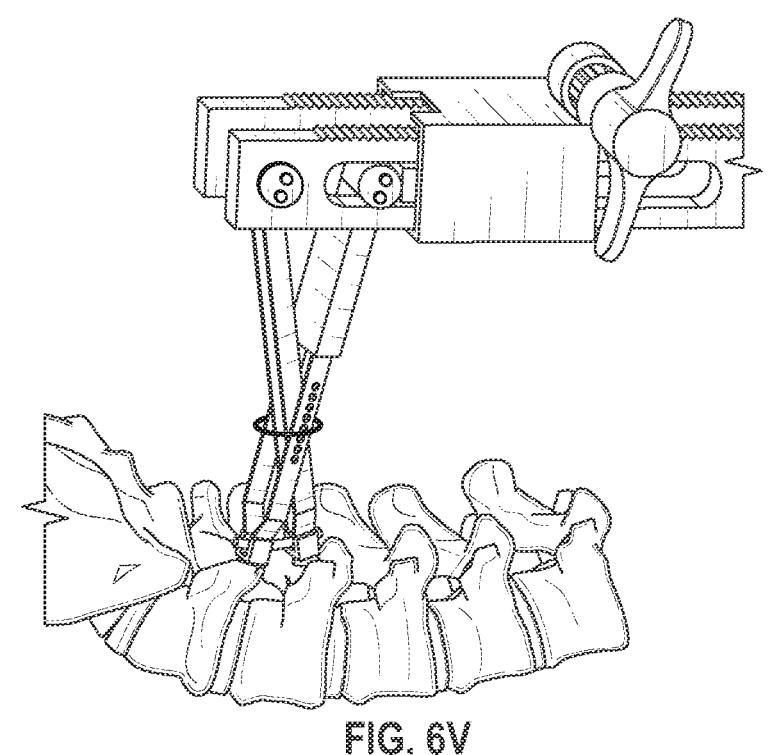

Systems, Devices and Methods of FIGS. 6A-6V

Embodiments disclosed herein are directed to a system 600 for stabilizing spinal vertebrae through a skin incision S. In any embodiments disclosed herein, any components, features, or other details of the system 600 can have any of the components, features, or other details of any other system embodiments disclosed herein or be used according to any of the steps of any other method embodiments disclosed herein, including without limitation any of the embodiments of the system 200, 300, 400 and/or 500 or methods of use thereof described above, in any combination with any of the components, features, or details of the system 600 or methods of use disclosed below. Similarly, any components, features, steps, or other details of any of the other system or method embodiments disclosed herein can have any of the components, features, steps, or other details of any embodiments of the system 600 or methods of use thereof disclosed herein in any combination with any of the components, features, or details of the system.

In any embodiments disclosed herein, the system 600 can have guiding elements that have varying widths or spacing between the blades of the guiding elements. The spacing between the blades can be sized and configured to allow other screws and towers or other guiding elements or extensions to pass between the blades thereof.

In some embodiments, the system 600 can include a first screw 612 that can include a first screw head 613, the first screw head 613 including a first side and a second side, the first side and the second side being opposite each other, and a first guiding element 610 configured to extend away from the first screw head 613. In any embodiments disclosed herein, the first guiding element 610 can include a first pair of blades 618 extending along a first longitudinal axis between a proximal end 610*a* and a distal end 610*b* of the first guiding element 610. The first pair of blades 618 can include a transition portion 616 between the proximal end 610*a* and a distal end 610*b* of the first guiding element 610 wherein a first spacing (also referred to herein as a separation distance) between an inside surface of the first pair of blades 618 in the transition portion 616 increases such that a proximal spacing between the first pair of blades at the proximal end 610*a* of the first guiding element 610 is greater than a distal spacing between the first pair of blades 618 at the distal portion 610*b* of the first guiding element. The distal end 610*b* of the first pair of blades 618 can be configured to engage with or couple with the first screw head 613.

The system 600 can further include a second screw 622 that can include a second screw head 623, the second screw head 623 including a first side and a second side, the first side and the second side being opposite each other, and a second guiding element 620 configured to extend away from the second screw head 623. In some embodiments, the second guiding element 620 can have straight blades. In any embodiments disclosed herein, the second guiding element 620 can include a second pair of blades 628 extending along a second longitudinal axis between a proximal end 620*a* and a distal end 620*b* of the second guiding element 620. The second pair of blades 628 can include a transition portion 626 between the proximal end 620*a* and a distal end 620*b* of the second guiding element 620 wherein a second spacing (also referred to herein as a separation distance) between an inside surface of the second pair of blades 628 in the transition portion 626 increases such that a proximal spacing between the second pair of blades 628 at the proximal end 620*a* of the second guiding element 620 is greater than a distal spacing between the second pair of blades 628 at the distal portion 620*b* of the second guiding element 620. The distal end 620*b* of the second pair of blades 628 can be configured to engage with or couple with the second screw head 622.

In any embodiments disclosed herein, the second spacing between the second pair of blades 628 can be less than the first spacing between the first pair of blades 618. In this configuration, the second guiding element 620 can be advanced through the first spacing between the first pair of blades 618 of the first guiding element 610.

Some embodiments of the system 600 can further include a third screw 632 that can include a third screw head 633, the third screw head 633 including a first side and a second side, the first side and the second side being opposite each other, and a third guiding element 630 configured to couple with and extend away from the third screw head 633. In some embodiments, the third guiding element 630 can have straight blades. In any embodiments disclosed herein, the third guiding element 630 can include a third pair of blades 638 extending along a third longitudinal axis between a proximal end 630*a* and a distal end 630*b* of the third guiding element 630. The third pair of blades 638 can include a transition portion 636 between the proximal end 630*a* and a distal end 630*b* of the third guiding element 630 wherein a third spacing (also referred to herein as a separation distance) between an inside surface of the third pair of blades 638 in the transition portion 636 increases such that a proximal spacing between the third pair of blades 638 at the proximal end 630*a* of the third guiding element 630 is greater than a distal spacing between the third pair of blades 638 at the distal portion 630*b* of the third guiding element 630. The distal end 630*b* of the third pair of blades 638 can be configured to engage with or couple with the third screw head 632.

In any embodiments disclosed herein, the third spacing between the third pair of blades 638 can be less than the second spacing between the second pair of blades 624. Further, the third spacing between the third pair of blades 638 can be less than the first spacing between the first pair of blades 614. In this configuration, the second guiding element 620 and the third guiding element 630 can be advanced through the first spacing between the first pair of blades in the first guiding element 614.

In any embodiments, the transition portion of the first guiding element 610, the second guiding element 620, the third guiding element 630, and/or any guiding element can be angled outwardly away from the longitudinal centerline axis, or bowed outwardly away from the longitudinal centerline axis, and can be straight along a length of the transition section, can be curved along a length of the transition section, or otherwise. Further, in any embodiments disclosed herein, each of the first pair of blades 618, the second pair of blades 624, the third pair of blades 638, and/or any blade of any guiding element disclosed herein can have a substantially uniform cross-sectional thickness from the proximal end to the distal end. In any embodiments disclosed herein, proximal portions of the first, second, and/or third pair of blades (i.e., from the proximal end to the proximal end of the transition portion) can be straight, planar, substantially straight, and/or substantially planar. Further, each of the blades of the proximal portions of the first, second, and/or third pair of blades can be parallel or substantially parallel to each other.

In some embodiments, the third spacing between the inner surfaces of the third pair of blades 638 of the third guiding element 630 can be less than the second spacing between the inner surfaces of the second pair of blades 624 of the second guiding element 620 by 25% (or approximately 25%), or from 15% (or approximately 15%) to 35% (or approximately 35%) or more. In any embodiments disclosed herein, the third spacing of the third guiding element 630 can be less than the second spacing of the second guiding element 620 by an amount that is greater than a thickness of each of the blades of the third pair of blades 638. Further, the second spacing between the inner surfaces of the second pair of blades 628 of the second guiding element 620 can be less than the first spacing between the inner surfaces of the first pair of blades 614 of the first guiding element 610 by 25% (or approximately 25%), or from 15% (or approximately 15%) to 35% (or approximately 35%) or more. In any embodiments disclosed herein, the second spacing of the second guiding element 620 can be less than the first spacing of the first guiding element 620 by an amount that is greater than a thickness of each of the blades of the second pair of blades 628.

In any embodiments disclosed herein, the guiding elements can have any of a range of lengths suitable for a range of differently sized anatomies, thereby permitting a surgeon to choose the desired length or lengths of the blades and positions of the enlarged openings after measurement of the depth of the tissue, for example.

Further, as shown in FIG. 6A, any embodiments of the system 600 can further have a restraint 650 configured to engage the first pair of blades 618 and/or the second pair of blades 628. In some embodiments, the restraint can be configured to engage an intermediate portion of the first pair of blades 618, the second pair of blades 628, and/or the third pair of blades 638. The restraint 650 can be configured in some embodiments to at least create a hinge point or fulcrum between the first, second, and/or third guiding elements 610, 620, 630. In some embodiments, the restraint 650 can be configured to surround at least the first, second, and/or third guiding elements 610, 620, 630 at intermediate portions thereof when the first, second, and/or third guiding element 610, 620, 630 passes through a portion of the other or others of the first, second, and/or third guiding element 610, 620, 630 and when the first, second, and/or third guiding elements 610, 620, 630 are engaged with the first, second, and/or third bone screws, respectively, and first, second, and/or third bone screws are implanted within a patient.

In some embodiments, the restraint 650 can be configured to limit relative movement between the first, second, and/or third guiding elements 610, 620, 630, and/or to restrain the first, second, and/or third guiding elements 610, 620, 630 at an intermediate portion thereof so that the first, second, and/or third guiding elements 610, 620, 630 are hinged or rotatably restrained to one another at the intermediate portion thereof. In any embodiments disclosed herein, the restraint 650 can be positioned at or approximately at the intersection of the first, second, and/or third guiding elements 610, 620, 630.

In some embodiments, the restraint 650 can be a ring configured to engage an outer portion along an intermediate portion of or intersection of the first, second, and/or third guiding elements 610, 620, 630. With reference to FIG. 6F, some embodiments of the restraint 650 can have an annular portion 652 (that can be permanently closed or openable, like a carbineer, hook, or keychain), a first and/or a second pin 654, and/or a first and a second restraint bars 658. In other embodiments, the restraint 650 can be configured such that the annular portion 652 coincides with the restraint bars 652 such that separate restraint bars are not needed. Any embodiments of the restraint 650 can be rigid and can be made from metal, plastic, rubber, or a composite material.

With reference to FIG. 6G, some embodiments of the first pair of blades 618 can include a plurality of holes 660 configured to receive pins 654 of the restraint 650. The restraint 650 can be selectively openable so that the restraint 650 can open to be advanced around the first, second, and/or third pair of blades, and closable to restrain the first, second, and/or third pair of blades.

Additionally, as shown in FIG. 6M on, any embodiments of the system 600 can further include caps 680, 682, 684 configured to be secured at the proximal ends of the first, second, and/or third pair of blades. The caps can provide an interface for other tools and devices, or robotic grippers, such as is shown in FIGS. 6S-6V. Additionally, some embodiments of the caps can be configured to limit relative movement of the first, second, and/or third pair of blades.

In some embodiments, the system can include a cap that extends from the proximal end of at least one of the first and the second pair of blades to an intermediate portion along at least one of the first and second pair of blades, the cap configured to block relative movement between the first and second pair of blades. Caps can be screwed on or otherwise attached to secure or lock the two blades together. By locking the blades together, an extension system comprising two blades is essentially turned into a tower by stabilizing the proximal ends of the blades. The difference between blades and a tower is essentially a connection of the proximal ends of the blades thereby stabilizing the blades on the distal and proximal ends. In some embodiments, the caps can be slid on, snapped on, screwed on or otherwise coupled with the proximal tips of the blades to stabilize the blades and/or to limit movement between different pairs of blades.

For example, with reference to FIG. 60, the first cap 680 coupled with a proximal end of the first guide element 610 can have a length that extends to a point where a distal edge or portion 680b of the cap 680 contacts the second guiding element 620 and the third guiding element 630 to provide an edge about which the second and the third guiding elements 620, 630 can rotate. Alternatively, as shown in FIG. 6P, the second cap 682 and the third cap 684 can have a length that extends to a point where a distal edge or portion 682b of the second cap 682 and/or a distal edge or portion 684b of the third cap 684 can contact the first guiding element 610 to provide an edge about which the second and the third guiding elements 620, 630 can rotate. Some embodiments of the system 600 can include a tool 690 configured to manipulate the proximal ends of the first, second, and/or third pair of blades to cause compression of a first, second, and/or third vertebra that the first, second, and/or third screw heads are respectively implanted into. Further, in any embodiments disclosed herein, a rod or connecting element 670 can be coupled with and of the first, second, and/or third the screw heads.

In this manner, the tool 690 coupled with caps 680, 682, 684, can allow for a single system to align the screw heads, provide a channel to insert the connecting element (rod), reduce the screw in settings of spondylolisthesis (FIGS. 6U and 6V), placement of locking cap, final tightening of the lock cap under compression, and/or counter torqueing of the rod and screw construct when locking cap is final tightened. In some embodiments, no other additional tools such as head turner, compressor, or countertorque tools are necessary.

Certain aspects of the systems, devices, components and/or methods described above or as illustrated with respect to FIGS. 6A-6V are also encompassed by the following numbered embodiments. These numbered embodiments are considered to be directed to systems, devices, components and/or methods that include but are not limited to the embodiments of FIGS. 6A-6V, and thus these numbered embodiments may encompass other embodiments as described throughout this specification.

1. A system for bone stabilization, comprising:
   a first guiding element comprising a first pair of blades extending at least partially along a first longitudinal axis, wherein each blade of the first pair of blades has a proximal end and a distal end, the distal ends of the first pair of blades configured to engage with a first bone screw, wherein each blade of the first pair of blades comprises a portion that deviates away from the first longitudinal axis to increase a separation distance between the first pair of blades when the distal ends of the first pair of blades are engaged with the first bone screw;
   a second guiding element comprising a second pair of blades extending at least partially along a first longitudinal axis, wherein each blade of the second pair of blades has a proximal end and a distal end, the distal ends of the second pair of blades configured to engage with a second bone screw, wherein each blade of the second pair of blades comprises a portion that deviates away from the second longitudinal axis to increase a separation distance between the second pair of blades when the distal ends of the second pair of blades are engaged with the second bone screw;

wherein the separation distance between the second pair of blades is less than the separation distance between the first pair of blades.

2. The system of Embodiment 1, further comprising: a third guiding element comprising a third pair of blades extending at least partially along a third longitudinal axis, wherein each blade of the third pair of blades has a proximal end and a distal end, the distal ends of the third pair of blades configured to engage with a third bone screw, wherein each blade of the third pair of blades comprises a portion that deviates away from the third longitudinal axis to increase a separation distance between the third pair of blades when the distal ends of the second pair of blades are engaged with the second bone screw;

wherein the separation distance between the third pair of blades is less than the separation distance between the second pair of blades.

3. The system of Embodiment 1 or 2, further comprising a restraint configured to engage an intermediate portion along either or both of the first pair of blades and the second pair of blades and limit relative movement between the first and second pair of blades.

4. The system of Embodiment 3, wherein the restraint is a ring configured to engage an outer portion along an intermediate portion of the first pair of blades.

5. The system of Embodiment 4, wherein the first pair of blades comprises a plurality of holes configured to receive pins on the ring.

6. The system of any one of Embodiments 3-5, wherein the restraint is adjustable to close around the intermediate portion along the first pair of blades.

7. The system of any one of the previous Embodiments, further comprising caps configured to be secured at the proximal ends of the first and second pair of blades to limit relative movement of each of the first and second pair of blades.

8. The system of any one of Embodiments 1-3, further comprising a cap that extends from the proximal end of at least one of the first and the second pair of blades to an intermediate portion along at least one of the first and second pair of blades, the cap configured to block relative movement between the first and second pair of blades.

9. The system of any one of the previous Embodiments, further comprising a tool configured to manipulate the proximal ends of the first and second pair of blades to cause compression of the first and second screw heads.

10. A system for bone stabilization, comprising:
a first guiding element extending at least partially along a first longitudinal axis and having a proximal end and a distal end, the distal end of the first guiding element configured to engage with a first bone screw;
a second guiding element extending at least partially along a second longitudinal axis and having a proximal end and a distal end, the distal end of the second guiding element configured to engage with a second bone screw, wherein the second guiding element is configured to pass through a portion of the first guiding element when the first and second guiding elements are engaged with the first and second bone screws, respectively, and the first and second bone screws are implanted within a patient; and
a restraint configured to surround at least one of the first and second guiding elements at intermediate portions thereof when the second guiding element passes through a portion of the first guiding element and when the first and second guiding elements are engaged with the first and second bone screws, respectively, and the first and second bone screws are implanted within a patient, wherein the restraint is configured to limit relative movement between the first and second guiding elements.

11. The system of Embodiment 10, wherein the restraint is a ring.

12. The system of Embodiment 10 or 11 wherein the restraint is adjustable to close around the first and second guiding elements.

13. The system of Embodiment 10, wherein the restraint comprises a cap extending distally from the proximal end of at least one of the first and second guiding elements.

14. The system of any one of Embodiments 10-13, further comprising a tool configured to manipulate the proximal ends of the first and second guiding elements when the second guiding element passes through a portion of the first guiding element and when the first and second guiding elements are engaged with the first and second bone screws, respectively, and the first and second bone screws are implanted within a patient.

15. The system of any one of Embodiments 10-14, further comprising a third guiding element extending at least partially along a third longitudinal axis and having a proximal end and a distal end, the distal end of the third guiding element configured to engage with a third bone screw, wherein the third guiding element is configured to pass through a portion of the second guiding element when the first, second and third guiding elements are engaged with the first, second and third bone screws, respectively, and the first, second and third bone screws are implanted within a patient.

Systems, Devices and Methods of FIGS. 7A-7H

Additional embodiments a device 700 (also referred to herein as a guidance tool or a guidance tool for delivering screws) for implanting screws spinal vertebrae through a skin incision S will now be described. In some embodiments, the device 700 can be used to sweep away or move tissue away from the target screw location using a hinged or rotatable blade. In some embodiments, the device can have a ring with a handle having a hinge with an extension that opens to spread out the tissue and clear the path to place the second screw. The second screw can be placed through the same incision through the "ring" or portal of the first screw guided by the tissue sweeper guide. With reference to FIGS. 7C-7E, FIG. 7C shows a closed tube 702 attached to the first screw 705. The device 700 can be inserted as one piece. The second blade 704 (also referred to herein as a tissue sweeper) can be opened as shown in FIG. 7D. Then, the second screw 707 can be inserted, as shown in FIG. 7E. The second screw can be attached to a tower, for example any of the towers, extensions, or guide elements of any of the embodiments disclosed herein. The rod or connecting element can then be inserted in a manner similar to any of the embodiments disclosed herein. The embodiments of the device 700 can also be used with or configured for use with robotic attachments or robotic surgical systems.

Figures 7A, 7B:
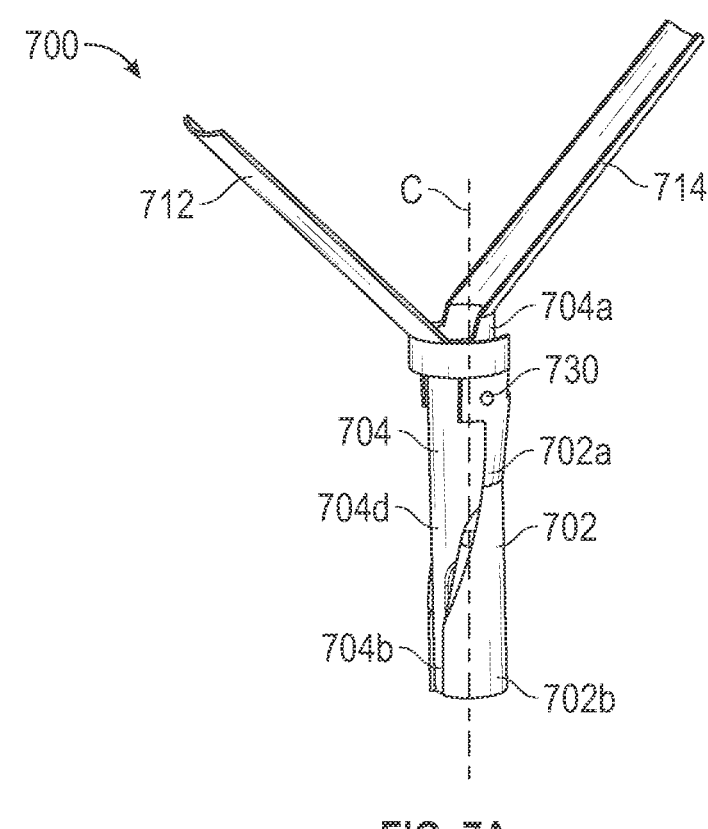
FIGS. 7A-7H illustrate another embodiment of a method and a system for stabilizing spinal vertebrae comprising spinal screws.
Figure 7C:
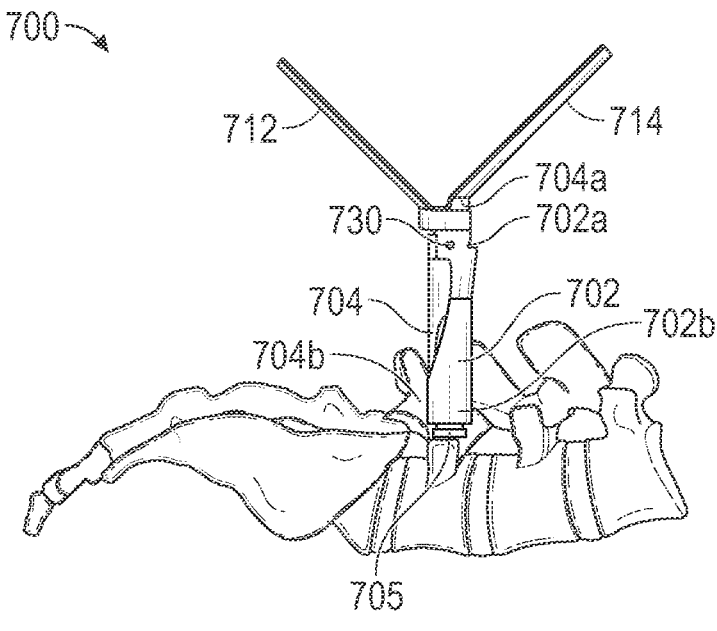
Figure 7D:
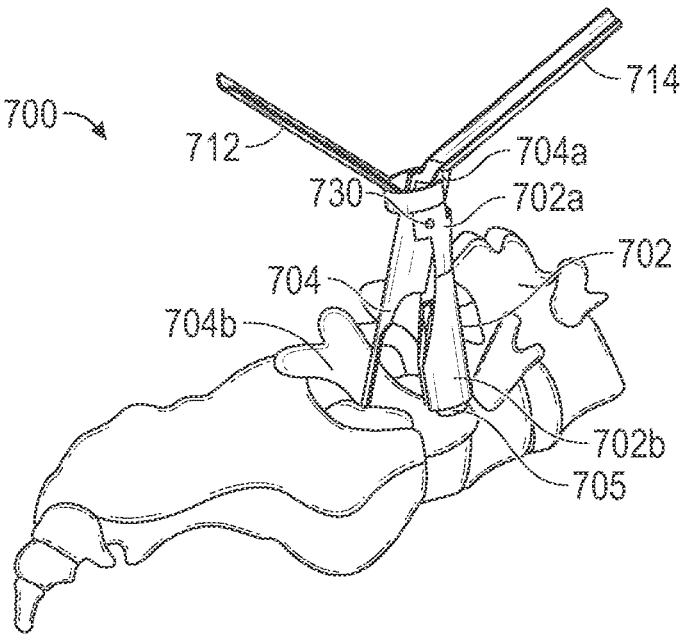
Figure 7E:
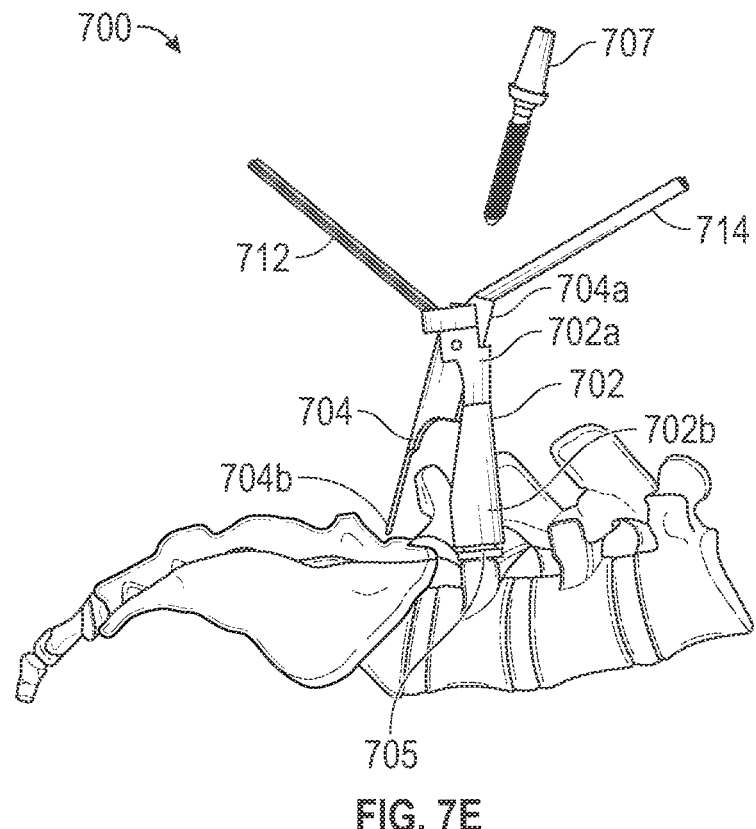
Figure 7F:
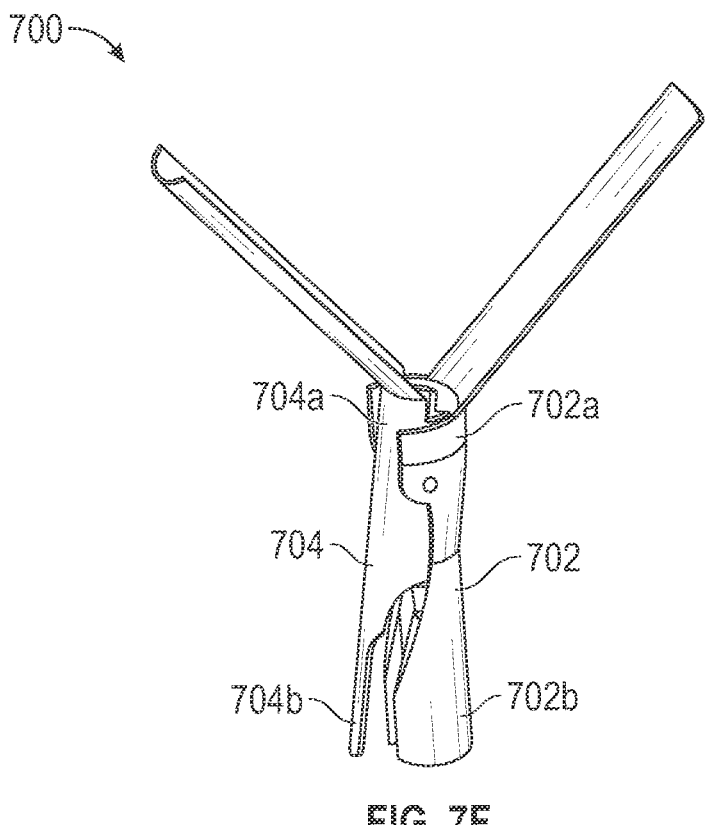
Figure 7G:
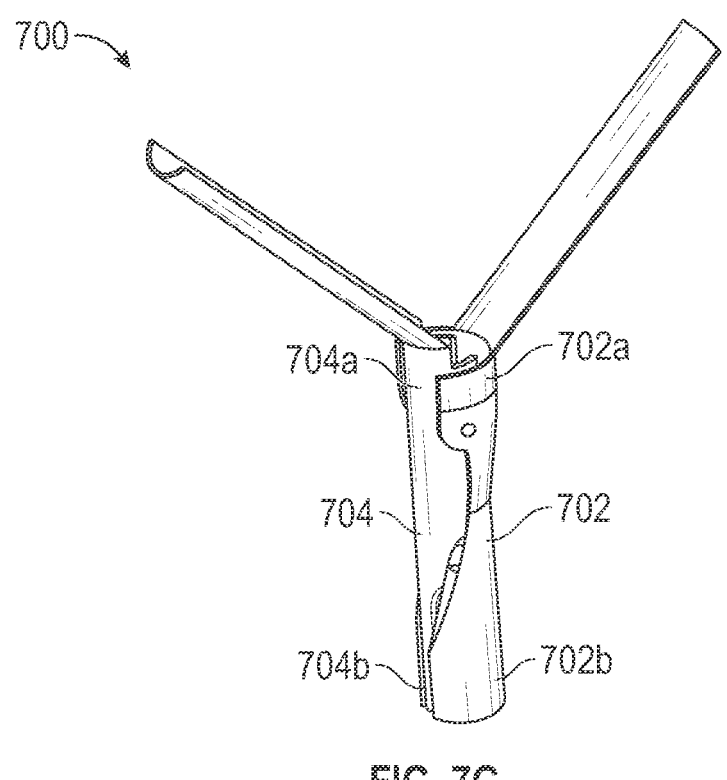
Figure 7H:
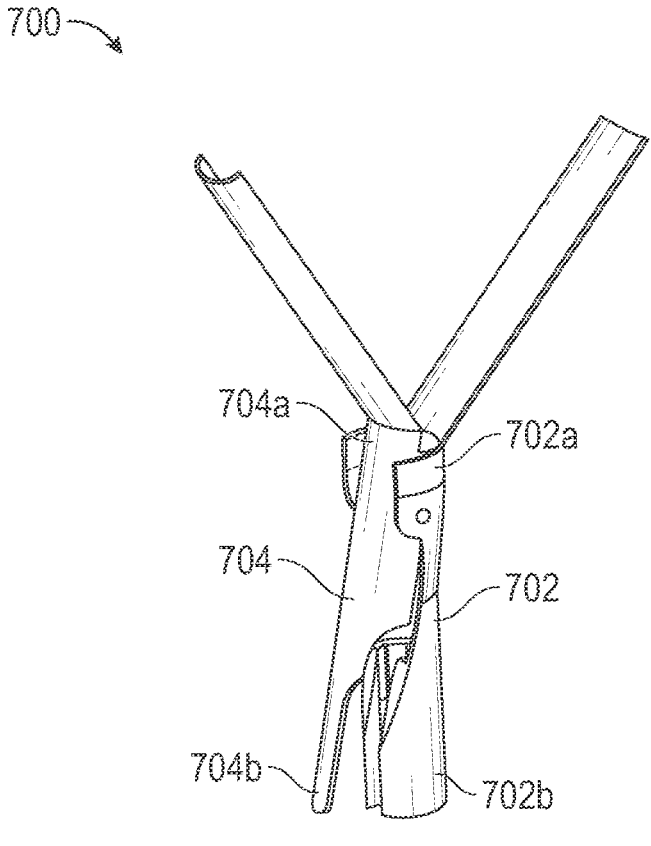

FIGS. 7F-7H illustrate an alternative version of the hinged tissue sweeper or device 700. In the embodiments shown therein, the blades 702, 704 and the handles 712, 714 do not cross sides. In other words, the handle 712 for the main tube 702 stays on the side of the main tube 702, which can increase the strength of the handle 712 and/or handle 714 and the device 700 in this configuration. A hinge 730 can be placed more superiorly and to the edge of the tube on the side of the sweeper (i.e., the second blade 704) to optimize the opening of the insertion of the second screw after the tissue sweeper 700 has been opened.

In any embodiments disclosed herein, any components, features, or other details of the device 700 can have any of the components, features, or other details of any other device embodiments disclosed herein, including without limitation any of the embodiments of the devices of system 200, 300, 400, 500 and/or 600 described above, in any combination with any of the components, features, or details of the device 700 disclosed below. Similarly, any components, features, or other details of any of the other device embodiments disclosed herein can have any of the components, features, or other details of any embodiments of the device 700 disclosed herein in any combination with any of the components, features, or details of the embodiments of the device 700.

In any embodiments disclosed herein, the device 700 can have a first blade 702 and a second blade 704, wherein the first blade 702 (also referred to herein as a first tube) can have a proximal end 702a, a distal end 702b, an inner surface 702c, and an outer surface 702d, and the second blade 704 can have a proximal end 704a, a distal end 704b, an inner surface 704c, and an outer surface 704d. In any embodiments disclosed herein, the device can have a hinge 730. The second blade 704 can be rotatably coupled with the first blade 702 using the hinge 730. The hinge 730 can include a shaft or rod, or a pin.

In some embodiments, with reference to FIG. 7C, the distal end of the first blade 702 can be configured to engage with a first bone screw 705. In any embodiments disclosed herein, the first and second blades 702, 704 can be moveable from a first configuration or position (as shown in FIG. 7A) in which the first and second blades 702, 704 form an at least partially enclosed passageway defined by the inner surfaces 702c, 704c of the first and second blades 702, 704 extending along a longitudinal axis or axial centerline C parallel to each of the first and second blades 702, 704, and a second configuration or position (as shown in FIG. 7B) in which the distal end 704b of the second blade 704 pivots relatively away from the distal end 702b of the first blade 702.

The first handle 712 can be connected to the proximal end 702a of the first blade 702. In some embodiments, the first handle 712 can be integrally formed with the first blade 702. The first handle 712 can extend at a first angle A1 relative to the longitudinal axis C when the first and second blades 702, 704 are in the first configuration. The second handle 714 can be connected to the proximal end 704a of the second blade 704. In some embodiments, the second handle 714 can be integrally formed with the first blade 704. The second handle 714 can extend at a second angle A2 relative to the longitudinal axis C when the first and second blades 702, 704 are in the first configuration. In some embodiments, the first and the second angles A1, A2 can diverge from each other on opposite sides of the longitudinal axis C. In some embodiments, the first and second angles can be fixed.

In some embodiments, when the device 700 is in the second configuration, with the first blade 702 remaining generally parallel to the longitudinal axis C of the passageway and the second blade 704 extending away from the longitudinal axis C on a first side of the longitudinal axis C, and the second handle 714 can extend away from the longitudinal axis C on a second side of the longitudinal axis C opposite to the first side of the longitudinal axis C (as shown in FIG. 7B).

In other embodiments, with the first handle 712 of the first blade 702 extending away from the longitudinal axis C on the first side of the longitudinal axis C in the second configuration and with the first blade 702 remaining parallel to the longitudinal axis C of the passageway, the second blade 704 can extend away from the longitudinal axis C on a first side of the longitudinal axis C, and the second handle 714 can extend away from the longitudinal axis C on the first side of the longitudinal axis C (as shown in FIGS. 7F and 7H). In some embodiments, the handle of the first blade 702 can extend away from the longitudinal axis on the second side of the longitudinal axis.

In some embodiments, the enclosed passageway defined by the inner surfaces of the first and second blades 702, 704 can be tubular, and the inner surfaces 702c, 704c of the first and second blades 702, 704 can be concave. Some embodiments of the device 700 can include a partial or complete ring surrounding the proximal ends 702a, 704a of the first and second blades 702, 704.

In some embodiments, the blade 704 can be used as a tissue sweeper as the blade 704 is opened from a closed position to an open position. However, then after the second screw 707 is inserted, then the blade 704 can be used as a compressor and even a counter torque. By adjusting the proximal handles 712 and 714 either closer together or farther apart (depending on the configuration of the blades if they cross sides or stay on the same side as the distal portion they are connected to), then compression of both screws 705 and 707 can be performed. Preferably blade 704 has a distal notch similar to notch 354 in FIG. 3B, and FIG. 481 in FIG. 4C. The blade 704 can also be wider in the distal margin to "hold" the screw head of screw 707. Preferably there is a corresponding notch at the distal tip of 702b to hold the rod as well. The notches at the tip of both distal arms (704b and 702b) hold the rod to be used as a counter-torque when the locking nut is tightened to the final torque when locking the connecting element/rod into the heads of the screw heads.

An embodiment of a method of delivering screws to a spinal location using any of the embodiments of the guidance tool or device 700 disclosed herein will now be described. With reference to FIGS. 7C-7E, a surgeon can deliver the guidance tool 700 to the desired or target spinal location so that the first blade 702 of the guidance tool 700 is engaged with a first bone screw implanted within a first vertebra. The surgeon can use the first and second handles 712, 714 to move the first and second blades 702, 704 from the first configuration to the second configuration so that that the distal end of the second blade 704 pivots away from the first blade 702 while the first blade 702 is engaged with the first bone screw. The surgeon can then deliver a second bone screw 707 between the proximal ends 702a, 704a of the first and second blades 702, 704 and between the inner surfaces 702c, 704c of the first and second blades 702, 704 and into a second vertebra.

Certain aspects of the systems, devices, components and/or methods described above or as illustrated with respect to FIGS. 7A-7H are also encompassed by the following numbered embodiments. These numbered embodiments are considered to be directed to systems, devices, components and/or methods that include but are not limited to the embodiments of FIGS. 7A-7H, and thus these numbered embodiments may encompass other embodiments as described throughout this specification.

1. A guidance tool for delivering screws to a spinal location, the guidance tool comprising:
  a first blade and a second blade, each of the first blade and the second blade having a proximal end, a distal end, an inner surface and an outer surface, the distal end of the first blade being configured to engage with a first bone screw, wherein the first and second blades are moveable from a first configuration in which the first and second blades form an at least partially enclosed passageway defined by the inner surfaces of the first and second blades extending along a longitudinal axis parallel to each of the first and second blades, and a second configuration in which the distal end of the second blade pivots relatively away from the distal end of the first blade;

a first handle connected to the proximal end of the first blade, the first handle extending at a first angle relative to the longitudinal axis when the first and second blades are in the first configuration; and a second handle connected to the proximal end of the second blade, the second handle extending at a second angle relative to the longitudinal axis when the first and second blades are in the first configuration, wherein the first and the second angle diverge from each other on opposite sides of the longitudinal axis.

2. The guidance tool of Embodiment 1, wherein in the second configuration, with the first blade remaining parallel to the longitudinal axis of the passageway, the second blade extends away from the longitudinal axis on a first side of the longitudinal axis, and the second handle extends away from the longitudinal axis on a second side of the longitudinal axis opposite to the first side.

3. The guidance tool of Embodiment 2, wherein the handle of the first blade extends away from the longitudinal axis on the first side of the longitudinal axis.

4. The guidance tool of Embodiment 1, wherein in the second configuration, with the first blade remaining parallel to the longitudinal axis of the passageway, the second blade extends away from the longitudinal axis on a first side of the longitudinal axis, and the second handle extends away from the longitudinal axis on the first side of the longitudinal axis.

5. The guidance tool of any one of Embodiment 4, wherein the handle of the first blade extends away from the longitudinal axis on the second side of the longitudinal axis.

6. The guidance tool of any one of Embodiments 1-5, wherein the enclosed passageway defined by the inner surfaces of the first and second blades is tubular.

7. The guidance tool of any one of Embodiments 1-6, wherein the inner surfaces of the first and second blades are concave.

8. The guidance tool of any one of Embodiments 1-7, further comprising a partial or complete ring surrounding the proximal ends of the first and second blades.

9. The guidance tool of any one of Embodiments 1-8, wherein the first and second angles are fixed.

10. A method of delivering screws to a spinal location using the guidance tool of any one of Embodiments 1-9, comprising:

delivering the guidance tool to the spinal location so that the first blade of the guidance tool is engaged with a first bone screw implanted within a first vertebra;

using the first and second handles to move the first and second blades from the first configuration to the second configuration so that that the distal end of the second blade pivots away from the first blade while the first blade is engaged with the first bone screw; and delivering a second bone screw between the proximal ends of the first and second blades and between the inner surfaces of the first and second blades and into a second vertebra.

Systems, Devices and Methods of FIGS. 8A-9P

Embodiments disclosed below and shown in FIGS. 8A-8G are related to show embodiments of a guidance tool 1500 for delivering screws to a spinal location. Sacroiliac (SI) fusion has been shown to be a useful and necessary adjunct to lumbar fusion. The SI joint is the next "joint" inferior to the L5-S1 joint. SI fusion usually requires placing 2-3 triangular metal implants (SI Fuse) through the iliac bone into the sacrum. By crossing the SI joint, the implants can stabilize the SI joint.

Conventional devices incorporate screws instead of triangular implants. In the conventional methods, each screw is usually placed individually in succession. The screws can be fully threaded or a lag screw with threads only in the sacral portion. Each screw typically requires a sequence of fluoroscopic images to position the trajectory of the screw in the correct 3 D position, which can be very time consuming and expose the patient to increased risks.

In some embodiments of the guidance tool 1500, by arranging three trajectories starting from a single incision at the skin, all three trajectories can be angled out to a small extent bit from the incision. Embodiments of the guidance tool 1500 can allow all three trajectories to be identified and confirmed in 3D space all at the same time (simultaneously), thus saving radiation from fluoroscopy and considerable time in surgery. All three screw trajectories can essentially be identified at the same time instead of serially-one after the other—of the conventional methods.

Figures 8A, 8B:
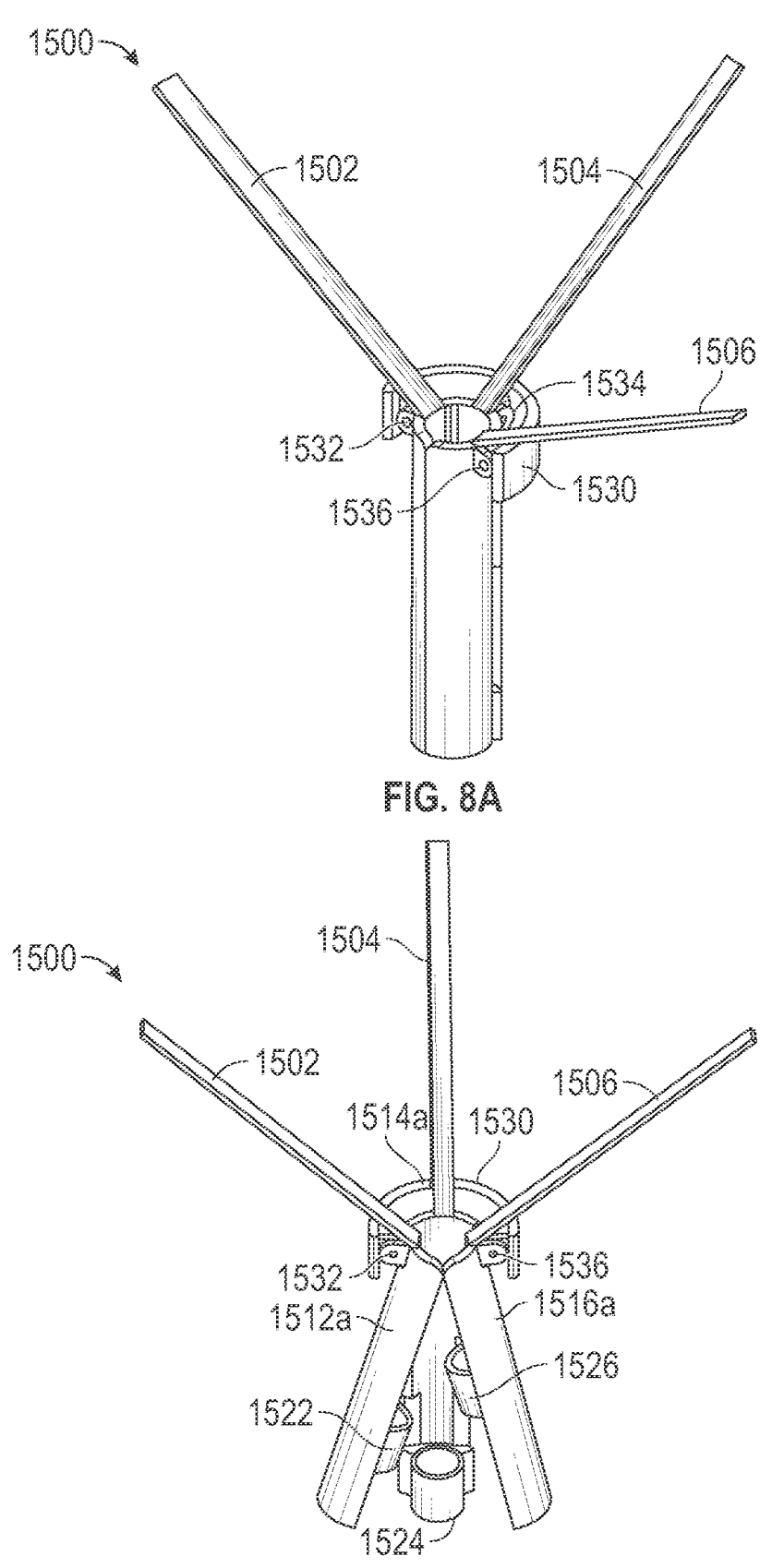
FIGS. 8A-8G illustrate another embodiment of a method and a system for delivering spinal screws to a spinal location.
Figures 8C, 8D:
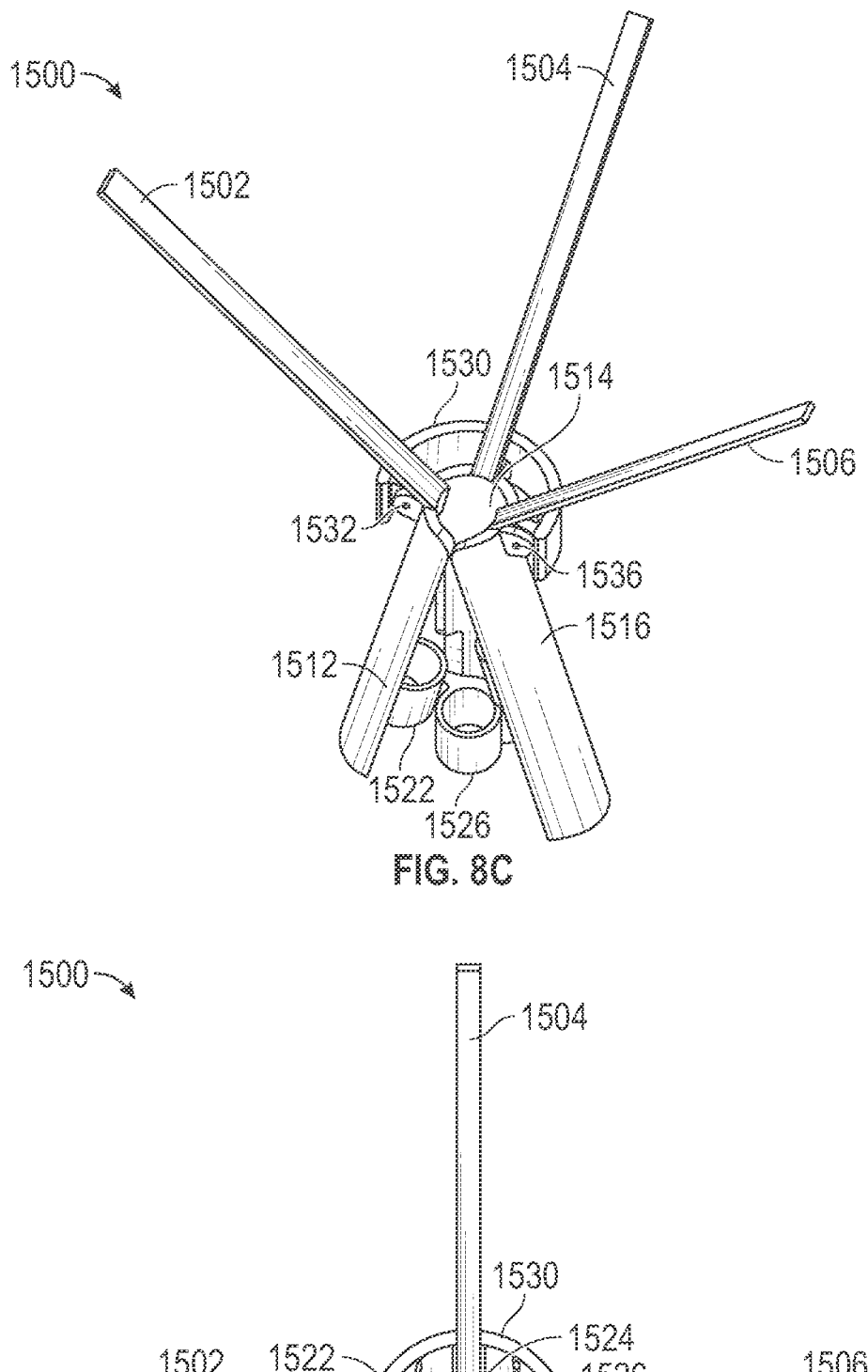
Figure 8E:
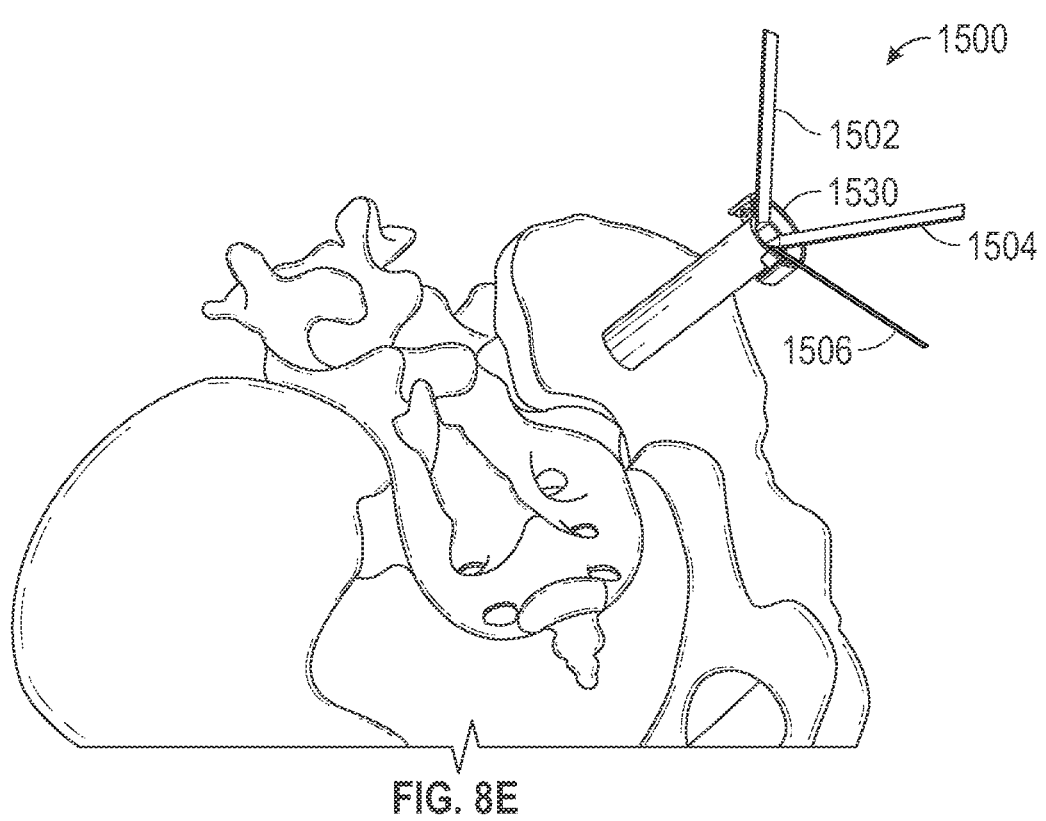

FIGS. 8C-8D show the guidance tool 1500, showing a trajectory view of the three implant trajectories. The three implants can be triangulated like shown in these figures, but can also be arranged in a linear pattern with all three implants in a single line or generally coaxially aligned. FIG. 8E shows a typical trajectory of the typical SI screw implant using the guidance tool 1500.

Figure 8F:
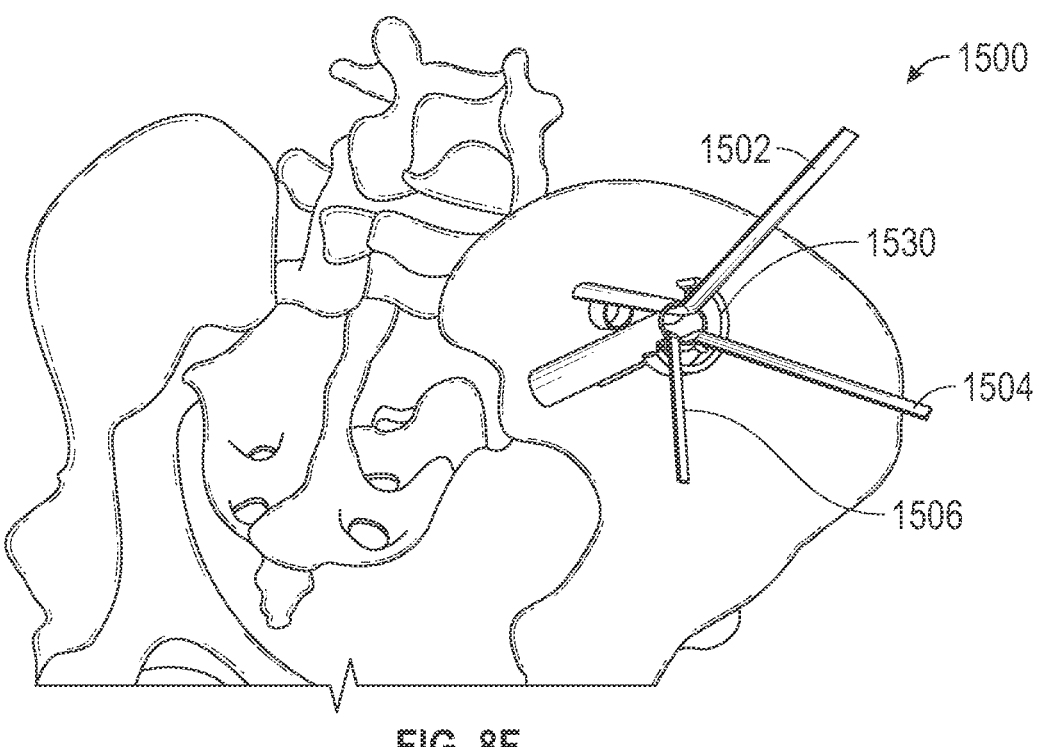
Figure 8G:
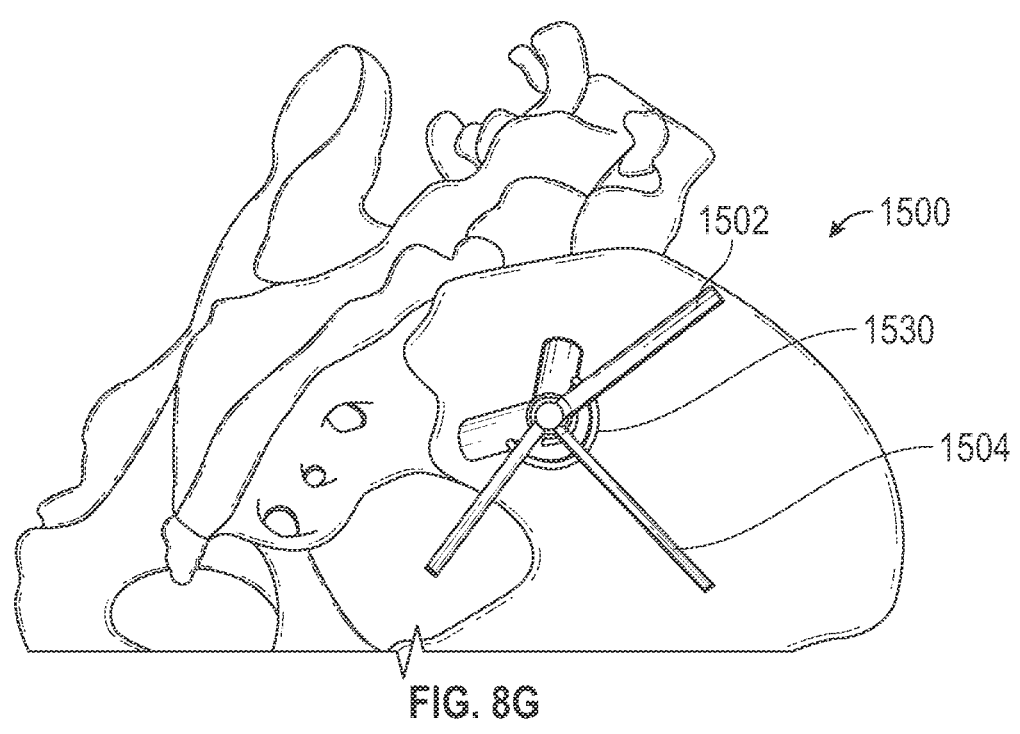

With reference to FIGS. 8F-8G, the three trajectories of the guidance tool 1500 are opened (or at least partially opened). All three trajectories of the guidance tool 1500 can be identified and verified by fluoroscopic guidance or intra-operative stereotactic navigation. The alignment of the trajectories of the guidance tool 1500 can be offset such as the corners of a flat triangle, but the trajectories can be linearly arranged also.

In any embodiments disclosed herein, the guidance tool 1500 can include a first handle 1502 coupled with a first blade 1512, a second handle 1504 coupled with a second blade 1514, and a third handle 1506 coupled with a third blade 1516. In some embodiments, the guidance tool 1500 can include only the first blade 1512 and the second blade 1514. In some embodiments, each of the three blades 1512, 1514, 1516 can have a proximal end proximal ends 1512*a*, 1514*a*, 1516*a*, a distal end proximal ends 1512*b*, 1514*b*, 1516*b*, an inner surface and an outer surface, respectively. In some embodiments, the guidance tool 1500 can have two blades, or more than three blades. In any embodiments disclosed herein, the handles 1502, 1504, 1506 can extend at an angle from the proximal end(s) 1512*a*, 1514*a*, 1516*a* of any one of the three blades 1512, 1514, 1516. In some embodiments, a handle can extend from the proximal end 1512*a*, 1514*a*, 1516*a* of all three blades 1512, 1514, 1516. The handles 1502, 1504, 1506 can be used to pivot a corresponding blade from a first configuration or position to a second configuration or position.

Further, in any embodiments of the guidance tool 1500, any of the three blades 1512, 1514, 1516 can have a guide 1522, 1524, 1526 (also referred to herein as a drill guide) coupled with an inside surface thereof, or integrally formed therewith. For example and without limitation, some embodiments of the guidance tool 1500 can have a guide 1522, 1524, 1526 on each of the three blades 1512, 1514, 1516. Each of the guides 1522, 1524, 1526 can be positioned at a different longitudinal location along the respective blades along the passageway when the three blades 1512, 1514, 1516 are in the first configuration. In some embodiments, the three blades 1512, 1514, 1516 can form a completely enclosed tubular passageway in the first configuration.

In any embodiments disclosed herein, as in the illustrated embodiments, the guides 1522, 1524, 1526 can be enclosed, partially open, tubular, C-shaped, U-shaped, or have any other desired shape. In some embodiments, the guides 1522, 1524, 1526 can extend longitudinally along a majority of a length of the inner surface of a corresponding blade 1512, 1514, 1516. Further, in some embodiments, the guides 1522, 1524, 1526 can be removably attachable to the inner surface of a corresponding blade 1512, 1514, 1516.

In some embodiments, at least two of the three blades 1512, 1514, 1516 can be moveable from a first configuration (as shown in FIG. 8A) in which each of the first, second and third blade 1516 can form an at least partially enclosed passageway defined by the inner surfaces of the three blades 1512, 1514, 1516 extending along a longitudinal axis parallel to each of the three blades 1512, 1514, 1516, and a second configuration (as shown in FIG. 8B) in which the distal ends of at least two of the three blades 1512, 1514, 1516 can be configured to pivot radially outward relative to their proximal ends 1512*a*, 1514*a*, 1516*a*. In some embodiments, all three blades 1512, 1514, 1516 can be moveable between the first configuration and the second configuration, wherein in the second configuration the distal ends of all three blades 1512, 1514, 1516 pivot radially outward relative to their proximal ends 1512*a*, 1514*a*, 1516*a*.

The guidance tool 1500 can, in some embodiments, can further include a mount 1530 coupled with the proximal ends 1512*a*, 1514*a*, 1516*a* of the three blades 1512, 1514, 1516, wherein the proximal ends 1512*a*, 1514*a*, 1516*a* of at least two of the three blades 1512, 1514, 1516 can be pivotally connected to the mount 1530. In some embodiments, as in the illustrate embodiments, the proximal ends 1512*a*, 1514*a*, 1516*a* of all three blades 1512, 1514, 1516 can be pivotally connected to or coupled with the mount 1530. In some embodiments, the mount 1530 can have a semi-circular shape that surrounds the proximal ends 1512*a*, 1514*a*, 1516*a* of the three blades 1512, 1514, 1516.

In any embodiments disclosed herein, each of the three blades 1512, 1514, 1516 can have a hinge, a bracket 1532, 1534, 1536, respectively, or other components that are configured to pivotally engage with corresponding components or structures on the mount 1530. A pin or a shaft can also be used to couple the blades 1512, 1514, 1516 and/or the brackets 1532, 1534, 1536 with the mount 1536.

In some embodiments, the guidance tool 1500 can, in the first configuration, be delivered to a location adjacent the sacroiliac joint. In the second configuration, the three blades 1512, 1514, 1516 can provide a trajectory along the inner surfaces of the three blades 1512, 1514, 1516 for delivering three screws to the sacroiliac joint.

FIGS. 9A-9E show an embodiment of a guidance tool 1600 for delivering pedicle screws. In any embodiments disclosed herein, any components, features, or other details of the guidance tool 1600 can have any of the components, features, or other details of any other guidance tool embodiments disclosed herein, including without limitation any of the embodiments of the guidance tool 1500 described above, in any combination with any of the components, features, or details of the guidance tool 1600 disclosed below. Similarly, any components, features, or other details of any of the other system embodiments disclosed herein can have any of the components, features, or other details of any embodiments of the guidance tool 1600 disclosed herein in any combination with any of the components, features, or details of the system.

The guidance tool is also referred to herein as a pedicle screw trajectory finder or a multi-prong trajectory finder. Currently, pedicle screw tracts are identified individually for each screw either by fluorscopic guidance, stereotactic navigation, or by robotic guidance. Embodiments of the guidance tool 1600 disclosed herein allow the surgeon or robot to insert a tubular structure containing two or three drill guides into the screw through the muscle and then opened so that all two or three drill guides are adjusted at the same time for each fluoroscopic shot. The drill guide tubes can be clipped into the clips 1622, 1626 coupled with or integrally formed with each of the blades 1612, 1616. Alternatively, in some embodiments, the blades 1612, 1614, 1616 can be elongated and extend all with way through the muscle and down to the bone. If a bilateral Wiltse approach is used, then two drill guides can be inserted simultaneously so that three screw trajectories can be adjusted at the same time for every fluoroscopy image taken. This would reduce the number of fluoscopic images by up to 6×.

Figure 9A:
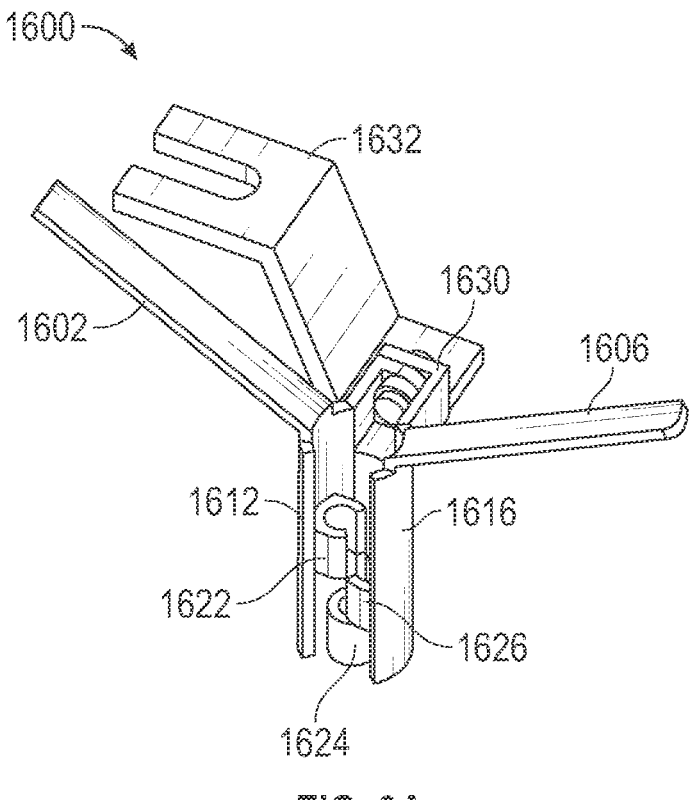
FIGS. 9A-9P illustrate another embodiment of a method and a system of a guidance tool for delivering pedicle screws.
Figure 9B:
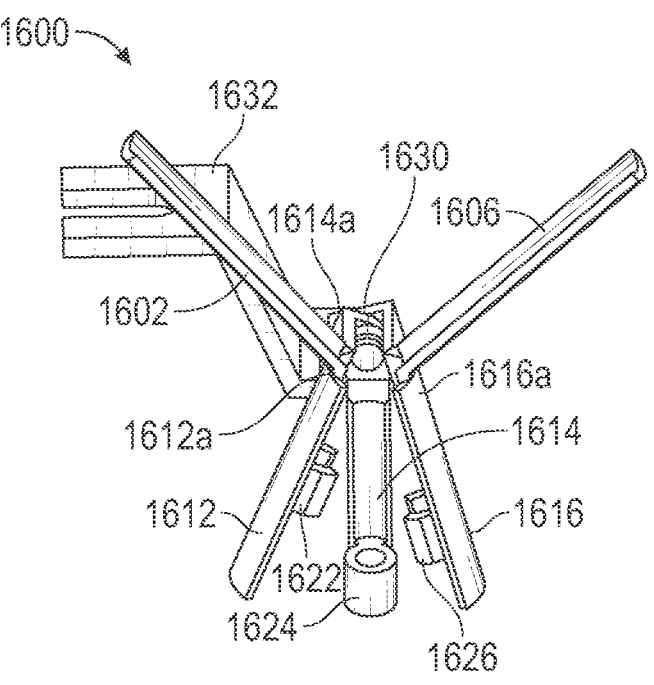
Figure 9C:
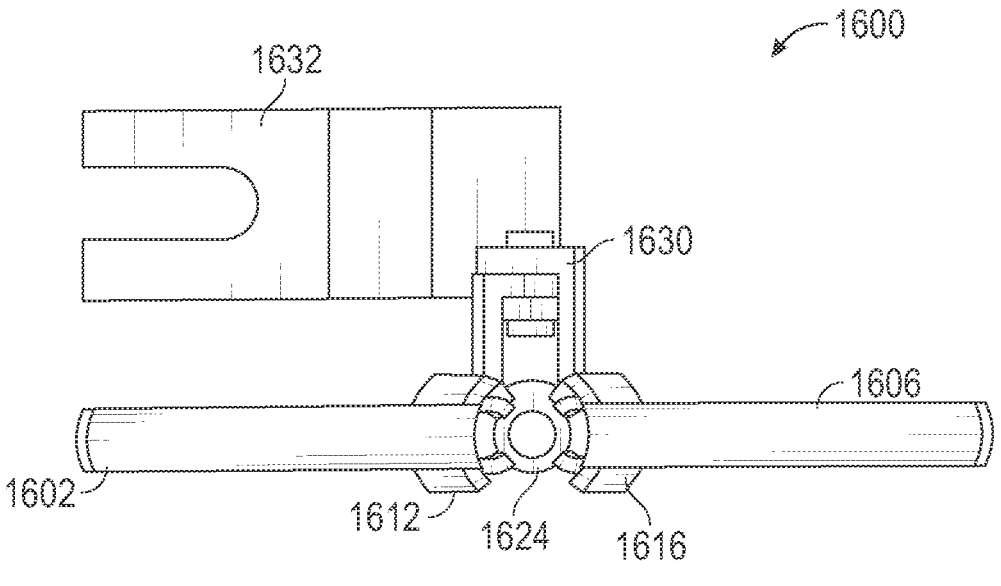
Figure 9D:
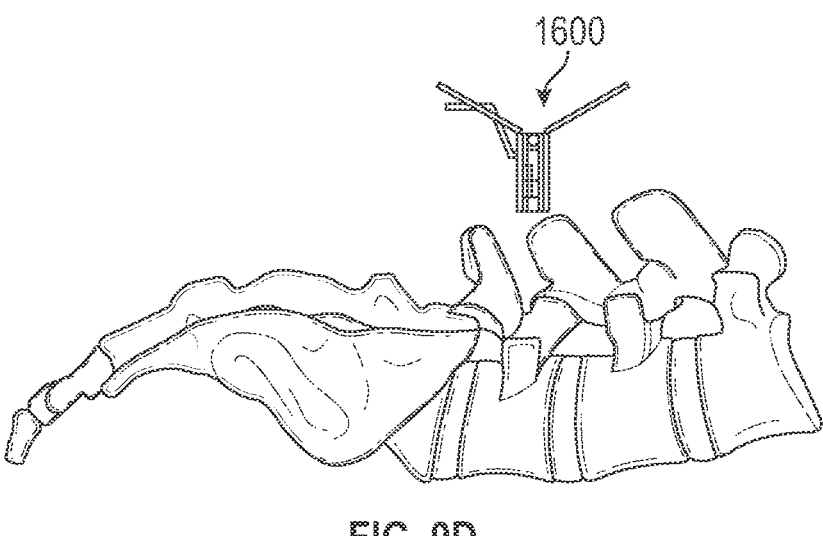
Figure 9E:
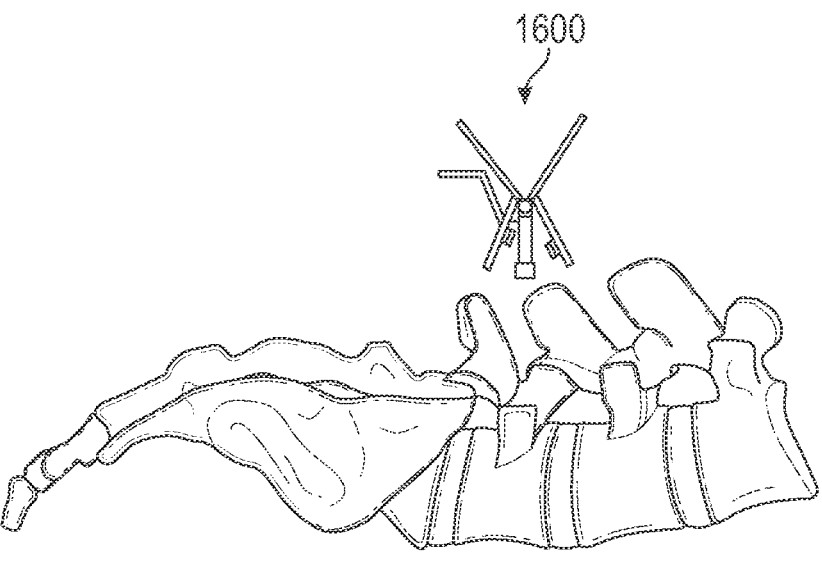
Figure 9F:
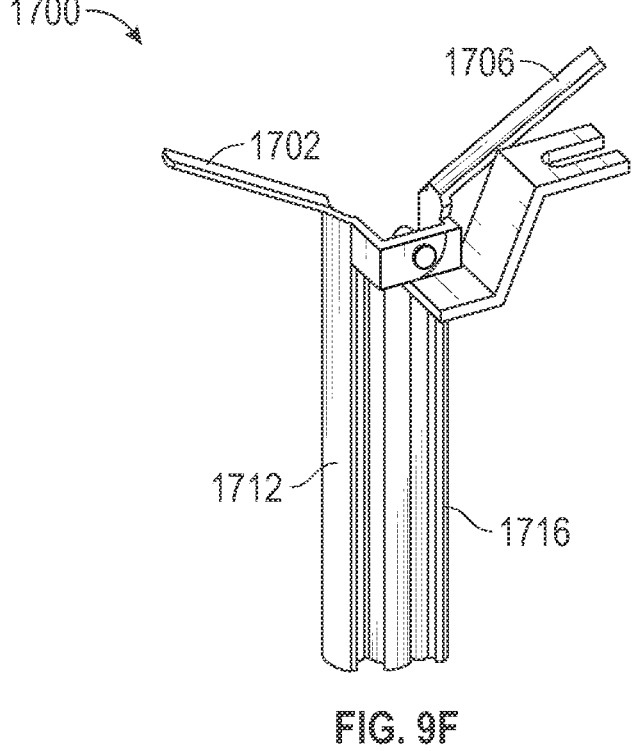
Figure 9G:
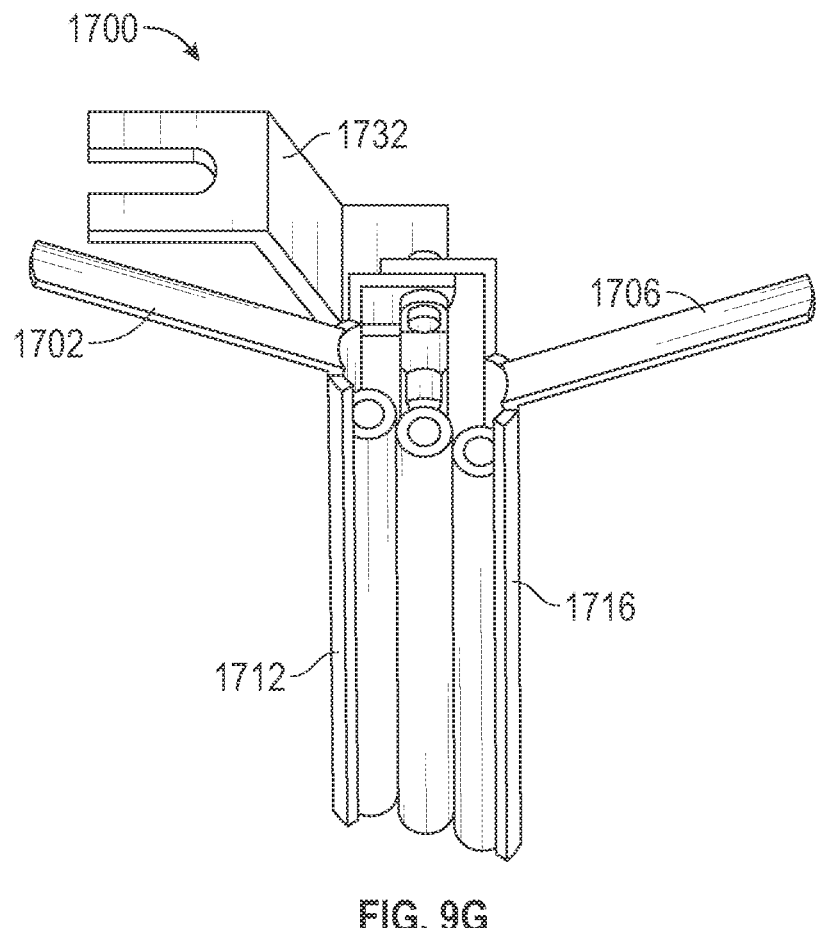
Figure 9H:
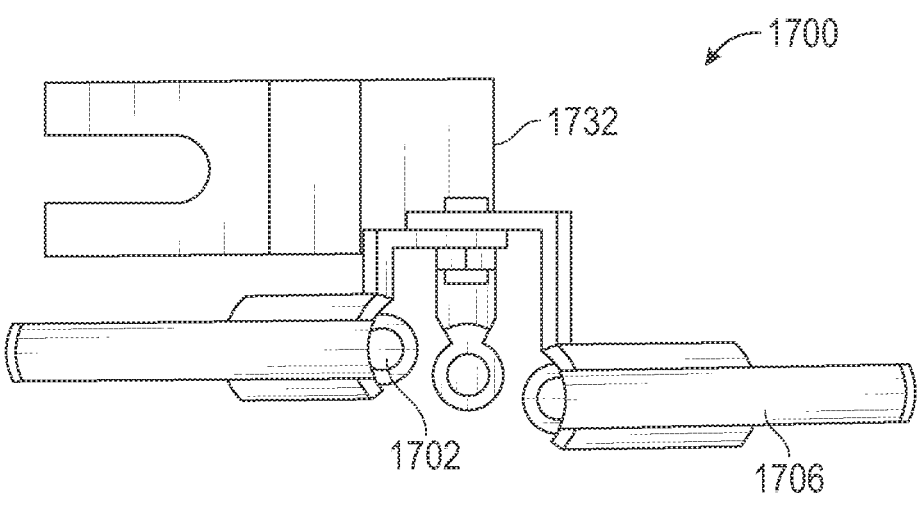
Figure 91:
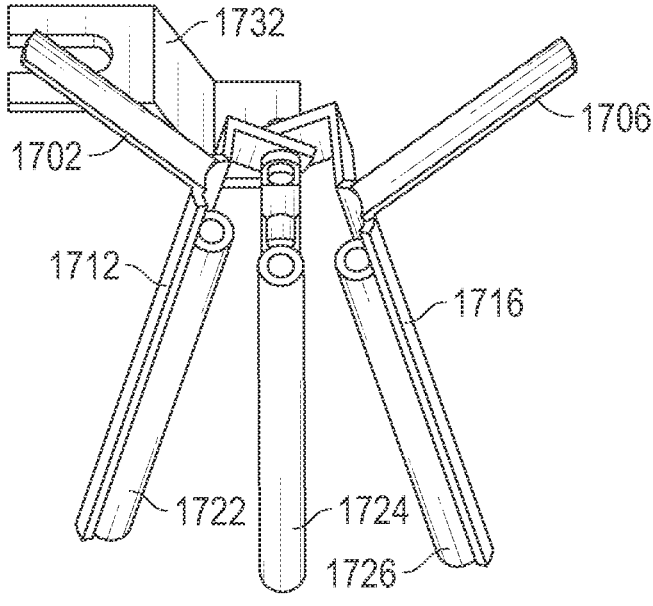
Figure 9J:
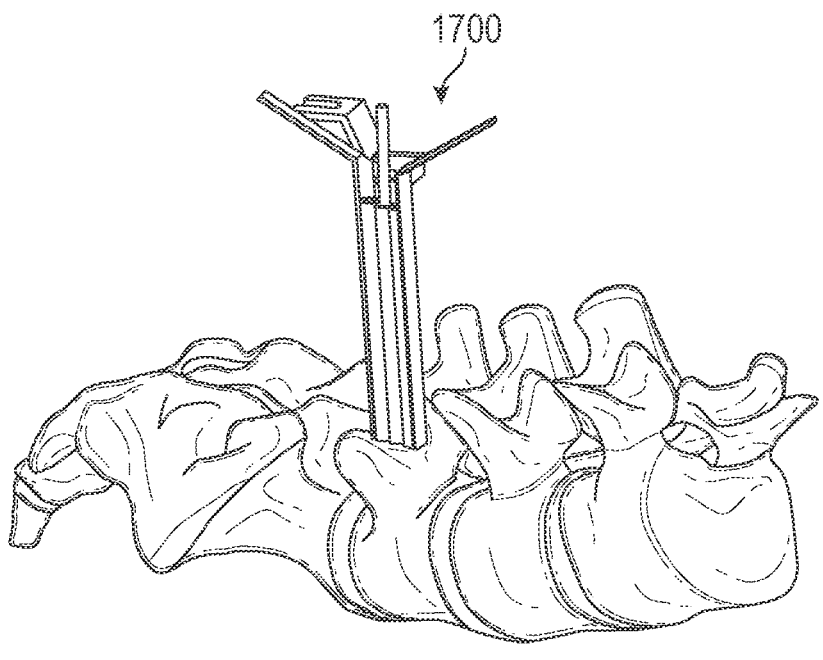
Figure 9K:
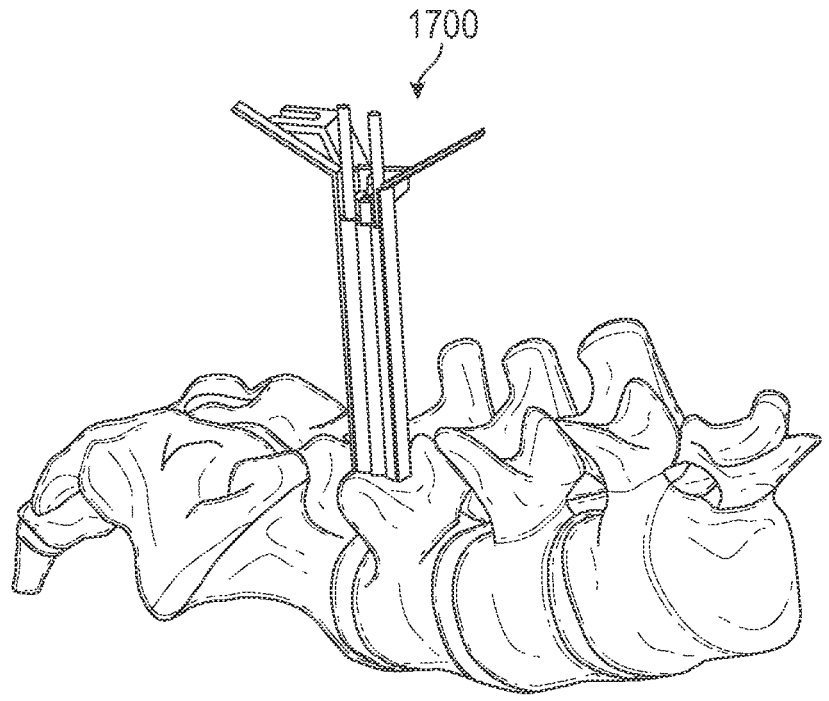

With reference to FIGS. 9D and 9E, the guidance tool 1600 can be inserted at the skin level and drill guides can be placed into the clips 1622, 1626 of each blade 1612, 1616. In some embodiments, a drill guide can be positioned in the guide 1624. The drill guides can be inserted together (closed) down through muscle and then opened similar to using a METRX dilator tube to dissect muscle off of bone. By placing the drill guide tubes down in a closed position then opening, this can help ensure that a single muscle plane contains all of the screws. Otherwise, the screws may be in different muscle planes which would require cutting of muscle when the rod or connecting element is inserted.

Also, this configuration of some embodiments allows for individual manipulation of each blade, permitting the robot to insert and open the blades and tubes to exact calculated positions and therefore trajectories of all three screws in one step. Thus, all screws trajectories can be identified in one step instead of three different steps, with some embodiments. Once drill guides are in the proper position, as confirmed by fluroscopic or stereotactic navigation means, then a drill can be used to create pedicle screw trajectories for the placement of pedicle screws.

With reference to FIGS. 9A-9E, some embodiments of the guidance tool 1600 for delivering pedicle screws can include blades 1612, 1614, and 1616. Each of the three blades 1612, 1614, 1616 can have a proximal end, a distal end, an inner surface and an outer surface. At least two of the three blades 1612, 1614, 1616 (for example and without limitation, blades 1612, 1616) can be moveable from a first configuration in which each of the blades 1612, 1614, 1616 form an at least partially enclosed passageway defined by the inner surfaces of the three blades 1612, 1614, 1616 extending along a longitudinal axis parallel to each of the three blades 1612, 1614, 1616, and a second configuration in which the distal ends of at least two of the three blades 1612, 1614, 1616 (for example and without limitation, blades 1612, 1616) pivot radially outward relative to their proximal ends 1612*a*, 1614*a*, 1616*a*. In some embodiments, the three blades 1612, 1614, 1616 can be configured in the first configuration for delivery to a location adjacent a first pedicle, and the three blades 1612, 1614, 1616 can be configured in the second configuration to provide a trajectory along the inner surfaces of the three blades 1612, 1614,

1616 for delivering three screws to the first pedicle, a second pedicle superior to the first pedicle, and a third pedicle inferior to the first pedicle.

In some embodiments, the second blade 1612 and the third blade 1616 can be pivotable away from the first blade 1614 along a common plane. Further, some embodiments of the guidance tool 1600 can include a mount 1630 connected to the proximal ends 1612a, 1614a, 1616a of the three blades 1612, 1614, 1616, wherein the proximal ends 1612a, 1614a, 1616a of at least two of the three blades 1612, 1614, 1616 can be pivotally connected to the mount 1630. The mount 1630 can have an arm 1632 extending away from the proximal ends 1612a, 1614a, 1616a of the three blades 1612, 1614, 1616, the arm 1632 being configured to be secured relative to a table, a positioning arm, a robotic arm, or other support structure. The tool 1600 can include handles 1602, 1606 extending at an angle from the proximal ends 1612a, 1616a of at least two of the three blades 1612, 1616, the handles 1602, 1606 being usable to pivot a corresponding blade from the first configuration to the second configuration. In any embodiments, all three of the blades 1612, 1614, 1616 can further have a guide 1622, 1624, 1626 on the inner surface thereof, which guides 1622, 1624, 1626 can be attached to or integrally formed with the blades. Further, in any embodiments, each of the guides 1622, 1624, 1626 can be positioned at a different longitudinal location along the passageway when the three blades 1612, 1614, 1616 can be in the first configuration. In some embodiments, the guides 1622, 1624, 1626 can be tubular, C-shaped, U-shaped, enclosed, open, or otherwise.

FIGS. 9F-9M show another embodiment of a guidance tool 1700 for delivering pedicle screws. The guidance tool is also referred to herein as a pedicle screw trajectory finder or a multi-prong trajectory finder. Currently pedicle screw tracts are identified individually for each screw either by fluorscopic guidance, stereotactic navigation, or by robotic guidance. This pedicle finder guidance tool can allow the surgeon or robot to insert a tubular structure containing two or three drill guides into the screw through the muscle and then opened so that all two or three drill guides are adjusted/manipulated at the same time for each fluoroscopic shot. If a bilateral Wiltse approach is used, then two drill guides can be inserted simultaneously so that six pedicle screw trajectories (for example, three on each side) can be adjusted at the same time for every fluoroscopy image taken. This would reduce the number of fluoscopic images by up to 6×. The drill guide tubes 1722, 1724, 1726 can be cylindrical and can be associated with or coupled with tissue spreaders. The purpose of expansion rather than inserting three tubes independently through muscle is that if all guide tubes on one side are inserted together initially and then opened, then the three tubes all occupy a single muscle plane. This spares any muscle cutting when the rod or connecting element is eventually inserted into the screw heads.

The guidance tool 1700 can be inserted at the skin level and drill guides can be placed into the clips of each blade. The drill guides can be inserted together (closed) down through muscle and then opened similar to using a Medtronic METRX dilator tube to dissect muscle off of bone. By placing the drill guide tubes down in a closed position then opening, this can help ensure that a single muscle plane contains all screws. Otherwise, screws may be in different muscle planes which would require cutting of muscle when the rod or connecting element is inserted. Handles 1702, 1704, 1706 on each of the guide tubes allow independent manipulation based on each fluoroscopic shot. If stereotactic navigation is used, then the trajectories can be manipulated continuously in response to the stereotactic guidance. The table arm bracket 1732 can allow the guidance tool 1700 to be stabilized in relation to the operating table. Also robotic manipulation of each blade can allow the robot to insert and open the blades 1702, 1704, 1706 and tubes to exact calculated positions and therefore trajectories of all three screws can be identified in one step instead of three different steps. Once drill guides are in the proper position as confirmed by fluroscopic or stereotactic navigation means, then a drill can be used to create pedicle screw trajectories for the placement of pedicle screws. Planning all three trajectories simultaneously better ensures that the screw heads will be aligned. Typically, most pedicle screw trajectories are aligned in a gentle curve in the lumbar spine. Linear approximation of this curve is usually straight forward.

Figure 9L:
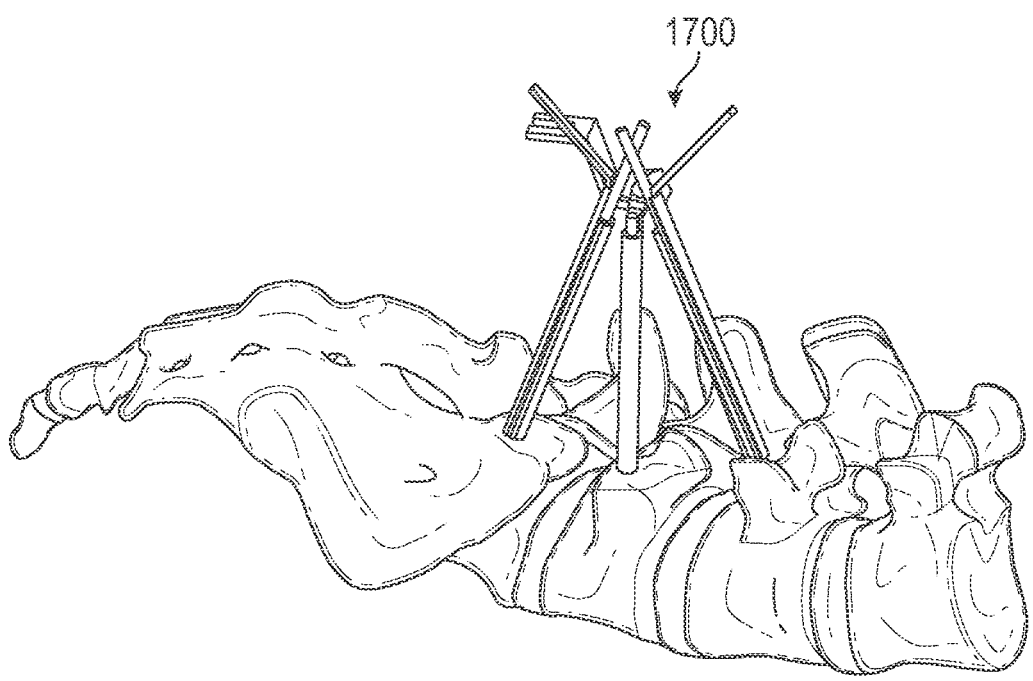
Figure 9M:
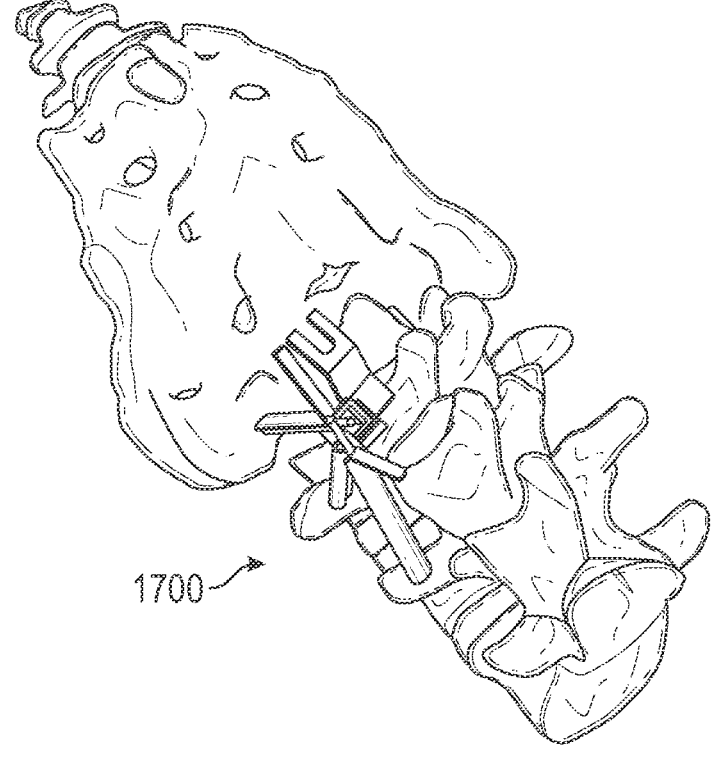

With reference to FIGS. 9L-9M, the guide tubes can be opened and can be manipulated deeper or more superficial depending on bony artifacts, osteophytes, etc. Inner tubes inside the guide can be positioned to accommodate these depth variations.

In any embodiments disclosed herein, any components, features, or other details of the guidance tool 1700 can have any of the components, features, or other details of any other guidance tool embodiments disclosed herein, including without limitation any of the embodiments of the guidance tool 1500, 1600 described above, in any combination with any of the components, features, or details of the guidance tool 1700 disclosed below. Similarly, any components, features, or other details of any of the other system embodiments disclosed herein can have any of the components, features, or other details of any embodiments of the guidance tool 1700 disclosed herein in any combination with any of the components, features, or details of the system.

In some embodiments, the guides 1722, 1724, 1726 can be cylindrical in shape and extend longitudinally along a majority of a length of the inner surface of a corresponding blade 1712, 1714, 1716. In some embodiments, the guides 1722, 1724, 1726 can be positioned side-by-side in the first configuration. Further, in some embodiments, the guides 1722, 1724, 1726 can be removably attachable to the inner surface of a corresponding blade 1712, 1714, 1716.

Figure 9N:
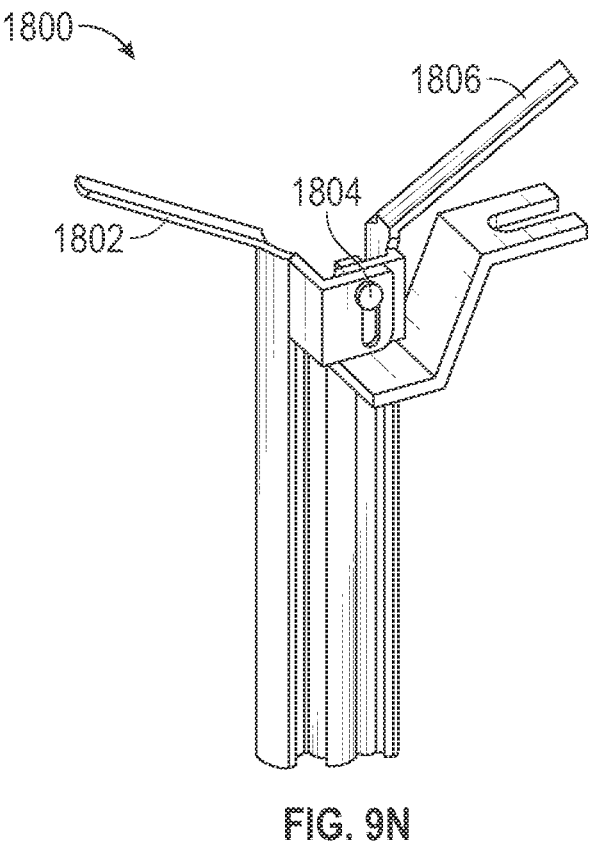
Figure 9O:
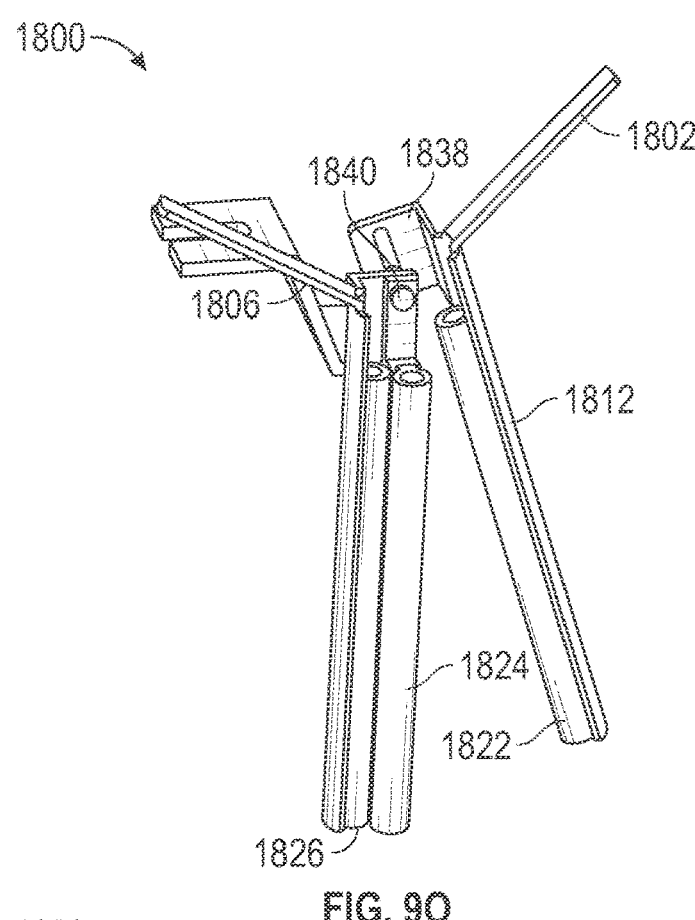
Figure 9P:
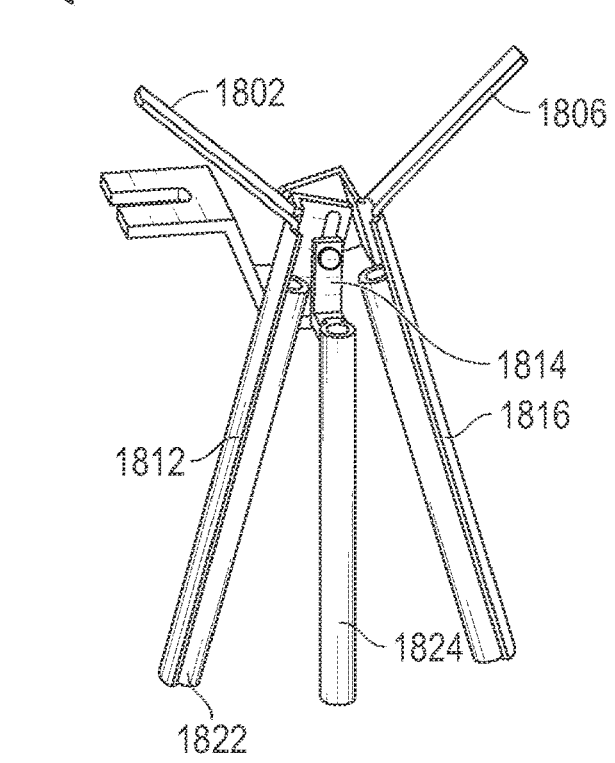

FIGS. 9N-9P show another embodiment of a guidance tool 1800 for delivering pedicle screws. In any embodiments disclosed herein, any components, features, or other details of the guidance tool 1800 can have any of the components, features, or other details of any other guidance tool embodiments disclosed herein, including without limitation any of the embodiments of the guidance tool 1500, 1600, and/or 1700 described above, in any combination with any of the components, features, or details of the guidance tool 1800 disclosed below. Similarly, any components, features, or other details of any of the other system embodiments disclosed herein can have any of the components, features, or other details of any embodiments of the guidance tool 1800 disclosed herein in any combination with any of the components, features, or details of the system. A variation of the stage of the guide tubes 1822, 1824, 1826 allows each tube 1822, 1824, 1826 to be varied in multiple° of freedom is necessary, independently of the other tubes. Preferably, a robot means allow calculated manipulation of the tubes 1822, 1824, 1826.

Additionally, with reference to FIGS. 9N-9P, some embodiments of the guidance tool 1800 can have a sliding hinge 1840 configured to permit the first blade 1812 to rotate and translate in an axial direction. For example and without limitation, in some embodiments, a bracket 1838 can be coupled with the first handle 1802 and/or first blade 1812. With reference to FIG. 90, in some embodiments, the second blade 1814 can be rotatable relative to the mount.

Certain aspects of the systems, devices, components and/or methods described above or as illustrated with respect to FIGS. 8A-9P are also encompassed by the following numbered embodiments. These numbered embodiments are considered to be directed to systems, devices, components and/or methods that include but are not limited to the embodiments of FIGS. 8A-9P, and thus these numbered embodiments may encompass other embodiments as described throughout this specification.

1. A guidance tool for delivering screws to a spinal location, the guidance tool comprising:

a first blade, a second blade and a third blade, each of the three blades having a proximal end, a distal end, an inner surface and an outer surface, wherein at least two of the three blades are moveable from a first configuration in which the first, second and third blades form an at least partially enclosed passageway defined by the inner surfaces of the three blades extending along a longitudinal axis parallel to each of the three blades, and a second configuration in which the distal ends of at least two of the three blades pivot radially outward relative to their proximal ends.

2. The guidance tool of Embodiment 1, wherein all three blades are moveable from the first configuration to the second configuration, wherein in the second configuration the distal ends of all three blades pivot radially outward relative to their proximal ends.

3. The guidance tool of Embodiment 1 or 2, further comprising a mount connected to the proximal ends of the three blades, wherein the proximal ends of at least two of the three blades are pivotally connected to the mount.

4. The guidance tool of Embodiment 3, wherein the proximal ends of all three blades are pivotally connected to the mount.

5. The guidance tool of Embodiment 3 or 4, wherein the mount has a semi-circular shape that surrounds the proximal ends of the three blades.

6. The guidance tool of any one of the preceding Embodiments, further comprising a handle extending at an angle from the proximal ends of at least two of the three blades, the handle being usable to pivot a corresponding blade from the first configuration to the second configuration.

7. The guidance tool of Embodiment 6, wherein a handle extends from the proximal end of all three blades.

8. The guidance tool of any one of the preceding Embodiments, wherein at least two of the three blades further comprise a drill guide on the inner surface thereof.

9. The guidance tool of any one of the preceding Embodiments, wherein all three of the blades further comprises a drill guide on the inner surface thereof.

10. The guidance tool of any one of Embodiment 8 or 9, wherein each of the drill guides is positioned at a different longitudinal location along the passageway when the three blades are in the first configuration.

11. The guidance tool of any one of Embodiments 8-10, wherein the drill guides are tubular.

12. The guidance tool of any one of Embodiments 8-10, wherein the drill guides are C-shaped.

13. The guidance tool of any one of Embodiments 8-12, wherein the drill guides extend longitudinally along a majority of a length of the inner surface of a corresponding blade.

14. The guidance tool of any one of Embodiments 8-13, wherein the drill guides are removably attachable to the inner surface of a corresponding blade.

15. The guidance tool of any one of the preceding Embodiments, wherein the three blades form a completely enclosed tubular passageway in the first configuration.

16. A guidance tool for delivering screws to a sacroiliac joint, the guidance tool comprising:

a first blade, a second blade and a third blade, each of the three blades having a proximal end, a distal end, an inner surface and an outer surface, wherein at least two of the three blades are moveable from a first configuration in which the first, second and third blades form an at least partially enclosed passageway defined by the inner surfaces of the three blades extending along a longitudinal axis parallel to each of the three blades, and a second configuration in which the distal ends of at least two of the three blades pivot radially outward relative to their proximal ends;

wherein the three blades are configured in the first configuration for delivery to a location adjacent the sacroiliac joint, and the three blades are configured in the second configuration to provide a trajectory along the inner surfaces of the three blades for delivering three screws to the sacroiliac joint.

17. The guidance tool of Embodiment 16, wherein all three blades are moveable from the first configuration to the second configuration, wherein in the second configuration the distal ends of all three blades pivot radially outward relative to their proximal ends.

18. The guidance tool of Embodiment 16 or 17, further comprising a mount connected to the proximal ends of the three blades, wherein the proximal ends of at least two of the three blades are pivotally connected to the mount.

19. The guidance tool of Embodiment 18, wherein the proximal ends of all three blades are pivotally connected to the mount.

20. The guidance tool of Embodiment 18 or 19, wherein the mount has a semi-circular shape that surrounds the proximal ends of the three blades.

21. The guidance tool of any one of Embodiments 16-20, further comprising a handle extending at an angle from the proximal ends of at least two of the three blades, the handle being usable to pivot a corresponding blade from the first configuration to the second configuration.

22. The guidance tool of Embodiment 21, wherein a handle extends from the proximal end of all three blades.

23. The guidance tool of any one of Embodiments 16-22, wherein all three of the blades further comprise a drill guide on the inner surface thereof.

24. The guidance tool of Embodiment 23, wherein each of the drill guides is positioned at a different longitudinal location along the passageway when the three blades are in the first configuration.

25. The guidance tool of any one of Embodiment 23 or 24, wherein the drill guides are tubular.

26. The guidance tool of any one of Embodiment 23 or 24, wherein the drill guides are C-shaped.

27. The guidance tool of any one of Embodiments 16-27, wherein the three blades form a completely enclosed tubular passageway in the first configuration.

28. A guidance tool for delivering pedicle screws, comprising:

a first blade, a second blade and a third blade, each of the three blades having a proximal end, a distal end, an inner surface and an outer surface, wherein at least two of the three blades are moveable from a first configuration in which the first, second and third blades form an at least partially enclosed passageway defined by the inner surfaces of the three blades extending along a longitudinal axis parallel to each of the three blades, and a second configuration in which the distal ends of at least two of the three blades pivot radially outward relative to their proximal ends;

wherein the three blades are configured in the first configuration for delivery to a location adjacent a first pedicle, and the three blades are configured in the second configuration to provide a trajectory along the inner surfaces of the three blades for delivering three screws to the first pedicle, a second pedicle superior to the first pedicle, and a third pedicle inferior to the first pedicle.

29. The guidance tool of Embodiment 28, wherein the second and third blades are pivotable away from the first blade along a common plane.

30. The guidance tool of Embodiment 28 or 29, further comprising a mount connected to the proximal ends of the three blades, wherein the proximal ends of at least two of the three blades are pivotally connected to the mount.

31. The guidance tool of Embodiment 30, wherein the mount comprises an arm extending away from the proximal ends of the three blades configured to be secured relative to a table.

32. The guidance tool of any one of Embodiments 28-31, further comprising a handle extending at an angle from the proximal ends of at least two of the three blades, the handle being usable to pivot a corresponding blade from the first configuration to the second configuration.

33. The guidance tool of any one of Embodiments 28-32, wherein all three of the blades further comprise a drill guide on the inner surface thereof.

34. The guidance tool of Embodiment 33, wherein each of the drill guides is positioned at a different longitudinal location along the passageway when the three blades are in the first configuration.

35. The guidance tool of Embodiment 33 or 34, wherein the drill guides are tubular.

36. The guidance tool of Embodiment 33 or 34, wherein the drill guides are C-shaped.

37. The guidance tool of any one of Embodiments 33-36, wherein the drill guides are cylindrical in shape and extend longitudinally along a majority of a length of the inner surface of a corresponding blade.

38. The guidance tool of Embodiment 37, wherein the drill guides are positioned side-by-side in the first configuration.

39. The guidance tool of any one of Embodiments 28-38, wherein the drill guides are removably attachable to the inner surface of a corresponding blade.

Systems, Devices and Methods of FIGS. 10A-10G

Additional embodiments of a system (e.g., system 2000) that can be used for stabilizing or treating spinal vertebrae through a skin incision S are disclosed below. In any embodiments disclosed herein, any components, features, or other details of the system 2000 can have any of the components, features, or other details of any other system embodiments disclosed herein or be used according to any of the steps of any other method embodiments disclosed herein, including without limitation any of the embodiments of the system 200, 300, and/or 400 or methods of use thereof described above, in any combination with any of the components, features, or details of the system 2000 or methods of use disclosed herein. Similarly, any components, features, steps, or other details of any of the other system or method embodiments disclosed herein can have any of the components, features, steps, or other details of any embodiments of the system 2000 or methods of use thereof disclosed herein in any combination with any of the components, features, or details of the system.

Some embodiments of the system 2000 for stabilizing spinal vertebrae through a skin incision S can include a first screw 2002 having a first screw head, a second screw 2004 having a second screw head, a third screw 2006 having a third screw head, a first tower 2012 having a distal portion 2012a and a proximal portion 2012b, a second tower 2014 having a distal portion 2014a and a proximal portion 2014b, and a third tower 2016 having a distal portion 2016a and a proximal portion 2016b. Note that the first tower, second tower, and third tower can also be referred to herein as a first extension, second extension, and third extension. The first tower 2012 can be configured to be removably coupled with the first screw 2002 at a distal end 2012a of the first tower 2012, the second tower 2014 can be configured to be removably coupled with the second screw 2004 at a distal end 2014a of the second tower 2014, and third tower 2016 can be configured to be removably coupled with the third screw 2006 at a distal end 2016a of the third tower 2016. In some embodiments, each of the first, second, and third screws 2002, 2004, 2006 can be positioned in different vertebra. In some embodiments, each of the first, second, and third screws 2002, 2004, 2006 can be positioned in adjacent vertebra. In any embodiments disclosed herein, any of the extensions can also be referred to as guiding elements, towers, or by other suitable terms understood in the industry. Additionally, note that, while the embodiments of the system 2000 disclosed herein may have included screws as part of the system, any embodiments of the system 2000 disclosed herein can exclude the screws such that the embodiments of the system 2000 include the towers and/or other components other than the screws.

Some MIS pedicle screw systems use towers mechanically coupled to pedicle screws while other MIS pedicle screw systems use extended tabs or blades that are created in a single piece of metal. In the extended tabs case the blades are manufactured as part of the screw from one single piece of metal. There is usually a scored transition between the top of the screw and the extended blade. The scored transition allows the blade to snap off at the end of the fusion after the rod has been final locked in place. From a manufacturing perspective, extended tabs or blades are more expensive because of the extra metal needed to manufacture the blade or tab that is eventually broken off and wasted.

In any of the embodiments disclosed herein, the first, second, and third towers can be configured to be removably coupled with the screw heads and otherwise configured to be reuseable. This can save a significant cost as compared with disposable blade designs that, once the blade has been separated from the screw head, is typically discarded and not reused. From a surgical perspective, towers are more firm an rigid and can be used to provide rigidity to as to provide counter-torque during final tightening of the locking cap onto the rod in the screw head. Extended blades usually do not have the same strength as a counter-torque device. The towers of any of the embodiments disclosed herein, with the rigidity that they provide, can therefore help prevent the walls of the pedicle screw from splaying during final tightening of the locking cap.

The towers of some embodiments disclosed herein can provide a more complete enclosure than the blades or tabs can, due to the additional wall portions of the towers that extend between the sides of the towers. In some embodiments, as shown in the figures, the wall portions that extend between the two side wall portions to provide additional strength and stiffness can be integrally formed with the side wall portions, or can be separately formed and coupled (removably or nonremovably) with the side wall portions to provide additional rigidity to the towers.

In some embodiments, at least a portion of the distal portions of any embodiments of the first and/or third towers 2012, 2016 can be enclosed about at least 320° (or at least approximately) 320° of the circumference or cross-section of the first and/or third towers 2012, 2016, or from 270° (or approximately) 270° to 330° (or approximately 330°, or at least) 330°, or from 290° (or approximately) 290° to 320° (or approximately) 320°, or enclosed about any value or range of value within the foregoing ranges. In some embodiments, at least a portion of the distal portions of any embodiments of the first and/or third towers 2012, 2016 can be can be completely enclosed, with the exception of the channel extending lengthwise along at least the distal portion of the first and/or third towers 2012, 2016 sized and configured to permit a passage of the rod or connecting element toward the screws. Additionally, for example and without limitation, at least a portion of the distal portion of any embodiments of the second tower 2014 can be enclosed about at least 270° (or at least approximately) 270° of the circumference or cross-section of the second tower 2014, or from 240° (or approximately) 240° to 320° (or approximately) 320°, or from 270° (or approximately) 270° to 300° (or approximately) 300°, or enclosed about any value or range of value within the foregoing ranges. In some embodiments, at least a portion of the distal portion of any embodiments of the second tower 2014 can be can be completely enclosed, with the exception of a channel on each side of the distal portion 2014b of the second tower 2014 extending lengthwise along at least the distal portion of the second tower 2014 sized and configured to permit a passage of the rod or connecting element toward the screws.

In some embodiments, at least a portion of the distal portions of any embodiments of the first and/or third towers 2012, 2016 can be enclosed about at least 80% (or at least approximately 80%) of the circumference or cross-section of the first and/or third towers 2012, 2016, or from 70% (or approximately 70%) to 90% (or approximately 90%, or more than 90%—e.g., 95% or 100%), or from 75% (or approximately 75%) to 85% (or approximately 85%), or enclosed about any value or range of value within the foregoing ranges. Additionally, for example and without limitation, at least a portion of the distal portion of any embodiments of the second tower 2014 can be enclosed about at least 75% (or at least approximately 75%) of the circumference or cross-section of the second tower 2014, or from 60% (or approximately 60%) to 80% (or approximately 80%), or from 65% (or approximately 65%) to 75% (or approximately 75%), or enclosed about any value or range of value within the foregoing ranges.

The additional wall portions of the towers disclosed herein are configured to prevent more muscle and tissue creep or invagination into the space within the tower or between the blades. For an MIS procedure in a large patient with excessive tissue, adipose tissue and muscle, a tower will protect the inside of the tower from tissue interference, whereas blades can allow tissue to creep in from both openings between the blades. In some embodiments, placement of the rod is then easier within a tower than using blades and there is a lower risk that patient tissue will be inadvertently severed or injured during rod placement. Placement of the rod using only blades often results in the rod getting "caught up" in the muscle that creeps into the opening between the blades.

In some embodiments, the first tower 2012 can have a slight bend between the distal portion 2012a and the proximal portion 2012b thereof. For example and without limitation, the distal portion 2012a can be angled relative to the proximal portion 2012b so that a longitudinal centerline of the proximal portion 2012b has an angle that is 20° or approximately 20° relative to a longitudinal centerline of the distal portion 2012a of the first tower 2012, or so that the longitudinal centerline of the proximal portion 2012b has an angle that is from 0° or approximately 0° to 40° or approximately 40°, or from 10° or approximately 10° to 30° or approximately 30° relative to the longitudinal centerline of the distal portion 2012a of the first tower, or of any value or range of values within any of the foregoing ranges. In any embodiments, the second tower 2014 can be generally straight along a length thereof, as shown, or can have a bend between the distal portion 2014a and the proximal portion 2014b thereof.

In some embodiments, the third tower 2016 can have a bend between the distal portion 2016a and the proximal portion 2016b thereof. The bend in the third tower 2016 may be greater than the bend in the first tower 2012. For example and without limitation, the distal portion 2016a can be angled relative to the proximal portion 2016b so that a longitudinal centerline of the proximal portion 2016b has an angle that is 85° or approximately 85° relative to a longitudinal centerline of the distal portion 2016a of the third tower 2016, or that is 90° or approximately 90° relative to a longitudinal centerline of the distal portion 2016a of the third tower 2016, or so that the longitudinal centerline of the proximal portion 2016b has an angle that is from 70° or approximately 70° to 110° or approximately 110°, or from 80° or approximately 80° to 100° or approximately 100° relative to the longitudinal centerline of the distal portion 2016a of the first tower 2012, or of any value or range of values within any of the foregoing ranges. In some embodiments, the bend between the distal and proximal portions of any of the towers can optionally be adjustable using an adjustable coupling such as a locking hinge.

Any embodiments of the system 2000 disclosed herein can be configured such that the first screw 2002, the second screw 2004, and the third screw 2006 can be implanted through the same skin incision S. Further, in any embodiments, a distal portion 2014a of the second tower 2014 can be positioned between the distal portions 2012a, 2016a of the first and third towers 2012, 2016 in an operable state of the system 2000.

In some embodiments, the first tower 2012 can have a two or more proximal portions 2012b extending away from the distal portion 2012a of the first tower 2012 at a variety of angles. For example and without limitation, the two or more proximal portions 2012b extending away from the distal portion 2012a of the first tower 2012 can provide two or more separate handles extending away from the distal portion 2012a that a surgeon can grasp and manipulate. In some embodiments, the first tower 2012 can removably couple with the first screw 2002 such that, when the first tower 2012 is coupled with the first screw 2002, an axial or longitudinal centerline C of the distal portion 2012a of the first tower 2012 is approximately collinear with an axial or longitudinal centerline C of the first screw 2002. The second tower 2014 can removably couple with the second screw 2004 such that, when the second tower 2014 is coupled with the second screw 2004, an axial centerline C of the distal portion 2014a of the second tower 2014 is approximately collinear with an axial centerline C of the second screw 2004. The third tower 2016 can removably couple with the third screw 2006 such that, when the third tower 2016 is coupled with the third screw 2006, an axial centerline C of the distal portion 2016*a* of the third tower 2016 is approximately collinear with an axial centerline C of the third screw 2006. In any embodiments, the first tower 2012 can be shorter than the second tower 2014 or the third tower 2016, longer than the second tower 2014 or the third tower 2016, or have approximately the same length as the second tower 2014 or the third tower 2016, and the second tower 2014 can be shorter than the third tower 2016, longer than the third tower 2016, or have approximately the same length as the third tower 2016.

In some embodiments, the angle between the proximal portion 2012*b* and distal portion 2012*a* of the first tower 2012 can be adjustable, an angle between the proximal portion 2014*b* and distal portion 2014*a* of the second tower 2014 can be adjustable, and/or the angle between the proximal portion 2016*b* and distal portion 2016*a* of the third tower 2016 can be adjustable. A common mechanism for adjustability is a gear or ratchet mechanism. In this way, the proximal portion of any of the extensions can be angled away from the centerline of the distal portion of the respective screw. By adjusting the angle, there may be more room to place the rod and locking caps. Also, by adjusting the angle, it may be easier for a surgeon to grip both proximal portions of the towers in order to squeeze the two or three proximal portions of the extensions in order to compress the heads of screws when locking the caps onto the connecting element or rod connecting the screw heads. In another embodiment, proximal portions 2012*b*, 2014*b*, and/or 2016*b* can be detachable from the distal portions 2012*a*, 2014*a*, and/or 2016*a*. In this manner, proximal portions with different angles in relation to centerline of the respective distal portions can be switched as needed and reconnected to the distal portions of the extensions.

Figure 10A:
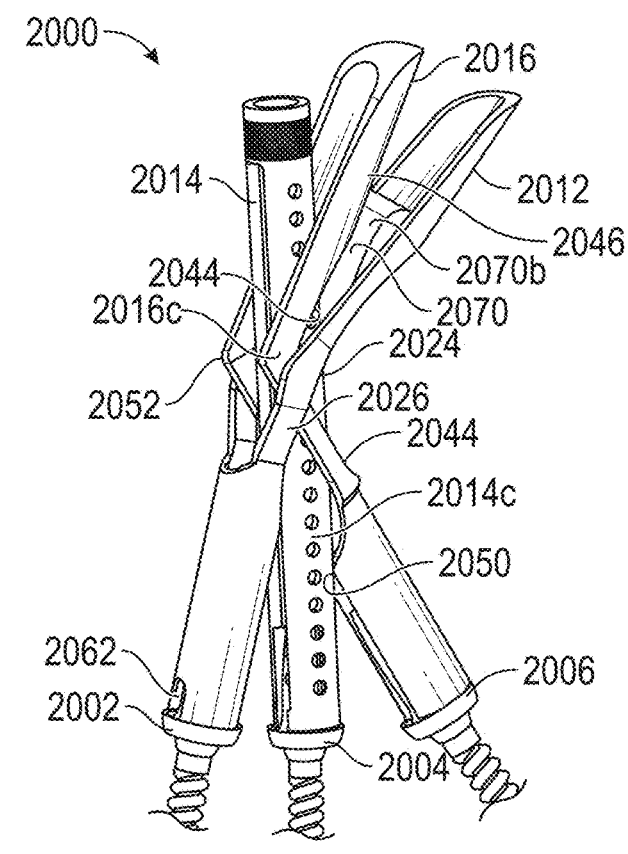
FIGS. 10A-10G illustrate another embodiment of a system for stabilizing spinal vertebrae comprising spinal screws.
Figure 10B:
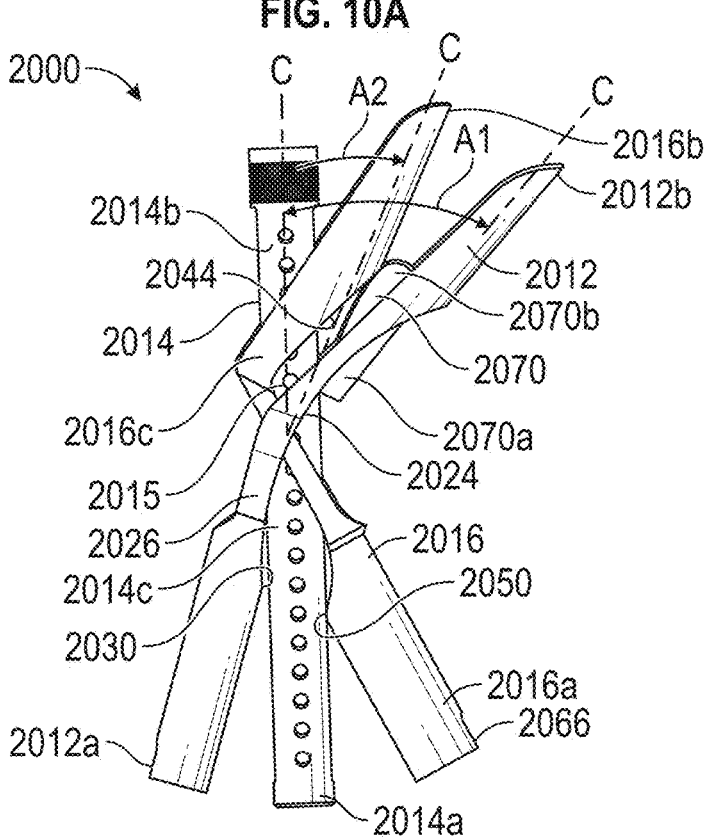
Figure 10C:
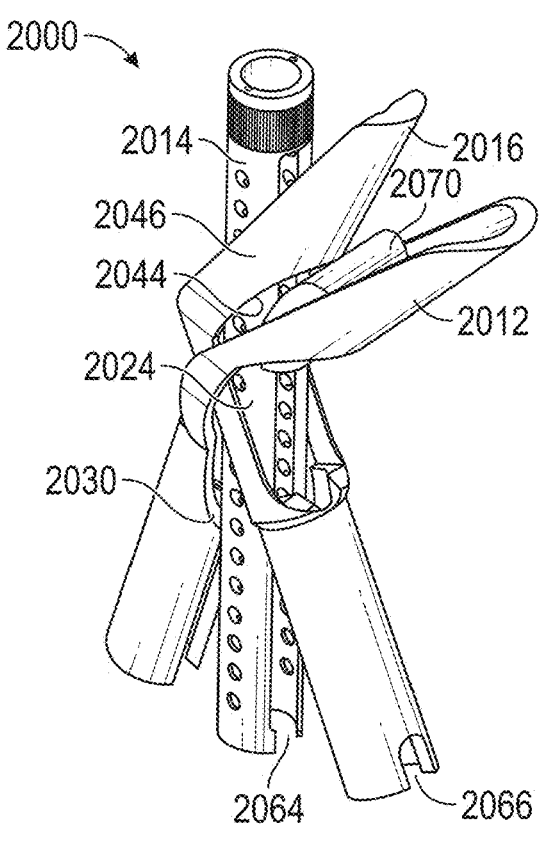
Figure 10D:
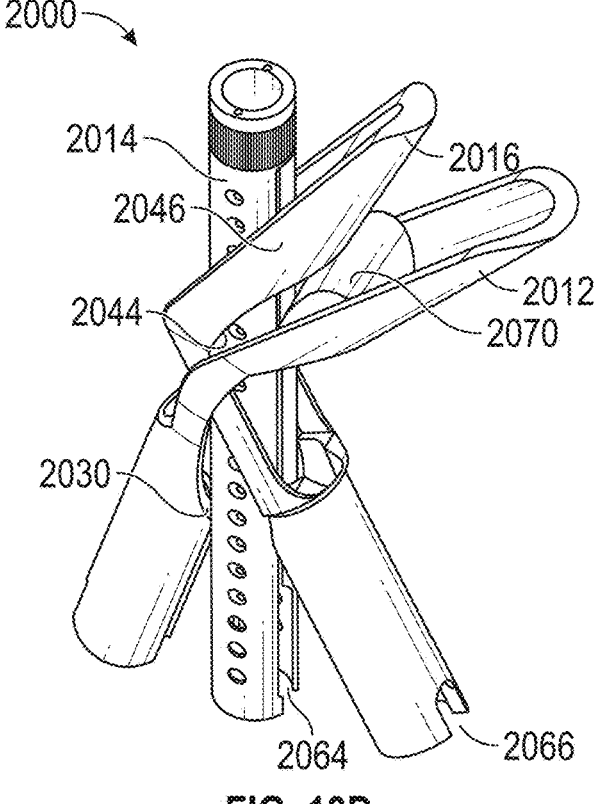
Figures 10E, 10F, 10G:
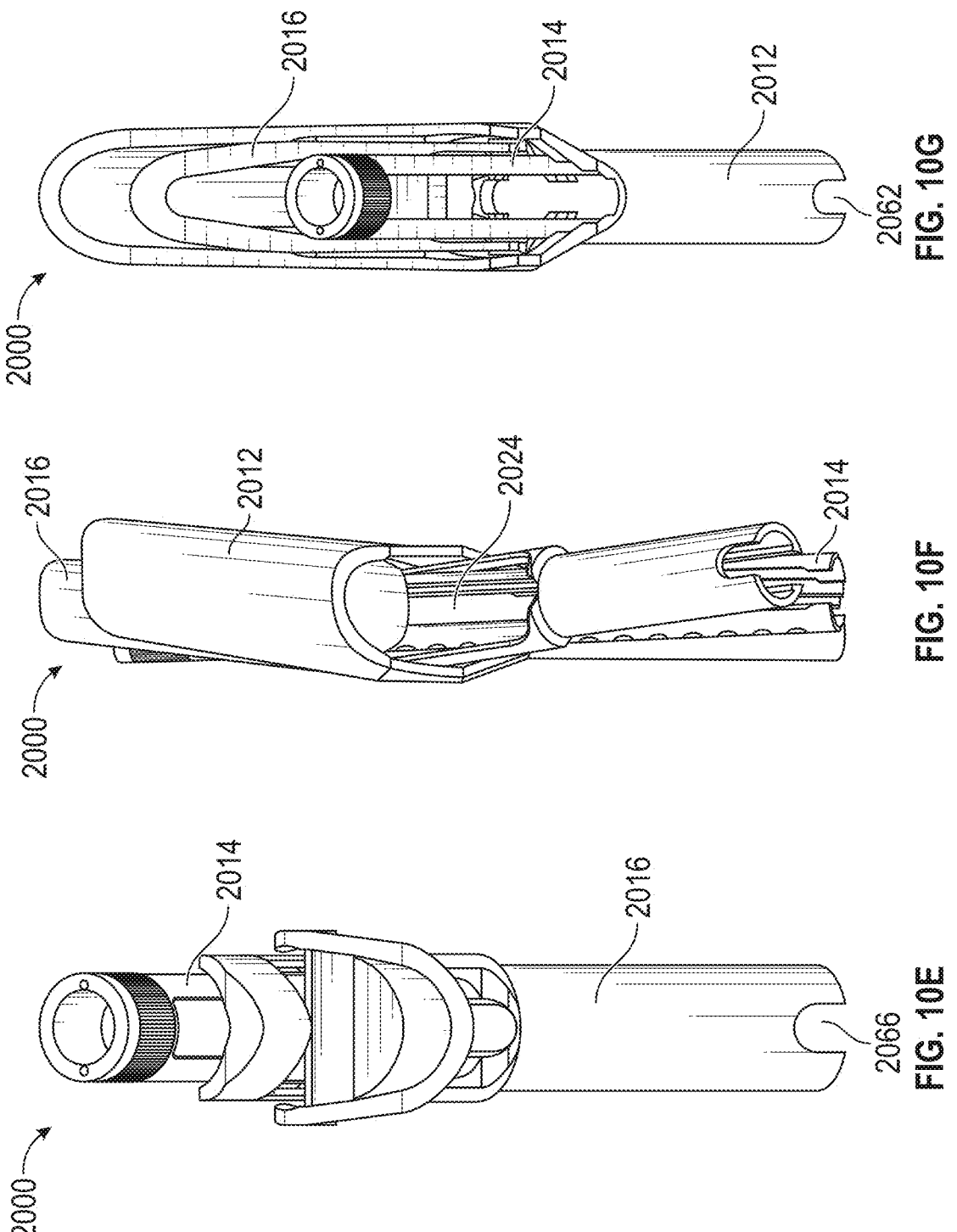

As mentioned, in some embodiments, the proximal portion 2012*b* of the first tower 2012 can extend at an angle away from the axial centerline C of the distal portion 2012*a* of the first tower 2012 such that an axial centerline of the proximal portion 2012*b* of the first tower 2012 is not approximately collinear with an axial centerline of the distal portion 2012*a* of the first tower 2012. Further, the first tower 2012 can be configured such that, in an operable state, an axial centerline of the proximal portion 2012*b* of the first tower 2012 can extend at an angle away from the axial centerline C of the proximal portion of the second tower 2014 so that the axial centerline of proximal portion 2012*b* of the first tower 2012 forms an acute angle A1 relative to the axial centerline of the proximal portion of the second tower 2014, as shown in FIG. 10B. In some embodiments, the angle A1 can be 50° (or approximately) 50°, or from 40° (or approximately) 40° or less to 70° (or approximately) 70° or more. The third tower 2016 can be configured such that, in an operable state, an axial centerline of the proximal portion 2016*b* of the third tower 2016 can extend at an angle away from the axial centerline C of the proximal portion of the second tower 2014 so that the axial centerline of proximal portion 2016*b* of the third tower 2016 forms an acute angle A2 relative to the axial centerline of the proximal portion of the second tower 2014 in an operable state, as shown in FIG. 10B. In some embodiments, the angle A2 can be 50° (or approximately) 50°, or from 40° (or approximately) 40° or less to 70° (or approximately) 70° or more.

In some embodiments, the first tower 2012 can be angled such that, in an operable state, the proximal portion 2012*b* of the first tower 2012 can extend away from the proximal portion 2014*b* of the second tower 2014 in a first direction, and the third tower 2016 can be angled such that, in an operable state, the proximal portion 2016*b* of the third tower 2016 can also extend away from the proximal portion of the second tower 2014 in the same direction or approximately the same direction as the proximal portion 2012*b* of the first tower—e.g., in the first direction. In some embodiments, the axial centerlines of the proximal portions 2012*b*, 2016*b* of the first and third towers 2012, 2016 can be within the same plane (e.g., a first plane) when the proximal portions 2012*b*, 2016*b* of the first and third towers 2012, 2016 extend away from the proximal portion of the second tower 2014 in the same direction. The first plane that contains the axial centerlines of the proximal portions 2012*b*, 2016*b* of the first and third towers 2012, 2016 can also intersect with the axial centerline of the second tower 2014, in some embodiments.

In some embodiments, the first tower 2012 can be sized and configured such that, in an operable state, the proximal portion 2012*b* of the first tower 2012 can extend away from the skin incision S toward the surgeon. In some embodiments, the first, second, and third towers 2012, 2014, and 2016 can be sized and configured such that the level of the patient's skin in an operable state of the system 2000 will be at or adjacent to the bend 2052 (e.g., just below the bend 2052) formed in the third tower 2016. In some embodiments, the distal portion 2012*a* of the first tower 2012 and the distal portion 2016*a* of the third tower 2016 can extend away from the first screw 2002 and the third screw 2006 to a height just below the skin incision S, or to a height level with the skin of a patient, when the first and third screws 2002, 2006 are fully implanted in a first vertebra and a third vertebra, respectively.

In some embodiments, the first tower 2012 can be sized such that only the proximal portion 2012*b* of the first tower 2012 is outside of the skin incision S when the first screw 2002 is implanted in a first vertebra, and the third tower 2016 can be sized such that only the proximal portion 2016*b* of the third tower 2016 is outside of the skin incision S when the third screw 2006 is implanted in a third vertebra. In any embodiments, the second tower 2014 can be sized to extend completely through the skin incision S when the second screw 2004 is implanted in a second vertebra.

The proximal portion 2012*b* of the first tower 2012 and the proximal portion 2016*b* of the third tower 2016 can be configured to be grasped by a surgeon to enable a surgeon to exert a rotational force on the first tower 2012 about at least the axial centerline C of the distal portion 2012*a* of the first tower 2012 about at least the axial centerline C of the distal portion 2012*a* of the first tower 2012 and/or a torque force on the first tower 2012 so as to cause the first tower 2012 to rotate about an axis that is perpendicular to an axial centerline C of the distal portion 2012*a* of the first tower 2012. The proximal portion 2016*b* of the third tower 2016 and the proximal portion 2016*b* of the third tower 2016 can be configured to be grasped by a surgeon to enable a surgeon to exert a rotational force on the third tower 2016 about at least the axial centerline C of the distal portion 2016*a* of the third tower 2016 about at least the axial centerline C of the distal portion 2016*a* of the third tower 2016 and/or a torque force on the third tower 2016 so as to cause the third tower 2016 to rotate about an axis that is perpendicular to an axial centerline C of the distal portion 2016*a* of the third tower 2016.

The proximal portion 2012*b* of the first tower 2012 can have a length that is approximately the same as a length of the distal portion 2012*a* of the first tower 2012, or can have a length that is at least 80% or less of a length of the distal portion 2012*a* of the first tower 2012. In some embodiments, the proximal portion 2012*b* of the first tower 2012 can be removably coupled with the distal portion 2012a of the first tower 2012. In other embodiments, the proximal portion 2012b of the first tower 2012 can be non-removably coupled with the distal portion 2012a of the first tower 2012. For example and without limitation, the proximal portion 2012b of the first tower 2012 can be integrally formed with the body portion of the first tower 2012. In any embodiments, the second and third towers 2014, 2016 can be similarly configured.

In some embodiments, at least the distal portion 2012a, the proximal portion 2012b of the first tower 2012, and/or the second tower 2014 can have a tubular or half-tubular shape. The first tower 2012 can have a cutout 2024 formed through a wall portion 2026 of the first tower 2012, the cutout 2024 being configured to receive a portion of an outside surface 2014c of the second tower 2014 therein in an operable state, as shown in the figures. In some embodiments, the cutout 2024 of the first tower 2012 can be large enough to also receive a portion of an outside surface 2016c of the third tower 2016 therein in an operable state, as shown in the figures. In some embodiments, the cutout 2024 can extend at least through a proximal end 2012c of the distal portion 2012a of the first tower 2012. The cutout 2024 can extend entirely through the first tower 2012 and be sized and configured such that, in an operable state, the second tower 2014 and the screw coupled with the second tower 2014 can pass entirely through the cutout 2024 in the first tower 2012 and the screw coupled with the third tower 2016 and at least the distal portion 2016b of the third tower 2016 can pass entirely through the cutout 2024.

In some embodiments, the cutout 2024 can extend entirely through the first tower 2012 such that, in an operable state, the second tower 2014 can pass entirely through the cutout 2024 and such that the wall portion 2026 of the first tower 2012 completely and continuously surrounds the outside surface 2014c of a portion of the second tower 2014 and the outside surface 2016c of a portion of the third tower 2016. Some embodiments of the cutout 2024 can have a distal edge 2030. In some embodiments, the distal edge 2030 can be lower to allow for a wider range of rotation or movement of the first tower 2012 relative to the second tower 2014. In some embodiments, the cutout 2024 can extend distally to be near to or adjacent to the distal end of the first tower. Some embodiments of the cutout 2024 can have an elongated or ovular shape.

In some embodiments, at least the distal portion 2016a and the proximal portion 2016b of the third tower 2016 can have a tubular or half-tubular shape. The third tower 2016 can have a cutout 2044 formed through a wall portion 2046 of the third tower 2016, the cutout 2044 being configured to receive a portion of an outside surface 2014c of the second tower 2014 therein in an operable state, as shown in the figures. In some embodiments, the cutout 2044 can extend at least through a proximal end 2016c of the distal portion 2016a of the third tower 2016. The cutout 2044 can extend entirely through the third tower 2016 such that, in an operable state, the second tower 2014 and the screw coupled with the second tower 2014 can pass entirely through the cutout 2044 in the third tower 2016.

In some embodiments, the cutout 2044 can be configured such that, in an operable state, the second tower 2014 can pass entirely through the cutout 2044 and such that the wall portion 2046 of the third tower 2016 completely and continuously surrounds the outside surface 2014c of a portion of the second tower 2014. Further, some embodiments of the cutout 2044 can have a distal edge 2050. In some embodiments, the distal edge 2050 can be lower to allow for a wider range of rotation or movement of the third tower 2016 relative to the second tower 2014. In some embodiments, the cutout 2044 can extend distally to be near to or adjacent to the distal end of the tower (e.g., the third tower 2016). Some embodiments of the cutout 2044 can have an elongated or ovular shape.

In some embodiments, at least the distal portion 2012a of the first tower 2012, the distal portion 2016a of the third tower 2016, and/or the distal portion 2014a of the second tower 2014 can have an adjustable length. Further, some embodiments of the first tower 2012, the second tower 2014, and the third tower 2016 can be generally cylindrically shaped. Other embodiments can have any other desired cross-sectional shape, including a generally square shape, a triangular cross-sectional shape, on ovular cross-sectional shape, a polygonal cross-sectional shape, or any combination of the foregoing.

The proximal portion 2012b of the first tower 2012 and/or the proximal portion 2016b of the third tower 2016 can have a cross-sectional profile that can have a curved shape. Further, the proximal portion 2012b of the first tower 2012 and/or the proximal portion 2016b of the third tower 2016 can have a cross-sectional profile that can have a semi-circular tubular shape. In some embodiments, the proximal portion 2012b of the first tower 2012 and/or the proximal portion 2016b of the third tower 2016 can have a cross-sectional profile that is approximately the same as one-half of the distal portion 2012a of the first tower 2012 and one-half of the distal portion 2016a of the third tower 2016. In some embodiments, the proximal portion 2012b of the first tower 2012 and/or the proximal portion 2016b of the third tower 2016 can have a planar shape.

Any of the embodiments of the system 2000 disclosed herein can have a rigid connecting element (not shown), similar to any of the other embodiments of the connecting elements disclosed herein, that can be implanted using any desired shape and configuration of a connecting element implantation device, such as the embodiment of the connecting element implantation device shown in FIGS. 3E-3F, or implanted using any other devices or methods disclosed herein or other desired devices or methods. A first receiving element coupled with the head of the first screw 2002, a second receiving element coupled with the head of the second screw 2004, and a third receiving element coupled with the head of the third screw 2006 can secure the connecting element to the screws 2002, 2004, 2006. The first, second, and third receiving elements can be configured to operably receive the connecting element that, in an operable state, can extend between the first, second, and third receiving elements when the first screw 2002, the second screw 2004, and the third screw 2006 are implanted in a first vertebra, a second vertebra, and a third vertebra, respectively.

In some embodiments, the first tower 2012 can have at least one window or slot 2062 extending through a side of the body portion thereof, the at least one slot 2062 configured to receive a connecting element 2051 or configured to permit a passage of a connecting element 2051 therethrough. Further, the second tower 2014 can have at least one slot or window 2064 extending through a side of the body portion of the second tower 2014, the at least one slot 2064 of the second tower 2014 configured to receive the connecting element 2051 that is configured to extend between the first screw 2002 and the third screw 2006 in an operable state. The third tower 2016 can have at least one slot or window 2066 extending through a side of the body portion of the third tower 2016, the at least one slot 2066 of the third tower

2016 configured to receive the connecting element 2051 that is configured to extend between the first screw 2002 and the third screw 2006 in an operable state. Lengthwise slots or channels can be formed in at least the distal portions of each of the first, second, and third towers to permit the connecting element to pass distally toward the screws.

In some embodiments of the system 2000, the first tower 2012 can have an insert or projection 2070 formed thereon or coupled therewith. The projection 2070 can have a distal portion 2070*a* that, in some embodiments, in an operable state, contacts the outside surface 2014*c* of the second tower 2014 to provide a point or a region of contact between the proximal portion 2012*a* of the first tower 2012 and the proximal portion 2014*b* of the second tower 2014. In some embodiments of this configuration, as the proximal portion 2012*b* of the first tower 2012 is squeezed relative to or otherwise rotated or moved toward the proximal portion 2014*b* of the second tower 2014, the distal portion 2070*a* of the projection 2070 can contact the outside surface 2014*c* of the second tower 2014 and the distal portion 2012*a* of the first tower 2012 can be moved toward the distal portion 2014*a* of the second tower 2014 to cause a compressive force to be exerted on a first vertebra that the first tower 2012 is coupled with relative to a second, adjacent vertebra that the second tower 2014 is coupled with. In other embodiments, the projection 2070 can be configured to rotate or otherwise move so that the point or region of contact and rotation between the first and second towers 2012, 2014 is only at the distal end 2030 of the opening 2024. In some embodiments of this configuration, as the proximal portion 2012*b* of the first tower 2012 is moved away from the proximal portion 2014*b* of the second tower 2014, the distal portion 2012*a* of the first tower 2012 can be moved away from the distal portion 2014*a* of the second tower 2014 to cause a traction force to be exerted on a first vertebra that the first tower 2012 is coupled with relative to a second, adjacent vertebra that the second tower 2014 is coupled with.

In some embodiments, the insert 2070 can be removably inserted into an interior space of the proximal portion 2012*b* of the first tower 2012 and positioned between the proximal portion 2012*b* of the first tower 2012 and the proximal portion 2016*b* of the third tower 2016, when needed or desired, to provide a fulcrum between the first and third towers 2012, 2016 during compression. In other embodiments, the insert 2070 can be nonremovably coupled with the proximal portion 2012*b* of the first tower 2012 or integrally formed with the proximal portion 2012*b* of the first tower 2012, or nonremovably coupled with an outside surface of the proximal portion 2016*b* of the third tower 2016 or integrally formed with the proximal portion 2016*b* of the third tower 2016 so as to be between the proximal portion 2016*b* of the third tower 2016 and the proximal portion 2012*b* of the first tower 2012.

In some embodiments, the projection 2070 can be configured to contact the outside surface 2016*c* of the third tower 2016, for example, in a proximal portion 2016*b* of the third tower 2016, to provide a point or a region of contact and rotation, or a fulcrum, between the proximal portion 2012*a* of the first tower 2012 and the proximal portion 2016*b* of the third tower 2016. In some embodiments of this configuration, as the proximal portion 2012*b* of the first tower 2012 is squeezed relative to or otherwise rotated or moved toward the proximal portion 2016*b* of the third tower 2016, a proximal portion 2070*b* of the projection 2070 can contact the outside surface 2016*c* of the proximal portion 2016*b* of the third tower 2016 to provide the point or a region of contact and rotation, or a fulcrum, between the proximal portion 2012*a* of the first tower 2012 and the proximal portion 2016*b* of the third tower 2016 to cause a compressive force to be exerted on a first vertebra that the first tower 2012 is coupled with relative to a third vertebra that the third tower 2016 is coupled with. In other embodiments, one or more rings, shafts, pins, pegs, and/or other mechanical connectors can be used to create the point or region of rotation, or fulcrum, between the first, second, and/or third towers 2012, 2014, 2016. For example and without limitation, with reference to FIG. 10B, a peg or a pair of pegs or pins advanced into the opening 2015 passing through the second tower 2014 that extends radially outwardly away from the outside surface 2014*c* of the second tower 2014 could be used to provide a pivot point or fulcrum between the first tower 2012 and the third tower 2016. The peg(s) or pin(s) that can extend through the openings 2015 can be used in lieu of the projection 2070 to provide the fulcrum between the first and third towers 2012, 2016. In some embodiments of this configuration, as the proximal portion 2012*b* of the first tower 2012 is moved away from the proximal portion 2016*b* of the third tower 2016, the system 2000 can be configured to cause the distal portion 2012*a* of the first tower 2012 to move away from the distal portion 2016*a* of the third tower 2016 to thereby cause a traction force to be exerted on a first vertebra that the first tower 2012 is coupled with relative to a third vertebra that the third tower 2016 is coupled with.

In some embodiments, the first, second, and third towers 2012, 2014, 2016 can be configured to be selectively removable from the first, second, and third screws 2002, 2004, 2006. For example and without limitation, some embodiments of the first, second, and third towers 2012, 2014, 2016 can have one or more creases, fracture lines, or lines of weakness (for example, two creases, fracture lines, or lines of weakness) along a length of a wall portion of any or all of the first, second, and third towers 2012, 2014, 2016. In some embodiments, a tool or other device can be used to fracture the first, second, and third towers 2012, 2014, 2016 along the one or more creases, fracture lines, or lines of weakness to remove the first, second, and third towers 2012, 2014, 2016 from the first, second, and third screws 2002, 2004, 2006. In some embodiments, the one or more creases, fracture lines, or lines of weakness can be circumferentially arranged and positioned at or adjacent to a top surface of the screws that the towers are attached to so that the towers can break along the one or more creases, fracture lines, or lines of weakness at or adjacent to the screws and be removed.

In some embodiments, the first, second, and third towers 2012, 2014, 2016 can have distal end portions having circumferential, helical, and/or discrete/intermittent projections, tabs, lip(s), flanges, grooves, channels, detents, or other mechanically locking features that engage with complementary locking features of the screw heads to cause the first, second, and third towers 2012, 2014, 2016 to be coupled with the screw heads when the first, second, and third towers 2012, 2014, 2016 are intact, but which can each be decoupled from the complementary locking features of the screw heads when the first, second, and/or third towers 2012, 2014, 2016 are fractured or split apart. As another example, a third wall or connecting wall connecting two sides of any of the first, second, and/or third towers 2012, 2014, 2016 can have an angled or "V" shaped profile wherein a fracture line or line of weakness extends along the apex or angle of the angled or "V" shaped profile such that, when the two sides of the first, second, and third towers 2012, 2014, 2016 are squeezed toward one another, such force from the squeezing can cause a fracture along the fracture line or line of weakness in the connecting portion, thereby allowing the first and second sides of the tower to separate so that tower can be removed from the screw head. In some embodiments, a slider ring can be slid down the tower to cause the two sides of the tower to be squeezed toward one another. In some embodiments, the first, second, and third towers 2012, 2014, 2016 can have tabs that extend from the first, second, and third screw heads that can be broken off from the screw heads after implantation. In some embodiments, the first, second, and/or third towers can be removably coupled with the first, second, and/or third screws by rotating the first, second, and/or third towers into engagement with the first, second, and/or third screws, and removed in the opposite manner.

In other embodiments, the extensions can be removably coupled with the screws so that the entire extension can be removed from the screw and the patient intact and be reused in subsequent procedures. For example and without limitation, ball and detent removable coupling mechanisms can be used to removably couple the first, second, and third towers 2012, 2014, 2016 with the first, second, and third screw heads. Other conventional or desired coupling mechanisms can be used to removably couple the first, second, and third towers 2012, 2014, 2016 with the first, second, and third screw heads. In other embodiments, a plurality of wires (such as, for example and without limitation, wires 140*a*, 140*b* shown in FIG. 1A) can be used to removably couple the first, second, and third towers 2012, 2014, 2016 with the first, second, and third screw heads, as described above with respect to the embodiments shown in FIGS. 1A-1Z.

Some embodiments of methods for treating a spinal defect include implanting a first screw 2002 that is coupled with a first tower 2012 through the incision into a first vertebra, advancing a third tower 2016 that is coupled with a third screw 2006 through the cutout 2024 formed in the first tower 2012 and implanting the third screw 2006 into a third vertebra, and advancing a second tower 2014 that is coupled with a second screw 2004 through the cutout 2044 formed in the third tower 2016 and implanting the second screw 2004 into a second vertebra. In some embodiments, the second vertebra can be between the first and third vertebrae.

The surgeon or medical practitioner can move a proximal portion 2012*b* of the first tower 2012 toward a proximal portion 2016*b* of the third tower 2016 to cause the distal portion 2012*a* of the first tower 2012 to move toward the distal portion 2016*a* of the third tower 2016, thereby causing a compressive force to be applied between the first, second, and third vertebrae. In some embodiments, the method can further include coupling a rigid connector or rod with the first screw 2002, the second screw 2004, and the third screw 2006 to generally fix a position of the first screw 2002 relative to the second screw 2004 and the third screw 2006. Thereafter, the first, second, and third towers 2012, 2014, 2016 can be removed from the first, second, and third screws 2002, 2004, 2006.

Any embodiments of the system 2000 disclosed herein can be configured for use in performing L4, L5 and S1 surgical procedures, as well as cortical screw trajectory procedures. Additionally, any embodiments of the system 2000 disclosed herein can be configured to enable compression, traction, and/or counter-torque all with one device, and the extensions can be configured to allow a tower, rod insertion, and rod reducer (using extended tabs with threads) with one device.

Certain aspects of the systems, devices, components and/or methods described above or as illustrated with respect to FIGS. 10A-10G are also encompassed by the following numbered embodiments. These numbered embodiments are considered to be directed to systems, devices, components and/or methods that include but are not limited to the embodiments of FIGS. 10A-10G, and thus these numbered embodiments may encompass other embodiments as described throughout this specification. Additionally, note that, while the embodiments of the system disclosed below may be described as including screws, any of the following embodiments may exclude any and all screws such that the embodiments only include the first tower, the second tower, and the third tower, plus any other components other than the screws (e.g., connecting element).

1. A system for stabilizing spinal vertebrae through a skin incision, comprising:

a first screw having a first screw head, a second screw having a second screw head, and a third screw having a third screw head;

a first tower having a distal portion and a proximal portion, the first tower being configured to be removably coupled with the first screw at a distal end of the first tower;

a second tower having a distal portion and a proximal portion, the second tower configured to be removably coupled with the second screw at a distal end of the second tower; and a third tower having a distal portion and a proximal portion, the third tower being configured to be removably coupled with the third screw at a distal end of the third tower;

wherein:

the first tower is configured to removably couple with the first screw such that, when the first tower is coupled with the first screw, an axial centerline of the distal portion of the first tower is approximately collinear with an axial centerline of the first screw;

the second tower is configured to removably couple with the second screw such that, when the second tower is coupled with the second screw, an axial centerline of the distal portion of the second tower is approximately collinear with an axial centerline of the second screw;

the third tower is configured to removably couple with the third screw such that, when the third tower is coupled with the third screw, an axial centerline of the distal portion of the third tower is approximately collinear with an axial centerline of the third screw;

the proximal portion of the first tower extends at an acute, nonzero angle away from the axial centerline of the distal portion of the first tower; and the proximal portion of the third tower extends at an acute, nonzero angle away from the axial centerline of the distal portion of the third tower.

2. The system of Embodiment 1, wherein the proximal portion of the first tower is configured such that, in an operable state of the system, the proximal portion of the first tower also extends at an acute, nonzero angle away from the axial centerline of the proximal portion of the second tower so that the proximal portion of the first tower forms an acute angle relative to the proximal portion of the second tower.

3. The system of any one of the previous Embodiments, wherein the first tower is sized and configured such that, in an operable state, the proximal portion of the first tower extends away from a skin incision toward a surgeon.

4. The system of any one of the previous Embodiments, wherein the distal portion of the first tower extends away from the first screw to a height just below the skin incision, or to a height level with the skin of a patient, when the first screw is fully implanted in a first vertebra.

5. The system of any one of the previous Embodiments, wherein the proximal portion of the first tower is configured to be grasped by a surgeon to enable a surgeon to exert a rotational force on the first tower about at least the axial centerline of the distal portion of the first tower and/or a torque force on the first tower so as to cause the first tower to rotate about an axis that is perpendicular to an axial centerline of the distal portion of the first tower.

6. The system of any one of the previous Embodiments, wherein the proximal portion of the third tower is configured to be grasped by a surgeon to enable a surgeon to exert a rotational force on the third tower about at least the axial centerline of the distal portion of the third tower and/or a torque force on the third tower so as to create a compressive force on a third vertebra that the third screw is coupled with relative to a first vertebra that the first screw is coupled with.

7. The system of any one of the previous Embodiments, wherein the first tower is sized such that only the proximal portion of the first tower is outside of a skin incision when the first screw is implanted in a first vertebra.

8. The system of any one of the previous Embodiments, wherein the third tower is sized such that only the proximal portion of the third tower is outside of a skin incision when the third screw is implanted in a third vertebra.

9. The system of any one of the previous Embodiments, wherein the second tower is sized to extend completely through a skin incision when the second screw is implanted in a second vertebra.

10. The system of any one of the previous Embodiments, wherein the system is configured such that the first, second, and third screws are implanted through the same skin incision.

11. The system of any one of the previous Embodiments, wherein the proximal portion of the first tower has a length that is approximately the same as a length of the distal portion of the first tower.

12. The system of any one of the previous Embodiments, wherein the proximal portion of the first tower has a length that is at least 80% of a length of the distal portion of the first tower.

13. The system of any one of the previous Embodiments, wherein the proximal portion of the first tower is removably coupled with the distal portion of the first tower and the proximal portion of the third tower is removably coupled with the distal portion of the third tower.

14. The system of any one of the previous Embodiments, wherein the proximal portion of the first tower is non-removably coupled with the distal portion of the first tower and the proximal portion of the third tower is non-removably coupled with the distal portion of the third tower.

15. The system of any one of the previous Embodiments, wherein the proximal portion of the first tower is integrally formed with the body portion of the first tower.

16. The system of any one of the previous Embodiments, wherein at least the proximal portions of the first tower and the second towers have a tubular shape.

17. The system of any one of the previous Embodiments, wherein the first tower has a cutout formed through a wall portion of the first tower, the cutout being configured to receive at least the second tower and the third tower therein in an operable state.

18. The system of Embodiment 17, wherein the cutout extends at least through a proximal end of the distal portion of the first tower.

19. The system of Embodiment 17, wherein the cutout extends entirely through the first tower such that, in an operable state, the second tower can pass entirely through the cutout.

20. The system of Embodiment 17, wherein the cutout extends entirely through the first tower such that, in an operable state, the second tower can pass entirely through the cutout and such that the wall portion of the first tower surrounds an outside surface of a portion of the second tower.

21. The system of any one of Embodiments 17-20, wherein the cutout is shaped such that a distal edge of the cutout is configured to contact an outside surface of the second tower in an operable state so that the second tower can be rotated about the distal edge of the cutout relative to the first tower.

22. The system of any one of Embodiments 17-21, wherein the cutout has an ovular or elongated shape.

23. The system of any one of Embodiments 17-22, wherein the cutout is adjacent to a proximal end of the distal portion of the first tower and a distal end of the proximal portion of the first tower.

24. The system of any one of the previous Embodiments, wherein the third tower has a cutout formed through a wall portion of the third tower, the cutout being configured to allow the second tower to pass through the cutout of the third tower in an operable state.

25. The system of Embodiment 24, wherein the cutout extends entirely through the third tower such that, in an operable state, the second tower can pass entirely through the cutout.

26. The system of any one of Embodiments 24-25, wherein the cutout has an ovular or elongated shape.

27. The system of any one of Embodiments 24-22, wherein the cutout is adjacent to a proximal end of the distal portion of the third tower and a distal end of the proximal portion of the third tower.

28. The system of any one of the previous Embodiments, wherein the proximal portion of the first tower and/or the third tower is open along one side thereof and not fully enclosed.

29. The system of any one of the previous Embodiments, wherein, in an operable state, an axial centerline of both the distal portion of the third tower and the proximal portion of the third tower extend at a nonzero angle away from the axial centerline of the second tower in a same direction.

30. The system of any one of the previous Embodiments, wherein, in an operable state, an axial centerline of both the proximal portion of the first tower and the proximal portion of the third tower extend at a nonzero angle away from the axial centerline of the second tower in a same direction.

31. The system of any one of the previous Embodiments, wherein at least the distal portion of the first tower and the distal portion of the third tower have an adjustable length.

32. The system of any one of the previous Embodiments, wherein at least the distal portion of the first tower, the distal portion of the second tower, and the distal portion of the third tower are generally cylindrically shaped.

33. The system of any one of the previous Embodiments, wherein the proximal portion of the first tower and the proximal portion of the third tower have a cross-sectional profile having a curved shape.

34. The system of any one of the previous Embodiments, wherein the proximal portion of the first tower and the proximal portion of the third tower have a cross-sectional profile having a semi-circular tubular shape.

35. The system of any one of the previous Embodiments, wherein the proximal portion of the first tower and the proximal portion of the third tower have a planar shape.

36. The system of any one of the previous Embodiments, further comprising: a rigid connecting element; a first receiving element coupled with the first screw head; a second receiving element coupled with the second screw head; and a third receiving element coupled with the third screw head; wherein the first, second, and third receiving elements are configured to operably receive the connecting element that, in an operable state, extends between the first, second, and third receiving elements when the first, second, and third screws are implanted in a first, second, and third vertebra, respectively.

37. The system of any one of the previous Embodiments, wherein the first tower has at least one window extending through a side of the body portion thereof, the at least one window configured to receive a connecting element that is configured to extend between the first, second, and third screws in an operable state.

38. The system of any one of the previous Embodiments, wherein the second tower has at least one window extending through a side of the body portion thereof, the at least one window of the second tower configured to receive a connecting element that is configured to extend between the first, second, and third screws in an operable state.

39. The system of any one of the previous Embodiments, wherein the third tower has at least one window extending through a side of the body portion thereof, the at least one window of the third tower configured to receive a connecting element that is configured to extend between the first, second, and third screws in an operable state.

40. The system of any one of the previous Embodiments, wherein the first tower is shorter than the second tower at least in an operable state.

41. The system of any one of the previous Embodiments, wherein the first tower has a projection which provides a fulcrum for rotation of the first tower relative to the third tower.

42. The system of any one of the previous Embodiments, wherein the first, second, and third towers are releasably mechanically coupled with the first, second, and third screws, respectively.

43. The system of any one of the previous Embodiments, comprising two or more of the first towers and/or two or more of the third towers, wherein each of the two or more of the first towers define a different angle between the proximal portion and the distal portion of the first towers and each of the two or more of the third towers define a different angle between the proximal portion and the distal portion of the third towers.

44. A method of stabilizing spinal vertebrae, comprising:
   implanting a first screw that is coupled with a first tower through an incision into a first vertebra;
   advancing a third tower that is coupled with a third screw through a cutout formed in the first tower and implanting the third screw into a third vertebra;
   advancing a second tower that is coupled with a second screw through a cutout formed in the third tower and implanting the second screw into a second vertebra; and
   moving a proximal portion of the first tower toward a proximal portion of the third tower to cause a compressive force on at least the third vertebra relative to the first vertebra.

45. The method of Embodiment 42, further comprising coupling a rigid connector with the first screw, the second screw, and the third screw to generally fix a position of the first screw relative to the second screw and the third screw. Systems, Devices and Methods of FIGS. 11A-11G Additional embodiments of a system 2200 that can be used for stabilizing or treating spinal vertebrae through a skin incision S are disclosed below. In any embodiments disclosed herein, any components, features, or other details of the system 2200 can have any of the components, features, or other details of any other system embodiments disclosed herein or be used according to any of the steps of any other method embodiments disclosed herein, including without limitation any of the embodiments of the system 200, 300, 400, and/or 2000 or methods of use thereof described herein, in any combination with any of the components, features, or details of the system 2200 or methods of use disclosed herein. Similarly, any components, features, steps, or other details of any of the other system or method embodiments disclosed herein can have any of the components, features, steps, or other details of any embodiments of the system 2200 or methods of use thereof disclosed herein in any combination with any of the components, features, or details of the system.

Some embodiments of the system 2200 can be configured and/or optimized for use in robotic surgical procedures. For example and without limitation, in some embodiments, the proximal portions of the towers can be configured and optimized for grasping and locating by end effectors or robotic arms of a surgical robot. An advantage of some embodiments of the system 2200 and other systems disclosed herein as compared to conventional spinal surgical systems is that two or more, or three or more towers of some embodiments of the system 2200 can be advanced and manipulated through a single incision in the patient's back. Another advantage of some embodiments of the system 2200 and other systems disclosed herein as compared to conventional spinal surgical systems is that the two or more or three or more towers of some embodiments of the system can be constrained by each other or otherwise configured to limit a range of movement of the towers relative to one another. This can assist in the ability to locate and/or control the towers of the system, particularly by a surgical robot. This can also make it easier to advance the connecting element (also referred to herein as a connecting rod) through the two or more towers or three or more towers because the two or more towers will be better aligned.

Some embodiments of the system 2200 can be configured such that any of the towers attached to screws can be placed robotically and allow rod placement, rod reduction, compression, and/or final tightening with counter-torque all to be performed robotically through a mechanical coupling of parts of the tower system with robotic arms. The robot, navigation system, and/or software can be configured to identify or determine the positions of all towers screws, rods and caps at any desired time. In some embodiments, the proximal portions of the towers of any embodiments disclosed herein can be configured to be compatible with graspers, coupling mechanisms, and/or end effectors of surgical robots. For example and without limitation, as disclosed herein, the proximal portions of some embodiments of the towers disclosed herein can have a flat profile that can more easily and controllably be grasped by graspers, coupling mechanisms, and/or end effectors of surgical robots.

In any embodiments, the first, second, and third towers coupled with the screws can extend outside the body through the incision, and the proximal ends thereof can provide "handles" to allow the surgeon to know the position and orientation of the three screw heads constantly. This arrangement can also permit a robotic system to determine the orientation and position of all screw heads so that a robotic system would be able to lower the rod or connecting element directly into the screw heads, including with rotating the connecting element from vertical to horizontal into the seat of the heads of the screws. Any of the towers or other components can have additional features added thereto or otherwise be configured to integrate into a robotic system. Thereafter, the towers can be removed and withdrawn from the body, manually or robotically.

Some embodiments of the system 2200 for stabilizing spinal vertebrae through a skin incision S can include a first screw 2202, a second screw 2204, a third screw 2206, a first tower 2212 having a distal portion 2212a and a proximal portion 2212b, a second tower 2214 having a distal portion 2214a and a proximal portion 2214b, and a third tower 2216 having a distal portion 2216a and a proximal portion 2216b. The first tower, second tower, and third tower can also be referred to herein as a first extension, second extension, and third extension, or guiding elements, or by other suitable terms understood in the industry. The first tower 2212 can be configured to be removably coupled with the first screw 2202 at a distal end 2212a of the first tower 2212, the second tower 2214 can be configured to be removably coupled with the second screw 2204 at a distal end 2214a of the second tower 2214, and third tower 2216 can be configured to be removably coupled with the third screw 2206 at a distal end 2216a of the third tower 2216. In some embodiments, each of the first, second, and third screws 2202, 2204, 2206 can be positioned in different vertebra. In some embodiments, each of the first, second, and third screws 2202, 2204, 2206 can be positioned in adjacent vertebra. Additionally, note that, while the embodiments of the system 2200 disclosed herein may have included screws as part of the system, any embodiments of the system 2200 disclosed herein can exclude the screws such that the embodiments of the system 2200 include the towers and/or other components other than the screws.

In any of the embodiments disclosed herein, the first, second, and third towers can be configured to be removably coupled with the screw heads and otherwise configured to be reuseable. This can save a significant cost as compared with disposable blade designs that, once the blade has been separated from the screw head, is typically discarded and not reused. From a surgical perspective, towers are more firm an rigid and can be used to provide rigidity to as to provide counter-torque during final tightening of the locking cap onto the rod in the screw head. Extended blades usually do not have the same strength as a counter-torque device. The towers of any of the embodiments disclosed herein, with the rigidity that they provide, can therefore help prevent the walls of the pedicle screw from splaying during final tightening of the locking cap.

The towers of some embodiments disclosed herein can provide a more complete enclosure than the blades or tabs can, due to the additional wall portions of the towers that extend between the sides of the towers. In some embodiments, as shown in the figures, the wall portions that extend between the two side wall portions to provide additional strength and stiffness can be integrally formed with the side wall portions, or can be separately formed and coupled (removably or nonremovably) with the side wall portions to provide additional rigidity to the towers.

In some embodiments, at least a portion of the distal portions of any embodiments of the first and/or third towers 2212, 2216 can be enclosed about at least 320° (or at least approximately) 320° of the circumference or cross-section of the first and/or third towers 2212, 2216, or from 180° (or approximately 180° or less) to 330° (or approximately 330°, or at least) 330°, or from 210° (or approximately) 210° to 320° (or approximately) 320°, or enclosed about any value or range of value within the foregoing ranges. In some embodiments, at least a portion of the distal portions of any embodiments of the first and/or third towers 2212, 2216 can be can be completely enclosed, with the optional exception of the channel extending lengthwise along at least the distal portion of the first and/or third towers 2212, 2216 sized and configured to permit a passage of the rod or connecting element toward the screws. Additionally, for example and without limitation, at least a portion of the distal portion of any embodiments of the second tower 2214 can be enclosed about at least 270° (or at least approximately) 270° of the circumference or cross-section of the second tower 2214, or from 240° (or approximately) 240° to 320° (or approximately) 320°, or from 270° (or approximately) 270° to 300° (or approximately) 300°, or enclosed about any value or range of value within the foregoing ranges. In some embodiments, at least a portion of the distal portion of any embodiments of the second tower 2214 can be can be completely enclosed, with the exception of a channel on each side of the distal portion 2214b of the second tower 2214 extending lengthwise along at least the distal portion of the second tower 2214 sized and configured to permit a passage of the rod or connecting element toward the screws.

In some embodiments, at least a portion of the distal portions of any embodiments of the first and/or third towers 2212, 2216 can be enclosed about at least 80% (or at least approximately 80%) of the circumference or cross-section of the first and/or third towers 2212, 2216, or from 70% (or approximately 70%) to 90% (or approximately 90%, or more than 90%—e.g., 95% or 100%), or from 75% (or approximately 75%) to 85% (or approximately 85%), or enclosed about any value or range of value within the foregoing ranges. Additionally, for example and without limitation, at least a portion of the distal portion of any embodiments of the second tower 2214 can be enclosed about at least 50% (or at least approximately 50%) of the circumference or cross-section of the second tower 2214, or from 60% (or approximately 60%) to 80% (or approximately 80%), or from 65% (or approximately 65%) to 75% (or approximately 75%), or enclosed about any value or range of value within the foregoing ranges.

Figures 11A, 11B:
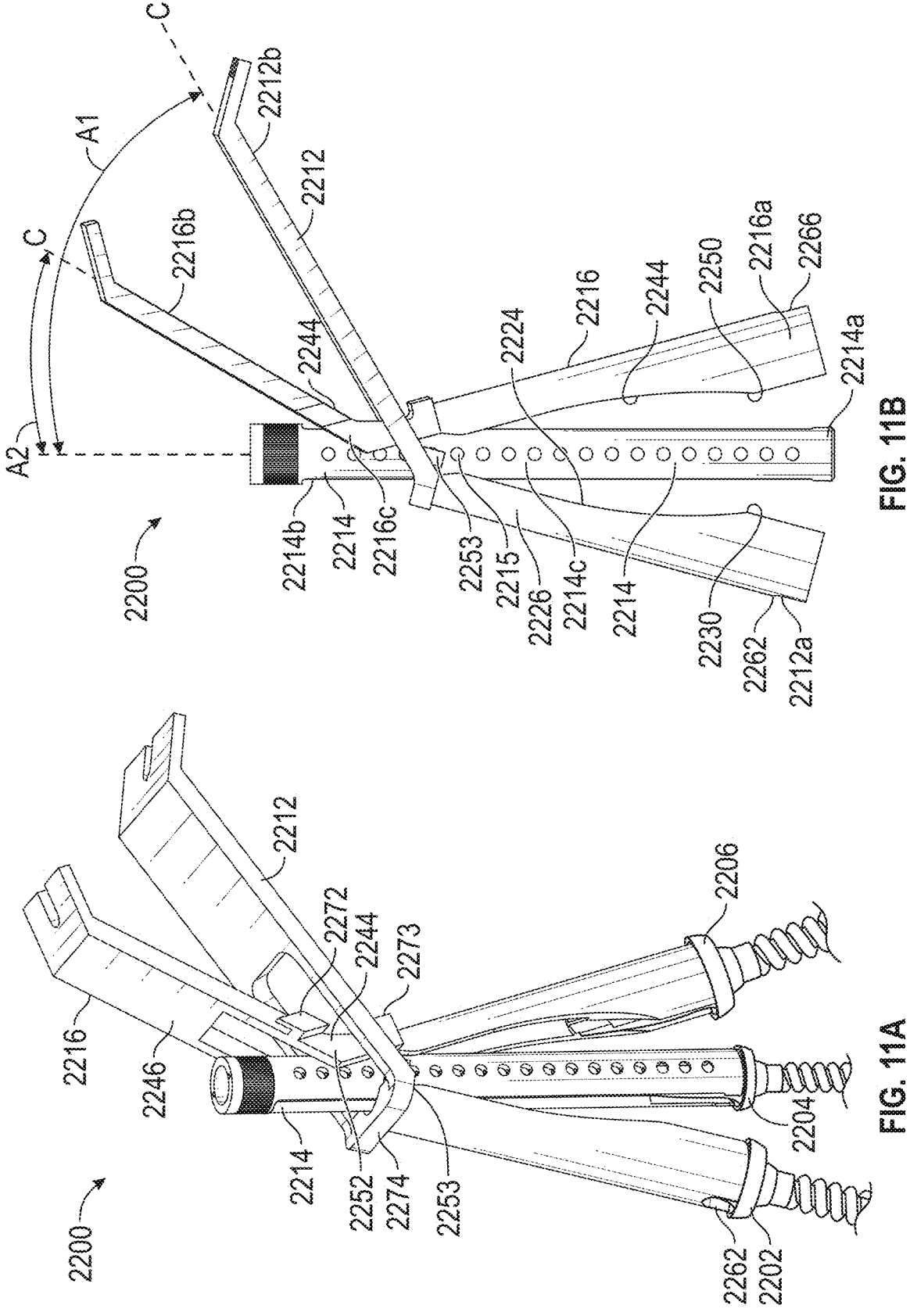
FIGS. 11A-11G illustrate another embodiment of a system for stabilizing spinal vertebrae comprising spinal screws.
Figures 11C, 11D:
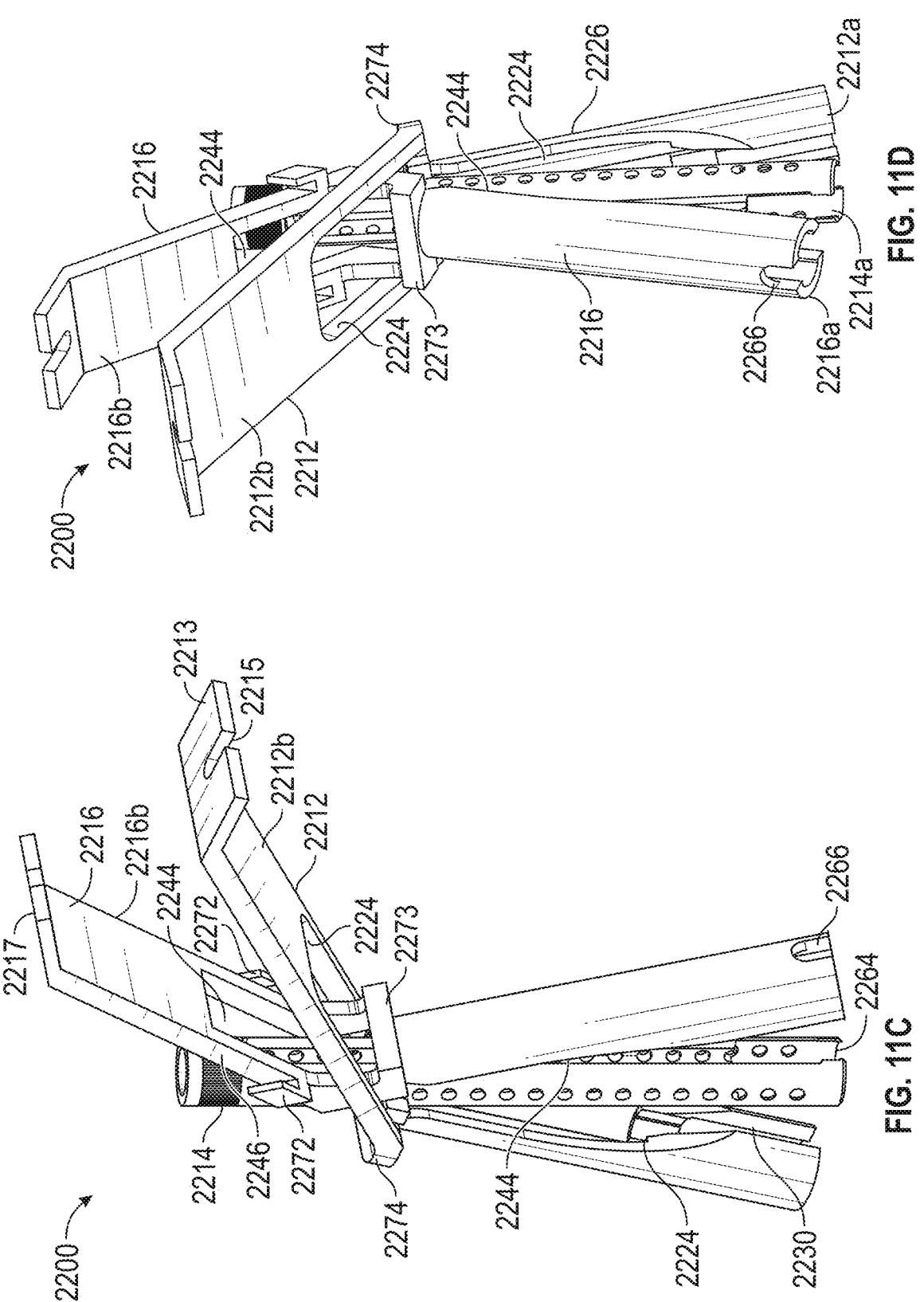
Figure 11E:
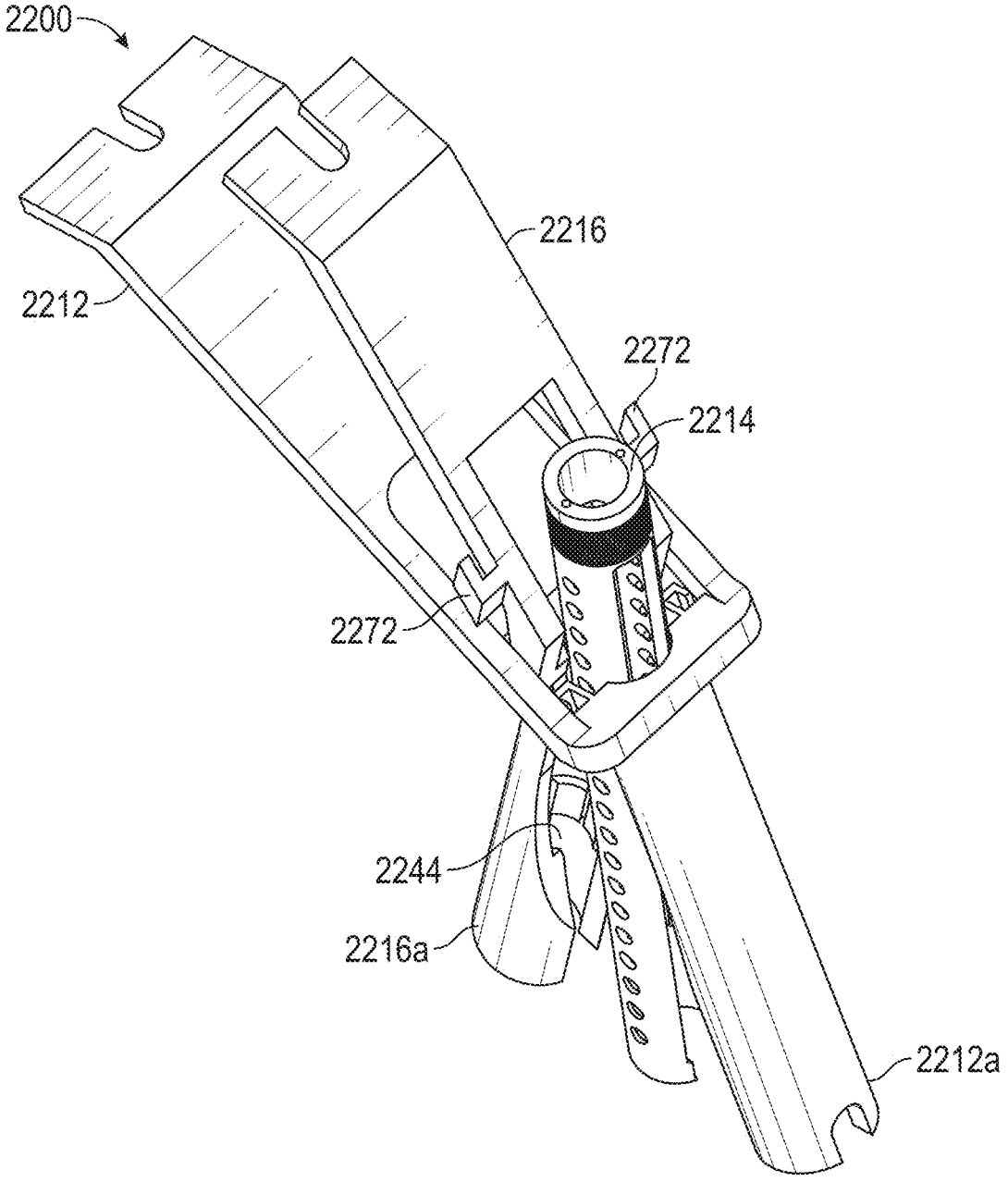

In some embodiments, with reference to FIG. 11B, the first tower 2212 can have a bend between the distal portion 2212a and the proximal portion 2212b thereof. For example and without limitation, the distal portion 2212a can be angled relative to the proximal portion 2212b so that a longitudinal centerline C of the proximal portion 2212b has an angle that is 45° or approximately 45° relative to a longitudinal centerline C of the distal portion 2212a of the first tower 2212, or so that the longitudinal centerline of the proximal portion 2212b has an angle that is from 30° or approximately 30° to 60° or approximately 60°, or from 40° or approximately 40° to 50° or approximately 50° relative to the longitudinal centerline of the distal portion 2212a of the first tower, or of any value or range of values within any of the foregoing ranges. In any embodiments, the second tower 2214 can be generally straight along a length thereof, as shown, or can have a bend between the distal portion 2214a and the proximal portion 2214b thereof within any of the ranges mentioned above for the first tower 2212.

In some embodiments, the third tower 2216 can have a bend between the distal portion 2216a and the proximal portion 2216b thereof. The bend in the third tower 2216 can be less than, can be greater than, or can be the same as the bend in the first tower 2212. For example and without limitation, the distal portion 2216a can be angled relative to the proximal portion 2216b so that a longitudinal centerline C of the proximal portion 2216b has an angle that is 45° or approximately 45° relative to a longitudinal centerline C of the distal portion 2216a of the third tower 2216, or that is 50° or approximately 50° relative to a longitudinal centerline C of the distal portion 2216a of the third tower 2216, or so that the longitudinal centerline C of the proximal portion 2216b has an angle that is from 30° or approximately 30° to 60° or approximately 60°, or from 40° or approximately 40° to 50° or approximately 50° relative to the longitudinal centerline of the distal portion 2216a of the first tower 2212, or of any value or range of values within any of the foregoing ranges.

Any embodiments of the system 2200 disclosed herein can be configured such that the first screw 2202, the second screw 2204, and the third screw 2206 can be implanted through the same skin incision S. Further, in any embodiments, a distal portion 2214a of the second tower 2214 can be positioned between the distal portions 2212a, 2216a of the first and third towers 2212, 2216 in an operable state of the system 2200.

In some embodiments, the first tower 2212 can have a two or more proximal portions 2212b extending away from the distal portion 2212a of the first tower 2212 at a variety of angles. For example and without limitation, the two or more proximal portions 2212b extending away from the distal portion 2212a of the first tower 2212 can provide two or more separate handles extending away from the distal portion 2212a that a surgeon can grasp and manipulate. In some embodiments, the first tower 2212 can removably couple with the first screw 2202 such that, when the first tower 2212 is coupled with the first screw 2202, an axial or longitudinal centerline C of the distal portion 2212a of the first tower 2212 is approximately collinear with an axial or longitudinal centerline C of the first screw 2202. The second tower 2214 can removably couple with the second screw 2204 such that, when the second tower 2214 is coupled with the second screw 2204, an axial centerline C of the distal portion 2214a of the second tower 2214 is approximately collinear with an axial centerline C of the second screw 2204. The third tower 2216 can removably couple with the third screw 2206 such that, when the third tower 2216 is coupled with the third screw 2206, an axial centerline C of the distal portion 2216a of the third tower 2216 is approximately collinear with an axial centerline C of the third screw 2206. In any embodiments, the first tower 2212 can be shorter than the second tower 2214 or the third tower 2216, longer than the second tower 2214 or the third tower 2216, or have approximately the same length as the second tower 2214 or the third tower 2216, and the second tower 2214 can be shorter than the third tower 2216, longer than the third tower 2216, or have approximately the same length as the third tower 2216.

In some embodiments, the angle between the proximal portion 2212b and distal portion 2212a of the first tower 2212 can be adjustable, an angle between the proximal portion 2214b and distal portion 2214a of the second tower 2214 can be adjustable, and/or the angle between the proximal portion 2216b and distal portion 2216a of the third tower 2216 can be adjustable. A common mechanism for adjustability is a gear or ratchet mechanism. In this way, the proximal portion of any of the extensions can be angled away from the centerline of the distal portion of the respective screw. By adjusting the angle, there may be more room to place the rod and locking caps. Also, by adjusting the angle, it may be easier for a surgeon to grip both proximal portions of the towers in order to squeeze the two or three proximal portions of the extensions in order to compress the heads of screws when locking the caps onto the connecting element or rod connecting the screw heads. In another embodiment, proximal portions 2212b, 2214b, and/or 2216b can be detachable from the distal portions 2212a, 2214a, and/or 2216a. In this manner, proximal portions with different angles in relation to centerline of the respective distal portions can be switched as needed and reconnected to the distal portions of the extensions.

As mentioned, in some embodiments, the proximal portion 2212b of the first tower 2212 can extend at an angle away from the axial centerline C of the distal portion 2212a of the first tower 2212 such that an axial centerline of the proximal portion 2212b of the first tower 2212 is not approximately collinear with an axial centerline of the distal portion 2212a of the first tower 2212. Further, the first tower 2212 can be configured such that, in an operable state, an axial centerline of the proximal portion 2212b of the first tower 2212 can extend at an angle away from the axial centerline C of the proximal portion of the second tower 2214 so that the axial centerline of proximal portion 2212b of the first tower 2212 forms an acute angle A1 relative to the axial centerline of the proximal portion of the second tower 2214, as shown in FIG. 11B. In some embodiments, the angle A1 can be 60° (or approximately) 60°, or from 40° (or approximately) 40° or less to 80° (or approximately) 80° or more, or of any value or range of values within any of the foregoing ranges. The third tower 2216 can be configured such that, in an operable state, an axial centerline of the proximal portion 2216b of the third tower 2216 can extend at an angle away from the axial centerline C of the proximal portion of the second tower 2214 so that the axial centerline of proximal portion 2216b of the third tower 2216 forms an acute angle A2 relative to the axial centerline of the proximal portion of the second tower 2214 in an operable state, as shown in FIG. 11B. In some embodiments, the angle A2 can be 30° (or approximately) 30°, or from 15° (or approximately) 15° or less to 45° (or approximately) 45° or more.

In some embodiments, the first tower 2212 can be angled such that, in an operable state, the proximal portion 2212b of the first tower 2212 can extend away from the proximal portion 2214b of the second tower 2214 in a first direction, and the third tower 2216 can be angled such that, in an operable state, the proximal portion 2216b of the third tower 2216 can also extend away from the proximal portion of the second tower 2214 in the same direction or approximately the same direction as the proximal portion 2212b of the first tower—e.g., in the first direction. In some embodiments, the axial centerlines of the proximal portions 2212b, 2216b of the first and third towers 2212, 2216 can be within the same plane (e.g., a first plane) or approximately the same plane when the proximal portions 2212b, 2216b of the first and third towers 2212, 2216 extend away from the proximal portion of the second tower 2214 in the same direction. The first plane that contains the axial centerlines of the proximal portions 2212b, 2216b of the first and third towers 2212, 2216 can also intersect with the axial centerline of the second tower 2214, in some embodiments.

In some embodiments, the first tower 2212 can be sized and configured such that, in an operable state, the proximal portion 2212b of the first tower 2212 can extend away from the skin incision S toward the surgeon. In some embodiments, the first, second, and third towers 2212, 2214, and 2216 can be sized and configured such that the level of the patient's skin in an operable state of the system 2200 will be at or adjacent to the bend 2252 (e.g., just below the bend 2252) formed in the third tower 2216 or at or adjacent to the bend 2253 (e.g., just below the bend 2253) formed in the first tower 2212. In some embodiments, the distal portion 2212*a* of the first tower 2212 and/or the distal portion 2216*a* of the third tower 2216 can extend away from the first screw 2202 and the third screw 2206 to a height just below the skin incision S (for example and without limitation, wherein a distance from the skin surface to the proximal most end of the distal portion of the first or third tower is less than or equal to 10% or approximately 10%, is less than or equal to 15% or approximately 15%, or is less than or equal to 20% or approximately 20% of a length of the distal portion of the first or third tower), or to a height level with the skin of a patient, or to a height just above the skin incision S (for example and without limitation, wherein a distance from the skin surface to the proximal most end of the distal portion of the first or third tower is less than or equal to 10% or approximately 10%, is less than or equal to 15% or approximately 15%, or is less than or equal to 20% or approximately 20%, of a length of the distal portion of the first or third tower), when the first and third screws 2202, 2206 are fully implanted in a first vertebra and a third vertebra, respectively.

In some embodiments, the first tower 2212, the second tower 2214, and/or the third tower 2216 can intersect at a height just below the skin incision S. For example and without limitation, the first tower 2212, the second tower 2214, and/or the third tower 2216 can intersect at an intersection point or points such that a distance from the skin surface to the point of intersection of the first tower 2212 and the second tower 2214, the first tower 2212 and the third tower 2216, the second tower 2214 and the third tower 2216, and/or the first tower 2212, the second tower 2214, and the third tower 2216 is less than or equal to 10% of the length of the distal portion of the first tower or the third tower, wherein the point of intersection is at the skin surface, or optionally below the skin surface, or optionally above the skin surface for the intersection of the first tower 2212 and the second tower 2214, the first tower 2212 and the third tower 2216, the second tower 2214 and the third tower 2216, and/or the first tower 2212, the second tower 2214, and the third tower 2216.

In some embodiments, the first tower 2212 can be sized such that only the proximal portion 2212*b* of the first tower 2212 is outside of the skin incision S when the first screw 2202 is implanted in a first vertebra, and the third tower 2216 can be sized such that only the proximal portion 2216*b* of the third tower 2216 is outside of the skin incision S when the third screw 2206 is implanted in a third vertebra. In any embodiments, the second tower 2214 can be sized to extend completely through the skin incision S when the second screw 2204 is implanted in a second vertebra.

The proximal portion 2212*b* of the first tower 2212 and the proximal portion 2216*b* of the third tower 2216 can be configured to be grasped by a surgeon to enable a surgeon to exert a rotational force on the first tower 2212 about at least the axial centerline C of the distal portion 2212*a* of the first tower 2212 about at least the axial centerline C of the distal portion 2212*a* of the first tower 2212 and/or a torque force on the first tower 2212 so as to cause the first tower 2212 to rotate about an axis that is perpendicular to an axial centerline C of the distal portion 2212*a* of the first tower 2212. The proximal portion 2216*b* of the third tower 2216 and the proximal portion 2216*b* of the third tower 2216 can be configured to be grasped by a surgeon to enable a surgeon to exert a rotational force on the third tower 2216 about at least the axial centerline C of the distal portion 2216*a* of the third tower 2216 about at least the axial centerline C of the distal portion 2216*a* of the third tower 2216 and/or a torque force on the third tower 2216 so as to cause the third tower 2216 to rotate about an axis that is perpendicular to an axial centerline C of the distal portion 2216*a* of the third tower 2216.

The proximal portion 2212*b* of the first tower 2212 can have a length that is approximately the same as a length of the distal portion 2212*a* of the first tower 2212, or can have a length that is at least 80% or less or 120% or less of a length of the distal portion 2212*a* of the first tower 2212. In some embodiments, the proximal portion 2212*b* of the first tower 2212 can be removably coupled with the distal portion 2212*a* of the first tower 2212. In other embodiments, the proximal portion 2212*b* of the first tower 2212 can be non-removably coupled with the distal portion 2212*a* of the first tower 2212. For example and without limitation, the proximal portion 2212*b* of the first tower 2212 can be integrally formed with the body portion of the first tower 2212. In any embodiments, the second and third towers 2214, 2216 can be similarly configured.

In some embodiments, at least the proximal portion 2212*b* of the first tower 2212 and/or the third tower 2216 can have a flat or rectangular shape—for example and without limitation, a solid rectangular shape wherein a width of the proximal portion can be significantly greater than a thickness of the proximal portion. In some embodiments, the width of the proximal portion of the first and/or third towers can be 6 times or approximately 6 times greater or more than a thickness of the proximal portion, or from 4 times or approximately 4 times greater to 8 times or approximately 8 times greater than a thickness of the proximal portion of the first and/or third towers, or of any values or from and to any values within the foregoing range. The first tower 2212 can have a cutout 2224 formed through a wall portion 2226 of the distal portion 2212*a* first tower 2212 and through the proximal portion 2212*b* of the first tower 2212. The cutout 2224 being configured to receive a portion of or permit the passage therethrough of an outside surface 2214*c* of the second tower 2214 therein in an operable state, as shown in the figures. In some embodiments, the cutout 2224 of the first tower 2212 can be large enough to also receive a portion of an outside surface 2216*c* of the third tower 2216 therein in an operable state, as shown in the figures. In some embodiments, the cutout 2224 can extend at least through a proximal end 2212*c* of the distal portion 2212*a* of the first tower 2212. The cutout 2224 can extend entirely through the first tower 2212 and be sized and configured such that, in an operable state, the second tower 2214 and the screw coupled with the second tower 2214 can pass entirely through the cutout 2224 in the first tower 2212 and the screw coupled with the third tower 2216 and at least the distal portion 2216*b* of the third tower 2216 can pass entirely through the cutout 2224.

In some embodiments, the proximal portion 2212*b* of the first tower 2212 can have an angled portion 2213 at a proximal most end of the proximal portion 2212*b*. The angled portion can be angled relative to the adjacent portion of the proximal portion 2212*b*. The angled portion can be angled at an angle of 45° or approximately 45° relative to the adjacent portion of the proximal portion 2212*b*, or from 35° or approximately 35° to 55° or approximately 55° relative to the adjacent portion of the proximal portion 2212*b*. The angled portion 2213 can have a slot 2215 formed therein. In some embodiments, the proximal portion 2212*b* of the first tower 2212 can have a cross-sectional shape, profile, and/or size that is the same as or similar to handle portion of METRX RETRACTOR TUBES. The third tower 2216 can be similarly configured.

In some embodiments, the cutout 2224 can extend entirely through the first tower 2212 such that, in an operable state, the second tower 2214 can pass entirely through the cutout 2224 and such that the wall portion 2226 of the first tower 2212 completely and continuously surrounds the outside surface 2214c of a portion of the second tower 2214 and the outside surface 2216c of a portion of the third tower 2216. Some embodiments of the cutout 2224 can have a distal edge 2230. In some embodiments, the distal edge 2230 can be lower to allow for a wider range of rotation or movement of the first tower 2212 relative to the second tower 2214. In some embodiments, the cutout 2224 can extend distally to be near to or adjacent to the distal end of the first tower. Some embodiments of the cutout 2224 can have an elongated or ovular shape.

In some embodiments, at least the distal portion 2216a of the third tower 2216 can have a tubular or half-tubular shape. The third tower 2216 can have a cutout 2244 formed through a wall portion 2246 of the distal portion 2216a of the third tower 2216 and through the proximal portion 2216b of the third tower 2216, the cutout 2244 being configured to receive a portion of an outside surface 2214c of the second tower 2214 therein and/or to permit a user to advance the second tower 2214 therethrough in an operable state, as shown in the figures. In some embodiments, the cutout 2244 can extend at least through a proximal end 2216c of the distal portion 2216a of the third tower 2216. The cutout 2244 can extend entirely through the third tower 2216 such that, in an operable state, the second tower 2214 and the screw coupled with the second tower 2214 can pass entirely through the cutout 2244 in the third tower 2216.

In some embodiments, the cutout 2244 can be configured such that, in an operable state, the second tower 2214 can pass entirely through the cutout 2244 and such that the wall portion 2246 of the third tower 2216 completely and continuously surrounds the outside surface 2214c of a portion of the second tower 2214. In some embodiments, a shown, the cutout 2244 can be configured such that, in an operable state, the outside surface 2214c of the second tower 2214 is only partially surrounded by the wall portion 2246 of the third tower 2216. For example and without limitation, the third tower 2216 can form an approximately U shape at the proximal end 2216c of the distal portion 2216a of the third tower 2216. Further, some embodiments of the cutout 2244 can have a distal edge 2250. In some embodiments, the distal edge 2250 can be lower to allow for a wider range of rotation or movement of the third tower 2216 relative to the second tower 2214. In some embodiments, the cutout 2244 can extend distally to be near to or adjacent to the distal end of the tower (e.g., the third tower 2216). Some embodiments of the cutout 2244 can have an elongated or ovular shape.

In some embodiments, at least the distal portion 2212a of the first tower 2212, the distal portion 2216a of the third tower 2216, and/or the distal portion 2214a of the second tower 2214 can have an adjustable length. Further, some embodiments of the distal portion of the first tower 2212, the second tower 2214, and/or the third tower 2216 can be generally cylindrically shaped. Other embodiments can have any other desired cross-sectional shape, including a generally square shape, a triangular cross-sectional shape, on ovular cross-sectional shape, a polygonal cross-sectional shape, or any combination of the foregoing.

The proximal portion 2212b of the first tower 2212 and/or the proximal portion 2216b of the third tower 2216 can have a cross-sectional profile that can have a curved shape. In some embodiments, the proximal portion 2212b of the first tower 2212 and/or the proximal portion 2216b of the third tower 2216 can have a planar shape.

Any of the embodiments of the system 2200 disclosed herein can include a rigid connecting element (not shown), similar to any of the other embodiments of the connecting elements disclosed herein, that can be implanted using any desired shape and configuration of a connecting element implantation device, such as the embodiment of the connecting element implantation device shown in FIGS. 3E-3F, or implanted using any other devices or methods disclosed herein or other desired devices or methods. For example and without limitation, any embodiments of the system disclosed herein (including embodiments of the system 2200) can be configured to implant the connecting element using the same or similar components of the MEDTRONIC SEXTANT II PERCUTANEOUS ROD SYSTEM, adapted for use with the embodiments disclosed herein. Any embodiments of the system disclosed herein (including embodiments of the system 2200) can be configured to implant the connecting element using a rotating implantation component that is configured to rotate about an axis outside of the body and to deliver the connection element in the desired location with respect to the towers and screws.

In some embodiments, a first receiving element coupled with the head of the first screw 2202, a second receiving element coupled with the head of the second screw 2204, and a third receiving element coupled with the head of the third screw 2206 can secure the connecting element to the screws 2202, 2204, 2206. The first, second, and third receiving elements can be configured to operably receive the connecting element that, in an operable state, can extend between the first, second, and third receiving elements when the first screw 2202, the second screw 2204, and the third screw 2206 are implanted in a first vertebra, a second vertebra, and a third vertebra, respectively.

In some embodiments, the first tower 2212 can have at least one window or slot 2262 extending through a side of the body portion thereof, the at least one slot 2262 configured to receive a connecting element 2250 or configured to permit a passage of a connecting element 2250 therethrough. Further, the second tower 2214 can have at least one slot or window 2264 extending through a side of the body portion of the second tower 2214, the at least one slot 2264 of the second tower 2214 configured to receive the connecting element 2250 that is configured to extend between the first screw 2202 and the third screw 2206 in an operable state. The third tower 2216 can have at least one slot or window 2266 extending through a side of the body portion of the third tower 2216, the at least one slot 2266 of the third tower 2216 configured to receive the connecting element 2250 that is configured to extend between the first screw 2202 and the third screw 2206 in an operable state. Lengthwise slots or channels can be formed in at least the distal portions of each of the first, second, and third towers to permit the connecting element to pass distally toward the screws.

In some embodiments of the system 2200, though not shown, the first tower 2212 can optionally have an insert or projection 2270 formed thereon or coupled therewith or positioned adjacent thereto. The projection 2270 can have a distal portion 2270a that, in some embodiments, in an operable state, contacts the outside surface 2214c of the second tower 2214 to provide a point or a region of contact between the proximal portion 2212a of the first tower 2212 and the proximal portion 2214b of the second tower 2214. In some embodiments of this configuration, as the proximal portion 2212b of the first tower 2212 is squeezed relative to or otherwise rotated or moved toward the proximal portion 2214b of the second tower 2214, the distal portion 2270a of the projection 2270 can contact the outside surface 2214c of the second tower 2214 and the distal portion 2212a of the first tower 2212 can be moved toward the distal portion 2214a of the second tower 2214 to cause a compressive force to be exerted on a first vertebra that the first tower 2212 is coupled with relative to a second, adjacent vertebra that the second tower 2214 is coupled with. In other embodiments, the projection 2270 can be configured to rotate or otherwise move so that the point or region of contact and rotation between the first and second towers 2212, 2214 is only at the distal end 2230 of the opening 2224. In some embodiments of this configuration, as the proximal portion 2212b of the first tower 2212 is moved away from the proximal portion 2214b of the second tower 2214, the distal portion 2212a of the first tower 2212 can be moved away from the distal portion 2214a of the second tower 2214 to cause a traction force to be exerted on a first vertebra that the first tower 2212 is coupled with relative to a second, adjacent vertebra that the second tower 2214 is coupled with.

In some embodiments, the insert 2270 can be removably or nonremovably positioned between the proximal portion 2212b of the first tower 2212 and the proximal portion 2216b of the third tower 2216, when needed or desired, to provide a fulcrum between the first and third towers 2212, 2216 during compression. In other embodiments, the insert 2270 can be nonremovably coupled with the proximal portion 2212b of the first tower 2212 or integrally formed with the proximal portion 2212b of the first tower 2212, or nonremovably coupled with an outside surface of the proximal portion 2216b of the third tower 2216 or integrally formed with the proximal portion 2216b of the third tower 2216 so as to be between the proximal portion 2216b of the third tower 2216 and the proximal portion 2212b of the first tower 2212.

In some embodiments, the projection 2270 can be configured to contact the outside surface 2216c of the third tower 2216, for example, in a proximal portion 2216b of the third tower 2216, to provide a point or a region of contact and rotation, or a fulcrum, between the proximal portion 2212a of the first tower 2212 and the proximal portion 2216b of the third tower 2216. In some embodiments of this configuration, as the proximal portion 2212b of the first tower 2212 is squeezed relative to or otherwise rotated or moved toward the proximal portion 2216b of the third tower 2216, a proximal portion 2270b of the projection 2270 can contact the outside surface 2216c of the proximal portion 2216b of the third tower 2216 to provide the point or a region of contact and rotation, or a fulcrum, between the proximal portion 2212a of the first tower 2212 and the proximal portion 2216b of the third tower 2216 to cause a compressive force to be exerted on a first vertebra that the first tower 2212 is coupled with relative to a third vertebra that the third tower 2216 is coupled with. In other embodiments, one or more rings, shafts, pins, pegs, and/or other mechanical connectors can be used to create the point or region of rotation, or fulcrum, between the first, second, and/or third towers 2212, 2214, 2216. For example and without limitation, with reference to FIG. 11B, a peg or a pair of pegs or pins advanced into the opening 2215 passing through the second tower 2214 that extends radially outwardly away from the outside surface 2214c of the second tower 2214 could be used to provide a pivot point or fulcrum between the first tower 2212 and the third tower 2216. The peg(s) or pin(s) that can extend through the openings 2215 can be used in lieu of the projection 2270 to provide the fulcrum between the first and third towers 2212, 2216. In some embodiments of this configuration, as the proximal portion 2212b of the first tower 2212 is moved away from the proximal portion 2216b of the third tower 2216, the system 2200 can be configured to cause the distal portion 2212a of the first tower 2212 to move away from the distal portion 2216a of the third tower 2216 to thereby cause a traction force to be exerted on a first vertebra that the first tower 2212 is coupled with relative to a third vertebra that the third tower 2216 is coupled with.

In some embodiments, the third tower 2216 can have one or more hooks 2272 (two being included in the illustrated embodiment) positioned at the sides of the proximal portion of the third tower 2216. The hooks 2272 can extend laterally away from the sides of the proximal portion of the third tower 2216. In some embodiments, the hooks 2272 can be used to constrain one or more wires (such as, without limitation, wires 140a, 140b) during a procedure. The hooks 2272 can also be used to create a pivot point or fulcrum against which a top surface of the proximal portion 2212b of the first tower 2212 can contact and about which the first tower 2212 can pivot or rotate.

Additionally, the first tower 2212 can have a reinforcing element 2274 at or adjacent to a proximal end of the distal portion 2212a of the first tower 2212. The reinforcing element 2274 can extend laterally across the first tower 2212 and can increase the stiffness of the first tower 2212 in bending and/or in torsion. Similarly, in some embodiments, the third tower 2216 can have a reinforcing element 2273 at or adjacent to a proximal end of the distal portion 2216a of the third tower 2216. The reinforcing element 2273 of the third tower 2216 can extend laterally across the third tower 2216 and can increase the stiffness of the third tower 2216 in bending and/or in torsion.

Figure 11G:
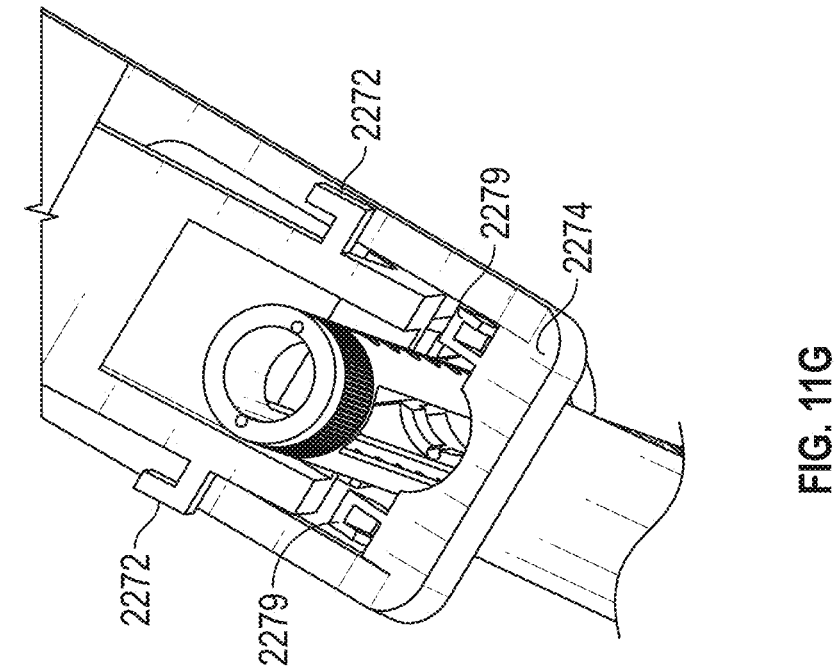

In some embodiments, with reference to FIG. 11G, the third tower 2212 can have one or more hooks 2279 (two being included in the illustrated embodiment) coupled with the reinforcing element 2274. In some embodiments, the hooks 2279 coupled with the reinforcing element 2274 can be used to constrain one or more wires (such as, without limitation, wires 140a, 140b) during a procedure.

Figure 11F:
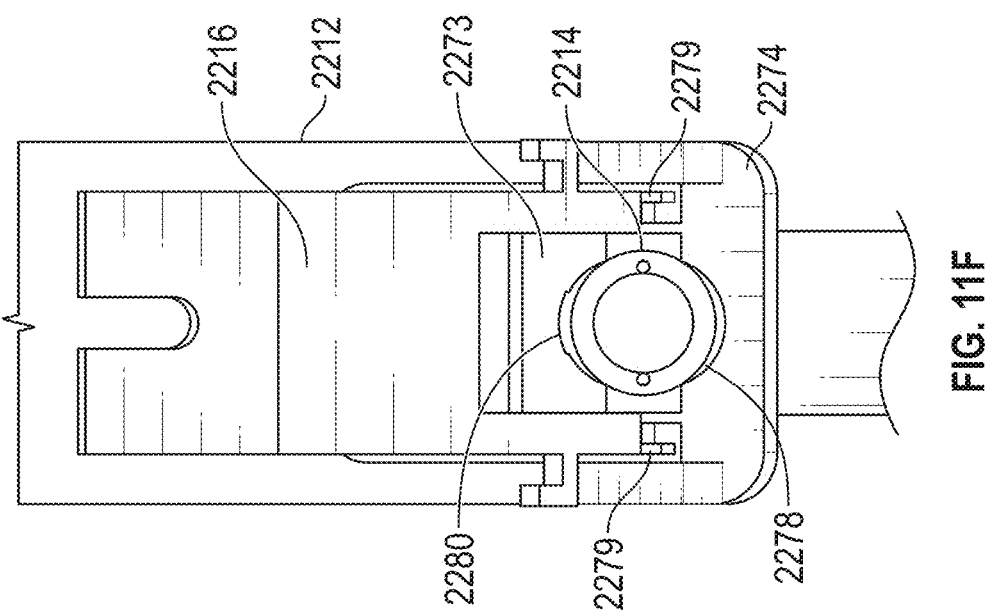

With reference to FIGS. 11F and 11G, some embodiments of the reinforcing element 2274 of the first tower 2212 can have a cutout 2278 (that can optionally be circular) formed therein that can receive a portion of an outside surface of the second tower 2214 therein. The cutout 2278 can be used to partially constrain the first tower 2212 with respect to the second tower 2214, particularly when the first tower 2212 is moved to force the cutout 2278 into contact with the outside surface of the second tower 2214. In some embodiments, the radius of the cutout 2278 can be less than a radius of the outside surface of the second tower 2214. In other embodiments, the cutout 2278 can have a V shape.

Additionally, some embodiments of the reinforcing element 2273 of the third tower 2216 can have a cutout 2280 (that can optionally be circular) formed therein that can receive a portion of an outside surface of the second tower 2214 therein. The cutout 2280 can be used to partially constrain the third tower 2216 with respect to the second tower 2214, particularly when the third tower 2216 is moved to force the cutout 2280 into contact with the outside surface of the second tower 2214. In some embodiments, the radius of the cutout 2280 can be less than a radius of the outside surface of the second tower 2214. In other embodiments, the cutout 2280 can have a V shape.

In some embodiments, the first, second, and third towers 2212, 2214, 2216 can be configured to be selectively removable from the first, second, and third screws 2202, 2204, 2206. For example and without limitation, some embodiments of the first, second, and third towers 2212, 2214, 2216 can have one or more creases, fracture lines, or lines of weakness (for example, two creases, fracture lines, or lines of weakness) along a length of a wall portion of any or all of the first, second, and third towers 2212, 2214, 2216. In some embodiments, a tool or other device can be used to fracture the first, second, and third towers 2212, 2214, 2216 along the one or more creases, fracture lines, or lines of weakness to remove the first, second, and third towers 2212, 2214, 2216 from the first, second, and third screws 2202, 2204, 2206. In some embodiments, the one or more creases, fracture lines, or lines of weakness can be circumferentially arranged and positioned at or adjacent to a top surface of the screws that the towers are attached to so that the towers can break along the one or more creases, fracture lines, or lines of weakness at or adjacent to the screws and be removed.

In some embodiments, the first, second, and third towers 2212, 2214, 2216 can have distal end portions having circumferential, helical, and/or discrete/intermittent projections, tabs, lip(s), flanges, grooves, channels, detents, or other mechanically locking features that engage with complementary locking features of the screw heads to cause the first, second, and third towers 2212, 2214, 2216 to be coupled with the screw heads when the first, second, and third towers 2212, 2214, 2216 are intact, but which can each be decoupled from the complementary locking features of the screw heads when the first, second, and/or third towers 2212, 2214, 2216 are fractured or split apart. As another example, a third wall or connecting wall connecting two sides of any of the first, second, and/or third towers 2212, 2214, 2216 can have an angled or "V" shaped profile wherein a fracture line or line of weakness extends along the apex or angle of the angled or "V" shaped profile such that, when the two sides of the first, second, and third towers 2212, 2214, 2216 are squeezed toward one another, such force from the squeezing can cause a fracture along the fracture line or line of weakness in the connecting portion, thereby allowing the first and second sides of the tower to separate so that tower can be removed from the screw head. In some embodiments, a slider ring can be slid down the tower to cause the two sides of the tower to be squeezed toward one another. In some embodiments, the first, second, and third towers 2212, 2214, 2216 can have tabs that extend from the first, second, and third screw heads that can be broken off from the screw heads after implantation. In some embodiments, the first, second, and/or third towers can be removably coupled with the first, second, and/or third screws by rotating the first, second, and/or third towers into engagement with the first, second, and/or third screws, and removed in the opposite manner.

In other embodiments, the extensions can be removably coupled with the screws so that the entire extension can be removed from the screw and the patient intact and be reused in subsequent procedures. For example and without limitation, ball and detent removable coupling mechanisms can be used to removably couple the first, second, and third towers 2212, 2214, 2216 with the first, second, and third screw heads. Other conventional or desired coupling mechanisms can be used to removably couple the first, second, and third towers 2212, 2214, 2216 with the first, second, and third screw heads. In other embodiments, a plurality of wires (such as, for example and without limitation, wires 140*a*, 140*b* shown in FIG. 1A) can be used to removably couple the first, second, and third towers 2212, 2214, 2216 with the first, second, and third screw heads, as described above with respect to the embodiments shown in FIGS. 1A-1Z.

Some embodiments of methods for treating a spinal defect include implanting a first screw 2202 that is coupled with a first tower 2212 through the incision into a first vertebra, advancing a third tower 2216 that is coupled with a third screw 2206 through the cutout 2224 formed in the first tower 2212 and implanting the third screw 2206 into a third vertebra, and advancing a second tower 2214 that is coupled with a second screw 2204 through the cutout 2244 formed in the third tower 2216 and implanting the second screw 2204 into a second vertebra. In some embodiments, the second vertebra can be between the first and third vertebrae.

The surgeon or medical practitioner can move a proximal portion 2212*b* of the first tower 2212 toward a proximal portion 2216*b* of the third tower 2216 to cause the distal portion 2212*a* of the first tower 2212 to move toward the distal portion 2216*a* of the third tower 2216, thereby causing a compressive force to be applied between the first, second, and third vertebrae. In some embodiments, the method can further include coupling a rigid connector or rod with the first screw 2202, the second screw 2204, and the third screw 2206 to generally fix a position of the first screw 2202 relative to the second screw 2204 and the third screw 2206. Thereafter, the first, second, and third towers 2212, 2214, 2216 can be removed from the first, second, and third screws 2202, 2204, 2206.

Any embodiments of the system 2200 disclosed herein can be configured for use in performing L4, L5 and S1 surgical procedures, as well as cortical screw trajectory procedures. Additionally, any embodiments of the system 2200 disclosed herein can be configured to enable compression, traction, and/or counter-torque all with one device, and the extensions can be configured to allow a tower, rod insertion, and rod reducer (using extended tabs with threads) with one device.

In any system embodiments disclosed herein, including without limitation the embodiments of the system 2000, 2200, any of the towers (also referred to herein as extensions) can have an open channel or opening along the length of at least a portion of the tower. The open channel or opening can, in some embodiments, reduce the torsional or bending stiffness of the tower during an implantation procedure—for example and without limitation, when counter-torque forces applied to the tower. Additional components and devices, such as the embodiments of the covers that are disclosed below, can be used to selectively reinforce or close at least a portion of the channel or opening to selectively increase a rigidity or stiffness of the tower. For example and without limitation, in some embodiments, a cover can be slid longitudinally over the channel or opening to selectively close the channel or opening or selectively increase a stiffness of the tower. The cover can have grooves or channels that can be used to guide the cover to be in contact with the tower at the desired location and also connect the cover to the tower to increase the stiffness of the tower at the location of the channel or opening. In some embodiments, the cover can be coupled with the tower after the rod or connecting element has been advanced or at least been partially advanced through the tower and/or screw heads. As mentioned, the closing of the open channel can, in some embodiments, aid in stabilizing the tower to aid final tightening of the locking cap and using the towers as a counter torque mechanism.

Systems, Devices and Methods of FIGS. 12A-12D

Additional embodiments of a system 3000 that can be used for stabilizing or treating spinal vertebrae through a skin incision are disclosed below. With reference to FIGS. 12A-12D, some embodiments of the system 3000 can have a first tower 3002, a second tower 3004, and a cover (also referred to herein as a support cover) that can be selectively coupled with at least one of the first tower 3002 and the second tower 3004, or any other towers of the system 3000.

In any embodiments disclosed herein, any components, features, or other details of the system 3000, including without limitation any embodiments of the first and second towers 3002, 3004, can have any of the components, features, or other details of any other system embodiments or towers or extensions of any of the other system embodiments disclosed herein or be used according to any of the steps of any other method embodiments disclosed herein, including without limitation any of the embodiments of the system 200, 300, 400, 2000, and/or 2200 or methods of use thereof described herein, in any combination with any of the components, features, or details of the system 3000 or methods of use disclosed herein. Similarly, any components, features, steps, or other details of any of the other system or method embodiments disclosed herein can have any of the components, features, steps, or other details of any embodiments of the system 3000 or methods of use thereof disclosed herein in any combination with any of the components, features, or details of the system.

Some embodiments of the system 3000 can be configured and/or optimized for use in robotic surgical procedures, just as with any of the other embodiments disclosed herein, including without limitation any embodiments of the system 2200. For example and without limitation, in some embodiments, the proximal portions of the towers can be configured and optimized for grasping and locating by end effectors or robotic arms of a surgical robot. The proximal portions of the first and second towers 3002, 3004 can have a curved portion for increased stiffness and a flat portion 3012, 3014, respectively, at a proximal end of the proximal portions of the first and second towers 3002, 3004. The flat portions 3012, 3014 can be better suited for graspers, end effectors, or coupling mechanisms of surgical robotic systems.

In any system embodiments of the system 3000 disclosed herein, any of the towers 3002, 3004 (also referred to herein as extensions) or any other towers of the system 3000 can have an open channel or opening along the length of at least a portion of the tower. In some embodiments, a cover 3006 (also referred to herein as a support cover) can be selectively coupled with the first tower 3002, the second tower 3004, and/or any other tower of the system 3000. In some embodiments, the cover 3006 can be used to selectively reinforce or close at least a portion of the channel or opening of one or more of the towers to selectively increase a rigidity or stiffness of the tower. For example and without limitation, in some embodiments, the cover 3006 can be slid longitudinally over the channel or opening to selectively close the channel or opening or selectively increase a stiffness of the tower.

Figure 12A:
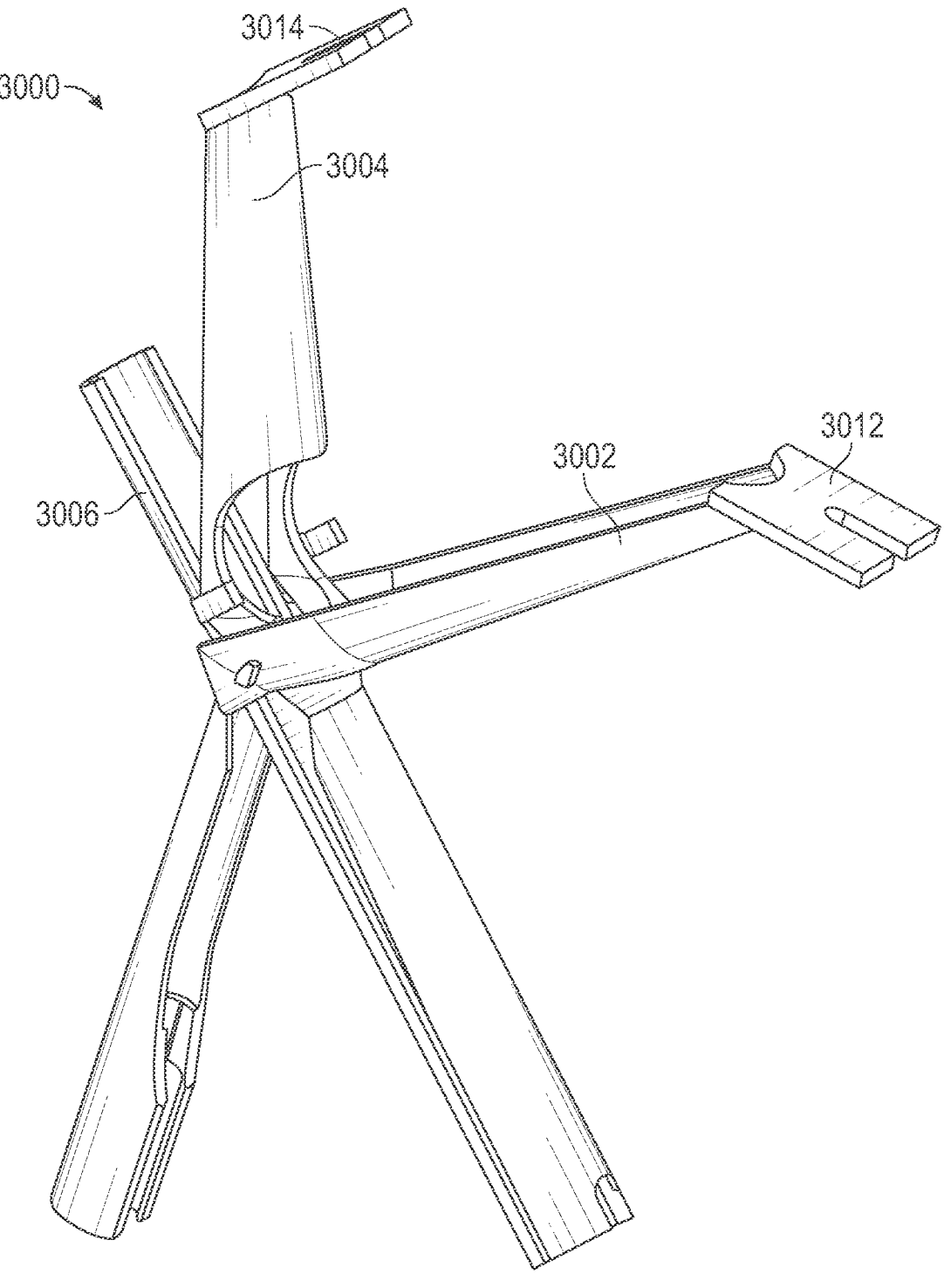
FIGS. 12A-12D illustrate another embodiment of a system for stabilizing spinal vertebrae comprising spinal screws.
Figure 12B:
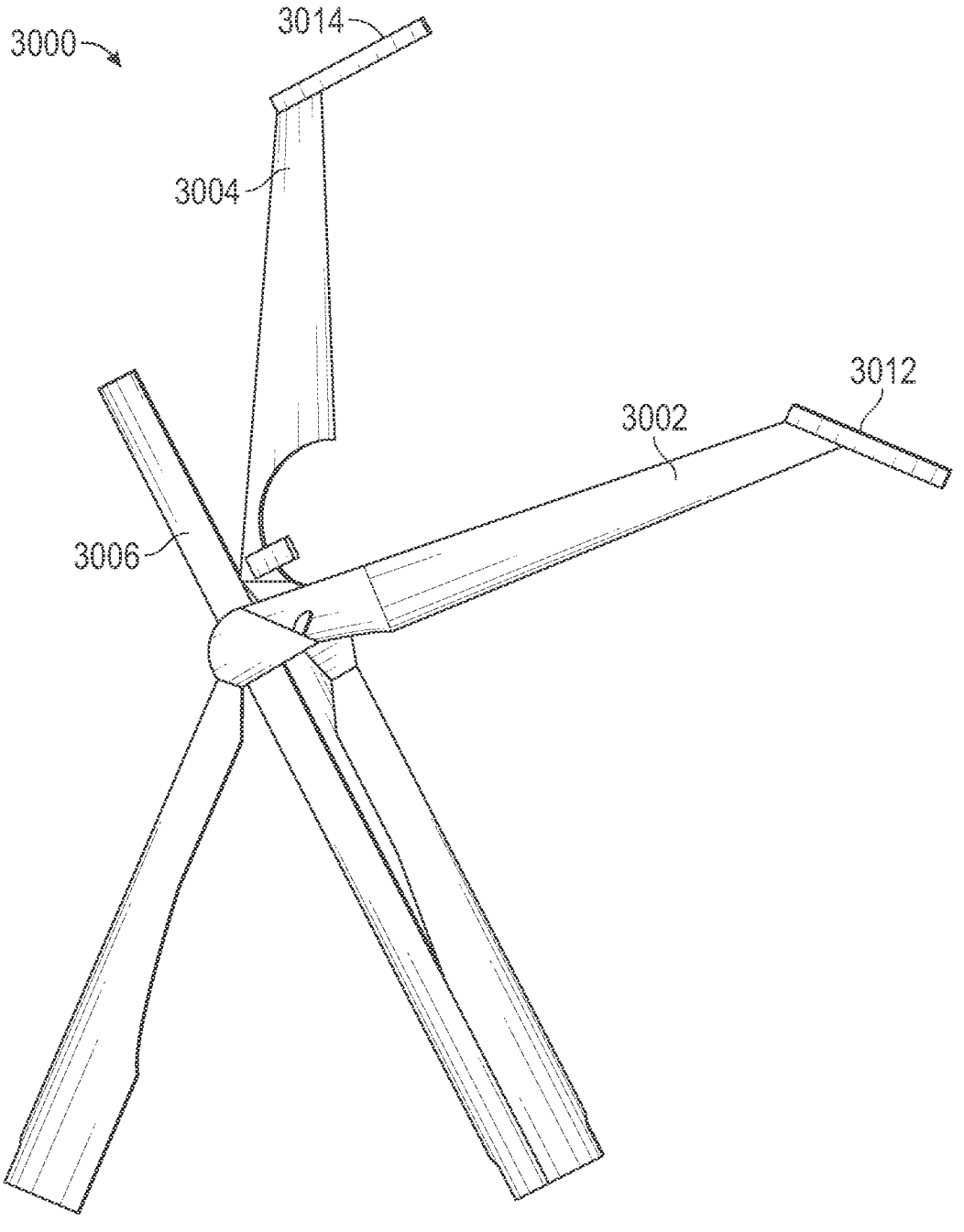
Figure 12C:
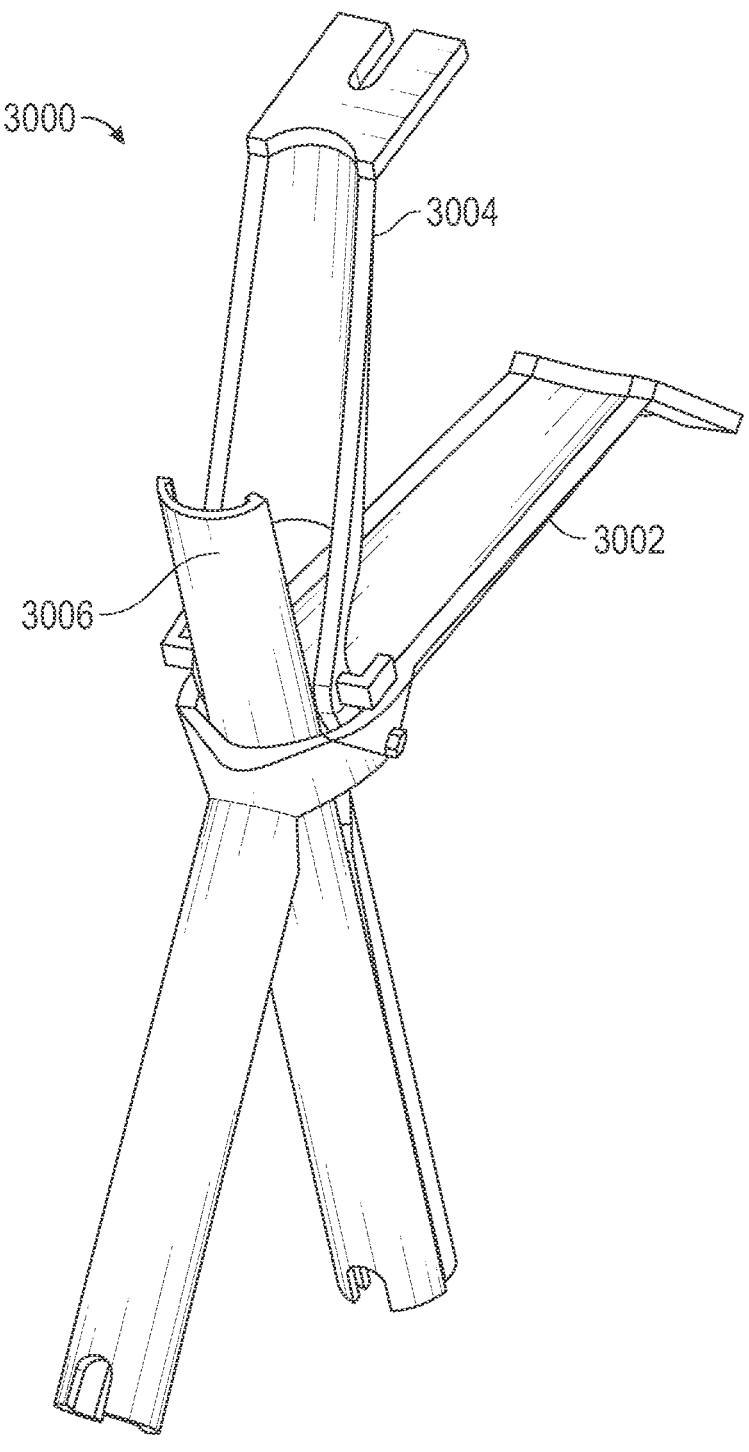
Figure 12D:
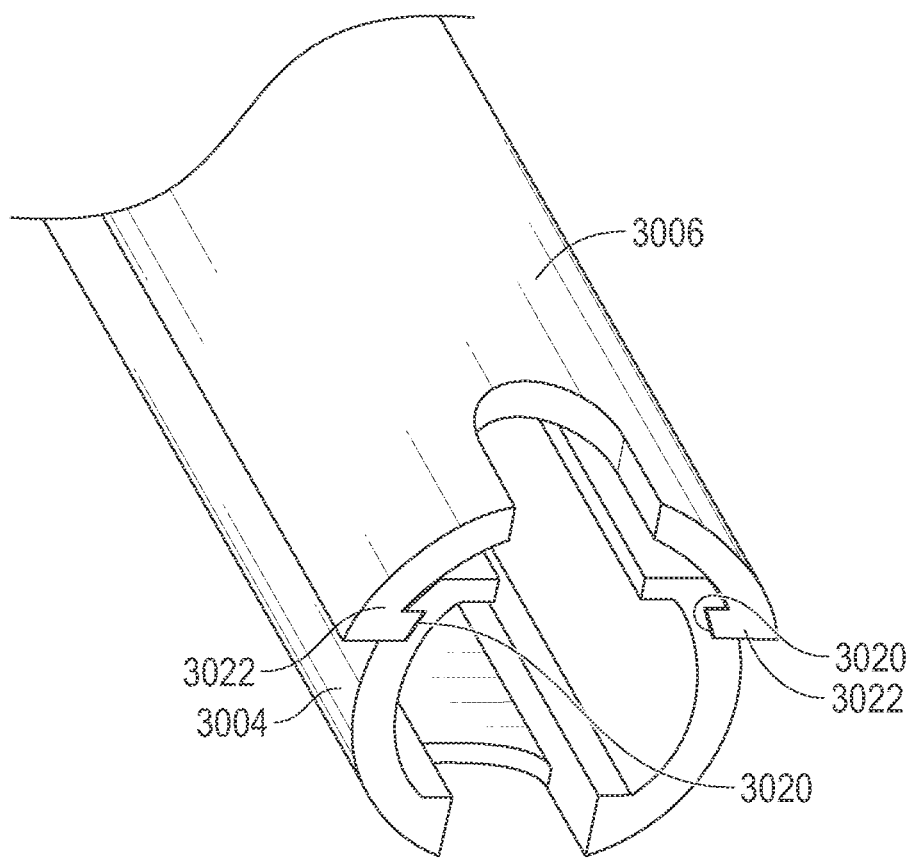

In some embodiments, with reference to FIG. 12D, the tower can have grooves or channels 3020 formed along at least a portion of a length of the tower, e.g., extending proximally from a distal end portion of the tower, which are configured to receive a mating tabbed feature or projection 3022 formed on the cover 3006. The grooves 3020 and projections 3022 can be configured to constrain the cover 3006 to the tower or couple the cover 3006 with the tower to increase the support that the cover 3006 provides to the tower when coupled together. The grooves 3020 and projections 3022 can be formed longitudinally along at least a portion of the length of the cover 3006 and the tower so that the projections 3022 may be slid into the channels 3020 as the cover 3006 is slid downward toward the distal end of the tower from outside the body. In some embodiments, the cover can be optimized for robotic surgical systems, such as by having a flat proximal portion that can be more easily grasped by the robot. In some embodiments, the cover can be coupled with the tower after the rod or connecting element has been advanced or at least been partially advanced through the tower and/or screw heads. As mentioned, the closing of the open channel can, in some embodiments, aid in stabilizing the tower to aid final tightening of the locking cap and using the towers as a counter torque mechanism.

While certain embodiments have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present embodiments is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations.

Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15°, 10°, 5°, 3°, 1°, or 0.1°.

Further, the ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±10%). For example, "about 7 mm" includes "7 mm" and numbers and ranges preceded by a term such as "about" or "approximately" should be interpreted as disclosing numbers and ranges with or without such a term such that this application supports claiming the number and ranges disclosed in the specification and/or claims with or without the term such as "about" or "approximately" before such numbers or ranges. Phrases preceded by a term such as "substantially" include the recited phrase and should be interpreted based on the circumstances (e.g., as much as reasonably possible under the circumstances). For example, "substantially straight" includes "straight."

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A system for stabilizing spinal vertebrae through a skin incision, comprising:

a first screw having a first screw head and a second screw having a second screw head;

a first tower having a distal portion, a proximal portion, and a bend between the distal portion and the proximal portion, the first tower being configured to be removably coupled with the first screw at a distal end of the first tower; and a second tower having a distal portion, a proximal portion, and a bend between the distal portion and the proximal portion, the second tower being configured to be removably coupled with the second screw at a distal end of the second tower;

wherein:

the first tower is configured to be removably coupled with the first screw such that, when the first tower is coupled with the first screw, an axial centerline of the distal portion of the first tower is approximately collinear with an axial centerline of the first screw;

the second tower is configured to be removably coupled with the second screw such that, when the second tower is coupled with the second screw, an axial centerline of the distal portion of the second tower is approximately collinear with an axial centerline of the second screw;

the proximal portion of the first tower extends at an acute, nonzero angle away from the axial centerline of the distal portion of the first tower;

the proximal portion of the second tower extends at an acute, nonzero angle away from the axial centerline of the distal portion of the second tower;

in an operable state, the first tower and the second tower are configured to intersect one another;

the first tower and the second tower are rigid; and in the operable state, the proximal portion of the first tower extends in a first direction at a first angle and the proximal portion of the second tower extends in the first direction at a second angle, wherein the second angle is less than the first angle.

2. The system of claim 1, wherein, in the operable state, the first tower and the second tower are configured to intersect at or adjacent to a skin level of a patient.

3. The system of claim 1, wherein, in the operable state, the first tower and the second tower are configured to intersect in an implanted state at or adjacent to a skin level of a patient such that a distance from the skin level to a proximal most end of the distal portion of the first tower is less than or equal to 10% of a length of the distal portion of the first tower and a distance from the skin level to a proximal most end of the distal portion of the second tower is less than or equal to 10% of a length of the distal portion of the second tower.

4. The system of claim 1, wherein the first tower has an opening therein, the opening being sized and configured to receive the second tower therein such that, in the operable state, an outer wall of a portion of the first tower surrounds an outer surface of a portion of the second tower.

5. The system of claim 4, wherein the opening extends at least through a proximal end of the distal portion of the first tower.

6. The system of claim 5, wherein the opening extends at least through a distal end of the proximal portion of the first tower.

7. The system of claim 1, wherein the distal portion of the first tower and/or the second tower has a curved cross-sectional profile and the proximal portion of the first tower and/or the second tower has a flat or rectangular cross-sectional profile.

8. The system of claim 1, wherein the proximal portion of the first tower is configured to be grasped by a surgeon to enable the surgeon to exert a counter-torque force on the first tower about at least the axial centerline of the distal portion of the first tower.

9. The system of claim 1, wherein, in the operable state, the system is configured such that moving the proximal portion of the first tower toward the proximal portion of the second tower will cause a compressive force on at least a first vertebra that the first screw is implanted in relative to a second vertebra that the second screw is implanted in.

10. The system of claim 1, wherein the first tower and the second tower are sized and configured such that only the proximal portion of the first tower and the proximal portion of the second tower are outside of the skin incision when the first screw is implanted in a first vertebra.

11. The system of claim 1, wherein the system is configured such that the first screw and the second screw are implanted through a common skin incision.

12. The system of claim 1, wherein the first tower has a pair of hooks configured to receive a pair of wires used during an implantation procedure.

13. The system of claim 1, wherein the first tower has a projection which provides a fulcrum for rotation of the second tower relative to the first tower.

14. The system of claim 1, further comprising: a rigid connecting element, a first receiving element coupled with the first screw head, and a second receiving element coupled with the second screw head, wherein the first receiving element and the second receiving element are configured to operably receive the rigid connecting element that, in the operable state, extends between the first receiving element and the second receiving element when the first screw and the second screw are implanted in a first and second vertebra, respectively.

15. The system of claim 1, further comprising a driver tool configured to rotate a cap to tighten the cap relative to at least one of the first screw and the second screw to secure a rod to at least the first screw or the second screw, the driver tool configured to be advanced through at least one of the first tower or the second tower.

16. The system of claim 1, wherein the first tower further comprises a first opening and, wherein, in the operable state a portion of the second tower is positioned within the first opening.

17. The system of claim 1, wherein the first direction is in the direction of a length of the spine.

18. A method of stabilizing spinal vertebrae, comprising:
providing the system of claim 4;
implanting the first screw that is coupled with the first tower through an incision into a first vertebra;
advancing the second tower that is coupled with the second screw through the opening formed in the first tower and implanting the second screw into a second vertebra; and
moving the proximal portion of the first tower toward the proximal portion of the second tower to move the first vertebra from a first position relative to the second vertebra to a second position relative to the second vertebra.

19. A system for stabilizing spinal vertebrae through a skin incision, comprising:
a first screw having a first screw head and a second screw having a second screw head;
a first tower having a distal portion and a proximal portion, the first tower being configured to be removably coupled with the first screw at a distal end of the first tower; and
a second tower having a distal portion and a proximal portion, the second tower being configured to be removably coupled with the second screw at a distal end of the second tower;
wherein:
the first tower is configured to be removably coupled with the first screw such that, when the first tower is coupled with the first screw, an axial centerline of the distal portion of the first tower is approximately collinear with an axial centerline of the first screw;
the second tower is configured to be removably coupled with the second screw such that, when the second tower is coupled with the second screw, an axial centerline of the distal portion of the second tower is approximately collinear with an axial centerline of the second screw;
the proximal portion of the first tower extends at an acute, nonzero angle away from the axial centerline of the distal portion of the first tower;
the proximal portion of the second tower extends at an acute, nonzero angle away from the axial centerline of the distal portion of the second tower;
in an operable state, the proximal portion of the first tower extends in a first direction and in a first plane and the proximal portion of the second tower also extends in the first direction and in the first plane;
wherein the first direction extends in the direction of a length of the spine.

20. The system of claim 19, wherein, in the operable state, the first tower and the second tower are configured to intersect at or adjacent to a skin level of a patient.

21. The system of claim 19, wherein, in the operable state, the first plane extends through the entire longitudinal centerlines of the first tower and the second tower in the operable state.

22. The system of claim 19, wherein the axial centerline of the distal portion of the first tower extends along the first plane.

23. The system of claim 19, wherein in the operable state the proximal portion of the first tower extends in the first direction at a first angle and the proximal portion of the second tower extends in the first direction at a second angle, wherein the second angle is less than the first angle.

24. A system for stabilizing spinal vertebrae through a skin incision, comprising:

a first screw having a first screw head and a second screw having a second screw head;

a first tower having a distal portion, a proximal portion, and a bend between the distal portion and the proximal portion, the first tower being configured to be removably coupled with the first screw at a distal end of the first tower; and a second tower having a distal portion, a proximal portion, and a bend between the distal portion and the proximal portion, the second tower being configured to be removably coupled with the second screw at a distal end of the second tower;

wherein:

the first tower is configured to be removably coupled with the first screw such that, when the first tower is coupled with the first screw, an axial centerline of the distal portion of the first tower is approximately collinear with an axial centerline of the first screw;

the second tower is configured to be removably coupled with the second screw such that, when the second tower is coupled with the second screw, an axial centerline of the distal portion of the second tower is approximately collinear with an axial centerline of the second screw;

the proximal portion of the first tower extends at an acute, nonzero angle away from the axial centerline of the distal portion of the first tower;

the proximal portion of the second tower extends at an acute, nonzero angle away from the axial centerline of the distal portion of the second tower; and in an operable state, the first tower and the second tower are configured to intersect one another;

the proximal portion of the first tower comprises a fulcrum; and the fulcrum is configured so that the second tower can contact the fulcrum and rotate about the fulcrum in an operable state during compression of the vertebrae.

25. The system of claim 24, wherein, the first tower has an opening therein, the opening being sized and configured to receive the second tower therein such that, in the operable state, an outer wall of a portion of the first tower surrounds an outer surface of a portion of the second tower.

26. The system of claim 24, wherein the distal portion of the first tower and/or the second tower has a curved cross-sectional profile and the proximal portion of the first tower and/or the second tower has a flat or rectangular cross-sectional profile.

* * * * *